(12) United States Patent
Roecklin et al.

(10) Patent No.: US 7,081,345 B1
(45) Date of Patent: Jul. 25, 2006

(54) USE OF A POLYPEPTIDE FOR DETECTING, PREVENTING OR TREATING A PATHOLOGICAL CONDITION ASSOCIATED WITH A DEGENERATIVE, NEUROLOGICAL OR AUTOIMMUNE DISEASE

(75) Inventors: Dominique Roecklin, Niederschaeffolsheim (FR); Hanno Kolbe, Achenheim (FR); Marie-Hélène Charles, Condrieu (FR); Carine Malcus, Brignais (FR); Lyse Santoro, Charbonnieres les Bains (FR); Hervé Perron, Lyons (FR)

(73) Assignee: Biomerieux Stelhys, Marcy L'Etoile (FR)

( * ) Notice: Subject to any disclaimer, the term of this patent is extended or adjusted under 35 U.S.C. 154(b) by 273 days.

(21) Appl. No.: 10/030,937

(22) PCT Filed: Jul. 17, 2000

(86) PCT No.: PCT/FR00/02057

§ 371 (c)(1),
(2), (4) Date: May 24, 2002

(87) PCT Pub. No.: WO01/05422

PCT Pub. Date: Jan. 25, 2001

(30) Foreign Application Priority Data

Jul. 15, 1999 (FR) .................................. 99 09372

(51) Int. Cl.
*G01N 33/53* (2006.01)
(52) U.S. Cl. ..................... 435/7.1; 536/23.1; 536/23.5; 530/350
(58) Field of Classification Search ................ 530/350, 530/387.1; 435/7.1
See application file for complete search history.

(56) References Cited

U.S. PATENT DOCUMENTS 5,876,954 A    3/1999   Perron et al. ................. 435/23

FOREIGN PATENT DOCUMENTS

| CA | 2214843 | 4/1999 |
|---|---|---|
| JP | A 8-308582 | 11/1996 |
| WO | WO 90/07712 | 7/1990 |
| WO | WO 97/33466 | 9/1997 |
| WO | WO 98/11439 | 3/1998 |

OTHER PUBLICATIONS

Xie et al, Biochem. Biophys. Res. Comm. 177: 1217 (1991).*
Nagarajan et al, Biochem. J. 282: 807 (1992).*
Li et al, J. Biol. Chem. 270: 24246 (1995).*
Rieger et al., "Un facteur gliotoxique et la sclerose en plaques", C.R. Acad. Sci. Paris, Sciences de la vie/Life sciences, XP 000602023, pp. 343-350, 1996.
Kisilevsky et al., "Arresting amyloidosis in vivo using small-molecule anionic sulphonates or sulphates: implications for Alzheimer's disease", Nature Medicine, vol. 1, No. 2, pp. 143-148, 1995.
Conzelmann et al., "Purification and Characterization of an Activator Protein for the Degradation of Glycolipis $G_{M2}$ and $G_{A2}$ by Hexosaminidase A", Hoppe-Seyler's Z. Physiol. Chem., pp. 1837-1849, 1979, vol. 360.
Hitomi et al., "A novel calcium-binding protein in amniotic fluid, CAAF1: its molecular cloning and tissue distribution", Journal of Cell Science, pp. 805-815, 1996, vol. 109.
Raftery et al., "Isolation of the murine S100 protein MRP14 (14 kDa migration-inhibitory-factor-related protein) from activated spleen cells: characterization of post-translational modifications and zinc binding", Biochem J., pp. 285-293, 1996, vol. 316.

(Continued)

*Primary Examiner*—James Martinell
(74) *Attorney, Agent, or Firm*—Oliff & Berridge, PLC

(57) ABSTRACT

The invention concerns the use of at least one polypeptide comprising a protein fragment to obtain a diagnostic, prognostic, prophylactic or therapeutic composition for detecting, preventing or treating a pathological condition associated with a degenerative and/or neurological and/or autoimmune disease, said protein being selected among the proteins whereof the peptide sequence in native state corresponds to SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, and SEQ ID No 29, and the peptide sequences having at least 70% identity, preferably at least 80% identity and advantageously at least 98% identity with any one of the peptide sequences SEQ ID No 1 to SEQ ID No 8 and SEQ ID No 10 to SEQ ID No 29, and the peptide sequences or fragments of said sequences belonging to a common family of proteins selected among perlecan, the precursor of the retinol-binding plasmatic protein, of the GM2 activator protein, of calgranulin B and of saponin B.

10 Claims, 18 Drawing Sheets

OTHER PUBLICATIONS

Kase et al., "Only sphingolipid activator protein B (SAP-B or saposin B) stimulates the degradation of globotriaosylceramide by recombinant human lysosomal α-galactosidase in a detergent-free liposomal system", FEBS Letters, pp. 74-76, 1996, vol. 393.

Bierfreund et al., "Recombinant GM2-Activator Protein Stimulates in Vivo Degradation of GA2 in GM2 Gangliosidosis AB Variant Fibroblasts But Exhibits No Detectable Binding of GA2 in an In Vitro Assay", Neurochemical Research, vol. 24, No. 2, pp. 295-300, 1999.

Longbottom et al., "Subunit structure of calgranulins A and B obtained from sputum, plasma, granulocytes and cultured epithelial cells", Biochimica et Biophysica Acta, pp. 215-222, 1992, vol. 1120.

Raftery et al., "Overexpression, Oxidative Refolding, and Zinc Binding of Recombinant Forms of the Murine S100 Protein MRP14 (S100A9)", Protein Expression and Purification, pp. 228-235, 1999, vol. 15.

Klempt et al., "The heterodimer of the $Ca^{2+}$-binding proteins MRP8 and MRP14 binds arachidonic acid", FEBS Letters, pp. 81-84, 1997, vol. 408.

Katz et al., "Colorimetric diagnosis of prolonged bluetongue viremia in sheep, using an enzyme-linked oligonucleotide sorbent assay of amplified viral nucleic acids", Am J Vet Res, vol. 54, No. 12, pp. 2021-2026, 1993.

Toes et al., "Protective anti-tumor immunity induced by vaccination with recombinant adenoviruses encloding multiple tumor-associated cytotoxic T lumphocyte epitopes in a string-of-beads fashion", Proc. Natl. Acad. Sci., vol. 94, pp. 14660-14665, 1997.

Bird et al., "Single-Chain Antigen-Binding Proteins", Science Reports, pp. 423-426, 1988, vol. 242.

Arakawa et al., "Cloning and Sequencing of the $V_H$ and $V_\kappa$ Genes of an Anti-CD3 Monoclonal Antibody, and Construction of a Mouse/Human Chimeric Antibody", J. Biochem, pp. 657-662, vol. 120, No. 3, 1996.

Chaudhary et al., "A recombinant immunotoxin consisting of two antibody variable domains fused to *Pseudomonas* exotoxin", Letters to Nature, vol. 339, pp. 394-397, 1989.

Behr et al., "Efficient gene transfer into mammalian primary endocrine cells with lipopolyamine-coated DNA", Proc. Natl. Acad. Sci, vol. 86, pp. 6982-6986, 1989.

Debrick et al., "Macrophages As Accessory Cells For Class I MHC-Restricted Immune Responses", The Journal of Immunology, vol. 147, No. 9, pp. 2846-2851, 1991.

Kovacsovics-Bankowski et al., "A Phagosome-to-Cytosol Pathway for Exogenous Antigens Presented on MHC Class I Molecules", Science Reports, vol. 267, pp. 243-246, 1995.

Kovacsovics-Bankowski et al., "Efficient major histocompatibility complex class I presentation of exogenous antigen upon phagocytosis by macrophages", Proc. Natl. Acad. Sci, vol. 90, pp. 4942-4946, 1993.

Racoosin et al., "M-CSF-induced macropinocytosis increases solute endocytosis but not receptor-mediated endocytosis in mouse macrophages", Journal of Cell Science, pp. 867-880, 1992, vol. 102.

Finke et al. "Increase of proliferation rate and enhancement of antitumor cytotoxicity of expanded human CD3+ CD56+ immunologic effector cells by receptor-mediated transfection with the interleukin-7 gene", Gene Therapy, pp. 31-39, 1998, vol. 5.

Haensler et al., "Polyamidoamine Cascade Polymers Mediate Efficient Transfection of Cells in Culture", Bioconjugate Chem., pp. 372-379, 1993, vol. 4.

Deo et al., "Clinical significance of IgG Fc receptors and FcγR-directed immunotherapies", Immunology Today, vol. 18, pp. 127-135, 1997.

Pession et al., "Molecular Cloning of NKp46: A Novel Member of the Immunoglobulin Superfamily Involved in Triggering of Natural Cytotoxicity", J. Exp. Med, vol. 188, No. 5, pp. 953-960, 1998.

Kawano et al., "Natural killer-like nonspecific tumor cell lysis mediated by specific ligand-activated Vα14 NKT cells", Proc. Natl. Acad. Sci., vol. 95, pp. 5690-5693, 1998.

McCoy et al., "Pulmonary Inflammation Induced by Incomplete or Inactivated Adenoviral Particles", Human Gene Therapy, pp. 1553-1560, 1995, vol. 6.

Cotten et al., "Non-viral approaches to gene therapy", Current Biology, pp. 705-710, 1993.

Felgner et al., "Cationic liposome-mediated transfection", Nature, vol. 337, pp. 387-388, 1989.

Felgner et al., "Lipofection: A highly efficient, lipid-mediated DNA-transfection procedure", Proc. Natl. Acad. Sci, vol. 84, pp. 7413-7417, 1987.

Felgner et al., "Cationic Lipid-Mediated Delivery of Polynucleotides", Methods, pp. 67-75, 1993, vol. 5.

Gao et al., "A Novel Cationic Liposome Reagent For Efficient Transfection of Mammalian Cells", Biochemical and Biophysical Research Communication, vol. 179, No. 1, pp. 280-285, 1991.

Groettrup et al., "Peptide antigen production by the proteasome: complexity provides efficiency", Immunology Today, vol. 17, No. 9, pp. 429-435, 1996.

Polydefkis et al., "Achor Sequence-Dependent Endogenous Processing of Human Immunodeficiency Virus 1 Envlope Glycoprotein gp160 For CD4+ T Cell Recognition", J. Exp Med, vol. 171, pp. 875-887, 1990.

Sallusto et al., "Dendritic Cells Use Macropinocytosis and the Mannose Receptor to Concentrate Macromolecules in the Major Histocompatibility Complex Class II Compartment: Downregulation by Cytokines and Bacterial Products", J. Exp. Med, vol. 182, pp. 389-400, 1995.

Melero et al., "Amplification of tumor immunity by gene transfer of the co-stimulatory 4-1BB ligand: synergy with the CD28 co-stimulatory pathway", Eur. J. Immunol., pp. 1116-1121, 1998, vol. 28.

Whitton et al., "A "String-of-Beads" Vaccine, Comprising Linked Minigenes, Confers Protection from Lethal-Dose Virus Challenge", Journal of Virology, vol. 67, No. 1, pp. 348-352, 1993.

Svensson et al., "Bone Marrow-Derived Dendritic Cells Can Process Bacteria for MHC-I and MHC-II Presentation to T Cells", The Journal of Immunology, pp. 4229-4236, 1997.

Norbury et al., "Constitutive macropinocytosis allows TAP-dependent major histocompatibility compex class I presentation of exogenous soluble antigen by bone marrow-derived dendritic cells", Eur. J. Immunol., pp. 280-288, 1997, vol. 27.

Routledge et al., "A humanized monovalent CD3 antibody which can activate homologous complement", Eur. J. Immunol, pp. 2717-2725, 1991, vol. 21.

Sousa et al., "Phagocytosis of Antigens by Langerhans Cells in Vitro", J. Exp. Med, vol. 178, pp. 509-519, 1993.

Klein et al., "Sphingolipid Activator Protein D (sap-D) Stimulates the Lysosomal Degradation of Ceramide *In Vivo*", Biochemical and Biophysical Research Communications, vol. 200, No. 3, pp. 1440-1448, 1994.

Murao et al., "A Protein Complex Expressed during Terminal Differentiation of Monomyelocytic Cells Is an Inhibitor of Cell Growth", Cell Growth & Differentiation, vol. 1, pp. 447-454, 1990.

Murthy et al., "In Vitro Candidastatic Properties of the Human Neutrophil Calprotectin Complex", Journal of Immunology, vol. 151, No. 11, pp. 6291-6301, 1993.

Murdoch et al., Primary Structure of the Human Heparan Sulfate Proteoglycan from Basement Membrane (HSPG2/Perlecan), The Journal of Biological Chemistry, vol. 267, No. 12, pp. 8544-8557, 1992.

Zaltash et al., "Secondary structure and limited proteolysis give experimental evidence that the precursor of pulmonary surfactant protein B contains three saposin-like domains", FEBS Letters, pp. 1-4, 1998, vol. 423.

Lagasse et al., "Cloning and Expression of Two Human Genes Encoding Calcium-Binding Priotenis That Are Regulated during Myeloid Differentiation", Molecular and Cellular Biology, vol. 8, No. 6, pp. 2402-2410, 1988.

Kleinschmidt et al., "Complete Amino-Acid Sequence of the Naturally Occuring $A_2$ Activator Protein for Enzymic Sphingomyelin Degradation: Identity to the Sulfatide Activator Protein (SAP-1)", Biol. Chem. Hoppe-Seyler, vol. 369, pp. 1361-1365, 1988.

O'Brein et al., "Saposin proteins: structure, function, and role in human lysosomal storage disorders", The FASEB Journal, vol 5, pp. 301-308, 1991.

Roda et al., "Production of a High-Titer Antibody to Bile Acids", Journal of Steroid Biochemistry, vol. 13, pp. 449-454, 1980.

Scheibenbogen et al., "A Sensitive ELISPOT Assay for Detection of CD8+ T Lymphocytes Specific for HLA Class I-binding Peptide Epitopes Derived from Influenza Proteins in the Blood of Healthy Donors and Melanoma Patients", Clinical Cancer Research, vol. 3, pp. 221-226, 1997.

Misasi et al., "Colocalization and Complex Formation Between Prosaposin and Monosialoganglioside GM3 in Neural Cells", Journal of Neurochemistry, vol. 71, No. 6, pp. 2313-2321, 1998.

Versteeg, "NK cells and T cells: mirror images?", Immunology Today, vol. 13, No. 7, pp. 244-247, 1992.

George et al., "Disease susceptibility, transplantation and the MHC", Immunology Today, vol. 16, No. 5, pp. 209-211, 1995.

Brittenden et al., "Natural Killer Cells and Cancer", Cancer, vol. 77, No. 7, pp. 1226-1243, 1996.

Blazar et al., "Anti-CD3∈F(ab')$_2$ Fragments Inhibit T Cell Expansion in Vivo During Graft-Versus-Host Disease or the Primary Immune Response to Nominal Antigen[1,2]", The Journal of Immunology, pp. 5821-5833, 1997.

McLachlan et al., "Evaluation in vitro and in vivo of cationic liposome-expression construct complexes for cystic fibrosis gene therapy", Gene Therapy, pp. 614-622, 1995, vol. 2.

Behr et al., "Efficient gene transfer into mammalian primary endocrine cells with lipopolyamine-coated DNA", Proc. Natl. Acad. Sci., vol. 96, pp. 6982-6986, 1989.

Waring et al., "Porcine Cerebroside Sulfate Activator (Saposin B) Secondary Structure: CD, FTIR, and NMR Studies", Molecular Genetics and Metabolism, pp. 14-25, 1998, vol. 63.

Anderson et al., "Antibodies to DNA", BioEssays, vol. 8, No. 2, pp. 69-75, 1988.

Kohler et al., "Continuous cultures of fused cells secreting antibody of predefined specificity", Nature, vol. 256, pp. 495-497, 1975.

Yajima et al., "SiC and $Si_3N_4$ sintered bodies with new borodiphenylsiloxane polymers as binder", Nature, vol. 266, pp. 522-524, 1977.

Lee et al., "Functional groups on 'Z' DNA recognized by monoclonal antibodies", FEBS Letters, vol. 168, No. 2, pp. 303-306, 1984.

Malfoy et al., "Interaction between Antibodies to Z-Form Deoxyribonucleic Acid and Double-Stranded Polynucleotides", Biochemistry, pp. 5463-5467, 1982.

Traincard et al., "Calibration of target amounts of DNA in hybridization experiments using monoclonal antinucleoside antibodies", Molecular and Cellular Probes, pp. 27-38, 1989, vol. 3.

Traincard et al., "Monoclonal anti-nucleoside antibodies Characterization and application in an enzyme immunoassay of single-stranded DNA", Journal of Immunological Methods, pp. 83-91, 1989, vol. 123.

Cros et al, "Monoclonal antibodies targeted to α-oligonucleotides. Characterisation and application in nucleic acid detection", Nucleic Acids Research, vol. 22, No. 15, pp. 2951-2957, 1994.

Li et al., "Presence of Activator Proteins for the Enzymic Hydrolysis of $G_{M1}$ and $G_{M2}$ Gangliosides in Normal Human Urine", Am J Hum Genet, pp. 629-634, 1983, vol. 35.

Li et al., "A Protein Activator for the Enzymic Hydrolysis of $G_{M2}$ Ganglioside", The Journal of Biological Chemistry, vol. 256, No. 12, p. 6234-6240, 1981.

Li et al., "An Activator Stimulating the Enzymic Hydrolysis of Sphingoglycolipids", The Journal of Biological Chemistry, vol. 251, No. 4, pp. 1159-1163, 1976.

Kishimoto et al., "Saposins: structure, function, distribution, and molecular genetics", Journal of Lipid Research, vol. 33, pp. 1255-1267, 1992.

Mallet et al., "Enzyme-Linked Oligosorbent Assay for Detection of Polymerase Chain Reaction-Amplified Human Immunodeficiency Virus Type 1", Journal of Clinical Microbiology, vol. 31, No. 6, pp. 1444-1449, 1993.

Saintigny et al., "Differential Expression of Calgranulin A and B in Various Epithelial Cell Lines and Reconstructed Epidermis", The Journal of Investigative Dermatology, pp. 639-644, 1992.

Goebeler et al., "The monoclonal antibody MAC387 detects an epitope on the calcium-binding protein MRP14", Journal of Leukocyte Biology, vol. 55, pp. 259-261, 1994.

Qi et al., "Functional Human Saposins Expressed in *Escherichia coli*", The Journal of Biological Chemistry, vol. 269, No. 24, pp. 16746-16753, 1994.

Yuziuk et al, "Specificity of Mouse $G_{M2}$ Activator Protein and β-N-Acetylhexosaminidass A and B", The Journal of Biological Chemistry, vol. 273, No. 1, pp. 66-72, 1998.

DeGasperi et al., "Isolation and characterization of an activator protein for the hydrolysis of ganglioside $G_{M2}$ from the roe of stiped mullet (*Mugil cephalus*)", Biochem J., pp. 777-783, 1989.

Vogel et al, "Identity of the Activator Proteins for the Enzymatic Hydrolysis of Sulfatide, Ganglioside $G_{M1}$, and Globotriaosylceramide", Archives of Biochemistry and Biophysics, vol. 259, No. 2, pp. 627-638, 1987.

Hirabayashi et al., "The Protein Activator Specific for the Enzymic Hydrolysis of $GM_2$ Ganglioside in Normal Human Brain and Brains of Three Types of $GM_2$ Gangliosidosis", Journal of Neurochemistry, vol. 40, No. 1, pp. 168-175, 1983.

Bos et al., "Copurification of P6, MRP8, and MRP14 from Human Granulocytes and Separation of Individual Proteins[1]", Protein Expression and Purification, pp. 313-318, 1998, vol. 13.

"Les Transcrits Subissent une Maturation Nucleaire Qui Debute Avant Que La Transcription Ne Soit Achevee", Du Genotype Au Phenotype, pp. 73-77.

"Molecular cloning-A laboratory manual", CHS Laboratory, Cold Spring, 1982, Table of Contents Only pp. v-x.

Remington's Pharmaceutical Sciences, Mack Publishing, 16th Edition, 1980, Table of Contents Only, p. xiii.

Li et al., "Characterization of a Nonspecific Activator Protein for the Enzymatic Hydrolysis of Glycolipids*", Journal of Biological Chemistry, vol. 263, No. 14, pp. 6588-6591, 1988.

Furst et al., "The complete amino-acid sequences of human ganglioside GM2 activator protein and cerebroside sulfate activator protein", Eur. J. Biochem, pp. 709-714, 1990.

Yang et al., "Monoclonal T Cells Identified in Early NOD Islet Infiltrates", Immunity, vol. 4, pp. 189-194, 1996.

* cited by examiner

Rabbits anti GM2

➤ Ganglioside GM2 activator
2 peptides of 13, 15 amino acids    rabbits 189 190
1 peptide of 18 amino acids    rabbit 191 and 192

MQSLMQAPLL IALGLLLATP AQAHLKKPSQ
LSSFSWDNCD EGKDPAVIRS LTLEPDPIVV
PGNVTLSVVG STSVPLSSPL KVDLVLEKEV
AGLWIKIPCT DYIGSCTFEH FCDVLDMLIP
TGEPCPEPLR TYGLPCHCPF KEGTYSLPKS
EFVVPDLELP SWLTTGNYRI ESVLSSSGKR
LGCIKIAASLKGI

FIG. 1

Rabbits anti MRP14

2 peptides of 13, 19 amino acids      rabbit 193
1 peptide of 17 amino acids      rabbit 195–196

MTCKMSQLER NIETIINTFH QYSVKLGHPD
TLNQGEFKEL VRKDLQNFLK KENKNEKVIE
HIMEDDLDTN ADKQLSFEEF IMLMARLTWA
SHEKMHEGDE GPGHHHKPGL GEGTP

FIG. 2

Rabbit anti Saposine 3 peptides of 12, 15, 15 amino acids     rabbit 74-75
3 peptides of 12, 15, 15 amino acids     rabbit 72-73

GDVCQDCIQM VTDIQTAVRT NSTFVQALVE
HVKEECDRLG PGMADICKNY ISQYSEIAIQ
MMMHMQDQQP KEICALVGFC DEV

FIG. 3

MS patient progressive remittent form

SapB & Gliotoxicity

GM2AP & Gliotoxicity

MS patient - Progressive

SEQUENCE LISTING

```
<160> NUMBER OF SEQ ID NOS: 75

<210> SEQ ID NO 1
<211> LENGTH: 4393
<212> TYPE: PRT
<213> ORGANISM: Homo sapiens

<400> SEQUENCE: 1

Met Gly Trp Arg Ala Pro Gly Ala Leu Leu Ala Leu Leu Leu His
 1               5                  10                  15

Gly Arg Leu Leu Ala Val Thr His Gly Leu Arg Ala Tyr Asp Gly Leu
                20                  25                  30

Ser Leu Pro Glu Asp Ile Glu Thr Val Thr Ala Ser Gln Met Arg Trp
            35                  40                  45

Thr His Ser Tyr Leu Ser Asp Asp Glu Asp Met Leu Ala Asp Ser Ile
        50                  55                  60

Ser Gly Asp Asp Leu Gly Ser Gly Asp Leu Gly Ser Gly Asp Phe Gln
    65                  70                  75                  80

Met Val Tyr Phe Arg Ala Leu Val Asn Phe Thr Arg Ser Ile Glu Tyr
                85                  90                  95

Ser Pro Gln Leu Glu Asp Ala Gly Ser Arg Glu Phe Arg Glu Val Ser
               100                 105                 110

Glu Ala Val Val Asp Thr Leu Val Ser Glu Tyr Leu Lys Ile Pro Gly
           115                 120                 125

Asp Gln Val Val Ser Val Val Phe Ile Lys Glu Leu Asp Gly Trp Val
       130                 135                 140
```

-continued

```
Phe Val Glu Leu Asp Val Gly Ser Glu Gly Asn Ala Asp Gly Ala Gln
145                 150                 155                 160

Ile Gln Glu Met Leu Leu Arg Val Ile Ser Ser Gly Ser Val Ala Ser
                165                 170                 175

Tyr Val Thr Ser Pro Gln Gly Phe Gln Phe Arg Arg Leu Gly Thr Val
            180                 185                 190

Pro Gln Phe Pro Arg Ala Cys Thr Glu Ala Phe Ala Cys His Ser
        195                 200                 205

Tyr Asn Glu Cys Val Ala Leu Glu Tyr Arg Cys Asp Arg Arg Pro Asp
    210                 215                 220

Cys Arg Asp Met Ser Asp Glu Leu Asn Cys Glu Glu Pro Val Leu Gly
225                 230                 235                 240

Ile Ser Pro Thr Phe Ser Leu Leu Val Glu Thr Thr Ser Leu Pro Pro
                245                 250                 255

Arg Pro Glu Thr Thr Ile Met Arg Gln Pro Pro Val Thr His Ala Pro
            260                 265                 270

Gln Pro Leu Leu Pro Gly Ser Val Arg Pro Leu Pro Cys Gly Pro Gln
        275                 280                 285

Glu Ala Ala Cys Arg Asn Gly His Cys Ile Pro Arg Asp Tyr Leu Cys
    290                 295                 300

Asp Gly Gln Glu Asp Cys Glu Asp Gly Ser Asp Glu Leu Asp Cys Gly
305                 310                 315                 320

Pro Pro Pro Pro Cys Glu Pro Asn Glu Phe Pro Cys Gly Asn Gly His
                325                 330                 335

Cys Ala Leu Lys Leu Trp Arg Cys Asp Gly Asp Phe Asp Cys Glu Asp
            340                 345                 350

Arg Thr Asp Glu Ala Asn Cys Pro Thr Lys Arg Pro Glu Glu Val Cys
        355                 360                 365

Gly Pro Thr Gln Phe Arg Cys Val Ser Thr Asn Met Cys Ile Pro Ala
    370                 375                 380

Ser Phe His Cys Asp Glu Glu Ser Asp Cys Pro Asp Arg Ser Asp Glu
385                 390                 395                 400

Phe Gly Cys Met Pro Pro Gln Val Val Thr Pro Pro Arg Glu Ser Ile
                405                 410                 415

Gln Ala Ser Arg Gly Gln Thr Val Thr Phe Thr Cys Val Ala Ile Gly
            420                 425                 430

Val Pro Ala Pro Phe Leu Ile Asn Trp Arg Leu Asn Trp Gly His Ile
        435                 440                 445

Pro Ser Gln Pro Arg Val Thr Val Thr Ser Glu Gly Gly Arg Gly Thr
    450                 455                 460

Leu Ile Ile Arg Asp Val Lys Glu Ser Asp Gln Gly Ala Tyr Thr Cys
465                 470                 475                 480

Glu Ala Met Asn Ala Arg Gly Met Val Phe Gly Ile Pro Asp Gly Val
                485                 490                 495

Leu Glu Leu Val Pro Gln Arg Ala Gly Pro Cys Pro Asp Gly His Phe
            500                 505                 510

Tyr Leu Glu His Ser Ala Ala Cys Leu Pro Cys Phe Cys Phe Gly Ile
        515                 520                 525

Thr Ser Val Cys Gln Ser Thr Arg Arg Phe Arg Asp Gln Ile Arg Leu
    530                 535                 540

Arg Phe Asp Gln Pro Asp Asp Phe Lys Gly Val Asn Val Thr Met Pro
545                 550                 555                 560
```

```
Ala Gln Pro Gly Thr Pro Pro Leu Ser Ser Thr Gln Leu Gln Ile Asp
                565                 570                 575

Pro Ser Leu His Glu Phe Gln Leu Val Asp Leu Ser Arg Arg Phe Leu
            580                 585                 590

Val His Asp Ser Phe Trp Ala Leu Pro Glu Gln Phe Leu Gly Asn Lys
            595                 600                 605

Val Asp Ser Tyr Gly Gly Ser Leu Arg Tyr Asn Val Arg Tyr Glu Leu
610                 615                 620

Ala Arg Gly Met Leu Glu Pro Val Gln Arg Pro Asp Val Val Leu Val
625                 630                 635                 640

Gly Ala Gly Tyr Arg Leu Leu Ser Arg Gly His Thr Pro Thr Gln Pro
                645                 650                 655

Gly Ala Leu Asn Gln Arg Gln Val Gln Phe Ser Glu Glu His Trp Val
            660                 665                 670

His Glu Ser Gly Arg Pro Val Gln Arg Ala Glu Leu Leu Gln Val Leu
            675                 680                 685

Gln Ser Leu Glu Ala Val Leu Ile Gln Thr Val Tyr Asn Thr Lys Met
690                 695                 700

Ala Ser Val Gly Leu Ser Asp Ile Ala Met Asp Thr Thr Val Thr His
705                 710                 715                 720

Ala Thr Ser His Gly Arg Ala His Ser Val Glu Glu Cys Arg Cys Pro
                725                 730                 735

Ile Gly Tyr Ser Gly Leu Ser Cys Glu Ser Cys Asp Ala His Phe Thr
            740                 745                 750

Arg Val Pro Gly Gly Pro Tyr Leu Gly Thr Cys Ser Gly Cys Ser Cys
            755                 760                 765

Asn Gly His Ala Ser Ser Cys Asp Pro Val Tyr Gly His Cys Leu Asn
770                 775                 780

Cys Gln His Asn Thr Glu Gly Pro Gln Cys Lys Lys Cys Lys Ala Gly
785                 790                 795                 800

Phe Phe Gly Asp Ala Met Lys Ala Thr Ala Thr Ser Cys Arg Pro Cys
                805                 810                 815

Pro Cys Pro Tyr Ile Asp Ala Ser Arg Arg Phe Ser Asp Thr Cys Phe
            820                 825                 830

Leu Asp Thr Asp Gly Gln Ala Thr Cys Asp Ala Cys Ala Pro Gly Tyr
            835                 840                 845

Thr Gly Arg Arg Cys Glu Ser Cys Ala Pro Gly Tyr Glu Gly Asn Pro
850                 855                 860

Ile Gln Pro Gly Gly Lys Cys Arg Pro Val Asn Gln Glu Ile Val Arg
865                 870                 875                 880

Cys Asp Glu Arg Gly Ser Met Gly Thr Ser Gly Glu Ala Cys Arg Cys
                885                 890                 895

Lys Asn Asn Val Val Gly Arg Leu Cys Asn Glu Cys Ala Asp Arg Ser
            900                 905                 910

Phe His Leu Ser Thr Arg Asn Pro Asp Gly Cys Leu Lys Cys Phe Cys
            915                 920                 925

Met Gly Val Ser Arg His Cys Thr Ser Ser Ser Trp Ser Arg Ala Gln
930                 935                 940

Leu His Gly Ala Ser Glu Glu Pro Gly His Phe Ser Leu Thr Asn Ala
945                 950                 955                 960

Ala Ser Thr His Thr Thr Asn Glu Gly Ile Phe Ser Pro Thr Pro Gly
                965                 970                 975

Glu Leu Gly Phe Ser Ser Phe His Arg Leu Leu Ser Gly Pro Tyr Phe
```

-continued

```
                980             985             990
Trp Ser Leu Pro Ser Arg Phe Leu Gly Asp Lys Val Thr Ser Tyr Gly
    995            1000            1005

Gly Glu Leu Arg Phe Thr Val Thr Gln Arg Ser Gln Pro Gly Ser Thr
   1010            1015            1020

Pro Leu His Gly Gln Pro Leu Val Val Leu Gln Gly Asn Asn Ile Ile
1025            1030            1035            1040

Leu Glu His His Val Ala Gln Glu Pro Ser Pro Gly Gln Pro Ser Thr
               1045            1050            1055

Phe Ile Val Pro Phe Arg Glu Gln Ala Trp Gln Arg Pro Asp Gly Gln
           1060            1065            1070

Pro Ala Thr Arg Glu His Leu Leu Met Ala Leu Ala Gly Ile Asp Thr
       1075            1080            1085

Leu Leu Ile Arg Ala Ser Tyr Ala Gln Gln Pro Ala Glu Ser Arg Val
   1090            1095            1100

Ser Gly Ile Ser Met Asp Val Ala Val Pro Glu Thr Gly Gln Asp
1105            1110            1115            1120

Pro Ala Leu Glu Val Glu Gln Cys Ser Cys Pro Pro Gly Tyr Arg Gly
               1125            1130            1135

Pro Ser Cys Gln Asp Cys Asp Thr Gly Tyr Thr Arg Thr Pro Ser Gly
           1140            1145            1150

Leu Tyr Leu Gly Thr Cys Glu Arg Cys Ser Cys His Gly His Ser Glu
       1155            1160            1165

Ala Cys Glu Pro Glu Thr Gly Ala Cys Gln Gly Cys Gln His His Thr
   1170            1175            1180

Glu Gly Pro Arg Cys Glu Gln Cys Gln Pro Gly Tyr Tyr Gly Asp Ala
1185            1190            1195            1200

Gln Arg Gly Thr Pro Gln Asp Cys Gln Leu Cys Pro Cys Tyr Gly Asp
           1205            1210            1215

Pro Ala Ala Gly Gln Ala Ala His Thr Cys Phe Leu Asp Thr Asp Gly
       1220            1225            1230

His Pro Thr Cys Asp Ala Cys Ser Pro Gly His Ser Gly Arg His Cys
   1235            1240            1245

Glu Arg Cys Ala Pro Gly Tyr Tyr Gly Asn Pro Ser Gln Gly Gln Pro
1250            1255            1260

Cys Gln Arg Asp Ser Gln Val Pro Gly Pro Ile Gly Cys Asn Cys Asp
1265            1270            1275            1280

Pro Gln Gly Ser Val Ser Ser Gln Cys Asp Ala Ala Gly Gln Cys Gln
           1285            1290            1295

Cys Lys Ala Gln Val Glu Gly Leu Thr Cys Ser His Cys Arg Pro His
       1300            1305            1310

His Phe His Leu Ser Ala Ser Asn Pro Asp Gly Cys Leu Pro Cys Phe
   1315            1320            1325

Cys Met Gly Ile Thr Gln Gln Cys Ala Ser Ser Ala Tyr Thr Arg His
   1330            1335            1340

Leu Ile Ser Thr His Phe Ala Pro Gly Asp Phe Gln Gly Phe Ala Leu
1345            1350            1355            1360

Val Asn Pro Gln Arg Asn Ser Arg Leu Thr Gly Glu Phe Thr Val Glu
               1365            1370            1375

Pro Val Pro Glu Gly Ala Gln Leu Ser Phe Gly Asn Phe Ala Gln Leu
           1380            1385            1390

Gly His Glu Ser Phe Tyr Trp Gln Leu Pro Glu Thr Tyr Gln Gly Asp
       1395            1400            1405
```

```
Lys Val Ala Ala Tyr Gly Gly Lys Leu Arg Tyr Thr Leu Ser Tyr Thr
    1410                1415                1420

Ala Gly Pro Gln Gly Ser Pro Leu Ser Asp Pro Asp Val Gln Ile Thr
1425                1430                1435                1440

Gly Asn Asn Ile Met Leu Val Ala Ser Gln Pro Ala Leu Gln Gly Pro
                1445                1450                1455

Glu Arg Arg Ser Tyr Glu Ile Met Phe Arg Glu Glu Phe Trp Arg Arg
            1460                1465                1470

Pro Asp Gly Gln Pro Ala Thr Arg Glu His Leu Leu Met Ala Leu Ala
        1475                1480                1485

Asp Leu Asp Glu Leu Leu Ile Arg Ala Thr Phe Ser Ser Val Pro Leu
    1490                1495                1500

Val Ala Ser Ile Ser Ala Val Ser Leu Glu Val Ala Gln Pro Gly Pro
1505                1510                1515                1520

Ser Asn Arg Pro Arg Ala Leu Glu Val Glu Glu Cys Arg Cys Pro Pro
                1525                1530                1535

Gly Tyr Ile Gly Leu Ser Cys Gln Asp Cys Ala Pro Gly Tyr Thr Arg
            1540                1545                1550

Thr Gly Ser Gly Leu Tyr Leu Gly His Cys Glu Leu Cys Glu Cys Asn
        1555                1560                1565

Gly His Ser Asp Leu Cys His Pro Glu Thr Gly Ala Cys Ser Gln Cys
    1570                1575                1580

Gln His Asn Ala Ala Gly Glu Phe Cys Glu Leu Cys Ala Pro Gly Tyr
1585                1590                1595                1600

Tyr Gly Asp Ala Thr Ala Gly Thr Pro Glu Asp Cys Gln Pro Cys Ala
                1605                1610                1615

Cys Pro Leu Thr Asn Pro Glu Asn Met Phe Ser Arg Thr Cys Glu Ser
            1620                1625                1630

Leu Gly Ala Gly Gly Tyr Arg Cys Thr Ala Cys Glu Pro Gly Tyr Thr
        1635                1640                1645

Gly Gln Tyr Cys Glu Gln Cys Gly Pro Gly Tyr Val Gly Asn Pro Ser
    1650                1655                1660

Val Gln Gly Gly Gln Cys Leu Pro Glu Thr Asn Gln Ala Pro Leu Val
1665                1670                1675                1680

Val Glu Val His Pro Ala Arg Ser Ile Val Pro Gln Gly Gly Ser His
                1685                1690                1695

Ser Leu Arg Cys Gln Val Ser Gly Arg Gly Pro His Tyr Phe Tyr Trp
            1700                1705                1710

Ser Arg Glu Asp Gly Arg Pro Val Pro Ser Gly Thr Gln Gln Arg His
        1715                1720                1725

Gln Gly Ser Glu Leu His Phe Pro Ser Val Gln Pro Ser Asp Ala Gly
    1730                1735                1740

Val Tyr Ile Cys Thr Cys Arg Asn Leu His Arg Ser Asn Thr Ser Arg
1745                1750                1755                1760

Ala Glu Leu Leu Val Thr Glu Ala Pro Ser Lys Pro Ile Thr Val Thr
                1765                1770                1775

Val Glu Glu Gln Arg Ser Gln Ser Val Arg Pro Gly Ala Asp Val Thr
            1780                1785                1790

Phe Ile Cys Thr Ala Lys Ser Lys Ser Pro Ala Tyr Thr Leu Val Trp
        1795                1800                1805

Thr Arg Leu His Asn Gly Lys Leu Pro Thr Arg Ala Met Asp Phe Asn
    1810                1815                1820
```

-continued

```
Gly Ile Leu Thr Ile Arg Asn Val Gln Leu Ser Asp Ala Gly Thr Tyr
1825                1830                1835                1840

Val Cys Thr Gly Ser Asn Met Phe Ala Met Asp Gln Gly Thr Ala Thr
            1845                1850                1855

Leu His Val Gln Ala Ser Gly Thr Leu Ser Ala Pro Val Val Ser Ile
        1860                1865                1870

His Pro Pro Gln Leu Thr Val Gln Pro Gly Gln Leu Ala Glu Phe Arg
    1875                1880                1885

Cys Ser Ala Thr Gly Ser Pro Thr Pro Thr Leu Glu Trp Thr Gly Gly
1890                1895                1900

Pro Gly Gly Gln Leu Pro Ala Lys Ala Gln Ile His Gly Gly Ile Leu
1905                1910                1915                1920

Arg Leu Pro Ala Val Glu Pro Thr Asp Gln Ala Gln Tyr Leu Cys Arg
            1925                1930                1935

Ala His Ser Ser Ala Gly Gln Gln Val Ala Arg Ala Val Leu His Val
        1940                1945                1950

His Gly Gly Gly Gly Pro Arg Val Gln Val Ser Pro Glu Arg Thr Gln
    1955                1960                1965

Val His Ala Gly Arg Thr Val Arg Leu Tyr Cys Arg Ala Ala Gly Val
1970                1975                1980

Pro Ser Ala Thr Ile Thr Trp Arg Lys Glu Gly Gly Ser Leu Pro Pro
1985                1990                1995                2000

Gln Ala Arg Ser Glu Arg Thr Asp Ile Ala Thr Leu Leu Ile Pro Ala
            2005                2010                2015

Ile Thr Thr Ala Asp Ala Gly Phe Tyr Leu Cys Val Ala Thr Ser Pro
        2020                2025                2030

Ala Gly Thr Ala Gln Ala Arg Ile Gln Val Val Val Leu Ser Ala Ser
    2035                2040                2045

Asp Ala Ser Gln Pro Pro Val Lys Ile Glu Ser Ser Ser Pro Ser Val
2050                2055                2060

Thr Glu Gly Gln Thr Leu Asp Leu Asn Cys Val Val Ala Gly Ser Ala
2065                2070                2075                2080

His Ala Gln Val Thr Trp Tyr Arg Arg Gly Gly Ser Leu Pro His His
            2085                2090                2095

Thr Gln Val His Gly Ser Arg Leu Arg Leu Pro Gln Val Ser Pro Ala
        2100                2105                2110

Asp Ser Gly Glu Tyr Val Cys Arg Val Glu Asn Gly Ser Gly Pro Lys
    2115                2120                2125

Glu Ala Ser Ile Thr Val Ser Val Leu His Gly Thr His Ser Gly Pro
2130                2135                2140

Ser Tyr Thr Pro Val Pro Gly Ser Thr Arg Pro Ile Arg Ile Glu Pro
2145                2150                2155                2160

Ser Ser Ser His Val Ala Glu Gly Gln Thr Leu Asp Leu Asn Cys Val
            2165                2170                2175

Val Pro Gly Gln Ala His Ala Gln Val Thr Trp His Lys Arg Gly Gly
        2180                2185                2190

Ser Leu Pro Ala Arg His Gln Thr His Gly Ser Leu Leu Arg Leu His
    2195                2200                2205

Gln Val Thr Pro Ala Asp Ser Gly Glu Tyr Val Cys His Val Val Gly
2210                2215                2220

Thr Ser Gly Pro Leu Glu Ala Ser Val Leu Val Thr Ile Glu Ala Ser
2225                2230                2235                2240

Val Ile Pro Gly Pro Ile Pro Pro Val Arg Ile Glu Ser Ser Ser Ser
```

-continued

```
                2245                2250                2255
Thr Val Ala Glu Gly Gln Thr Leu Asp Leu Ser Cys Val Val Ala Gly
            2260                2265                2270
Gln Ala His Ala Gln Val Thr Trp Tyr Lys Arg Gly Gly Ser Leu Pro
        2275                2280                2285
Ala Arg His Gln Val Arg Gly Ser Arg Leu Tyr Ile Phe Gln Ala Ser
    2290                2295                2300
Pro Ala Asp Ala Gly Gln Tyr Val Cys Arg Ala Ser Asn Gly Met Glu
2305                2310                2315                2320
Ala Ser Ile Thr Val Thr Val Thr Gly Thr Gln Gly Ala Asn Leu Ala
            2325                2330                2335
Tyr Pro Ala Gly Ser Thr Gln Pro Ile Arg Ile Glu Pro Ser Ser Ser
        2340                2345                2350
Gln Val Ala Glu Gly Gln Thr Leu Asp Leu Asn Cys Val Val Pro Gly
    2355                2360                2365
Gln Ser His Ala Gln Val Thr Trp His Lys Arg Gly Gly Ser Leu Pro
    2370                2375                2380
Val Arg His Gln Thr His Gly Ser Leu Leu Arg Leu Tyr Gln Ala Ser
2385                2390                2395                2400
Pro Ala Asp Ser Gly Glu Tyr Val Cys Arg Val Leu Gly Ser Ser Val
        2405                2410                2415
Pro Leu Glu Ala Ser Val Leu Val Thr Ile Glu Pro Ala Gly Ser Val
            2420                2425                2430
Pro Ala Leu Gly Val Thr Pro Thr Val Arg Ile Glu Ser Ser Ser Ser
        2435                2440                2445
Gln Val Ala Glu Gly Gln Thr Leu Asp Leu Asn Cys Leu Val Ala Gly
    2450                2455                2460
Gln Ala His Ala Gln Val Thr Trp His Lys Arg Gly Gly Ser Leu Pro
2465                2470                2475                2480
Ala Arg His Gln Val His Gly Ser Arg Leu Arg Leu Leu Gln Val Thr
            2485                2490                2495
Pro Ala Asp Ser Gly Glu Tyr Val Cys Arg Val Val Gly Ser Ser Gly
        2500                2505                2510
Thr Gln Glu Ala Ser Val Leu Val Thr Ile Gln Gln Arg Leu Ser Gly
    2515                2520                2525
Ser His Ser Gln Gly Val Ala Tyr Pro Val Arg Ile Glu Ser Ser Ser
    2530                2535                2540
Ala Ser Leu Ala Asn Gly His Thr Leu Asp Leu Asn Cys Leu Val Ala
2545                2550                2555                2560
Ser Gln Ala Pro His Thr Ile Thr Trp Tyr Lys Arg Gly Gly Ser Leu
            2565                2570                2575
Pro Ser Arg His Gln Ile Val Gly Ser Arg Leu Arg Ile Pro Gln Val
        2580                2585                2590
Thr Pro Ala Asp Ser Gly Glu Tyr Val Cys His Val Ser Asn Gly Ala
    2595                2600                2605
Gly Ser Arg Glu Thr Ser Leu Ile Val Thr Ile Gln Gly Ser Gly Ser
    2610                2615                2620
Ser His Val Pro Arg Val Ser Pro Ile Arg Ile Glu Ser Ser Ser
2625                2630                2635                2640
Pro Thr Val Val Glu Gly Gln Thr Leu Asp Leu Asn Cys Val Val Ala
            2645                2650                2655
Arg Gln Pro Gln Ala Ile Ile Thr Trp Tyr Lys Arg Gly Gly Ser Leu
        2660                2665                2670
```

-continued

Pro Ser Arg His Gln Thr His Gly Ser His Leu Arg Leu His Gln Met
    2675                2680                2685

Ser Val Ala Asp Ser Gly Glu Tyr Val Cys Arg Ala Asn Asn Asn Ile
    2690                2695                2700

Asp Ala Leu Glu Ala Ser Ile Val Ile Ser Val Ser Pro Ser Ala Gly
2705                2710                2715                2720

Ser Pro Ser Ala Pro Gly Ser Ser Met Pro Ile Arg Ile Glu Ser Ser
        2725                2730                2735

Ser Ser His Val Ala Glu Gly Glu Thr Leu Asp Leu Asn Cys Val Val
            2740                2745                2750

Pro Gly Gln Ala His Ala Gln Val Thr Trp His Lys Arg Gly Gly Ser
        2755                2760                2765

Leu Pro Ser Tyr His Gln Thr Arg Gly Ser Arg Leu Arg Leu His His
    2770                2775                2780

Val Ser Pro Ala Asp Ser Gly Glu Tyr Val Cys Arg Val Met Gly Ser
2785                2790                2795                2800

Ser Gly Pro Leu Glu Ala Ser Val Leu Val Thr Ile Glu Ala Ser Gly
        2805                2810                2815

Ser Ser Ala Val His Val Pro Ala Pro Gly Gly Ala Pro Pro Ile Arg
            2820                2825                2830

Ile Glu Pro Ser Ser Arg Val Ala Glu Gly Gln Thr Leu Asp Leu
    2835                2840                2845

Lys Cys Val Val Pro Gly Gln Ala His Ala Gln Val Thr Trp His Lys
    2850                2855                2860

Arg Gly Gly Asn Leu Pro Ala Arg His Gln Val His Gly Pro Leu Leu
2865                2870                2875                2880

Arg Leu Asn Gln Val Ser Pro Ala Asp Ser Gly Glu Tyr Ser Cys Gln
        2885                2890                2895

Val Thr Gly Ser Ser Gly Thr Leu Glu Ala Ser Val Leu Val Thr Ile
            2900                2905                2910

Glu Pro Ser Ser Pro Gly Pro Ile Pro Ala Pro Gly Leu Ala Gln Pro
    2915                2920                2925

Ile Tyr Ile Glu Ala Ser Ser Ser His Val Thr Glu Gly Gln Thr Leu
    2930                2935                2940

Asp Leu Asn Cys Val Val Pro Gly Gln Ala His Ala Gln Val Thr Trp
2945                2950                2955                2960

Tyr Lys Arg Gly Gly Ser Leu Pro Ala Arg His Gln Thr His Gly Ser
        2965                2970                2975

Gln Leu Arg Leu His His Val Ser Pro Ala Asp Ser Gly Glu Tyr Val
            2980                2985                2990

Cys Arg Ala Ala Gly Gly Pro Gly Pro Glu Gln Glu Ala Ser Phe Thr
    2995                3000                3005

Val Thr Val Pro Pro Ser Glu Gly Ser Ser Tyr Arg Leu Arg Ser Pro
    3010                3015                3020

Val Ile Ser Ile Asp Pro Pro Ser Ser Thr Val Gln Gln Gly Gln Asp
3025                3030                3035                3040

Ala Ser Phe Lys Cys Leu Ile His Asp Gly Ala Ala Pro Ile Ser Leu
        3045                3050                3055

Glu Trp Lys Thr Arg Asn Gln Glu Leu Glu Asp Asn Val His Ile Ser
            3060                3065                3070

Pro Asn Gly Ser Ile Ile Thr Ile Val Gly Thr Arg Pro Ser Asn His
    3075                3080                3085

-continued

Gly Thr Tyr Arg Cys Val Ala Ser Asn Ala Tyr Gly Val Ala Gln Ser
    3090            3095            3100

Val Val Asn Leu Ser Val His Gly Pro Pro Thr Val Ser Val Leu Pro
3105            3110            3115            3120

Glu Gly Pro Val Trp Val Lys Val Gly Lys Ala Val Thr Leu Glu Cys
        3125            3130            3135

Val Ser Ala Gly Glu Pro Arg Ser Ser Ala Arg Trp Thr Arg Ile Ser
        3140            3145            3150

Ser Thr Pro Ala Lys Leu Glu Gln Arg Thr Tyr Gly Leu Met Asp Ser
    3155            3160            3165

His Thr Val Leu Gln Ile Ser Ser Ala Lys Pro Ser Asp Ala Gly Thr
    3170            3175            3180

Tyr Val Cys Leu Ala Gln Asn Ala Leu Gly Thr Ala Gln Lys Gln Val
3185            3190            3195            3200

Glu Val Ile Val Asp Thr Gly Ala Met Ala Pro Gly Ala Pro Gln Val
        3205            3210            3215

Gln Ala Glu Glu Ala Glu Leu Thr Val Glu Ala Gly His Thr Ala Thr
        3220            3225            3230

Leu Arg Cys Ser Ala Thr Gly Ser Pro Ala Arg Thr Ile His Trp Ser
    3235            3240            3245

Lys Leu Arg Ser Pro Leu Pro Trp Gln His Arg Leu Glu Gly Asp Thr
    3250            3255            3260

Leu Ile Ile Pro Arg Val Ala Gln Gln Asp Ser Gly Gln Tyr Ile Cys
3265            3270            3275            3280

Asn Ala Thr Ser Pro Ala Gly His Ala Glu Ala Thr Ile Ile Leu His
        3285            3290            3295

Val Glu Ser Pro Pro Tyr Ala Thr Thr Val Pro Glu His Ala Ser Val
        3300            3305            3310

Gln Ala Gly Glu Thr Val Gln Leu Gln Cys Leu Ala His Gly Thr Pro
    3315            3320            3325

Pro Leu Thr Phe Gln Trp Ser Arg Val Gly Ser Ser Leu Pro Gly Arg
    3330            3335            3340

Ala Thr Ala Arg Asn Glu Leu Leu His Phe Glu Arg Ala Ala Pro Glu
3345            3350            3355            3360

Asp Ser Gly Arg Tyr Arg Cys Arg Val Thr Asn Lys Val Gly Ser Ala
        3365            3370            3375

Glu Ala Phe Ala Gln Leu Leu Val Gln Gly Pro Pro Gly Ser Leu Pro
        3380            3385            3390

Ala Thr Ser Ile Pro Ala Gly Ser Thr Pro Thr Val Gln Val Thr Pro
    3395            3400            3405

Gln Leu Glu Thr Lys Ser Ile Gly Ala Ser Val Glu Phe His Cys Ala
    3410            3415            3420

Val Pro Ser Asp Arg Gly Thr Gln Leu Arg Trp Phe Lys Glu Gly Gly
3425            3430            3435            3440

Gln Leu Pro Pro Gly His Ser Val Gln Asp Gly Val Leu Arg Ile Gln
        3445            3450            3455

Asn Leu Asp Gln Ser Cys Gln Gly Thr Tyr Ile Cys Gln Ala His Gly
        3460            3465            3470

Pro Trp Gly Lys Ala Gln Ala Ser Ala Gln Leu Val Ile Gln Ala Leu
    3475            3480            3485

Pro Ser Val Leu Ile Asn Ile Arg Thr Ser Val Gln Thr Val Val Val
    3490            3495            3500

Gly His Ala Val Glu Phe Glu Cys Leu Ala Leu Gly Asp Pro Lys Pro

-continued

```
      3505                3510                3515                3520
Gln Val Thr Trp Ser Lys Val Gly Gly His Leu Arg Pro Gly Ile Val
              3525                3530                3535
Gln Ser Gly Gly Val Val Arg Ile Ala His Val Glu Leu Ala Asp Ala
        3540                3545                3550
Gly Gln Tyr Arg Cys Thr Ala Thr Asn Ala Ala Gly Thr Thr Gln Ser
        3555                3560                3565
His Val Leu Leu Val Gln Ala Leu Pro Gln Ile Ser Met Pro Gln
    3570                3575                3580
Glu Val Arg Val Pro Ala Gly Ser Ala Ala Val Phe Pro Cys Ile Ala
3585                3590                3595                3600
Ser Gly Tyr Pro Thr Pro Asp Ile Ser Trp Ser Lys Leu Asp Gly Ser
              3605                3610                3615
Leu Pro Pro Asp Ser Arg Leu Glu Asn Asn Met Leu Met Leu Pro Ser
        3620                3625                3630
Val Gln Pro Gln Asp Ala Gly Thr Tyr Val Cys Thr Ala Thr Asn Arg
        3635                3640                3645
Gln Gly Lys Val Lys Ala Phe Ala His Leu Gln Val Pro Glu Arg Val
        3650                3655                3660
Val Pro Tyr Phe Thr Gln Thr Pro Tyr Ser Phe Leu Pro Leu Pro Thr
3665                3670                3675                3680
Ile Lys Asp Ala Tyr Arg Lys Phe Glu Ile Lys Ile Thr Phe Arg Pro
              3685                3690                3695
Asp Ser Ala Asp Gly Met Leu Leu Tyr Asn Gly Gln Lys Arg Val Pro
              3700                3705                3710
Gly Ser Pro Thr Asn Leu Ala Asn Arg Gln Pro Asp Phe Ile Ser Phe
        3715                3720                3725
Gly Leu Val Gly Gly Arg Pro Glu Phe Arg Phe Asp Ala Gly Ser Gly
              3730                3735                3740
Met Ala Thr Ile Arg His Pro Thr Pro Leu Ala Leu Gly His Phe His
3745                3750                3755                3760
Thr Val Thr Leu Leu Arg Ser Leu Thr Gln Gly Ser Leu Ile Val Gly
              3765                3770                3775
Asp Leu Ala Pro Val Asn Gly Thr Ser Gln Gly Lys Phe Gln Gly Leu
        3780                3785                3790
Asp Leu Asn Glu Glu Leu Tyr Leu Gly Gly Tyr Pro Asp Tyr Gly Ala
              3795                3800                3805
Ile Pro Lys Ala Gly Leu Ser Ser Gly Phe Ile Gly Cys Val Arg Glu
    3810                3815                3820
Leu Arg Ile Gln Gly Glu Glu Ile Val Phe His Asp Leu Asn Leu Thr
3825                3830                3835                3840
Ala His Gly Ile Ser His Cys Pro Thr Cys Arg Asp Arg Pro Cys Gln
              3845                3850                3855
Asn Gly Gly Gln Cys His Asp Ser Glu Ser Ser Ser Tyr Val Cys Val
              3860                3865                3870
Cys Pro Ala Gly Phe Thr Gly Ser Arg Cys Glu His Ser Gln Ala Leu
        3875                3880                3885
His Cys His Pro Glu Ala Cys Gly Pro Asp Ala Thr Cys Val Asn Arg
        3890                3895                3900
Pro Asp Gly Arg Gly Tyr Thr Cys Arg Cys His Leu Gly Arg Ser Gly
3905                3910                3915                3920
Leu Arg Cys Glu Glu Gly Val Thr Val Thr Thr Pro Ser Leu Ser Gly
              3925                3930                3935
```

-continued

```
Ala Gly Ser Tyr Leu Ala Leu Pro Ala Leu Thr Asn Thr His His Glu
        3940            3945                3950

Leu Arg Leu Asp Val Glu Phe Lys Pro Leu Ala Pro Asp Gly Val Leu
    3955                3960                3965

Leu Phe Ser Gly Gly Lys Ser Gly Pro Val Glu Asp Phe Val Ser Leu
3970                3975                3980

Ala Met Val Gly Gly His Leu Glu Phe Arg Tyr Glu Leu Gly Ser Gly
3985                3990                3995                4000

Leu Ala Val Leu Arg Thr Ala Glu Pro Leu Ala Leu Gly Arg Trp His
        4005                4010                4015

Arg Val Ser Ala Glu Arg Leu Asn Lys Asp Gly Ser Leu Arg Val Asn
    4020                4025                4030

Gly Gly Arg Pro Val Leu Arg Ser Pro Gly Lys Ser Gln Gly Leu
        4035                4040                4045

Asn Leu His Thr Leu Leu Tyr Leu Gly Gly Val Glu Pro Ser Val Pro
    4050                4055                4060

Leu Ser Pro Ala Thr Asn Met Ser Ala His Phe Arg Gly Cys Val Gly
4065                4070                4075                4080

Glu Val Ser Val Asn Gly Lys Arg Leu Asp Leu Thr Tyr Ser Phe Leu
        4085                4090                4095

Gly Ser Gln Gly Ile Gly Gln Cys Tyr Asp Ser Ser Pro Cys Glu Arg
    4100                4105                4110

Gln Pro Cys Gln His Gly Ala Thr Cys Met Pro Ala Gly Glu Tyr Glu
        4115                4120                4125

Phe Gln Cys Leu Cys Arg Asp Gly Ile Lys Gly Asp Leu Cys Glu His
    4130                4135                4140

Glu Glu Asn Pro Cys Gln Leu Arg Glu Pro Cys Leu His Gly Gly Thr
4145                4150                4155                4160

Cys Gln Gly Thr Arg Cys Leu Cys Leu Pro Gly Phe Ser Gly Pro Arg
        4165                4170                4175

Cys Gln Gln Gly Ser Gly His Gly Ile Ala Glu Ser Asp Trp His Leu
    4180                4185                4190

Glu Gly Ser Gly Gly Asn Asp Ala Pro Gly Gln Tyr Gly Ala Tyr Phe
    4195                4200                4205

His Asp Asp Gly Phe Leu Ala Phe Pro Gly His Val Phe Ser Arg Ser
    4210                4215                4220

Leu Pro Glu Val Pro Glu Thr Ile Glu Leu Glu Val Arg Thr Ser Thr
4225                4230                4235                4240

Ala Ser Gly Leu Leu Leu Trp Gln Gly Val Glu Val Gly Glu Ala Gly
        4245                4250                4255

Gln Gly Lys Asp Phe Ile Ser Leu Gly Leu Gln Asp Gly His Leu Val
        4260                4265                4270

Phe Arg Tyr Gln Leu Gly Ser Gly Glu Ala Arg Leu Val Ser Glu Asp
    4275                4280                4285

Pro Ile Asn Asp Gly Glu Trp His Arg Val Thr Ala Leu Arg Glu Gly
    4290                4295                4300

Arg Arg Gly Ser Ile Gln Val Asp Gly Glu Glu Leu Val Ser Gly Arg
4305                4310                4315                4320

Ser Pro Gly Pro Asn Val Ala Val Asn Ala Lys Gly Ser Ile Tyr Ile
        4325                4330                4335

Gly Gly Ala Pro Asp Val Ala Thr Leu Thr Gly Gly Arg Phe Ser Ser
        4340                4345                4350
```

```
Gly Ile Thr Gly Cys Val Lys Asn Leu Val Leu His Ser Ala Arg Pro
    4355            4360            4365

Gly Ala Pro Pro Gln Pro Leu Asp Leu Gln His Arg Ala Gln Ala
    4370            4375            4380

Gly Ala Asn Thr Arg Pro Cys Pro Ser
4385            4390

<210> SEQ ID NO 2
<211> LENGTH: 195
<212> TYPE: PRT
<213> ORGANISM: Homo sapiens

<400> SEQUENCE: 2

Asp Ala Pro Gly Gln Tyr Gly Ala Tyr Phe His Asp Asp Gly Phe Leu
 1               5                  10                  15

Ala Phe Pro Gly His Val Phe Ser Arg Ser Leu Pro Glu Val Pro Glu
                20                  25                  30

Thr Ile Glu Leu Glu Val Arg Thr Ser Thr Ala Ser Gly Leu Leu Leu
            35                  40                  45

Trp Gln Gly Val Glu Val Gly Glu Ala Gly Gln Gly Lys Asp Phe Ile
        50                  55                  60

Ser Leu Gly Leu Gln Asp Gly His Leu Val Phe Arg Tyr Gln Leu Gly
65                  70                  75                  80

Ser Gly Glu Ala Arg Leu Val Ser Glu Asp Pro Ile Asn Asp Gly Glu
                85                  90                  95

Trp His Arg Val Thr Ala Leu Arg Glu Gly Arg Gly Ser Ile Gln
                100                 105                 110

Val Asp Gly Glu Glu Leu Val Ser Gly Arg Ser Pro Gly Pro Asn Val
            115                 120                 125

Ala Val Asn Ala Lys Gly Ser Val Tyr Ile Gly Gly Ala Pro Asp Val
        130                 135                 140

Ala Thr Leu Thr Gly Gly Arg Phe Ser Ser Gly Ile Thr Gly Cys Val
145                 150                 155                 160

Lys Asn Leu Val Leu His Ser Arg Pro Gly Ala Pro Pro Gln
                165                 170                 175

Pro Leu Asp Leu Gln His Arg Ala Gln Ala Gly Ala Asn Thr Arg Pro
            180                 185                 190

Cys Pro Ser
    195

<210> SEQ ID NO 3
<211> LENGTH: 508
<212> TYPE: PRT
<213> ORGANISM: Homo sapiens

<400> SEQUENCE: 3

Arg Thr Cys Arg Cys Lys Asn Asn Val Val Gly Arg Leu Cys Asn Glu
 1               5                  10                  15

Cys Ala Asp Arg Ser Phe His Leu Ser Thr Arg Asn Pro Asp Gly Cys
                20                  25                  30

Leu Lys Cys Phe Cys Met Gly Val Ser Arg His Cys Thr Ser Ser Ser
            35                  40                  45

Trp Ser Arg Ala Gln Leu His Gly Ala Ser Glu Glu Pro Gly His Phe
        50                  55                  60

Ser Leu Thr Asn Ala Ala Ser Thr His Thr Thr Asn Glu Gly Ile Phe
65                  70                  75                  80
```

-continued

```
Ser Pro Thr Pro Gly Glu Leu Gly Phe Ser Ser Phe His Arg Leu Leu
            85                  90                  95

Ser Gly Pro Tyr Phe Trp Ser Leu Pro Ser Arg Phe Leu Gly Asp Lys
            100                 105                 110

Val Thr Ser Tyr Gly Gly Glu Leu Arg Phe Thr Val Thr Gln Arg Ser
            115                 120                 125

Gln Pro Gly Ser Thr Pro Leu His Gly Gln Pro Leu Val Val Leu Gln
130             135                 140

Gly Asn Asn Ile Ile Leu Glu His His Val Ala Gln Glu Pro Ser Pro
145             150                 155                 160

Gly Gln Pro Ser Thr Phe Ile Val Pro Phe Arg Glu Gln Ala Trp Gln
                165                 170                 175

Arg Pro Asp Gly Gln Pro Ala Thr Arg Glu His Leu Leu Met Ala Leu
            180                 185                 190

Ala Gly Ile Asp Thr Leu Leu Ile Arg Ala Ser Tyr Ala Gln Gln Pro
            195                 200                 205

Ala Glu Ser Arg Leu Ser Gly Ile Ser Met Asp Val Ala Val Pro Glu
            210                 215                 220

Glu Thr Gly Gln Asp Pro Ala Leu Glu Val Gln Cys Ser Cys Pro
225             230                 235                 240

Pro Gly Tyr Leu Gly Pro Ser Cys Gln Asp Cys Asp Thr Gly Tyr Thr
            245                 250                 255

Arg Thr Pro Ser Gly Leu Tyr Leu Gly Thr Cys Glu Arg Cys Ser Cys
            260                 265                 270

His Gly His Ser Glu Ala Cys Glu Pro Glu Thr Gly Ala Cys Gln Gly
            275                 280                 285

Cys Gln His His Thr Glu Gly Pro Arg Cys Glu Gln Cys Gln Pro Gly
            290                 295                 300

Tyr Tyr Gly Asp Ala Gln Arg Gly Thr Pro Gln Asp Cys Gln Leu Cys
305             310                 315                 320

Pro Cys Tyr Gly Asp Pro Ala Ala Gly Gln Ala Ala Leu Thr Cys Phe
            325                 330                 335

Leu Asp Thr Asp Gly His Pro Thr Cys Asp Ala Cys Ser Pro Gly His
            340                 345                 350

Ser Gly Arg His Cys Glu Arg Cys Ala Pro Gly Tyr Tyr Gly Asn Pro
            355                 360                 365

Ser Gln Gly Gln Pro Cys Gln Arg Asp Ser Gln Val Pro Gly Pro Ile
370             375                 380

Gly Cys Asn Cys Asp Pro Gln Gly Ser Val Ser Ser Gln Cys Asp Ala
385             390                 395                 400

Ala Gly Gln Cys Gln Cys Lys Ala Gln Val Glu Gly Leu Thr Cys Ser
            405                 410                 415

His Cys Arg Pro His His Phe His Leu Ser Ala Ser Asn Pro Asp Gly
            420                 425                 430

Cys Leu Pro Cys Phe Cys Met Gly Ile Thr Gln Gln Cys Ala Ser Ser
            435                 440                 445

Ala Tyr Thr Arg His Leu Ile Ser Thr His Phe Ala Pro Gly Asp Phe
450                 455                 460

Gln Gly Phe Ala Leu Val Asn Pro Gln Arg Asn Ser Arg Leu Thr Gly
465                 470                 475                 480

Glu Phe Thr Val Glu Pro Val Pro Glu Gly Ala Gln Leu Ser Phe Gly
                485                 490                 495

Asn Phe Ala Gln Leu Gly His Glu Ser Phe Tyr Trp
```

```
                      500             505

<210> SEQ ID NO 4
<211> LENGTH: 199
<212> TYPE: PRT
<213> ORGANISM: Homo sapiens

<400> SEQUENCE: 4

Met Lys Trp Val Trp Ala Leu Leu Leu Ala Ala Trp Ala Ala Ala
 1               5                  10                  15

Glu Arg Asp Cys Arg Val Ser Ser Phe Arg Val Lys Glu Asn Phe Asp
                20                  25                  30

Lys Ala Arg Phe Ser Gly Thr Trp Tyr Ala Met Ala Lys Lys Asp Pro
            35                  40                  45

Glu Gly Leu Phe Leu Gln Asp Asn Ile Val Ala Glu Phe Ser Val Asp
        50                  55                  60

Glu Thr Gly Gln Met Ser Ala Thr Ala Lys Gly Arg Val Arg Leu Leu
65                  70                  75                  80

Asn Asn Trp Asp Val Cys Ala Asp Met Val Gly Thr Phe Thr Asp Thr
                85                  90                  95

Glu Asp Pro Ala Lys Phe Lys Met Lys Tyr Trp Gly Val Ala Ser Phe
            100                 105                 110

Leu Gln Lys Gly Asn Asp Asp His Trp Ile Val Asp Thr Asp Tyr Asp
        115                 120                 125

Thr Tyr Ala Val Gln Tyr Ser Cys Arg Leu Leu Asn Leu Asp Gly Thr
    130                 135                 140

Cys Ala Asp Ser Tyr Ser Phe Val Phe Ser Arg Asp Pro Asn Gly Leu
145                 150                 155                 160

Pro Pro Glu Ala Gln Lys Ile Val Arg Gln Arg Gln Glu Glu Leu Cys
                165                 170                 175

Leu Ala Arg Gln Tyr Arg Leu Ile Val His Asn Gly Tyr Cys Asp Gly
            180                 185                 190

Arg Ser Glu Arg Asn Leu Leu
        195

<210> SEQ ID NO 5
<211> LENGTH: 199
<212> TYPE: PRT
<213> ORGANISM: Homo sapiens

<400> SEQUENCE: 5

Met Lys Trp Val Trp Ala Leu Leu Leu Ala Ala Trp Ala Ala Ala
 1               5                  10                  15

Glu Arg Asp Cys Arg Val Ser Ser Phe Arg Val Lys Glu Asn Phe Asp
                20                  25                  30

Lys Ala Arg Phe Ser Gly Thr Trp Tyr Ala Met Ala Lys Lys Asp Pro
            35                  40                  45

Glu Gly Leu Phe Leu Gln Asp Asn Ile Val Ala Glu Phe Ser Val Asp
        50                  55                  60

Glu Thr Gly Gln Met Ser Ala Thr Ala Lys Gly Arg Val Arg Leu Leu
65                  70                  75                  80

Asn Asn Trp Asp Val Cys Ala Asp Met Val Gly Thr Phe Thr Asp Thr
                85                  90                  95

Glu Asp Pro Ala Lys Phe Lys Met Lys Tyr Trp Gly Val Ala Ser Phe
            100                 105                 110

Leu Gln Lys Gly Asn Asp Asp His Trp Ile Val Asp Thr Asp Tyr Asp
```

```
                115                 120                 125
Thr Tyr Ala Val Gln Tyr Ser Cys Arg Leu Leu Asn Leu Asp Gly Thr
        130                 135                 140

Cys Ala Asp Ser Tyr Ser Phe Val Phe Ser Arg Asp Pro Asn Gly Leu
145                 150                 155                 160

Pro Pro Glu Ala Gln Lys Ile Val Arg Gln Arg Gln Glu Glu Leu Cys
                165                 170                 175

Leu Ala Arg Gln Tyr Arg Leu Ile Val His Asn Gly Tyr Cys Asp Gly
                180                 185                 190

Arg Ser Glu Arg Asn Leu Leu
            195

<210> SEQ ID NO 6
<211> LENGTH: 199
<212> TYPE: PRT
<213> ORGANISM: Homo sapiens

<400> SEQUENCE: 6

Met Lys Trp Val Trp Ala Leu Leu Leu Ala Ala Trp Ala Ala Ala
  1               5                  10                  15

Glu Arg Asp Cys Arg Val Ser Ser Phe Arg Val Lys Glu Asn Phe Asp
                 20                  25                  30

Lys Ala Arg Phe Ser Gly Thr Trp Tyr Ala Met Ala Lys Lys Asp Pro
             35                  40                  45

Glu Gly Leu Phe Leu Gln Asp Asn Ile Val Ala Glu Phe Ser Val Asp
         50                  55                  60

Glu Thr Gly Gln Met Ser Ala Thr Ala Lys Gly Arg Val Arg Leu Leu
 65                  70                  75                  80

Asn Asn Trp Asp Val Cys Ala Asp Met Val Gly Thr Phe Thr Asp Thr
                 85                  90                  95

Glu Asp Pro Ala Lys Phe Lys Met Lys Tyr Trp Gly Val Ala Ser Phe
            100                 105                 110

Leu Gln Lys Gly Asn Asp Asp His Trp Ile Val Asp Thr Asp Tyr Asp
        115                 120                 125

Thr Tyr Ala Val Gln Tyr Ser Cys Arg Leu Leu Asn Leu Asp Gly Thr
        130                 135                 140

Cys Ala Asp Ser Tyr Ser Phe Val Phe Ser Arg Asp Pro Asn Gly Leu
145                 150                 155                 160

Pro Pro Glu Ala Gln Lys Ile Val Arg Gln Arg Gln Glu Glu Leu Cys
                165                 170                 175

Leu Ala Arg Gln Tyr Arg Leu Ile Val His Asn Gly Tyr Cys Asp Gly
                180                 185                 190

Arg Ser Glu Arg Asn Leu Leu
            195

<210> SEQ ID NO 7
<211> LENGTH: 182
<212> TYPE: PRT
<213> ORGANISM: Homo sapiens

<400> SEQUENCE: 7

Glu Arg Asp Cys Arg Val Ser Ser Phe Arg Val Lys Glu Asn Phe Asp
  1               5                  10                  15

Lys Ala Arg Phe Ser Gly Thr Trp Tyr Ala Met Ala Lys Lys Asp Pro
                 20                  25                  30

Glu Gly Leu Phe Leu Gln Asp Asn Ile Val Ala Glu Phe Ser Val Asp
```

```
                35                  40                  45
Glu Thr Gly Gln Met Ser Ala Thr Ala Lys Gly Arg Val Arg Leu Leu
 50                  55                  60

Asn Asn Trp Asp Val Cys Ala Asp Met Val Gly Thr Phe Thr Asp Thr
 65                  70                  75                  80

Glu Asp Pro Ala Lys Phe Lys Met Lys Tyr Trp Gly Val Ala Ser Phe
                 85                  90                  95

Leu Gln Lys Gly Asn Asp Asp His Trp Ile Val Asp Thr Asp Tyr Asp
                100                 105                 110

Thr Tyr Ala Val Gln Tyr Ser Cys Arg Leu Leu Asn Leu Asp Gly Thr
            115                 120                 125

Cys Ala Asp Ser Tyr Ser Phe Val Phe Ser Arg Asp Pro Asn Gly Leu
130                 135                 140

Pro Pro Glu Ala Gln Lys Ile Val Arg Gln Arg Gln Glu Glu Leu Cys
145                 150                 155                 160

Leu Ala Arg Gln Tyr Arg Leu Ile Val His Asn Gly Tyr Cys Asp Gly
                165                 170                 175

Arg Ser Glu Arg Asn Leu
                180

<210> SEQ ID NO 8
<211> LENGTH: 193
<212> TYPE: PRT
<213> ORGANISM: Homo sapiens

<400> SEQUENCE: 8

Met Gln Ser Leu Met Gln Ala Pro Leu Leu Ile Ala Leu Gly Leu Leu
  1               5                  10                  15

Leu Ala Thr Pro Ala Gln Ala His Leu Lys Lys Pro Ser Gln Leu Ser
                 20                  25                  30

Ser Phe Ser Trp Asp Asn Cys Asp Glu Gly Lys Asp Pro Ala Val Ile
             35                  40                  45

Arg Ser Leu Thr Leu Glu Pro Asp Pro Ile Val Val Pro Gly Asn Val
 50                  55                  60

Thr Leu Ser Val Val Gly Ser Thr Ser Val Pro Leu Ser Ser Pro Leu
 65                  70                  75                  80

Lys Val Asp Leu Val Leu Glu Lys Glu Val Ala Gly Leu Trp Ile Lys
                 85                  90                  95

Ile Pro Cys Thr Asp Tyr Ile Gly Ser Cys Thr Phe Glu His Phe Cys
                100                 105                 110

Asp Val Leu Asp Met Leu Ile Pro Thr Gly Glu Pro Cys Pro Glu Pro
            115                 120                 125

Leu Arg Thr Tyr Gly Leu Pro Cys His Cys Pro Phe Lys Glu Gly Thr
130                 135                 140

Tyr Ser Leu Pro Lys Ser Glu Phe Val Val Pro Asp Leu Glu Leu Pro
145                 150                 155                 160

Ser Trp Leu Thr Thr Gly Asn Tyr Arg Ile Glu Ser Val Leu Ser Ser
                165                 170                 175

Ser Gly Lys Arg Leu Gly Cys Ile Lys Ile Ala Ala Ser Leu Lys Gly
                180                 185                 190

Ile

<210> SEQ ID NO 9
<211> LENGTH: 193
<212> TYPE: PRT
```

<213> ORGANISM: Homo sapiens

<400> SEQUENCE: 9

```
Met Gln Ser Leu Met Gln Ala Pro Leu Leu Ile Ala Leu Gly Leu Leu
  1               5                  10                  15
Leu Ala Thr Pro Ala Gln Ala His Leu Lys Lys Pro Ser Gln Leu Ser
             20                  25                  30
Ser Phe Ser Trp Asp Asn Cys Phe Glu Gly Lys Asp Pro Ala Val Ile
         35                  40                  45
Arg Ser Leu Thr Leu Glu Pro Asp Pro Ile Val Val Pro Gly Asn Val
     50                  55                  60
Thr Leu Ser Val Val Gly Ser Thr Ser Val Pro Leu Ser Ser Pro Leu
 65                  70                  75                  80
Lys Val Asp Leu Val Leu Glu Lys Glu Val Ala Gly Leu Trp Ile Lys
                 85                  90                  95
Ile Pro Cys Thr Asp Tyr Ile Gly Ser Cys Thr Phe Glu His Phe Cys
            100                 105                 110
Asp Val Leu Asp Met Leu Ile Pro Thr Gly Glu Pro Cys Pro Glu Pro
            115                 120                 125
Leu Arg Thr Tyr Gly Leu Pro Cys His Cys Pro Phe Lys Glu Gly Thr
        130                 135                 140
Tyr Ser Leu Pro Lys Ser Glu Phe Ala Val Pro Asp Leu Glu Leu Pro
145                 150                 155                 160
Ser Trp Leu Thr Thr Gly Asn Tyr Arg Ile Glu Ser Val Leu Ser Ser
                165                 170                 175
Ser Gly Lys Arg Leu Gly Cys Ile Lys Ile Ala Ala Ser Leu Lys Gly
            180                 185                 190
Ile
```

<210> SEQ ID NO 10
<211> LENGTH: 178
<212> TYPE: PRT
<213> ORGANISM: Homo sapiens

<400> SEQUENCE: 10

```
Leu Leu Ala Thr Pro Ala Gln Ala His Leu Lys Lys Pro Ser Gln Leu
  1               5                  10                  15
Ser Ser Phe Ser Trp Asp Asn Cys Asp Glu Gly Lys Asp Pro Ala Val
             20                  25                  30
Ile Arg Ser Leu Thr Leu Glu Pro Asp Pro Ile Val Val Pro Gly Asn
         35                  40                  45
Val Thr Leu Ser Val Val Gly Ser Thr Ser Val Pro Leu Ser Ser Pro
     50                  55                  60
Leu Lys Val Asp Leu Val Leu Glu Lys Glu Val Ala Gly Leu Trp Ile
 65                  70                  75                  80
Lys Ile Pro Cys Thr Asp Tyr Ile Gly Ser Cys Thr Phe Glu His Phe
                 85                  90                  95
Cys Asp Val Leu Asp Met Leu Ile Pro Thr Gly Glu Pro Cys Pro Glu
            100                 105                 110
Pro Leu Arg Thr Tyr Gly Leu Pro Cys His Cys Pro Phe Lys Glu Gly
            115                 120                 125
Thr Tyr Ser Leu Pro Lys Ser Glu Phe Val Val Pro Asp Leu Glu Leu
        130                 135                 140
Pro Ser Trp Leu Thr Thr Gly Asn Tyr Arg Ile Glu Ser Val Leu Ser
145                 150                 155                 160
```

```
Ser Ser Gly Lys Arg Leu Gly Cys Ile Lys Ile Ala Ala Ser Leu Lys
            165                 170                 175

Gly Ile

<210> SEQ ID NO 11
<211> LENGTH: 200
<212> TYPE: PRT
<213> ORGANISM: Homo sapiens

<400> SEQUENCE: 11

Arg Ala Gly Pro Pro Phe Pro Met Gln Ser Leu Met Gln Ala Pro Leu
  1               5                  10                  15

Leu Ile Ala Leu Gly Leu Leu Leu Ala Ala Pro Ala Gln Ala His Leu
                 20                  25                  30

Lys Lys Pro Ser Gln Leu Ser Ser Phe Ser Trp Asp Asn Cys Asp Glu
             35                  40                  45

Gly Lys Asp Pro Ala Val Ile Arg Ser Leu Thr Leu Glu Pro Asp Pro
 50                  55                  60

Ile Ile Val Pro Gly Asn Val Thr Leu Ser Val Met Gly Ser Thr Ser
 65                  70                  75                  80

Val Pro Leu Ser Ser Pro Leu Lys Val Asp Leu Val Leu Glu Lys Glu
                 85                  90                  95

Val Ala Gly Leu Trp Ile Lys Ile Pro Cys Thr Asp Tyr Ile Gly Ser
                100                 105                 110

Cys Thr Phe Glu His Phe Cys Asp Val Leu Asp Met Leu Ile Pro Thr
            115                 120                 125

Gly Glu Pro Cys Pro Glu Pro Leu Arg Thr Tyr Gly Leu Pro Cys His
        130                 135                 140

Cys Pro Phe Lys Glu Gly Thr Tyr Ser Leu Pro Lys Ser Glu Phe Val
145                 150                 155                 160

Val Pro Asp Leu Glu Leu Pro Ser Trp Leu Thr Thr Gly Asn Tyr Arg
                165                 170                 175

Ile Glu Ser Val Leu Ser Ser Gly Lys Arg Leu Gly Cys Ile Lys
            180                 185                 190

Ile Ala Ala Ser Leu Lys Gly Ile
            195                 200

<210> SEQ ID NO 12
<211> LENGTH: 189
<212> TYPE: PRT
<213> ORGANISM: Homo sapiens

<400> SEQUENCE: 12

Met Gln Ala Pro Leu Leu Ile Ala Leu Gly Leu Leu Leu Ala Thr Pro
  1               5                  10                  15

Ala Gln Ala His Leu Lys Lys Pro Ser Gln Leu Ser Ser Phe Ser Trp
                 20                  25                  30

Asp Asn Cys Asp Glu Gly Lys Asp Pro Ala Val Ile Arg Ser Leu Thr
             35                  40                  45

Leu Glu Pro Asp Pro Ile Val Val Pro Gly Asn Val Thr Leu Ser Val
 50                  55                  60

Val Gly Ser Thr Ser Val Pro Leu Ser Ser Pro Leu Lys Val Asp Leu
 65                  70                  75                  80

Val Leu Glu Lys Glu Val Ala Gly Leu Trp Ile Lys Ile Pro Cys Thr
                 85                  90                  95
```

```
Asp Tyr Ile Gly Ser Cys Thr Phe Glu His Phe Cys Asp Val Leu Asp
            100                 105                 110
Met Leu Ile Pro Thr Gly Glu Pro Cys Pro Glu Pro Leu Arg Thr Tyr
        115                 120                 125
Gly Leu Pro Cys His Cys Pro Phe Lys Glu Gly Thr Tyr Ser Leu Pro
    130                 135                 140
Lys Ser Glu Phe Val Val Pro Asp Leu Glu Leu Pro Ser Trp Leu Thr
145                 150                 155                 160
Thr Gly Asn Tyr Arg Ile Glu Ser Val Leu Ser Ser Gly Lys Arg
                165                 170                 175
Leu Gly Cys Ile Lys Ile Ala Ala Ser Leu Lys Gly Ile
            180                 185
```

<210> SEQ ID NO 13
<211> LENGTH: 193
<212> TYPE: PRT
<213> ORGANISM: Homo sapiens

<400> SEQUENCE: 13

```
Met Gln Ser Leu Met Gln Ala Pro Leu Leu Ile Ala Leu Gly Leu Leu
 1               5                  10                  15
Leu Ala Thr Pro Ala Gln Ala His Leu Lys Lys Pro Ser Gln Leu Ser
                20                  25                  30
Ser Phe Ser Trp Asp Asn Cys Asp Glu Gly Lys Asp Pro Ala Val Ile
            35                  40                  45
Arg Ser Leu Thr Leu Glu Pro Asp Pro Ile Val Val Pro Gly Asn Val
    50                  55                  60
Thr Leu Ser Val Val Gly Ser Thr Ser Val Pro Leu Ser Ser Pro Leu
65                  70                  75                  80
Lys Val Asp Leu Val Leu Glu Lys Glu Val Ala Gly Leu Trp Ile Lys
                85                  90                  95
Ile Pro Cys Thr Asp Tyr Ile Gly Ser Cys Thr Phe Glu His Phe Cys
            100                 105                 110
Asp Val Leu Asp Met Leu Ile Pro Thr Gly Glu Pro Cys Pro Glu Pro
        115                 120                 125
Leu Arg Thr Tyr Gly Leu Pro Cys His Cys Pro Phe Lys Glu Gly Thr
    130                 135                 140
Tyr Ser Leu Pro Lys Ser Glu Phe Val Val Pro Asp Leu Glu Leu Pro
145                 150                 155                 160
Ser Trp Leu Thr Thr Gly Asn Tyr Arg Ile Glu Ser Val Leu Ser Ser
                165                 170                 175
Ser Gly Lys Arg Leu Gly Cys Ile Lys Ile Ala Ala Ser Leu Lys Gly
            180                 185                 190
Ile
```

<210> SEQ ID NO 14
<211> LENGTH: 193
<212> TYPE: PRT
<213> ORGANISM: Homo sapiens

<400> SEQUENCE: 14

```
Met Gln Ser Leu Met Gln Ala Pro Leu Leu Ile Ala Leu Gly Leu Leu
 1               5                  10                  15
Leu Ala Thr Pro Ala Gln Ala His Leu Lys Lys Pro Ser Gln Leu Ser
                20                  25                  30
Ser Phe Ser Trp Asp Asn Cys Asp Glu Gly Lys Asp Pro Ala Val Ile
```

```
                    35                  40                  45
Arg Ser Leu Thr Leu Glu Pro Asp Pro Ile Val Val Pro Gly Asn Val
         50                  55                  60

Thr Leu Ser Val Val Gly Ser Thr Ser Val Pro Leu Ser Ser Pro Leu
 65                  70                  75                  80

Lys Val Asp Leu Val Leu Glu Lys Glu Val Ala Gly Leu Trp Ile Lys
                 85                  90                  95

Ile Pro Cys Thr Asp Tyr Ile Gly Ser Cys Thr Phe Glu His Phe Cys
                100                 105                 110

Asp Val Leu Asp Met Leu Ile Pro Thr Gly Glu Pro Cys Pro Glu Pro
                115                 120                 125

Leu Arg Thr Tyr Gly Leu Pro Cys His Cys Pro Phe Lys Glu Gly Thr
        130                 135                 140

Tyr Ser Leu Pro Lys Ser Glu Phe Val Val Pro Asp Leu Glu Leu Pro
145                 150                 155                 160

Ser Trp Leu Thr Thr Gly Asn Tyr Arg Ile Glu Ser Val Leu Ser Ser
                165                 170                 175

Ser Gly Lys Arg Leu Gly Cys Ile Lys Ile Ala Ala Ser Leu Lys Gly
                180                 185                 190

Ile

<210> SEQ ID NO 15
<211> LENGTH: 193
<212> TYPE: PRT
<213> ORGANISM: Homo sapiens

<400> SEQUENCE: 15

Met Gln Ser Leu Met Gln Ala Pro Leu Leu Ile Ala Leu Gly Leu Leu
  1               5                  10                  15

Leu Ala Thr Pro Ala Gln Ala His Leu Lys Lys Pro Ser Gln Leu Ser
                 20                  25                  30

Ser Phe Ser Trp Asp Asn Cys Asp Glu Gly Lys Asp Pro Ala Val Ile
             35                  40                  45

Arg Ser Leu Thr Leu Glu Pro Asp Pro Ile Val Val Pro Gly Asn Val
         50                  55                  60

Thr Leu Ser Val Val Gly Ser Thr Ser Val Pro Leu Ser Ser Pro Leu
 65                  70                  75                  80

Lys Val Asp Leu Val Leu Glu Lys Glu Val Ala Gly Leu Trp Ile Lys
                 85                  90                  95

Ile Pro Cys Thr Asp Tyr Ile Gly Ser Cys Thr Phe Glu His Phe Cys
                100                 105                 110

Asp Val Leu Asp Met Leu Ile Pro Thr Gly Glu Pro Cys Pro Glu Pro
                115                 120                 125

Leu Arg Thr Tyr Gly Leu Pro Cys His Cys Pro Phe Lys Glu Gly Thr
        130                 135                 140

Tyr Ser Leu Pro Lys Ser Glu Phe Val Val Pro Asp Leu Glu Leu Pro
145                 150                 155                 160

Ser Trp Leu Thr Thr Gly Asn Tyr Arg Ile Glu Ser Val Leu Ser Ser
                165                 170                 175

Ser Gly Lys Arg Leu Gly Cys Ile Lys Ile Ala Ala Ser Leu Lys Gly
                180                 185                 190

Ile

<210> SEQ ID NO 16
```

<211> LENGTH: 193
<212> TYPE: PRT
<213> ORGANISM: Homo sapiens

<400> SEQUENCE: 16

```
Met Gln Ser Leu Met Gln Ala Pro Leu Leu Ile Ala Leu Gly Leu Leu
 1               5                  10                  15
Leu Ala Thr Pro Ala Gln Ala His Leu Lys Lys Pro Ser Gln Leu Ser
            20                  25                  30
Ser Phe Ser Trp Asp Asn Cys Asp Glu Gly Lys Asp Pro Ala Val Ile
        35                  40                  45
Arg Ser Leu Thr Leu Glu Pro Asp Pro Ile Val Val Pro Gly Asn Val
 50                  55                  60
Thr Leu Ser Val Val Gly Ser Thr Ser Val Pro Leu Ser Ser Pro Leu
 65                  70                  75                  80
Lys Val Asp Leu Val Leu Glu Lys Glu Val Ala Gly Leu Trp Ile Lys
                 85                  90                  95
Ile Pro Cys Thr Asp Tyr Ile Gly Ser Cys Thr Phe Glu His Phe Cys
            100                 105                 110
Asp Val Leu Asp Met Leu Ile Pro Thr Gly Glu Pro Cys Pro Glu Pro
        115                 120                 125
Leu Arg Thr Tyr Gly Leu Pro Cys His Cys Pro Phe Lys Glu Gly Thr
    130                 135                 140
Tyr Ser Leu Pro Lys Ser Glu Phe Val Val Pro Asp Leu Glu Leu Pro
145                 150                 155                 160
Ser Trp Leu Thr Thr Gly Asn Tyr Arg Ile Glu Ser Val Leu Ser Ser
                165                 170                 175
Ser Gly Lys Arg Leu Gly Cys Ile Lys Ile Ala Ala Ser Leu Lys Gly
            180                 185                 190
Ile
```

<210> SEQ ID NO 17
<211> LENGTH: 114
<212> TYPE: PRT
<213> ORGANISM: Homo sapiens

<400> SEQUENCE: 17

```
Met Thr Cys Lys Met Ser Gln Leu Glu Arg Asn Ile Glu Thr Ile Ile
 1               5                  10                  15
Asn Thr Phe His Gln Tyr Ser Val Lys Leu Gly His Pro Asp Thr Leu
            20                  25                  30
Asn Gln Gly Glu Phe Lys Glu Leu Val Arg Lys Asp Leu Gln Asn Phe
        35                  40                  45
Leu Lys Lys Glu Asn Lys Asn Glu Lys Val Ile Glu His Ile Met Glu
 50                  55                  60
Asp Leu Asp Thr Asn Ala Asp Lys Gln Leu Ser Phe Glu Glu Phe Ile
 65                  70                  75                  80
Met Leu Met Ala Arg Leu Thr Trp Ala Ser His Glu Lys Met His Glu
                 85                  90                  95
Gly Asp Glu Gly Pro Gly His His Lys Pro Gly Leu Gly Glu Gly
            100                 105                 110
Thr Pro
```

<210> SEQ ID NO 18
<211> LENGTH: 93
<212> TYPE: PRT

<213> ORGANISM: Homo sapiens

<400> SEQUENCE: 18

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
    50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90

<210> SEQ ID NO 19
<211> LENGTH: 92
<212> TYPE: PRT
<213> ORGANISM: Homo sapiens

<400> SEQUENCE: 19

Met Thr Lys Leu Glu Glu His Leu Glu Gly Ile Val Asn Ile Phe His
1               5                   10                  15

Gln Tyr Ser Val Arg Lys Gly His Phe Asp Thr Leu Ser Lys Gly Glu
            20                  25                  30

Leu Lys Gln Leu Leu Thr Lys Glu Leu Ala Asn Thr Ile Lys Asn Ile
        35                  40                  45

Lys Asp Lys Ala Val Ile Asp Glu Ile Phe Gln Gly Leu Asp Ala Asn
    50                  55                  60

Gln Asp Glu Gln Val Asp Phe Gln Glu Phe Ile Ser Leu Val Ala Ile
65                  70                  75                  80

Ala Leu Lys Ala Ala His Tyr His Thr His Lys Glu
                85                  90

<210> SEQ ID NO 20
<211> LENGTH: 92
<212> TYPE: PRT
<213> ORGANISM: Homo sapiens

<400> SEQUENCE: 20

Met Thr Lys Leu Glu Glu His Leu Glu Gly Ile Val Asn Ile Phe His
1               5                   10                  15

Gln Tyr Ser Val Arg Lys Gly His Phe Asp Thr Leu Ser Lys Gly Glu
            20                  25                  30

Leu Lys Gln Leu Leu Thr Lys Glu Leu Ala Asn Thr Ile Lys Asn Ile
        35                  40                  45

Lys Asp Lys Ala Val Ile Asp Glu Ile Phe Gln Gly Leu Asp Ala Asn
    50                  55                  60

Gln Asp Glu Gln Val Asp Phe Gln Glu Phe Ile Ser Leu Val Ala Ile
65                  70                  75                  80

Ala Leu Lys Ala Ala His Tyr His Thr His Lys Glu
                85                  90

<210> SEQ ID NO 21
<211> LENGTH: 91
<212> TYPE: PRT
<213> ORGANISM: Homo sapiens

<400> SEQUENCE: 21

Thr Lys Leu Glu Glu His Leu Glu Gly Ile Val Asn Ile Phe His Gln
1               5                   10                  15

Tyr Ser Val Arg Lys Gly His Phe Asp Thr Leu Ser Lys Gly Glu Leu
            20                  25                  30

Lys Gln Leu Leu Thr Lys Glu Leu Ala Asn Thr Ile Lys Asn Ile Lys
        35                  40                  45

Asp Lys Ala Val Ile Asp Glu Ile Phe Gln Gly Leu Asp Ala Asn Gln
    50                  55                  60

Asp Glu Gln Val Asp Phe Gln Glu Phe Ile Ser Leu Val Ala Ile Ala
65                  70                  75                  80

Leu Lys Ala Ala His Tyr His Thr His Lys Glu
                85                  90

<210> SEQ ID NO 22
<211> LENGTH: 93
<212> TYPE: PRT
<213> ORGANISM: Homo sapiens

<400> SEQUENCE: 22

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
    50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90

<210> SEQ ID NO 23
<211> LENGTH: 92
<212> TYPE: PRT
<213> ORGANISM: Homo sapiens

<400> SEQUENCE: 23

Met Thr Lys Leu Glu Glu His Leu Glu Gly Ile Val Asn Ile Phe His
1               5                   10                  15

Gln Tyr Ser Val Arg Lys Gly His Phe Asp Thr Leu Ser Lys Gly Glu
            20                  25                  30

Leu Lys Gln Leu Leu Thr Lys Glu Leu Ala Asn Thr Ile Lys Asn Ile
        35                  40                  45

Lys Asp Lys Ala Val Ile Asp Glu Ile Phe Gln Gly Leu Asp Ala Asn
    50                  55                  60

Gln Asp Glu Gln Val Asp Phe Gln Glu Phe Ile Ser Leu Val Ala Ile
65                  70                  75                  80

Ala Leu Lys Ala Ala His Tyr His Thr His Lys Glu
                85                  90

<210> SEQ ID NO 24
<211> LENGTH: 85
<212> TYPE: PRT
<213> ORGANISM: Homo sapiens

```
<400> SEQUENCE: 24

Asp Asn Gly Asp Val Cys Gln Asp Cys Ile Gln Met Val Thr Asp Ile
  1               5                  10                  15

Gln Thr Ala Val Arg Thr Asn Ser Thr Phe Val Gln Ala Leu Val Glu
             20                  25                  30

His Val Lys Glu Glu Cys Asp Arg Leu Gly Pro Gly Met Ala Asp Ile
         35                  40                  45

Cys Lys Asn Tyr Ile Ser Gln Tyr Ser Glu Ile Ala Ile Gln Met Met
     50                  55                  60

Met His Met Gln Asp Gln Gln Pro Lys Glu Ile Cys Ala Leu Val Gly
 65                  70                  75                  80

Phe Cys Asp Glu Val
             85

<210> SEQ ID NO 25
<211> LENGTH: 381
<212> TYPE: PRT
<213> ORGANISM: Homo sapiens

<400> SEQUENCE: 25

Met Ala Glu Ser His Leu Leu Gln Trp Leu Leu Leu Leu Leu Pro Thr
  1               5                  10                  15

Leu Cys Gly Pro Gly Thr Ala Ala Trp Thr Thr Ser Ser Leu Ala Cys
             20                  25                  30

Ala Gln Gly Pro Glu Phe Trp Cys Gln Ser Leu Glu Gln Ala Leu Gln
         35                  40                  45

Cys Arg Ala Leu Gly His Cys Leu Gln Glu Val Trp Gly His Val Gly
     50                  55                  60

Ala Asp Asp Leu Cys Gln Glu Cys Glu Asp Ile Val His Ile Leu Asn
 65                  70                  75                  80

Lys Met Ala Lys Glu Ala Ile Phe Gln Asp Thr Met Arg Lys Phe Leu
             85                  90                  95

Glu Gln Glu Cys Asn Val Leu Pro Leu Lys Leu Leu Met Pro Gln Cys
        100                 105                 110

Asn Gln Val Leu Asp Asp Tyr Phe Pro Leu Val Ile Asp Tyr Phe Gln
        115                 120                 125

Asn Gln Ile Asp Ser Asn Gly Ile Cys Met His Leu Gly Leu Cys Lys
        130                 135                 140

Ser Arg Gln Pro Glu Pro Glu Gln Glu Pro Gly Met Ser Asp Pro Leu
145                 150                 155                 160

Pro Lys Pro Leu Arg Asp Pro Leu Pro Asp Pro Leu Leu Asp Lys Leu
                165                 170                 175

Val Leu Pro Val Leu Pro Gly Ala Leu Gln Ala Arg Pro Gly Pro His
                180                 185                 190

Thr Gln Asp Leu Ser Glu Gln Gln Phe Pro Ile Pro Leu Pro Tyr Cys
                195                 200                 205

Trp Leu Cys Arg Ala Leu Ile Lys Arg Ile Gln Ala Met Ile Pro Lys
        210                 215                 220

Gly Ala Leu Arg Val Ala Val Ala Gln Val Cys Arg Val Val Pro Leu
225                 230                 235                 240

Val Ala Gly Gly Ile Cys Gln Cys Leu Ala Glu Arg Tyr Ser Val Ile
                245                 250                 255

Leu Leu Asp Thr Leu Leu Gly Arg Met Leu Pro Gln Leu Val Cys Arg
                260                 265                 270
```

-continued

```
Leu Val Leu Arg Cys Ser Met Asp Asp Ser Ala Gly Pro Arg Ser Pro
            275                 280                 285

Thr Gly Glu Trp Leu Pro Arg Asp Ser Glu Cys His Leu Cys Met Ser
        290                 295                 300

Val Thr Thr Gln Ala Gly Asn Ser Ser Glu Gln Ala Ile Pro Gln Ala
305                 310                 315                 320

Met Leu Gln Ala Cys Val Gly Ser Trp Leu Asp Arg Glu Lys Cys Lys
                325                 330                 335

Gln Phe Val Glu Gln His Thr Pro Gln Leu Leu Thr Leu Val Pro Arg
            340                 345                 350

Gly Trp Asp Ala His Thr Thr Cys Gln Ala Leu Gly Val Cys Gly Thr
        355                 360                 365

Met Ser Ser Pro Leu Gln Cys Ile His Ser Pro Asp Leu
    370                 375                 380

<210> SEQ ID NO 26
<211> LENGTH: 379
<212> TYPE: PRT
<213> ORGANISM: Homo sapiens

<400> SEQUENCE: 26

Met Ala Glu Ser His Leu Leu Gln Trp Leu Leu Leu Leu Pro Thr
1               5                   10                  15

Leu Cys Gly Pro Gly Thr Ala Ala Trp Thr Thr Ser Ser Leu Ala Cys
                20                  25                  30

Ala Gln Gly Pro Glu Phe Trp Cys Gln Ser Leu Glu Gln Ala Leu Gln
            35                  40                  45

Cys Arg Ala Leu Gly His Cys Leu Gln Glu Val Trp Gly His Val Gly
        50                  55                  60

Ala Asp Asp Leu Cys Gln Glu Cys Glu Asp Ile Val His Ile Leu Asn
65                  70                  75                  80

Lys Met Ala Lys Glu Ala Ile Phe Gln Asp Thr Met Arg Lys Phe Leu
                85                  90                  95

Glu Gln Glu Cys Asn Val Leu Pro Leu Lys Leu Leu Met Pro Gln Cys
            100                 105                 110

Asn Gln Val Leu Asp Asp Tyr Phe Pro Leu Val Ile Asp Tyr Phe Gln
        115                 120                 125

Asn Gln Thr Asp Ser Asn Gly Ile Cys Met His Leu Gly Cys Lys Ser
130                 135                 140

Arg Gln Pro Glu Pro Glu Gln Glu Pro Gly Met Ser Asp Pro Leu Pro
145                 150                 155                 160

Lys Pro Leu Arg Asp Pro Leu Pro Asp Pro Leu Leu Asp Lys Leu Val
                165                 170                 175

Leu Pro Val Leu Pro Gly Ala Leu Gln Ala Arg Pro Gly Pro His Thr
            180                 185                 190

Gln Asp Leu Ser Glu Gln Gln Phe Pro Ile Pro Leu Pro Tyr Cys Trp
        195                 200                 205

Cys Arg Ala Leu Ile Lys Arg Ile Gln Ala Met Ile Pro Lys Gly Ala
    210                 215                 220

Leu Arg Val Ala Val Ala Gln Val Cys Arg Val Val Pro Leu Val Ala
225                 230                 235                 240

Gly Gly Ile Cys Gln Cys Leu Ala Glu Arg Tyr Ser Val Ile Leu Leu
                245                 250                 255

Asp Thr Leu Leu Gly Arg Met Leu Pro Gln Leu Val Cys Arg Leu Val
            260                 265                 270
```

-continued

```
Leu Arg Cys Ser Met Asp Asp Ser Ala Gly Pro Arg Ser Pro Thr Gly
            275                 280                 285
Glu Trp Leu Pro Arg Asp Ser Glu Cys His Leu Cys Met Ser Val Thr
        290                 295                 300
Thr Gln Ala Gly Asn Ser Ser Glu Gln Ala Ile Pro Gln Ala Met Leu
305                 310                 315                 320
Gln Ala Cys Val Gly Ser Trp Leu Asp Arg Glu Lys Cys Lys Gln Phe
                325                 330                 335
Val Glu Gln His Thr Pro Gln Leu Leu Thr Leu Val Pro Arg Gly Trp
            340                 345                 350
Asp Ala His Thr Thr Cys Gln Ala Leu Gly Val Cys Gly Thr Met Ser
            355                 360                 365
Ser Pro Leu Gln Cys Ile His Ser Pro Asp Leu
        370                 375
```

<210> SEQ ID NO 27
<211> LENGTH: 527
<212> TYPE: PRT
<213> ORGANISM: Homo sapiens

<400> SEQUENCE: 27

```
Met Tyr Ala Leu Phe Leu Leu Ala Ser Leu Leu Gly Ala Ala Leu Ala
  1               5                  10                  15
Gly Pro Val Leu Gly Leu Lys Glu Cys Thr Arg Gly Ser Ala Val Trp
             20                  25                  30
Cys Gln Asn Val Lys Thr Ala Ser Asp Cys Gly Ala Val Lys His Cys
         35                  40                  45
Leu Gln Thr Val Trp Asn Lys Pro Thr Val Lys Ser Leu Pro Cys Asp
     50                  55                  60
Ile Cys Lys Asp Val Val Thr Ala Ala Gly Asp Met Leu Lys Asp Asn
 65                  70                  75                  80
Ala Thr Glu Glu Glu Ile Leu Val Tyr Leu Glu Lys Thr Cys Asp Trp
                 85                  90                  95
Leu Pro Lys Pro Asn Met Ser Ala Ser Cys Lys Glu Ile Val Asp Ser
            100                 105                 110
Tyr Leu Pro Val Ile Leu Asp Ile Ile Lys Gly Glu Met Ser Arg Pro
        115                 120                 125
Gly Glu Val Cys Ser Ala Leu Asn Leu Cys Glu Ser Leu Gln Lys His
    130                 135                 140
Leu Ala Glu Leu Asn His Gln Lys Gln Leu Glu Ser Asn Lys Ile Pro
145                 150                 155                 160
Glu Leu Asp Met Thr Glu Val Val Ala Pro Phe Met Ala Asn Ile Pro
                165                 170                 175
Leu Leu Leu Tyr Pro Gln Asp Gly Pro Arg Ser Lys Pro Gln Pro Lys
            180                 185                 190
Asp Asn Gly Asp Val Cys Gln Asp Cys Ile Gln Met Val Thr Asp Ile
        195                 200                 205
Gln Thr Ala Val Arg Thr Asn Ser Thr Phe Val Gln Ala Leu Val Glu
    210                 215                 220
His Val Lys Glu Glu Cys Asp Arg Leu Gly Pro Gly Met Ala Asp Ile
225                 230                 235                 240
Cys Lys Asn Tyr Ile Ser Gln Tyr Ser Glu Ile Ala Ile Gln Met Met
                245                 250                 255
Met His Met Gln Asp Gln Gln Pro Lys Glu Ile Cys Ala Leu Val Gly
```

```
                    260                 265                 270
Phe Cys Asp Glu Val Lys Glu Met Pro Met Gln Thr Leu Val Pro Ala
            275                 280                 285
Lys Val Ala Ser Lys Asn Val Ile Pro Ala Leu Glu Leu Val Glu Pro
        290                 295                 300
Ile Lys Lys His Glu Val Pro Ala Lys Ser Asp Val Tyr Cys Glu Val
305                 310                 315                 320
Cys Glu Phe Leu Val Lys Glu Val Thr Lys Leu Ile Asp Asn Asn Lys
                325                 330                 335
Thr Glu Lys Glu Ile Leu Asp Ala Phe Asp Lys Met Cys Ser Lys Leu
            340                 345                 350
Pro Lys Ser Leu Ser Glu Glu Cys Gln Glu Val Val Asp Thr Tyr Gly
        355                 360                 365
Ser Ser Ile Leu Ser Ile Leu Leu Glu Glu Val Ser Pro Glu Leu Val
    370                 375                 380
Cys Ser Met Leu His Leu Cys Ser Gly Thr Arg Leu Pro Ala Leu Thr
385                 390                 395                 400
Val His Val Thr Gln Pro Lys Asp Gly Gly Phe Cys Glu Val Cys Lys
                405                 410                 415
Lys Leu Val Gly Tyr Leu Asp Arg Asn Leu Glu Lys Asn Ser Thr Lys
            420                 425                 430
Gln Glu Ile Leu Ala Ala Leu Glu Lys Gly Cys Ser Phe Leu Pro Asp
        435                 440                 445
Pro Tyr Gln Lys Gln Cys Asp Gln Phe Val Ala Glu Tyr Glu Pro Val
    450                 455                 460
Leu Ile Glu Ile Leu Val Glu Val Met Asp Pro Ser Phe Val Cys Leu
465                 470                 475                 480
Lys Ile Gly Ala Cys Pro Ser Ala His Lys Pro Leu Leu Gly Thr Glu
                485                 490                 495
Lys Cys Ile Trp Gly Pro Ser Tyr Trp Cys Gln Asn Thr Glu Thr Ala
            500                 505                 510
Ala Gln Cys Asn Ala Val Glu His Cys Lys Arg His Val Trp Asn
        515                 520                 525

<210> SEQ ID NO 28
<211> LENGTH: 523
<212> TYPE: PRT
<213> ORGANISM: Homo sapiens

<400> SEQUENCE: 28

Met Tyr Ala Leu Phe Leu Leu Ala Ser Leu Leu Gly Ala Ala Leu Ala
1               5                   10                  15
Gly Pro Val Leu Gly Leu Lys Glu Cys Thr Arg Gly Ser Ala Val Trp
            20                  25                  30
Cys Gln Asn Val Lys Thr Ala Ser Asp Cys Gly Ala Val Lys His Cys
        35                  40                  45
Leu Gln Thr Val Trp Asn Lys Pro Thr Val Lys Ser Leu Pro Cys Asp
    50                  55                  60
Ile Cys Lys Asp Val Val Thr Ala Ala Gly Asp Met Leu Lys Asp Asn
65                  70                  75                  80
Ala Thr Glu Glu Glu Ile Leu Val Tyr Leu Glu Lys Thr Cys Asp Trp
                85                  90                  95
Leu Pro Lys Pro Asn Met Ser Ala Ser Cys Lys Glu Ile Val Asp Ser
            100                 105                 110
```

-continued

```
Tyr Leu Pro Val Ile Leu Asp Ile Ile Lys Gly Glu Met Ser Arg Pro
            115                 120                 125
Gly Glu Val Cys Ser Ala Leu Leu Cys Glu Ser Leu Gln Lys His Leu
        130                 135                 140
Ala Glu Leu Asn His Gln Lys Gln Leu Glu Ser Asn Lys Ile Pro Glu
145                 150                 155                 160
Leu Asp Met Thr Glu Val Val Ala Pro Phe Met Ala Asn Ile Pro Leu
                165                 170                 175
Leu Leu Tyr Pro Gln Asp Gly Pro Arg Ser Lys Pro Gln Pro Lys Asp
            180                 185                 190
Asn Gly Asp Val Cys Gln Asp Cys Ile Gln Met Val Thr Asp Ile Gln
        195                 200                 205
Thr Ala Val Arg Thr Asn Ser Thr Phe Val Gln Ala Leu Val Glu His
210                 215                 220
Val Lys Glu Glu Cys Asp Arg Leu Gly Pro Gly Met Ala Asp Ile Cys
225                 230                 235                 240
Lys Asn Tyr Ile Ser Gln Tyr Ser Glu Ile Ala Ile Gln Met Met Met
                245                 250                 255
His Met Gln Pro Lys Glu Ile Cys Ala Leu Val Gly Phe Cys Asp Glu
            260                 265                 270
Val Lys Glu Met Pro Met Gln Thr Leu Val Pro Ala Lys Val Ala Ser
        275                 280                 285
Lys Asn Val Ile Pro Ala Leu Glu Leu Val Glu Pro Ile Lys Lys His
        290                 295                 300
Glu Val Pro Ala Lys Ser Asp Val Tyr Cys Glu Val Cys Glu Phe Leu
305                 310                 315                 320
Val Lys Glu Val Thr Lys Leu Ile Asp Asn Asn Lys Thr Glu Lys Glu
                325                 330                 335
Ile Leu Asp Ala Phe Asp Lys Met Cys Ser Lys Leu Pro Lys Ser Leu
            340                 345                 350
Ser Glu Glu Cys Gln Glu Val Val Asp Thr Tyr Gly Ser Ser Ile Leu
        355                 360                 365
Ser Ile Leu Leu Glu Glu Val Ser Pro Glu Leu Val Cys Ser Met Leu
370                 375                 380
His Leu Cys Ser Gly Thr Arg Leu Pro Ala Leu Thr Val His Val Thr
385                 390                 395                 400
Gln Pro Lys Asp Gly Gly Phe Cys Glu Val Cys Lys Lys Leu Val Gly
                405                 410                 415
Tyr Leu Asp Arg Asn Leu Glu Lys Asn Ser Thr Lys Gln Glu Ile Leu
            420                 425                 430
Ala Ala Leu Glu Lys Gly Cys Ser Phe Leu Pro Asp Pro Tyr Gln Lys
        435                 440                 445
Gln Cys Asp Gln Phe Val Ala Glu Tyr Glu Pro Val Leu Ile Glu Ile
    450                 455                 460
Leu Val Glu Val Met Asp Pro Ser Phe Val Cys Leu Lys Ile Gly Ala
465                 470                 475                 480
Cys Pro Ser Ala His Lys Pro Leu Leu Gly Thr Glu Lys Cys Ile Trp
                485                 490                 495
Gly Pro Ser Tyr Trp Cys Gln Asn Thr Glu Thr Ala Ala Gln Cys Asn
            500                 505                 510
Ala Val Glu His Cys Lys Arg His Val Trp Asn
        515                 520
```

```
<210> SEQ ID NO 29
<211> LENGTH: 380
<212> TYPE: PRT
<213> ORGANISM: Homo sapiens

<400> SEQUENCE: 29

Met Ala Glu Ser His Leu Leu Gln Trp Leu Leu Leu Leu Pro Thr
  1               5                  10                  15

Leu Cys Gly Pro Gly Thr Ala Ala Trp Thr Thr Ser Ser Leu Ala Cys
             20                  25                  30

Ala Gln Gly Pro Glu Phe Trp Cys Gln Ser Leu Glu Gln Ala Leu Gln
         35                  40                  45

Cys Arg Ala Leu Gly His Cys Leu Gln Glu Val Trp Gly His Val Gly
     50                  55                  60

Ala Asp Asp Leu Cys Gln Glu Cys Glu Asp Ile Val His Ile Leu Asn
 65                  70                  75                  80

Lys Met Ala Lys Glu Ala Ile Phe Gln Asp Thr Met Arg Lys Phe Leu
                 85                  90                  95

Glu Gln Glu Cys Asn Val Leu Pro Leu Lys Leu Leu Met Pro Gln Cys
                100                 105                 110

Asn Gln Val Leu Asp Asp Tyr Phe Pro Leu Val Ile Asp Tyr Phe Gln
                115                 120                 125

Asn Gln Thr Asp Ser Asn Gly Ile Cys Met His Gly Leu Cys Lys Ser
            130                 135                 140

Arg Gln Pro Glu Pro Glu Gln Glu Pro Gly Met Ser Asp Pro Leu Pro
145                 150                 155                 160

Lys Pro Leu Arg Asp Pro Leu Pro Asp Pro Leu Leu Asp Lys Leu Val
                165                 170                 175

Leu Pro Val Leu Pro Gly Ala Leu Gln Ala Arg Pro Gly Pro His Thr
                180                 185                 190

Gln Asp Leu Ser Glu Gln Gln Phe Pro Ile Pro Leu Pro Tyr Cys Trp
            195                 200                 205

Leu Cys Arg Ala Leu Ile Lys Arg Ile Gln Ala Met Ile Pro Lys Gly
210                 215                 220

Ala Leu Ala Val Ala Val Ala Gln Val Cys Arg Val Val Pro Leu Val
225                 230                 235                 240

Ala Gly Gly Ile Cys Gln Cys Leu Ala Glu Arg Tyr Ser Val Ile Leu
                245                 250                 255

Leu Asp Thr Leu Leu Gly Arg Met Leu Pro Gln Leu Val Cys Arg Leu
            260                 265                 270

Val Leu Arg Cys Ser Met Asp Asp Ser Ala Gly Pro Arg Ser Pro Thr
        275                 280                 285

Gly Glu Trp Leu Pro Arg Asp Ser Glu Cys His Leu Cys Met Ser Val
290                 295                 300

Thr Thr Gln Ala Gly Asn Ser Ser Glu Gln Ala Ile Pro Gln Ala Met
305                 310                 315                 320

Leu Gln Ala Cys Val Gly Ser Trp Leu Asp Arg Glu Lys Cys Lys Gln
                325                 330                 335

Phe Val Glu Gln His Thr Pro Gln Leu Leu Thr Leu Val Pro Arg Gly
            340                 345                 350

Trp Asp Ala His Thr Thr Cys Gln Ala Leu Gly Val Cys Gly Thr Met
        355                 360                 365

Ser Ser Pro Leu Gln Cys Ile His Ser Pro Asp Leu
    370                 375                 380
```

<210> SEQ ID NO 30
<211> LENGTH: 4124
<212> TYPE: DNA
<213> ORGANISM: Homo sapiens

<400> SEQUENCE: 30

| | | | | | |
|---|---|---|---|---|---|
| atgagagaat | gggttctgct | catgtccgtg | ctgctctgtg | gcctggctgg | ccccacacac | 60 |
| ctgttccagc | caagcctggt | gctggacatg | gccaaggtcc | tcttggataa | ctactgcttc | 120 |
| ccggagaacc | tgctgggcat | gcaggaagcc | atccagcagg | ccatcaagag | ccatgagatt | 180 |
| ctgagcatct | cagacccgca | gacgctggcc | agtgtgctga | cagccgggt | gcagagctcc | 240 |
| ctgaacgatc | tcgcctggt | catctcctat | gagcccagca | ccccgagcc | tcccccacaa | 300 |
| gtcccagcac | tcaccagcct | tcagaagag | gaactgcttg | cctggctgca | aaggggcctc | 360 |
| cgccatgagg | ttctggaggg | taatgtgggc | tacctgcggg | tggacagcgt | cccgggccag | 420 |
| gaggtgctga | gcatgatggg | ggagttcctg | gtgcccacg | tgtgggggaa | tctcatgggc | 480 |
| acctccgcct | tagtgctgga | tctccggcac | tgcacaggag | gccaggtctc | tggcattccc | 540 |
| tacatcatct | cctacctgca | cccagggaac | caatcctgc | acgtggacac | tatctacaac | 600 |
| cgcccctcca | acaccaccac | ggagatctgg | accttgcccc | aggtcctggg | agaaaggtac | 660 |
| ggtgccgaca | aggatgtggt | ggtcctcacc | agcagccaga | ccagggggcgt | ggccgaggac | 720 |
| atcgcgcaca | tccttaagca | gatgcgcagg | gccatcgtgg | tgggcgagcg | gactggggga | 780 |
| ggggccctgg | acctccggaa | gctgaggata | ggcgagtctg | acttcttctt | cacggtgccc | 840 |
| gtgtccaggt | ccctgggggcc | ccttggtgga | ggcagccaga | cgtgggaggg | cagcggggtg | 900 |
| ctgccctgtg | tggggactcc | ggccgagcag | gccctggaga | aagccctggc | catcctcact | 960 |
| ctgcgcagcg | cccttccagg | ggtagtccac | tgcctccagg | aggtcctgaa | ggactactac | 1020 |
| acgctggtgg | accgtgtgcc | caccctgctg | cagcacttgg | ccagcatgga | cttctccacg | 1080 |
| gtggtctccg | aggaagatct | ggtcaccaag | ctcaatgccg | gcctgcaggc | tgcgtctgag | 1140 |
| gatcccaggc | tcctggtgcg | agccatcggg | cccacagaaa | ctccttcttg | gcccgcgccc | 1200 |
| gacgctgcag | ccgaagactc | accagggggtg | gccccagagt | tgcctgagga | cgaggctatc | 1260 |
| cggcaagcac | tggtggactc | tgtgttccag | gtgtcggtgc | tgccaggcaa | tgtgggctac | 1320 |
| ctgcgcttcg | atagttttgc | tgacgcctcc | gtcctgggtg | tgttggcccc | atatgtcctg | 1380 |
| cgccaggtgt | gggagccgct | acaggacacg | gagcacctca | tcatggacct | gcgccacaac | 1440 |
| cctggagggc | catcctctgc | tgtgcccctg | ctcctgtcct | acttccaggg | ccctgaggcc | 1500 |
| ggccccgtgc | acctcttcac | cacctatgat | cgccgcacca | acatcacgca | ggagcacttc | 1560 |
| agccacatgg | agctcccggg | cccacgctac | agcacccaac | gtgggggtgta | tctgctcacc | 1620 |
| agccaccgca | ccgccacggc | cgcggaggag | ttcgccttcc | ttatgcagtc | gctgggctgg | 1680 |
| gccacactgg | taggtgagat | caccgcgggc | aacctgctgc | acaccgcac | ggtgcgctg | 1740 |
| ctggacacac | ccgaaggcag | cctcgcgctc | accgtgccgg | tcctcacctt | catcgacaat | 1800 |
| cacggcgagg | cctggctggg | tggtggagtg | gtgcccgatg | ccatcgtgct | ggccgaggag | 1860 |
| gccctggaca | aagcccagga | agtgctggag | ttccaccaaa | gcctgggggc | cttggtggag | 1920 |
| ggcacagggc | acctgctgga | ggccactat | gctcggccag | aggtcgtggg | gcagaccagt | 1980 |
| gccctcctgc | gggccaagct | ggccagggc | gcctaccgca | cagctgtgga | cttggagtct | 2040 |
| ctggcctctc | agctcacagc | agacctccag | gaggtgtctg | ggaccaccg | cttgctagtg | 2100 |
| ttccacagcc | ctggcgagct | ggtggtagag | gaagcacccc | caccacccc | tgctgtcccc | 2160 |

```
tctccagagg agctcaccta ccttattgag gccctgttca agacagaggt gctgcccggc    2220
cagctgggct acctgcgttt tgacgccatg gctgaactgg agacagtgaa ggccgtgggg    2280
ccacagctgg tgcggctggt atggcaacag ctggtggaca cggctgcgct ggtgatcgac    2340
ctgcgctaca accctggcag ctactccacg gccatcccgc tgctctgctc ctacttcttt    2400
gaggcagagc cccgccagca cctgtattct gtctttgaca gggccacctc aaaagtcacg    2460
gaggtgtgga ccttgcccca ggtcgccggc cagcgctacg gctcacacaa ggacctctac    2520
atcctgatga ccacaccag tggctctgcg gccgaggcct ttgcacacac catgcaggac    2580
ctgcagcggg ccacggtcat tggggagccc acggccggag gcgcactctc tgtgggcatc    2640
taccaggtgg gcagcagccc cttatatgca tccatgccca cccagatggc catgagtgcc    2700
accacaggca aggcctggga cctggctggt gtggagcccg acatcactgt gcccatgagc    2760
gaagcccttt ccatagccca ggacatagtg gctctgcgtg ccaaggtgcc cacggtgctg    2820
cagacggccg ggaagctggt ggctgataac tatgcctctg ccgagctggg ggccaagatg    2880
gccaccaaac tgagcggtct gcagagccgc tactccaggg tgacctcaga agtggcccta    2940
gccgagatcc tgggggctga cctgcagatg ctctccggag acccacacct gaaggcagcc    3000
catatccctg agaatgccaa ggaccgcatt cctggaattg tgcccatgca gatcccttcc    3060
cctgaagtat ttgaagagct gatcaagttt tccttccaca ctaacgtgct tgaggacaac    3120
attggctact tgaggtttga catgtttggg gacggtgagc tgctcaccca ggtctccagg    3180
ctgctggtgg agcacatctg gaagaagatc atgcacacgg atgccatgat catcgacatg    3240
aggttcaaca tcggtggccc cacatcctcc attcccatct tgtgctccta cttctttgat    3300
gaaggccctc cagttctgct ggacaagatc tacagccggc tgatgactc tgtcagtgaa    3360 ctctggacac acgcccaggt tgtaggtgaa cgctatggct ccaagaagag catggtcatt    3420
ctgaccagca gtgtgacggc cggcaccgcg gaggagttca cctatatcat gaagaggctg    3480
ggccgggccc tggtcattgg ggaggtgacc agtgggggct gccagccacc acagacctac    3540
cacgtggatg acaccaacct ctacctcact atccccacgg cccgttctgt gggggcctcg    3600
gatggcagct cctgggaagg ggtgggggtg acaccccatg tggttgtccc tgcagaagag    3660
gctctcgcca gggccaagga gatgctccag cacaaccagc tgagggtgaa gcggagccca    3720
ggcctgcagg accacctgta gggaagggcc ccataggcag agccccaggg cagacagaac    3780
ctctgggaca cacaccaagg gcactcctgc aggtggcccg gcctgaggtt cccaggagca    3840
gcaaaggggc ctgctgagct ctggttaggt tacagctgga ggtgtgtata tatacacaca    3900
cacacatgta tatacacata tatatgtgta tgtatatata tgtatatata tatggctttc    3960
caataaccac ctaaattta acaaaggttc cttctaagtg gtagaacttg gggtggtatt    4020
tttaccttcc ttcttcatac tttgctcttt tccttaaata ctcattaatg tgcatatatc    4080
attattttca gatgcagcta tcattattcc aaaatacaaa ataa                    4124
```

<210> SEQ ID NO 31
<211> LENGTH: 579
<212> TYPE: DNA
<213> ORGANISM: Homo sapiens
<220> FEATURE:
<221> NAME/KEY: misc_feature
<222> LOCATION: 9
<223> OTHER INFORMATION: n is a or g or c or t
<220> FEATURE:
<221> NAME/KEY: misc_feature
<222> LOCATION: 12

-continued

```
<223> OTHER INFORMATION: n is a or g or c or t
<220> FEATURE:
<221> NAME/KEY: misc_feature
<222> LOCATION: 21
<223> OTHER INFORMATION: n is a or g or c or t
<220> FEATURE:
<221> NAME/KEY: misc_feature
<222> LOCATION: 24
<223> OTHER INFORMATION: n is a or g or c or t
<220> FEATURE:
<221> NAME/KEY: misc_feature
<222> LOCATION: 27
<223> OTHER INFORMATION: n is a or g or c or t
<220> FEATURE:
<221> NAME/KEY: misc_feature
<222> LOCATION: 30
<223> OTHER INFORMATION: n is a or g or c or t
<220> FEATURE:
<221> NAME/KEY: misc_feature
<222> LOCATION: 36
<223> OTHER INFORMATION: n is a or g or c or t
<220> FEATURE:
<221> NAME/KEY: misc_feature
<222> LOCATION: 39
<223> OTHER INFORMATION: n is a or g or c or t
<220> FEATURE:
<221> NAME/KEY: misc_feature
<222> LOCATION: 42
<223> OTHER INFORMATION: n is a or g or c or t
<220> FEATURE:
<221> NAME/KEY: misc_feature
<222> LOCATION: 45
<223> OTHER INFORMATION: n is a or g or c or t
<220> FEATURE:
<221> NAME/KEY: misc_feature
<222> LOCATION: 48
<223> OTHER INFORMATION: n is a or g or c or t
<220> FEATURE:
<221> NAME/KEY: misc_feature
<222> LOCATION: 51
<223> OTHER INFORMATION: n is a or g or c or t
<220> FEATURE:
<221> NAME/KEY: misc_feature
<222> LOCATION: 54
<223> OTHER INFORMATION: n is a or g or c or t
<220> FEATURE:
<221> NAME/KEY: misc_feature
<222> LOCATION: 57
<223> OTHER INFORMATION: n is a or g or c or t
<220> FEATURE:
<221> NAME/KEY: misc_feature
<222> LOCATION: 60
<223> OTHER INFORMATION: n is a or g or c or t
<220> FEATURE:
<221> NAME/KEY: misc_feature
<222> LOCATION: 63
<223> OTHER INFORMATION: n is a or g or c or t
<220> FEATURE:
<221> NAME/KEY: misc_feature
<222> LOCATION: 69
<223> OTHER INFORMATION: n is a or g or c or t
<220> FEATURE:
<221> NAME/KEY: misc_feature
<222> LOCATION: 75
<223> OTHER INFORMATION: n is a or g or c or t
<220> FEATURE:
<221> NAME/KEY: misc_feature
<222> LOCATION: 84
<223> OTHER INFORMATION: n is a or g or c or t
<220> FEATURE:
<221> NAME/KEY: misc_feature
<222> LOCATION: 87
<223> OTHER INFORMATION: n is a or g or c or t
<220> FEATURE:
<221> NAME/KEY: misc_feature
<222> LOCATION: 93
<223> OTHER INFORMATION: n is a or g or c or t
<220> FEATURE:
<221> NAME/KEY: misc_feature
```

-continued

```
<222> LOCATION: 96
<223> OTHER INFORMATION: n is a or g or c or t
<220> FEATURE:
<221> NAME/KEY: misc_feature
<222> LOCATION: 99
<223> OTHER INFORMATION: n is a or g or c or t
<220> FEATURE:
<221> NAME/KEY: misc_feature
<222> LOCATION: 105
<223> OTHER INFORMATION: n is a or g or c or t
<220> FEATURE:
<221> NAME/KEY: misc_feature
<222> LOCATION: 126
<223> OTHER INFORMATION: n is a or g or c or t
<220> FEATURE:
<221> NAME/KEY: misc_feature
<222> LOCATION: 135
<223> OTHER INFORMATION: n is a or g or c or t
<220> FEATURE:
<221> NAME/KEY: misc_feature
<222> LOCATION: 138
<223> OTHER INFORMATION: n is a or g or c or t
<220> FEATURE:
<221> NAME/KEY: misc_feature
<222> LOCATION: 141
<223> OTHER INFORMATION: n is a or g or c or t
<220> FEATURE:
<221> NAME/KEY: misc_feature
<222> LOCATION: 147
<223> OTHER INFORMATION: n is a or g or c or t
<220> FEATURE:
<221> NAME/KEY: misc_feature
<222> LOCATION: 150
<223> OTHER INFORMATION: n is a or g or c or t
<220> FEATURE:
<221> NAME/KEY: misc_feature
<222> LOCATION: 153
<223> OTHER INFORMATION: n is a or g or c or t
<220> FEATURE:
<221> NAME/KEY: misc_feature
<222> LOCATION: 156
<223> OTHER INFORMATION: n is a or g or c or t
<220> FEATURE:
<221> NAME/KEY: misc_feature
<222> LOCATION: 159
<223> OTHER INFORMATION: n is a or g or c or t
<220> FEATURE:
<221> NAME/KEY: misc_feature
<222> LOCATION: 165
<223> OTHER INFORMATION: n is a or g or c or t
<220> FEATURE:
<221> NAME/KEY: misc_feature
<222> LOCATION: 171
<223> OTHER INFORMATION: n is a or g or c or t
<220> FEATURE:
<221> NAME/KEY: misc_feature
<222> LOCATION: 177
<223> OTHER INFORMATION: n is a or g or c or t
<220> FEATURE:
<221> NAME/KEY: misc_feature
<222> LOCATION: 180
<223> OTHER INFORMATION: n is a or g or c or t
<220> FEATURE:
<221> NAME/KEY: misc_feature
<222> LOCATION: 183
<223> OTHER INFORMATION: n is a or g or c or t
<220> FEATURE:
<221> NAME/KEY: misc_feature
<222> LOCATION: 186
<223> OTHER INFORMATION: n is a or g or c or t
<220> FEATURE:
<221> NAME/KEY: misc_feature
<222> LOCATION: 192
<223> OTHER INFORMATION: n is a or g or c or t
<220> FEATURE:
<221> NAME/KEY: misc_feature
<222> LOCATION: 195
<223> OTHER INFORMATION: n is a or g or c or t
<220> FEATURE:
```

-continued

```
<221> NAME/KEY: misc_feature
<222> LOCATION: 198
<223> OTHER INFORMATION: n is a or g or c or t
<220> FEATURE:
<221> NAME/KEY: misc_feature
<222> LOCATION: 201
<223> OTHER INFORMATION: n is a or g or c or t
<220> FEATURE:
<221> NAME/KEY: misc_feature
<222> LOCATION: 204
<223> OTHER INFORMATION: n is a or g or c or t
<220> FEATURE:
<221> NAME/KEY: misc_feature
<222> LOCATION: 207
<223> OTHER INFORMATION: n is a or g or c or t
<220> FEATURE:
<221> NAME/KEY: misc_feature
<222> LOCATION: 210
<223> OTHER INFORMATION: n is a or g or c or t
<220> FEATURE:
<221> NAME/KEY: misc_feature
<222> LOCATION: 213
<223> OTHER INFORMATION: n is a or g or c or t
<220> FEATURE:
<221> NAME/KEY: misc_feature
<222> LOCATION: 216
<223> OTHER INFORMATION: n is a or g or c or t
<220> FEATURE:
<221> NAME/KEY: misc_feature
<222> LOCATION: 219
<223> OTHER INFORMATION: n is a or g or c or t
<220> FEATURE:
<221> NAME/KEY: misc_feature
<222> LOCATION: 222
<223> OTHER INFORMATION: n is a or g or c or t
<220> FEATURE:
<221> NAME/KEY: misc_feature
<222> LOCATION: 225
<223> OTHER INFORMATION: n is a or g or c or t
<220> FEATURE:
<221> NAME/KEY: misc_feature
<222> LOCATION: 228
<223> OTHER INFORMATION: n is a or g or c or t
<220> FEATURE:
<221> NAME/KEY: misc_feature
<222> LOCATION: 231
<223> OTHER INFORMATION: n is a or g or c or t
<220> FEATURE:
<221> NAME/KEY: misc_feature
<222> LOCATION: 234
<223> OTHER INFORMATION: n is a or g or c or t
<220> FEATURE:
<221> NAME/KEY: misc_feature
<222> LOCATION: 237
<223> OTHER INFORMATION: n is a or g or c or t
<220> FEATURE:
<221> NAME/KEY: misc_feature
<222> LOCATION: 240
<223> OTHER INFORMATION: n is a or g or c or t
<220> FEATURE:
<221> NAME/KEY: misc_feature
<222> LOCATION: 246
<223> OTHER INFORMATION: n is a or g or c or t
<220> FEATURE:
<221> NAME/KEY: misc_feature
<222> LOCATION: 252
<223> OTHER INFORMATION: n is a or g or c or t
<220> FEATURE:
<221> NAME/KEY: misc_feature
<222> LOCATION: 255
<223> OTHER INFORMATION: n is a or g or c or t
<220> FEATURE:
<221> NAME/KEY: misc_feature
<222> LOCATION: 258
<223> OTHER INFORMATION: n is a or g or c or t
<220> FEATURE:
<221> NAME/KEY: misc_feature
<222> LOCATION: 270
<223> OTHER INFORMATION: n is a or g or c or t
```

-continued

```
<220> FEATURE:
<221> NAME/KEY: misc_feature
<222> LOCATION: 273
<223> OTHER INFORMATION: n is a or g or c or t
<220> FEATURE:
<221> NAME/KEY: misc_feature
<222> LOCATION: 276
<223> OTHER INFORMATION: n is a or g or c or t
<220> FEATURE:
<221> NAME/KEY: misc_feature
<222> LOCATION: 279
<223> OTHER INFORMATION: n is a or g or c or t
<220> FEATURE:
<221> NAME/KEY: misc_feature
<222> LOCATION: 294
<223> OTHER INFORMATION: n is a or g or c or t
<220> FEATURE:
<221> NAME/KEY: misc_feature
<222> LOCATION: 300
<223> OTHER INFORMATION: n is a or g or c or t
<220> FEATURE:
<221> NAME/KEY: misc_feature
<222> LOCATION: 312
<223> OTHER INFORMATION: n is a or g or c or t
<220> FEATURE:
<221> NAME/KEY: misc_feature
<222> LOCATION: 315
<223> OTHER INFORMATION: n is a or g or c or t
<220> FEATURE:
<221> NAME/KEY: misc_feature
<222> LOCATION: 321
<223> OTHER INFORMATION: n is a or g or c or t
<220> FEATURE:
<221> NAME/KEY: misc_feature
<222> LOCATION: 342
<223> OTHER INFORMATION: n is a or g or c or t
<220> FEATURE:
<221> NAME/KEY: misc_feature
<222> LOCATION: 345
<223> OTHER INFORMATION: n is a or g or c or t
<220> FEATURE:
<221> NAME/KEY: misc_feature
<222> LOCATION: 354
<223> OTHER INFORMATION: n is a or g or c or t
<220> FEATURE:
<221> NAME/KEY: misc_feature
<222> LOCATION: 360
<223> OTHER INFORMATION: n is a or g or c or t
<220> FEATURE:
<221> NAME/KEY: misc_feature
<222> LOCATION: 363
<223> OTHER INFORMATION: n is a or g or c or t
<220> FEATURE:
<221> NAME/KEY: misc_feature
<222> LOCATION: 366
<223> OTHER INFORMATION: n is a or g or c or t
<220> FEATURE:
<221> NAME/KEY: misc_feature
<222> LOCATION: 372
<223> OTHER INFORMATION: n is a or g or c or t
<220> FEATURE:
<221> NAME/KEY: misc_feature
<222> LOCATION: 378
<223> OTHER INFORMATION: n is a or g or c or t
<220> FEATURE:
<221> NAME/KEY: misc_feature
<222> LOCATION: 384
<223> OTHER INFORMATION: n is a or g or c or t
<220> FEATURE:
<221> NAME/KEY: misc_feature
<222> LOCATION: 387
<223> OTHER INFORMATION: n is a or g or c or t
<220> FEATURE:
<221> NAME/KEY: misc_feature
<222> LOCATION: 390
<223> OTHER INFORMATION: n is a or g or c or t
<220> FEATURE:
<221> NAME/KEY: misc_feature
<222> LOCATION: 393
```

-continued

```
<223> OTHER INFORMATION: n is a or g or c or t
<220> FEATURE:
<221> NAME/KEY: misc_feature
<222> LOCATION: 399
<223> OTHER INFORMATION: n is a or g or c or t
<220> FEATURE:
<221> NAME/KEY: misc_feature
<222> LOCATION: 402
<223> OTHER INFORMATION: n is a or g or c or t
<220> FEATURE:
<221> NAME/KEY: misc_feature
<222> LOCATION: 405
<223> OTHER INFORMATION: n is a or g or c or t
<220> FEATURE:
<221> NAME/KEY: misc_feature
<222> LOCATION: 417
<223> OTHER INFORMATION: n is a or g or c or t
<220> FEATURE:
<221> NAME/KEY: misc_feature
<222> LOCATION: 429
<223> OTHER INFORMATION: n is a or g or c or t
<220> FEATURE:
<221> NAME/KEY: misc_feature
<222> LOCATION: 432
<223> OTHER INFORMATION: n is a or g or c or t
<220> FEATURE:
<221> NAME/KEY: misc_feature
<222> LOCATION: 438
<223> OTHER INFORMATION: n is a or g or c or t
<220> FEATURE:
<221> NAME/KEY: misc_feature
<222> LOCATION: 441
<223> OTHER INFORMATION: n is a or g or c or t
<220> FEATURE:
<221> NAME/KEY: misc_feature
<222> LOCATION: 444
<223> OTHER INFORMATION: n is a or g or c or t
<220> FEATURE:
<221> NAME/KEY: misc_feature
<222> LOCATION: 450
<223> OTHER INFORMATION: n is a or g or c or t
<220> FEATURE:
<221> NAME/KEY: misc_feature
<222> LOCATION: 459
<223> OTHER INFORMATION: n is a or g or c or t
<220> FEATURE:
<221> NAME/KEY: misc_feature
<222> LOCATION: 462
<223> OTHER INFORMATION: n is a or g or c or t
<220> FEATURE:
<221> NAME/KEY: misc_feature
<222> LOCATION: 465
<223> OTHER INFORMATION: n is a or g or c or t
<220> FEATURE:
<221> NAME/KEY: misc_feature
<222> LOCATION: 471
<223> OTHER INFORMATION: n is a or g or c or t
<220> FEATURE:
<221> NAME/KEY: misc_feature
<222> LOCATION: 477
<223> OTHER INFORMATION: n is a or g or c or t
<220> FEATURE:
<221> NAME/KEY: misc_feature
<222> LOCATION: 480
<223> OTHER INFORMATION: n is a or g or c or t
<220> FEATURE:
<221> NAME/KEY: misc_feature
<222> LOCATION: 483
<223> OTHER INFORMATION: n is a or g or c or t
<220> FEATURE:
<221> NAME/KEY: misc_feature
<222> LOCATION: 489
<223> OTHER INFORMATION: n is a or g or c or t
<220> FEATURE:
<221> NAME/KEY: misc_feature
<222> LOCATION: 492
<223> OTHER INFORMATION: n is a or g or c or t
<220> FEATURE:
<221> NAME/KEY: misc_feature
```

-continued

<222> LOCATION: 495
<223> OTHER INFORMATION: n is a or g or c or t
<220> FEATURE:
<221> NAME/KEY: misc_feature
<222> LOCATION: 498
<223> OTHER INFORMATION: n is a or g or c or t
<220> FEATURE:
<221> NAME/KEY: misc_feature
<222> LOCATION: 507
<223> OTHER INFORMATION: n is a or g or c or t
<220> FEATURE:
<221> NAME/KEY: misc_feature
<222> LOCATION: 516
<223> OTHER INFORMATION: n is a or g or c or t
<220> FEATURE:
<221> NAME/KEY: misc_feature
<222> LOCATION: 519
<223> OTHER INFORMATION: n is a or g or c or t
<220> FEATURE:
<221> NAME/KEY: misc_feature
<222> LOCATION: 522
<223> OTHER INFORMATION: n is a or g or c or t
<220> FEATURE:
<221> NAME/KEY: misc_feature
<222> LOCATION: 525
<223> OTHER INFORMATION: n is a or g or c or t
<220> FEATURE:
<221> NAME/KEY: misc_feature
<222> LOCATION: 528
<223> OTHER INFORMATION: n is a or g or c or t
<220> FEATURE:
<221> NAME/KEY: misc_feature
<222> LOCATION: 531
<223> OTHER INFORMATION: n is a or g or c or t
<220> FEATURE:
<221> NAME/KEY: misc_feature
<222> LOCATION: 534
<223> OTHER INFORMATION: n is a or g or c or t
<220> FEATURE:
<221> NAME/KEY: misc_feature
<222> LOCATION: 540
<223> OTHER INFORMATION: n is a or g or c or t
<220> FEATURE:
<221> NAME/KEY: misc_feature
<222> LOCATION: 543
<223> OTHER INFORMATION: n is a or g or c or t
<220> FEATURE:
<221> NAME/KEY: misc_feature
<222> LOCATION: 546
<223> OTHER INFORMATION: n is a or g or c or t
<220> FEATURE:
<221> NAME/KEY: misc_feature
<222> LOCATION: 561
<223> OTHER INFORMATION: n is a or g or c or t
<220> FEATURE:
<221> NAME/KEY: misc_feature
<222> LOCATION: 564
<223> OTHER INFORMATION: n is a or g or c or t
<220> FEATURE:
<221> NAME/KEY: misc_feature
<222> LOCATION: 567
<223> OTHER INFORMATION: n is a or g or c or t
<220> FEATURE:
<221> NAME/KEY: misc_feature
<222> LOCATION: 570
<223> OTHER INFORMATION: n is a or g or c or t
<220> FEATURE:
<221> NAME/KEY: misc_feature
<222> LOCATION: 576
<223> OTHER INFORMATION: n is a or g or c or t

<400> SEQUENCE: 31
atgcarwsny tnatgcargc nccnytnytn athgcnytng gnytnytnyt ngcnacnccn 60
gcncargcnc ayytnaaraa rccnwsncar ytnwsnwsnt tywsntggga yaaytgygay 120
garggnaarg ayccngcngt nathmgnwsn ytnacnytng arccngaycc nathgtngtn 180

| ccnggnaayg | tnacnytnws | ngtngtnggn | wsnacnwsng | tnccnytnws | nwsnccnytn | 240 |
| aargtngayy | tngtnytnga | raargargtn | gcnggnytnt | ggathaarat | hccntgyacn | 300 |
| gaytayathg | gnwsntgyac | nttygarcay | ttytgygayg | tnytngayat | gytnathccn | 360 |
| acnggngarc | cntgyccnga | rccnytnmgn | acntayggny | tnccntgyca | ytgyccntty | 420 |
| aargarggna | cntayswsnyt | nccnaarwsn | garttygtng | tnccngayyt | ngarytnccn | 480 |
| wsntggytna | cnacnggnaa | ytaymgnath | garwsngtny | tnwsnwsnws | nggnaarmgn | 540 |
| ytnggntgya | thaarathgc | ngcnwsnytn | aarggnath  |            |            | 579 |

<210> SEQ ID NO 32
<211> LENGTH: 633
<212> TYPE: DNA
<213> ORGANISM: Homo sapiens

<400> SEQUENCE: 32

| tttctttgcg | taaccaatac | tggaaggcat | ttaaaggacc | tctgccgcct | cagaccttgc | 60 |
| agttaactcc | gccctgaccc | acccttcccg | atgcagtccc | tgatgcaggc | tcccctcctg | 120 |
| atcgccctgg | gcttgcttct | cgcgacccct | gcgcaagccc | acctgaaaaa | ggtgagtgca | 180 |
| ccctctttta | agagtctgtt | tgcagcctcc | tggcccagct | acgggtgtgc | gggtctggct | 240 |
| gagatatggg | ggtggccact | ccgttctcta | gaattggttc | tctgcactag | agccttccaa | 300 |
| agtaactaat | tatgggattc | tggtctgtac | aatgagggtg | gcctctaaag | acttgttctg | 360 |
| ctccaggccc | tttttggaga | gattaatctc | acgtctgcac | tctcctgccc | tccctccaag | 420 |
| cgccggagtg | aaaatgcaga | cagccttaaa | actaaggcat | tgccccccaag | agattcagtc | 480 |
| ctgttaaccc | tgcaccttac | tcctgacccc | cactccttat | gtcccccatg | ataaggcctg | 540 |
| ctgcctcatc | tcttcccctg | ctcgaatgcc | ctgaggtctt | cctgagagtt | gggagggttt | 600 |
| gagagctttc | caaggccaag | aggattcact | aag        |            |            | 633 |

<210> SEQ ID NO 33
<211> LENGTH: 1047
<212> TYPE: DNA
<213> ORGANISM: Homo sapiens

<400> SEQUENCE: 33

| caggagcttg | ccctcttgct | gggattccaa | cgctggctgg | agaggagtgg | gcagcaggga | 60 |
| ggtgggaagt | cagagaaggt | gcccaccaaa | ggcctattag | gtcagtctcc | tgtttggaag | 120 |
| ttccaggtct | atcatatcct | gccttatagt | ttacaataca | cttttgggag | attatgtctt | 180 |
| ttgagtcttt | tagtttagtc | ctgcctataa | aatgagtagg | ataagtgtta | tcccaggttc | 240 |
| ataggtatgg | agtctcatag | atgaggctca | gggacggggg | tgcctcaccc | aaggtcacac | 300 |
| tgccaggagc | tcattttttcc | tgtgatctgt | gatagtttct | tttgtcaacc | ttttttcttct | 360 |
| tctccttcct | tgctgcctga | ttgtccccag | ccatcccagc | tcagtagctt | ttcctgggat | 420 |
| aactgtgatg | aagggaagga | ccctgcggtg | atcagaagcc | tgactctgga | gcctgacccc | 480 |
| atcgtcgttc | ctggaaatgt | gaccctcagt | gtcgtgggca | gcaccagtgt | cccccctgagt | 540 |
| tctcctctga | aggtgagcct | gggggtgggt | ggagaagggg | aggtgcgagg | gtctggccag | 600 |
| cagggtact | gggcatgta | tgcttgggga | actgtgaaga | atttcagaat | cctggattcc | 660 |
| cagagaatag | tacaggacat | gtagattcag | acactctttc | acaggttcat | ggaatctcag | 720 |
| gatcataaga | ttgaaaggaa | tctctgatgt | cagcgccagc | aacttcctgg | tgagggcagg | 780 |
| agtgacggat | accttgcacc | tggcagaagc | gtcctggcct | tctctgggcc | tggtggccaa | 840 |

-continued

| ctgctcatta ttatctgaca gctctggttg gccaatttgg ttttgctgtt aattataaaa | 900 |
| ttgatatacc aattagccag taatatatag tcactttaga aaacacaagt ggtcaaaaaa | 960 |
| taaataaaat aggccaagtg tggtaacttc atgcctgtaa ttcccacacc cttaggaggc | 1020 |
| tgaaggtggg tgggatcctt tttgagg | 1047 |

<210> SEQ ID NO 34
<211> LENGTH: 1706
<212> TYPE: DNA
<213> ORGANISM: Homo sapiens

<400> SEQUENCE: 34

| acagtagatg ccagtgcatt tcaatgcaag tgttagagcc aatcaatggg tagtgactac | 60 |
| ctaaagaatt ttaagactat ggattgagca tgatggctca cggcctgtaa tcccagcctt | 120 |
| tggaaggtga aggtgaaagg attgcttgag gccaggagtt ccagaccagc ttgggcaaca | 180 |
| aagtgagccc catctctaca aaaatacaa aattagctgg gtgtggtggc atgtgcctgt | 240 |
| ctgtgtttcc cacctacatg ggaggctgag gcaggaggat cgtctgagcc caggagtttg | 300 |
| aggctgcagt gagtgcagtg agccatgata caaaaaaaaa aataaagaa ttctaagtct | 360 |
| atgtatagtt cagtgtaggg ggaaaattca catttgatta ttaatgtctg ccatgggcac | 420 |
| aataatacac tatactcaca catgggccac aatgttgcca ttcctagaac agactatctc | 480 |
| taagatctca tccagttaaa aattctatga ttaaaatata ttgctgcttt tttgaagaca | 540 |
| gaagagctgg tatgtttgcc ctggaattta cacttataac cttttttcaaa cctttgtttt | 600 |
| attttttttt accaggtgga tttagttttg gagaaggagg tggctggcct ctggatcaag | 660 |
| atcccatgca cagactacat tggcagctgt acctttgaac acttctgtga tgtgcttgac | 720 |
| atgttaattc ctactgggga gccctgccca gagcccctgc gtacctatgg gcttccttgc | 780 |
| cactgtccct tcaaagaagt aagtacttag ggaggagaga gcgttacccc tgtggctaaa | 840 |
| gagatggggt ttggagagaa gggtcttttgc attctccttc tgcagatctg catgtctctg | 900 |
| gatttgtaag ccagtgtgac ctatcaggaa tcacttatct tccgggagcc tcagttatcc | 960 |
| atctacgaaa tgggagactt gaacttagat gtgatcttca gggcccttta tccatataat | 1020 |
| ccatgctcta cagtgctatg gccgtctctc atcttgtgcg gctgttttga gaatgggaag | 1080 |
| aggggtggta gttcatggct gcaatcctag cagtggctct aggagaaaga ccccatcagt | 1140 |
| aggctcccac tgactggcgg tccactggct ttcccgcagg gaacctactc actgcccaag | 1200 |
| agcgaattcg ttgtgcctga cctggagctg cccagttggc tcaccaccgg gaactaccgc | 1260 |
| atagagagcg tcctgagcag cagtgggaag cgtctgggct gcatcaagat cgctgcctct | 1320 |
| ctaaagggca tatagcatgg catctgccac agcagaatgg agcggtgtga ggaaggtccc | 1380 |
| ttttcctctg ttttgtgttt gccaaggcca aactcccact ctctgccccc ctttaatccc | 1440 |
| cttttctacag tgagtccact accctcactg aaaatcattt tgtaccactt acattttagg | 1500 |
| ctggggcaag cagccctgac ctaagggaga atgagttgga cagttcttga tagcccaggg | 1560 |
| catctgctgg gctgaccacg ttactcatcc ccgttaacat tctctctaaa gagcctcgtt | 1620 |
| catttccaaa gcagttaagg aatgggaaca gagtgtttta ggacctgaag aatctttatg | 1680 |
| actctctctc tttctctctt tttttt | 1706 |

<210> SEQ ID NO 35
<211> LENGTH: 633
<212> TYPE: DNA

-continued

<213> ORGANISM: Homo sapiens

<400> SEQUENCE: 35

```
tttctttgcg taaccaatac tggaaggcat ttaaaggacc tctgccgcct cagaccttgc      60
agttaactcc gccctgaccc acccttcccg atgcagtccc tgatgcaggc tcccctcctg     120
atcgccctgg gcttgcttct cgcgacccct gcgcaagccc acctgaaaaa ggtgagtgca     180
ccctcttta  agagtctgtt tgcagcctcc tggcccagct acgggtgtgc gggtctggct     240
gagatatggg ggtggccact ccgttctcta gaattggttc tctgcactag agccttccaa     300
agtaactaat tatgggattc tggtctgtac aatgagggtg gcctctaaag acttgttctg     360
ctccaggccc tttttggaga gattaatctc acgtctgcac tctcctgccc tccctccaag     420
cgccggagtg aaaatgcaga cagccttaaa actaaggcat gcccccaag  agattcagtc     480
ctgttaaccc tgcaccttac tcctgacccc cactccttat gtcccccatg ataaggcctg     540
ctgcctcatc tcttcccctg ctcgaatgcc ctgaggtctt cctgagagtt gggagggttt     600
gagagctttc caaggccaag aggattcact aag                                   633
```

<210> SEQ ID NO 36
<211> LENGTH: 1047
<212> TYPE: DNA
<213> ORGANISM: Homo sapiens

<400> SEQUENCE: 36

```
caggagcttg ccctcttgct gggattccaa cgctggctgg agaggagtgg gcagcaggga      60
ggtgggaagt cagagaaggt gcccaccaaa ggcctattag gtcagtctcc tgtttggaag     120
ttccaggtct atcatatcct gcctatagt  ttacaataca cttttgggag attatgtctt     180
ttgagtcttt tagtttagtc ctgcctataa aatgagtagg ataagtgtta tcccaggttc     240
ataggtatgg agtctcatag atgaggctca gggacggggg tgcctcaccc aaggtcacac     300
tgccaggagc tcattttcc  tgtgatctgt gatagtttct tttgtcaacc ttttcttct      360
tctccttcct tgctgcctga ttgtccccag ccatcccagc tcagtagctt ttcctgggat     420
aactgtgatg aagggaagga ccctgcggtg atcagaagcc tgactctgga gcctgacccc     480
atcgtcgttc ctggaaatgt gaccctcagt gtcgtgggca gcaccagtgt cccctgagt      540
tctcctctga aggtgagcct gggggtgggt ggagaagggg aggtgcgagg gtctggccag     600
caggggtact gggcatgta  tgcttgggga actgtgaaga atttcagaat cctggattcc     660
cagagaatag tacaggacat gtagattcag acactctttc acaggttcat ggaatctcag     720
gatcataaga ttgaaaggaa tctctgatgt cagcgccagc aacttcctgg tgagggcagg     780
agtgacggat accttgcacc tggcagaagc gtcctggcct tctctgggcc tggtggccaa     840
ctgctcatta ttatctgaca gctctggttg gccaatttgg ttttgctgtt aattataaaa     900
ttgatatacc aattagccag taatatatag tcacttaga  aaacaagt   ggtcaaaaaa     960
taaataaaat aggccaagtg tggtaacttc atgcctgtaa ttcccacacc cttaggaggc    1020
tgaaggtggg tgggatcctt tttgagg                                        1047
```

<210> SEQ ID NO 37
<211> LENGTH: 1706
<212> TYPE: DNA
<213> ORGANISM: Homo sapiens

<400> SEQUENCE: 37

```
acagtagatg ccagtgcatt tcaatgcaag tgttagagcc aatcaatggg tagtgactac       60
```

-continued

```
ctaaagaatt ttaagactat ggattgagca tgatggctca cggcctgtaa tcccagcctt      120
tggaaggtga aggtgaaagg attgcttgag gccaggagtt ccagaccagc ttgggcaaca      180
aagtgagccc catctctaca aaaaatacaa aattagctgg gtgtggtggc atgtgcctgt      240
ctgtgtttcc cacctacatg ggaggctgag gcaggaggat cgtctgagcc caggagtttg      300
aggctgcagt gagtgcagtg agccatgata caaaaaaaaa aaataaagaa ttctaagtct      360
atgtatagtt cagtgtaggg ggaaaattca catttgatta ttaatgtctg ccatgggcac      420
aataatacac tatactcaca catgggccac aatgttgcca ttcctagaac agactatctc      480
taagatctca tccagttaaa aattctatga ttaaaatata ttgctgcttt tttgaagaca      540
gaagagctgg tatgtttgcc ctggaattta cacttataac cttttttcaaa cctttgtttt      600
attttttttt accaggtgga tttagttttg gagaaggagg tggctggcct ctggatcaag      660
atcccatgca cagactacat tggcagctgt acctttgaac acttctgtga tgtgcttgac      720
atgttaattc ctactgggga gccctgccca gagcccctgc gtacctatgg gcttccttgc      780
cactgtccct tcaaagaagt aagtacttag ggaggagaga gcgttacccc tgtggctaaa      840
gagatggggt ttggagagaa gggtctttgc attctccttc tgcagatctg catgtctctg      900
gatttgtaag ccagtgtgac ctatcaggaa tcacttatct tccgggagcc tcagttatcc      960
atctacgaaa tgggagactt gaacttagat gtgatcttca gggcccttta tccatataat     1020
ccatgctcta cagtgctatg gccgtctctc atcttgtgcg gctgttttga gaatgggaag     1080
agggtggta gttcatggct gcaatcctag cagtggctct aggagaaaga ccccatcagt     1140
aggctcccac tgactggcgg tccactggct ttcccgcagg gaacctactc actgcccaag     1200
agcgaattcg ttgtgcctga cctggagctg cccagttggc tcaccaccgg gaactaccgc     1260
atagagagcg tcctgagcag cagtgggaag cgtctgggct gcatcaagat cgctgcctct     1320
ctaaagggca tatagcatgg catctgccac agcagaatgg agcggtgtga ggaaggtccc     1380
ttttcctctg ttttgtgttt gccaaggcca aactcccact ctctgccccc ctttaatccc     1440
cttttctacag tgagtccact accctcactg aaaatcattt tgtaccactt acattttagg     1500
ctggggcaag cagccctgac ctaagggaga atgagttgga cagttcttga tagcccaggg     1560
catctgctgg gctgaccacg ttactcatcc ccgttaacat tctctctaaa gagcctcgtt     1620
catttccaaa gcagttaagg aatgggaaca gagtgttttta ggacctgaag aatctttatg     1680
actctctctc tttctctctt tttttt                                          1706
```

<210> SEQ ID NO 38
<211> LENGTH: 1043
<212> TYPE: DNA
<213> ORGANISM: Homo sapiens

<400> SEQUENCE: 38

```
tttctttgcg taaccaatac tggaaggcat ttaaaggacc tctgccgcct cagaccttgc       60
agttaactcc gccctgaccc acccttcccg atgcagtccc tgatgcaggc tcccctcctg      120
atcgccctgg gcttgcttct cgcgaccccct gcgcaagccc acctgaaaaa gccatcccag      180
ctcagtagct tttcctggga taactgtgat gaagggaagg accctgcggt gatcagaagc      240
ctgactctgg agcctgaccc catcgtcgtt cctggaaatg tgaccctcag tgtcgtgggc      300
agcaccagtg tccccctgag ttctcctctg aaggtggatt tagttttgga gaaggaggtg      360
gctggcctct ggatcaagat cccatgcaca gactacattg gcagctgtac ctttgaacac      420
```

| | |
|---|---:|
| ttctgtgatg tgcttgacat gttaattcct actggggagc cctgcccaga gcccctgcgt | 480 |
| acctatgggc ttccttgcca ctgtcccttc aaagaaggaa cctactcact gcccaagagc | 540 |
| gaattcgttg tgcctgacct ggagctgccc agttggctca ccaccgggaa ctaccgcata | 600 |
| gagagcgtcc tgagcagcag tgggaagcgt ctgggctgca tcaagatcgc tgcctctcta | 660 |
| aagggcatat agcatggcat ctgccacagc agaatgagc ggtgtgagga aggtcccttt | 720 |
| tcctctgttt tgtgtttgcc aaggccaaac tcccactctc tgccccctt taatcccctt | 780 |
| tctacagtga gtccactacc ctcactgaaa atcattttgt accacttaca ttttaggctg | 840 |
| gggcaagcag ccctgaccta agggagaatg agttggacag ttcttgatag cccagggcat | 900 |
| ctgctgggct gaccacgtta ctcatccccg ttaacattct ctctaaagag cctcgttcat | 960 |
| ttccaaagca gttaaggaat gggaacagag tgttttagga cctgaagaat ctttatgact | 1020 |
| ctctctcttt ctctcttttt ttt | 1043 |

<210> SEQ ID NO 39
<211> LENGTH: 1047
<212> TYPE: DNA
<213> ORGANISM: Homo sapiens

<400> SEQUENCE: 39

| | |
|---|---:|
| caggagcttg ccctcttgct gggattccaa cgctggctgg agaggagtgg gcagcaggga | 60 |
| ggtgggaagt cagagaaggt gcccaccaaa ggcctattag gtcagtctcc tgtttggaag | 120 |
| ttccaggtct atcatatcct gccttatagt ttacaataca cttttgggag attatgtctt | 180 |
| ttgagtcttt tagtttagtc ctgcctataa aatgagtagg ataagtgtta tcccaggttc | 240 |
| ataggtatgg agtctcatag atgaggctca gggacggggg tgcctcaccc aaggtcacac | 300 |
| tgccaggagc tcattttttcc tgtgatctgt gatagtttct tttgtcaacc ttttttcttct | 360 |
| tctccttcct tgctgcctga ttgtcccag ccatcccagc tcagtagctt ttcctgggat | 420 |
| aactgtgatg aagggaagga ccctgcggtg atcagaagcc tgactctgga gcctgaccc | 480 |
| atcgtcgttc ctggaaatgt gaccctcagt gtcgtgggca gcaccagtgt cccctgagt | 540 |
| tctcctctga aggtgagcct ggggtgggt ggagaagggg aggtgcgagg gtctggccag | 600 |
| caggggtact ggggcatgta tgcttgggga actgtgaaga atttcagaat cctggattcc | 660 |
| cagagaatag tacaggacat gtagattcag acactctttc acaggttcat ggaatctcag | 720 |
| gatcataaga ttgaaaggaa tctctgatgt cagcgccagc aacttcctgg tgagggcagg | 780 |
| agtgacggat accttgcacc tggcagaagc gtcctggcct tctctgggcc tggtggccaa | 840 |
| ctgctcatta ttatctgaca gctctggttg gccaatttgg ttttgctgtt aattataaaa | 900 |
| ttgatatacc aattagccag taatatatag tcacttaga aaacacaagt ggtcaaaaaa | 960 |
| taaataaaat aggccaagtg tggtaacttc atgcctgtaa ttcccacacc cttaggaggc | 1020 |
| tgaaggtggg tgggatcctt tttgagg | 1047 |

<210> SEQ ID NO 40
<211> LENGTH: 1705
<212> TYPE: DNA
<213> ORGANISM: Homo sapiens

<400> SEQUENCE: 40

| | |
|---|---:|
| acagtagatg ccagtgattt caatgcaagt gttagagcca atcaatgggt agtgactacc | 60 |
| taaagaattt taagactatg gattgagcat gatggctcac ggcctgtaat cccagccttt | 120 |
| ggaaggtgaa ggtgaaagga ttgcttgagg ccaggagttc cagaccagct tgggcaacaa | 180 |

```
agtgagcccc atctctacaa aaatacaaa attagctggg tgtggtggca tgtgcctgtc        240
tgtgtttccc acctacatgg gaggctgagg caggaggatc gtctgagccc aggagtttga        300
ggctgcagtg agtgcagtga gccatgatac aaaaaaaaaa aataaagaat tctaagtcta        360
tgtatagttc agtgtagggg gaaaattcac atttgattat taatgtctgc catgggcaca        420
ataatacact atactcacac atgggccaca atgttgccat tcctagaaca gactatctct        480
aagatctcat ccagttaaaa attctatgat taaaatatat tgctgctttt ttgaagacag        540
aagagctggt atgtttgccc tggaatttac acttataacc tttttcaaac ctttgtttta        600 tttttttta  ccaggtggat ttagttttgg agaaggaggt ggctggcctc tggatcaaga        660
tcccatgcac agactacatt ggcagctgta cctttgaaca cttctgtgat gtgcttgaca        720
tgttaattcc tactggggag ccctgcccag agccctgcg  tacctatggg cttccttgcc        780
actgtccctt caaagaagta agtacttagg gaggagagag cgttacccct gtggctaaag        840
agatggggtt tggagagaag ggtctttgca ttctccttct gcagatctgc atgtctctgg        900
atttgtaagc cagtgtgacc tatcaggaat cacttatctt ccgggagcct cagtatccca        960
tctacgaaat gggagacttg aacttagatg tgatcttcag ggccctttat ccatataatc       1020
catgctctac agtgctatgg ccgtctctca tcttgtgcgg ctgttttgag aatgggaaga       1080
ggggtggtag ttcatggctg caatcctagc agtggctcta ggagaaagac cccatcagta       1140
ggctcccact gactggcggt ccactggctt cccgcaggg  aacctactca ctgcccaaga       1200
gcgaattcgt tgtgcctgac ctggagctgc ccagttggct caccaccggg aactaccgca       1260
tagagagcgt cctgagcagc agtgggaagc gtctgggctg catcaagatc gctgcctctc       1320
taaagggcat atagcatggc atctgccaca gcagaatgga gcggtgtgag gaaggtccct       1380
tttcctctgt tttgtgtttg ccaaggccaa actcccactc tctgccccc  tttaatcccc       1440 tttctacagt gagtccacta ccctcactga aaatcattt  gtaccactta cattttaggc       1500
tggggcaagc agccctgacc taagggagaa tgagttggac agttcttgat agcccagggc       1560
atctgctggg ctgaccacgt tactcatccc cgttaacatt ctctctaaag agcctcgttc       1620
atttccaaag cagttaagga atgggaacag agtgttttag gacctgaaga atctttatga       1680
ctctctctct ttctctcttt ttttt                                             1705

<210> SEQ ID NO 41
<211> LENGTH: 1043
<212> TYPE: DNA
<213> ORGANISM: Homo sapiens

<400> SEQUENCE: 41
tttctttgcg taaccaatac tggaaggcat ttaaaggacc tctgccgcct cagaccttgc         60
agttaactcc gccctgaccc acccttcccg atgcagtccc tgatgcaggc tcccctcctg        120
atcgccctgg gcttgcttct cgcgaccct  gcgcaagccc acctgaaaaa gccatcccag        180
ctcagtagct tttcctggga taactgtgat gaagggaagg accctgcggt gatcagaagc        240
ctgactctgg agcctgaccc catcgtcgtt cctggaaatg tgaccctcag tgtcgtgggc        300
agcaccagtg tcccctgag  ttctcctctg aaggtggatt tagttttgga gaaggaggtg        360
gctggcctct ggatcaagat cccatgcaca gactacattg gcagctgtac ctttgaacac        420
ttctgtgatg tgcttgacat gttaattcct actggggagc cctgcccaga gcccctgcgt        480
acctatgggc ttccttgcca ctgtcccttc aaagaaggaa cctactcact gcccaagagc        540
```

```
gaattcgttg tgcctgacct ggagctgccc agttggctca ccaccgggaa ctaccgcata      600
gagagcgtcc tgagcagcag tgggaagcgt ctgggctgca tcaagatcgc tgcctctcta      660
aagggcatat agcatggcat ctgccacagc agaatggagc ggtgtgagga aggtcccttt      720
tcctctgttt tgtgtttgcc aaggccaaac tcccactctc tgccccctt  taatccccctt      780 tctacagtga gtccactacc ctcactgaaa atcattttgt accacttaca ttttaggctg      840
gggcaagcag ccctgaccta agggagaatg agttggacag ttcttgatag cccagggcat      900
ctgctgggct gaccacgtta ctcatccccg ttaacattct ctctaaagag cctcgttcat      960
ttccaaagca gttaaggaat gggaacagag tgttttagga cctgaagaat ctttatgact     1020
ctctctcttt ctctcttttt ttt                                              1043
```

<210> SEQ ID NO 42
<211> LENGTH: 342
<212> TYPE: DNA
<213> ORGANISM: Homo sapiens
<220> FEATURE:
<221> NAME/KEY: misc_feature
<222> LOCATION: 6
<223> OTHER INFORMATION: n is a or g or c or t
<220> FEATURE:
<221> NAME/KEY: misc_feature
<222> LOCATION: 18
<223> OTHER INFORMATION: n is a or g or c or t
<220> FEATURE:
<221> NAME/KEY: misc_feature
<222> LOCATION: 24
<223> OTHER INFORMATION: n is a or g or c or t
<220> FEATURE:
<221> NAME/KEY: misc_feature
<222> LOCATION: 30
<223> OTHER INFORMATION: n is a or g or c or t
<220> FEATURE:
<221> NAME/KEY: misc_feature
<222> LOCATION: 42
<223> OTHER INFORMATION: n is a or g or c or t
<220> FEATURE:
<221> NAME/KEY: misc_feature
<222> LOCATION: 54
<223> OTHER INFORMATION: n is a or g or c or t
<220> FEATURE:
<221> NAME/KEY: misc_feature
<222> LOCATION: 69
<223> OTHER INFORMATION: n is a or g or c or t
<220> FEATURE:
<221> NAME/KEY: misc_feature
<222> LOCATION: 72
<223> OTHER INFORMATION: n is a or g or c or t
<220> FEATURE:
<221> NAME/KEY: misc_feature
<222> LOCATION: 78
<223> OTHER INFORMATION: n is a or g or c or t
<220> FEATURE:
<221> NAME/KEY: misc_feature
<222> LOCATION: 81
<223> OTHER INFORMATION: n is a or g or c or t
<220> FEATURE:
<221> NAME/KEY: misc_feature
<222> LOCATION: 87
<223> OTHER INFORMATION: n is a or g or c or t
<220> FEATURE:
<221> NAME/KEY: misc_feature
<222> LOCATION: 93
<223> OTHER INFORMATION: n is a or g or c or t
<220> FEATURE:
<221> NAME/KEY: misc_feature
<222> LOCATION: 96
<223> OTHER INFORMATION: n is a or g or c or t
<220> FEATURE:
<221> NAME/KEY: misc_feature
<222> LOCATION: 105
<223> OTHER INFORMATION: n is a or g or c or t -continued

```
<220> FEATURE:
<221> NAME/KEY: misc_feature
<222> LOCATION: 120
<223> OTHER INFORMATION: n is a or g or c or t
<220> FEATURE:
<221> NAME/KEY: misc_feature
<222> LOCATION: 123
<223> OTHER INFORMATION: n is a or g or c or t
<220> FEATURE:
<221> NAME/KEY: misc_feature
<222> LOCATION: 126
<223> OTHER INFORMATION: n is a or g or c or t
<220> FEATURE:
<221> NAME/KEY: misc_feature
<222> LOCATION: 135
<223> OTHER INFORMATION: n is a or g or c or t
<220> FEATURE:
<221> NAME/KEY: misc_feature
<222> LOCATION: 147
<223> OTHER INFORMATION: n is a or g or c or t
<220> FEATURE:
<221> NAME/KEY: misc_feature
<222> LOCATION: 174
<223> OTHER INFORMATION: n is a or g or c or t
<220> FEATURE:
<221> NAME/KEY: misc_feature
<222> LOCATION: 198
<223> OTHER INFORMATION: n is a or g or c or t
<220> FEATURE:
<221> NAME/KEY: misc_feature
<222> LOCATION: 204
<223> OTHER INFORMATION: n is a or g or c or t
<220> FEATURE:
<221> NAME/KEY: misc_feature
<222> LOCATION: 210
<223> OTHER INFORMATION: n is a or g or c or t
<220> FEATURE:
<221> NAME/KEY: misc_feature
<222> LOCATION: 222
<223> OTHER INFORMATION: n is a or g or c or t
<220> FEATURE:
<221> NAME/KEY: misc_feature
<222> LOCATION: 225
<223> OTHER INFORMATION: n is a or g or c or t
<220> FEATURE:
<221> NAME/KEY: misc_feature
<222> LOCATION: 246
<223> OTHER INFORMATION: n is a or g or c or t
<220> FEATURE:
<221> NAME/KEY: misc_feature
<222> LOCATION: 252
<223> OTHER INFORMATION: n is a or g or c or t
<220> FEATURE:
<221> NAME/KEY: misc_feature
<222> LOCATION: 255
<223> OTHER INFORMATION: n is a or g or c or t
<220> FEATURE:
<221> NAME/KEY: misc_feature
<222> LOCATION: 258
<223> OTHER INFORMATION: n is a or g or c or t
<220> FEATURE:
<221> NAME/KEY: misc_feature
<222> LOCATION: 261
<223> OTHER INFORMATION: n is a or g or c or t
<220> FEATURE:
<221> NAME/KEY: misc_feature
<222> LOCATION: 267
<223> OTHER INFORMATION: n is a or g or c or t
<220> FEATURE:
<221> NAME/KEY: misc_feature
<222> LOCATION: 270
<223> OTHER INFORMATION: n is a or g or c or t
<220> FEATURE:
<221> NAME/KEY: misc_feature
<222> LOCATION: 291
<223> OTHER INFORMATION: n is a or g or c or t
<220> FEATURE:
<221> NAME/KEY: misc_feature
<222> LOCATION: 300
```

-continued

<223> OTHER INFORMATION: n is a or g or c or t
<220> FEATURE:
<221> NAME/KEY: misc_feature
<222> LOCATION: 303
<223> OTHER INFORMATION: n is a or g or c or t
<220> FEATURE:
<221> NAME/KEY: misc_feature
<222> LOCATION: 306
<223> OTHER INFORMATION: n is a or g or c or t
<220> FEATURE:
<221> NAME/KEY: misc_feature
<222> LOCATION: 321
<223> OTHER INFORMATION: n is a or g or c or t
<220> FEATURE:
<221> NAME/KEY: misc_feature
<222> LOCATION: 324
<223> OTHER INFORMATION: n is a or g or c or t
<220> FEATURE:
<221> NAME/KEY: misc_feature
<222> LOCATION: 327
<223> OTHER INFORMATION: n is a or g or c or t
<220> FEATURE:
<221> NAME/KEY: misc_feature
<222> LOCATION: 330
<223> OTHER INFORMATION: n is a or g or c or t
<220> FEATURE:
<221> NAME/KEY: misc_feature
<222> LOCATION: 336
<223> OTHER INFORMATION: n is a or g or c or t
<220> FEATURE:
<221> NAME/KEY: misc_feature
<222> LOCATION: 339
<223> OTHER INFORMATION: n is a or g or c or t
<220> FEATURE:
<221> NAME/KEY: misc_feature
<222> LOCATION: 342
<223> OTHER INFORMATION: n is a or g or c or t

<400> SEQUENCE: 42
atgacntgya aratgwsnca rytngarmgn aayathgara cnathathaa yacnttycay 60
cartaywsng tnaarytngg ncayccngay acnytnaayc arggngartt yaargarytn 120
gtnmgnaarg ayytncaraa yttyytnaar aargaraaya araaygaraa rgtnathgar 180
cayathatgg argayytnga yacnaaygcn gayaarcary tnwsnttyga rgarttyath 240
atgytnatgg cnmgnytnac ntgggcnwsn caygaraara tgcaygargg ngaygarggn 300
ccnggncayc aycayaarcc nggnytnggn garggnacnc cn 342

<210> SEQ ID NO 43
<211> LENGTH: 4195
<212> TYPE: DNA
<213> ORGANISM: Homo sapiens

<400> SEQUENCE: 43
ttccaccttt tggctcttgt aaataatgct gctatgaaca tgaatgtaca aacatctgtt 60
tgaatccctg cattcaattc ttttgcatat atacccagga gcagaatgat ggatcatatg 120
gtaattctgt gtttatttat ttgaggaaca aacttgccgt tttccataac agctgcacta 180
ttttacattc ccactaacag tgcattaggc ttccaattct ctatgccctc accaacactt 240
gttttctggg ttttaaaaga agtagtagtc atccttgtag gtgtcaggtg gtatctcatt 300
gtcgttttgc ttcatgtttt cctaaagatt agtaattttc atatgcttat tgaccatttg 360
tatatcttct tcggagaagt gtctatttga gtctttcccc aattttgatt ggtttgtttg 420
ttttttgttg ttgagttgta gggattcttt tatattctgg atattaatcc cttatcagat 480
atttgtttta caaatatttt ctttgtaaca acagaaacac accacagtct tcaaggttgg 540
aagccagtta atctgagtag cattttgtta gtggtgggga gaggatttgt tcctcctgaa 600

-continued

```
atcctgggga attggccacc tcctcttctc ctcttaggca tgaagcgcgt ctggcttctc      660
caaagaactc ttcccctcca ctacctcaga gttagcttcc tctcttcagc cagtgatcct      720
ggggtcccag acacaataat taaccaagag agggtgaaag gctccctgct gtgtttatgc      780
aatggctcag gcccttgtga agtgccgagg acccccaagc agcctccatc tcccagggca      840
tggtccatcc ccagctttca cagaacagga aagctgtgga ggagtgtggg cagcagggta      900
ggaatggata tagcccttgg caacaacaca tttccccaca aagcacccac ccaaaagaac      960
aacaacgata gttttagttt ttagtaatga gaacaatagt tctcatgact aaaagccatc     1020
agccaggaca ctgttctcaa ccctttttgcg gtctttggac cctttgaaac tctgacagaa     1080
gccatggagg aatgttctca ctgagtgcat gcactcaaaa tgatgcattc aacttcaatt     1140
cagtttcagg gatgtatggc ctgaccacca atgcagggga ttagcaatcg caatagtgga     1200
gagggcatgg gagtgggaat ctggctggat caagcaagtg gatgccagca gcccagaaaa     1260
agagcccccc tacctgcttt ttccttcctg ggcactattg cccagcaaat gccttcctct     1320
ttccgcttct cctacctccc cacccaaaat tttcattctg cacagtgatt gccacattca     1380
ctggttgaga aacagagact gtagcaactc tggcaggag aagctgtctc tgatggcctg      1440
aagctgtggg cagctggcca agcctaaccg ctataaaaag gagctgcctc tcagccctgc     1500
atgtctcttg tcagctgtct ttcagaagac ctggtaagtg ggactgtctg ggttggcccc     1560
gcactttggg cttctcttgg ggagggtcag ggaagtggag cagccttcct gagagaggag     1620
agagaaagct cagggaggtc tggagcaaag atactcctgg aggtggggag tgaggcaggg     1680
ataaggaagg agagtatcct ccagcacctt ccagtgggta agggcacatt gtctcctagg     1740
ctggactttt cttgagcaga gggtgggtg gtaaggaaag tctacgggcc ccgtgtgtg      1800 tgcacatgtc tctgtgtgaa tggaccctcc cccttcccac acgtgtatcc ctatcatccc     1860
acccttccca ccagaggcca tagccatctg ctggtttggt tatttgagag tgcaggccag     1920
gacaaggcca tcgcttgggg catgaatcct ctgcgtactg ccctggccag atgcaaattc     1980
cctgccatgg gattcccag aaggttctgt ttttcaggtg gggcaagttc cgtgggcatc      2040
atgttgaccg agctggagaa agccttgaac tctatcatcg acgtctacca caagtactcc     2100
ctgataaagg ggaatttcca tgccgtctac agggatgacc tgaagaaatt gctagagacc     2160
gagtgtcctc agtatatcag ggtgaggagg ggctgggtgt ggcgggggct ctctgcctgg     2220 tcctgggggct gccctgggcc agcggtcctc cctgccaccc ttcatagatg ctatgcctcg     2280
gctctctctg agatctttaa actctggctt cttcctcctc aatcttgaca gaaaaagggt     2340
gcagacgtct ggttcaaaga gttggatatc aacactgatg gtgcagttaa cttccaggag     2400
ttcctcattc tggtgataaa gatgggcgtg gcagcccaca aaaaagccaa tgaagaaagc     2460
cacaaagagt agctgagtta ctgggcccag aggctgggcc cctggacatg tacctgcaga     2520
ataataaagt catcaatacc tcatgcctct ctcttatgct tttgtggaat gaggttcctc     2580
ggtgtggagg gagggttgga aaacccaaag gaagaaaaag aaatctatgt tatcccaccc     2640
tacctctcac aagcctttcc tgctttaccc ctcacctggc ctctgcccca cattccttca     2700
gcccctcatt tcgagcattg gatttgaggc ttaaggattc aaaagtcgt catgaatata     2760 gctgatgatt ttatagtggt tctgaaatgg gtcggggatt tgggaacagg gtggtagtat     2820
aagaacaact gatactgttc tctaagctaa atcttagctt ccagctacct gtcttagatg     2880
tggctcttgg gaaccttaga gtgatagcta catagaagtg tgtgggtgtg tgtgtgtgtg     2940
```

```
tctgtgtgtg tgtgtgtgag agagagacag acagaaagag agcaagagag ggaaggggggg    3000 agaggctgat tgtgtgtgtg gtgtgatgta ggtggacaat gttcagagtc ctccattaac    3060
aggataatcc tcacacctgt ccacatacct gtagtttgtc cttggggatt ttgaaaattt    3120
ttcctccctc tccactccca aactcccaac tcaattaaat gataaaggaa taggcaaata    3180
ggaaaataaa ttagtaaaac ttaagtcaaa gaataggtta ttcatacgct gcctatggga    3240
ttctatgctt tgtgatcaga aaattatcta aaaaatactt cccaagggct ggtacaaggg    3300
aggccagaag acgagtggtt cttctctgag gtggacatta aaaaagaag aaaatgaagg    3360 ggaaccttttt gacaagaatg tcaccccaaa ctggattttc atgctgtggt gtggggaatt    3420
ttctgttgtc ctcacttagg tgctggggca gtggtgttag tgatgggtaa aaaggtagga    3480
agctgtcaca gaatcactaa accagggttc ttaacttgtc tgtctataca tctctgaaat    3540
tgggttgaag ttgtgtgcat cattttgagt gacgcactga gaacattcct ccacggcttc    3600
catcgagagt ctcgaaaagg cccaacacct caaaaaggtt aagaacactt gtcctgctta    3660
ctggttttta gtaacaaatg gcagagtatt tctctctgtc tctctctctt tttttttttt    3720 ttttttttgag acacagggtc ttgtctgtca cgtggactag agtacaatgg gcatgatcat    3780
gggctcactg tagcctcgaa cacctgggct caagtaatcc tcccacctca gcctctttag    3840
tagctgggac tacagcatga gccactgccc ttggctaatt tttaaattat ttttttgtag    3900
agatggaaac ttgctatgtt gcccaggcta gtctcaaact cctggactca agcgatcctc    3960
ctaccttggc ctcccaaagt gctgagatta cagtgtgatc cacaccacac ctggccaaag    4020
attggagtat ttttattgct attgttgtgc tgggtgggtg ggtgggtgta tgctttgtgg    4080
ggacgtgtgt tgttgccaag ggctaaatca gttcctaccc tgctgcccac agtcctccac    4140
agctttcctg ctctgtgaag ctaaggatac accccgatga taagctgtca acata          4195

<210> SEQ ID NO 44
<211> LENGTH: 477
<212> TYPE: DNA
<213> ORGANISM: Homo sapiens
<220> FEATURE:
<221> NAME/KEY: misc_feature
<222> LOCATION: 389
<223> OTHER INFORMATION: n is a or g or c or t

<400> SEQUENCE: 44
tttttttttt ttttttttgg ataaagactt atttattatt tatcttatca tttcccagaa    60
caaaggccat tgagtaagcc attccctttta aacttggttg ggcagctgtc acatggctga    120
cctcttaatt acttcccaca gcctttgcca tgactgtggc catgcccacg tgggttgttc    180
tcatgcagct tctcatgaca ggcaaagatc aactttgcca tcagcatcat acactcctca    240
aagctcagct gattgtcctg gtttgtgtcc aggtcctcca tgatgtcatt tatgagggct    300
tcatttctct tctctttctt cataaaaggt tgccaaactg tgcttccac catttggtct    360 gaattccttc ttgctcaggg tgtaggggng ggtcttcctt cttaaagtat tgatgaaagg    420
gggccagatg ggggggttat gctgcgctcc atctgaaaag tggctttggt gggccat      477

<210> SEQ ID NO 45
<211> LENGTH: 406
<212> TYPE: DNA
<213> ORGANISM: Homo sapiens

<400> SEQUENCE: 45
tttttttttt tttttttttt ttttggagga agagacttta tttggcccca gcccctagcc    60
```

```
ccacagccaa gacagtttga cataacaggc cccggggccc tggttgggta gaggcagggt    120
ggcctggcct cctgattagt ggctgtggcc gtggccacca tgactgtggc cgtggccggg    180
gccactgtga tcttggccac tgtggtctta ggggtgccc tccccgaggc ctggcttatg    240
gtggtggcca gggccctcgt caccctcgtg cattttttcg tgggaggccc aggttagcct    300
cgccatcagc atgatgaact cctggagctc agctgcttgt ctgcatttgg gtccaggtcc    360
tccatgatgt gttctatgac cttttcattc ttattctcct tcttga                  406

<210> SEQ ID NO 46
<211> LENGTH: 425
<212> TYPE: DNA
<213> ORGANISM: Homo sapiens
<220> FEATURE:
<221> NAME/KEY: misc_feature
<222> LOCATION: 417
<223> OTHER INFORMATION: n is a or g or c or t

<400> SEQUENCE: 46
ggaggaagag actttatttg gccccagccc ctatccccac agccaagaca gtttgacata    60
acaggccccg ggccctggt tgggtaaagg caggtggcc tggcctcctg attagtggct    120
gtggccgtgg ccaccatgac tgtggccgtg ccgtggcca ctgtgatctt ggccactgtg    180
gtcttagggg gtgccctccc cgaggcctgg cttatggtgg tggccaggc cctcgtcacc    240 ctcgtgcatc ttctcgtggg aggcccaggt tagcctcgcc atcagcatga tgaactcctc    300
gaagctcagc tgcttgtctg catttgtgtc caggtcctcc atgatgtgtt ctatgacctt    360
ttcattctta ttctccttct tgagaaaatt ttgcagatct tttcgcacca gctcttngaa    420
ttccc                                                                425

<210> SEQ ID NO 47
<211> LENGTH: 565
<212> TYPE: DNA
<213> ORGANISM: Homo sapiens

<400> SEQUENCE: 47
aattcgctcg gctttgacag agtgcaagac gatgacttgc aaaatgtcgc agctggaacg    60
caacatagag accatcatca acaccttcca ccaatactct gtgaagctgg ggcacccaga    120
caccctgaac caggggggaat tcaaagagct ggtgcgaaaa gatctgcaaa attttctcaa    180
gaaggagaat aagaatgaaa aggtcataga acacatcatg gaggacctgg acacaaatgc    240
agacaagcag ctgagcttcg aggagttcat catgctgatg gcgaggctaa cctgggcctc    300
ccacgagaag atgcacgagg gtgacgaggg ccctggccac caccataagc caggcctcgg    360
ggagggcacc ccctaagacc acagtggcca agatcacagt ggccacggcc atggccacag    420
tcatggtggc cacggccaca ggccactaat caggaggcca ggccaccctg cctctaccca    480
accagggccc cgggggcctgt tatgtcaaac tgtcttggct gtggggctag gggctggggc    540
caaataaagt ctcttcctcc aagct                                          565

<210> SEQ ID NO 48
<211> LENGTH: 430
<212> TYPE: DNA
<213> ORGANISM: Homo sapiens

<400> SEQUENCE: 48
gacttggagg aagagacttt atttggcccc agccctagc cccacagcca agacagtttg    60
```

```
acataacagg ccccggggcc ctggttgggt agaggcaggg tggcctggcc tcctgattag    120
tggctgtggc cgtggccacc atgactgtgg ccgtggccgt ggccactgtg atcttggcca    180
ctgtggtctt aggggtgcc ctccccgagg cctggcttat ggtggtggcc agggccctcg     240
tcaccctcgt gcatcttctc gtgggaggcc caggttagcc tcgccatcag catgatgaac    300
tcctcgaagc tcagctgctt gtctgcattt gtgtccaggt cctccatgat gtgttctatg    360
accttttcat tcttattctc cttcttgaga aaattttgca gatctttcg caccagctct     420 ttgaattccc                                                           430

<210> SEQ ID NO 49
<211> LENGTH: 305
<212> TYPE: DNA
<213> ORGANISM: Homo sapiens

<400> SEQUENCE: 49
tgacttggag gaaaaaactt tatttggccc cagcccctag ccccacagcc aaaacagttt     60
gacataacag gccccggggc cctggttggg tagaggcagg ggggcctggc ctcctgatta    120
gtggctgtgg ccggggccac catgactgtg gccggggccg ggccactgt gatcttgcca     180 ctggggtctt aggggtgcc ctccccgagg cctggtttat ggtggtggcc agggcccttg     240
tcacccttgt gcatttttc gtgggaggcc caggttagcc tcgccatcag catgatgaac    300
tcctc                                                                305

<210> SEQ ID NO 50
<211> LENGTH: 452
<212> TYPE: DNA
<213> ORGANISM: Homo sapiens

<400> SEQUENCE: 50
ggaggaagag actttatttg gccccagccc ctagccccac agccaagaca gtttgacata     60
acaggccccg ggccctggt tgggtagagg caggtggcc tggcctcctg attagtggct     120
gtggccgtgg ccaccatgac tgtggccgtg gccgtggcca ctgtgatctt ggccactgtg    180
gtcttagggg gtgccctccc cgaggcctgg cttatggtgg tggccagggc cctcgtcacc    240
ctcgtgcatt ttctcgtggg aggcccaggt tagcctcgcc atcagcatga tgaactcctc    300
gaagctcagc tgcttgtctg catttgtgtc caggtcctcc atgatgtgtt ctatgacctt    360
ttcattctta ttctccttct tgagaaaatt ttgcagatct tttcgcacca gctctttgaa    420 ttcccccctgg ttcagggtgt ctgggtgccc ca                                 452

<210> SEQ ID NO 51
<211> LENGTH: 4439
<212> TYPE: DNA
<213> ORGANISM: Homo sapiens

<400> SEQUENCE: 51
atcactgtgg agtaggggaa gggcactcct ggggtggcaa ggtgggaggt gggccctgtg     60
ttcccacagt gggcagggag gtagtgaaag ggaagctggc cggacaggaa gggccattcc    120
aagagggctt tgtgcgcagg gctaagccaa gctttctcca taggcaatgg ggagcaactg    180
gaggttcgta gcaggagaag gacacatcaa gcccaccagg aggctaagta aaaacagttg    240
tctcccaagt tataagttcc tggaacccctt gctgggagca ggatttagaa aaatgatgct    300
gagagatgct agaaacatat tcgccctgag gctctctcac tcagactgca agaggaaggt    360
atcatcagaa ttgcccttaa ccaggaacca gaatagctgg gtccccttcc tgccaagtca    420
```

```
gcaaccagct atgtgacctt gctcaggtcc atctccgggt gtcagtttct tcatctacaa   480
tgcaagaggg ttgcccacct ctgagaaccc ttctaacccc aaatctcacc ctatgaatct   540
aagaacacaa cccctcgcca tcctaagtat cacagagcca ggcaagcatg ggtgagagct   600
cagaccatcc ttgttggact aaaaggaagg ggcagactgc catgggggc agccgagagg   660 gtcaggcccc cataggtcct cagcctgctt caacctcaaa ggggatgggg ggctgagtgg   720
tgccagagga gcagcaggct cgctcgggga gagtagggcc ttaggataga agggaaatga   780
actaaacaac cagcttcctg caaaccagtt tcaggccagg gctgggaatt tcacaaaaaa   840
gcagaaggcg ctctgtgaac atttcctgcc ccgccccagc ccccttcctg gcagcattag   900
cacactgctc acctgtgaag caatcttccg gagacagggc caaagggcaa gtgcccagt   960 caggagctgc ctataaatgc cgagcctgca cagctctggc aaacactctg tgtggctcct  1020
cggctttggt aagtgagctg ccagcttccc caggcagaag cctgcctgcc gattccttct  1080
ttccttccct gacccaactt ccttccaaat cctcctccta gaagccctcc ttggttggcc  1140
ctgcctactt taaagcttct ttcacatttt cttaggtcat gttcccctgg ggcctcctgc  1200
cctcaaatgc tttgcttttt ggcactctgt agatattcta aaaaatcatt ttgtacatgt  1260
gtgtgacagg ccatctccca gttaagttgc agcctgtgct ttctttttat tttgcacttc  1320
ccccactatt tctgtgagtg cttagtagga agtgtcaaag aagcttgaca gcattttctt  1380
ctaagtgtcc caactcttgg ttttccatta cacagacaga gtgcaagacg atgacttgca  1440
aaatgtcgca gctggaacgc aacatagaga ccatcatcaa caccttccac caatactctg  1500
tgaagctggg gcacccagac accctgaacc aggggggaatt caaagagctg gtgcgaaaag  1560
atctgcaaaa ttttctcaag gtagggctgg actctggcag gtctgaccca gcctcaccgc  1620
agtttgggtt gacaagggag gatgggagta tgggctacag caatcaaggg gaagatttga  1680
gctcctggag cccagcccca agacgcagcg agtgtcctgt tatacagggc aggtgctcac  1740
agttacacag gacgacaggg tcaagaaatt gctcaattga acacctgcta tttgtcgggc  1800
cctgttctgg gcagagggat gtagtggtaa atggagcccc actattccat gaggagacac  1860
acagtaaagt tgttggccaa taaagagcac agataaagcc aaatgccaat aagtgcctgg  1920
aagaaaatga gatagagtgc gctgtgggca atggggctgg gtggggtgga ggtgaccagt  1980
tagggtacat gagaagggcc tctttgagga ggtaacattt gagctgagcc ccgaatgttg  2040
gggagggaag cccctgagga tgacacttgg cacaaagctg aggagaccct aagcctcagg  2100
gcgaacttgg ggtggaagac ttgggggctt ttctaatcct aagggtctgc ggtggaaaat  2160
gaatgcataa agagcacatg gagagcacct gcacagcact cagggaactg ggaggttttt  2220
cccccgctcc aaaaatgatt aggcagttct aagaaaaagg ctgagcactt ccaacagcct  2280
ttttgttttc ttttcaaatt tggggaaagt cgggaaacag aggcctgcat taagaagggt  2340
ggaacacatg ggtctcagtc tcagttccag tcccggagcc agacatcctg gggtaggtcc  2400
ccagccctcc cagtgcccct ccctccgcct tggtaaggtg gagaattgca gccttcagag  2460
ttaggggccc tgacagctct ccataggtgg aggcctcagg caggcaggat gctgggtggg  2520
gtaggcaaga aagggcccag cagagaggcc gcatcggaaa actatcctcc atgtgacccc  2580
ctatgcccgc ttcaccccc acctgacatc ccccaccaga agcaaagcga tgctgtggga  2640
aaggaagcag agcctcatgg atgggctgca caggagagtg ctcgcattgg ctgggtaccc  2700
cacaggttct ggggagggga c ttagcgaggt gactcagtgc ctcggcctcc caaagtgctg  2760
```

-continued

```
ggattacaag catgagccac cctgtccgac catctcccct tttatacttt atcacaccct      2820
tgaggtcagc ggagcacata ctctgctctc tgaccctcca tctcccctgc ccacacctag      2880 gttttttctag tgtttccccg ttgtattggt tgaaataagt ttcactaatt ggtaacctcc     2940
agagggaagg aagggaggg caggggaagg agtgaagtgc agaggggtag cagagtggaa       3000
ctggcctcta agtcagatct gaatttgcat gccctcaata gtcaagcctg tgaaaactaa     3060
tgaccctctc taggactggt ttcaagtctt cctccaggaa gataccattc ctagctgtta    3120
aagttgttat aaggaccaaa tgaggtgaca tttccaggct tactcatgcc atgaccaggg    3180
caagaccctg gaactcagct tcctcttcta taaatagaa atcagcaccc aagtcacagg      3240
gtcatggagg gaataaactg gagagcgttt ggtatgtgct cagtgtctgc tccattgtgc     3300
gcactcagcc tatggtcatt tttaattttt aaatccagcc ccagggtcga ggcttccttg     3360
tacatttgcc agctggtcat ttactgtgct cccagtcccc acctctggcc acacccagct     3420
ctcacagcct tctctcccca cccgcagaag gagaataaga atgaaaaggt catagaacac    3480
atcatggagg acctggacac aaatgcagac aagcagctga gcttcgagga gttcatcatg    3540
ctgatggcga ggctaacctg gcctccac gagaagatgc acgagggtga cgagggccct      3600
ggccaccacc ataagccagg cctcggggag ggcacccct aagaccacag tggccaagat     3660
cacagtggcc acggccacgg ccacagtcat ggtggcacg gccacaggcc actaatcagg     3720
aggccaggcc accctgcctc tacccaacca gggccccggg gctgttatgt caaactgtct    3780
tggctgtggg gctaggggct ggggcaaata agtctcttcc tccaagtcag tgctctgtgt    3840
gcttcttcca cctcttctcc aaccctgcct tcccagggct ctggcattta gacagccctg    3900
tccttatctg tgactcagcc ccctcattca gtattaacaa aatgagaagc agcaaaacat    3960
gggtctgtgc tgggccccctt ggctcacctc cctgaccatg tcctcacctc tgacttcagg  4020 cccccactgtt cagatcccag gctccctgcc ccatctcaga caccctgtcc agcctgtcca   4080
gcctgacaaa tggcccttgt cactgtacac tgtagaaagc aaaaaggcat atctctaccc   4140
cttgatatgc ctgctacctc accaaccagc cccaagcctg tcttcaccca tcactgtcta   4200
cacagccctc tctctctcct aacagaattc tattcctctg aaagtcttca gaaactggac   4260
ctagatagtg ccatgtctgg ggaggaatat ggcaccaggc agtggaaaca aggacagatc   4320
ggtgtgttat ctcacatttg atcagagagc atgatctctc ttaacagacc tgccacccta   4380
atcaacggga gtgctcacac aagtgggagt ctgagagctt agccctatgc ccaccctgg    4439
```

<210> SEQ ID NO 52
<211> LENGTH: 565
<212> TYPE: DNA
<213> ORGANISM: Homo sapiens

<400> SEQUENCE: 52

```
aattcgctcg gctttgacag agtgcaagac gatgacttgc aaaatgtcgc agctggaacg      60
caacatagag accatcatca acaccttcca ccaatactct gtgaagctgg ggcacccaga    120 cacccctgaac caggggggaat tcaaagagct ggtgcgaaaa gatctgcaaa attttctcaa   180
gaaggagaat aagaatgaaa aggtcataga acacatcatg gaggacctgg acacaaatgc   240
agacaagcag ctgagcttcg aggagttcat catgctgatg gcgaggctaa cctgggcctc   300
ccacgagaag atgcacgagg gtgacgaggg ccctggccac caccataagc caggcctcgg   360
ggagggcacc ccctaagacc acagtggcca agatcacagt ggccacggcc atggccacag   420
tcatggtggc cacggccaca ggccactaat caggaggcca ggccacccctg cctctaccca   480
```

-continued accagggccc cggggcctgt tatgtcaaac tgtcttggct gtggggctag gggctggggc    540
caaataaagt ctcttcctcc aagct    565

<210> SEQ ID NO 53
<211> LENGTH: 255
<212> TYPE: DNA
<213> ORGANISM: Homo sapiens
<220> FEATURE:
<221> NAME/KEY: misc_feature
<222> LOCATION: 9
<223> OTHER INFORMATION: n is a or g or c or t
<220> FEATURE:
<221> NAME/KEY: misc_feature
<222> LOCATION: 14
<223> OTHER INFORMATION: n is a or g or c or t
<220> FEATURE:
<221> NAME/KEY: misc_feature
<222> LOCATION: 39
<223> OTHER INFORMATION: n is a or g or c or t
<220> FEATURE:
<221> NAME/KEY: misc_feature
<222> LOCATION: 42
<223> OTHER INFORMATION: n is a or g or c or t
<220> FEATURE:
<221> NAME/KEY: misc_feature
<222> LOCATION: 54
<223> OTHER INFORMATION: n is a or g or c or t
<220> FEATURE:
<221> NAME/KEY: misc_feature
<222> LOCATION: 57
<223> OTHER INFORMATION: n is a or g or c or t
<220> FEATURE:
<221> NAME/KEY: misc_feature
<222> LOCATION: 60
<223> OTHER INFORMATION: n is a or g or c or t
<220> FEATURE:
<221> NAME/KEY: misc_feature
<222> LOCATION: 63
<223> OTHER INFORMATION: n is a or g or c or t
<220> FEATURE:
<221> NAME/KEY: misc_feature
<222> LOCATION: 66
<223> OTHER INFORMATION: n is a or g or c or t
<220> FEATURE:
<221> NAME/KEY: misc_feature
<222> LOCATION: 72
<223> OTHER INFORMATION: n is a or g or c or t
<220> FEATURE:
<221> NAME/KEY: misc_feature
<222> LOCATION: 75
<223> OTHER INFORMATION: n is a or g or c or t
<220> FEATURE:
<221> NAME/KEY: misc_feature
<222> LOCATION: 81
<223> OTHER INFORMATION: n is a or g or c or t
<220> FEATURE:
<221> NAME/KEY: misc_feature
<222> LOCATION: 87
<223> OTHER INFORMATION: n is a or g or c or t
<220> FEATURE:
<221> NAME/KEY: misc_feature
<222> LOCATION: 90
<223> OTHER INFORMATION: n is a or g or c or t
<220> FEATURE:
<221> NAME/KEY: misc_feature
<222> LOCATION: 93
<223> OTHER INFORMATION: n is a or g or c or t
<220> FEATURE:
<221> NAME/KEY: misc_feature
<222> LOCATION: 102
<223> OTHER INFORMATION: n is a or g or c or t
<220> FEATURE:
<221> NAME/KEY: misc_feature
<222> LOCATION: 120
<223> OTHER INFORMATION: n is a or g or c or t
<220> FEATURE:

```
<221> NAME/KEY: misc_feature
<222> LOCATION: 123
<223> OTHER INFORMATION: n is a or g or c or t
<220> FEATURE:
<221> NAME/KEY: misc_feature
<222> LOCATION: 126
<223> OTHER INFORMATION: n is a or g or c or t
<220> FEATURE:
<221> NAME/KEY: misc_feature
<222> LOCATION: 129
<223> OTHER INFORMATION: n is a or g or c or t
<220> FEATURE:
<221> NAME/KEY: misc_feature
<222> LOCATION: 132
<223> OTHER INFORMATION: n is a or g or c or t
<220> FEATURE:
<221> NAME/KEY: misc_feature
<222> LOCATION: 138
<223> OTHER INFORMATION: n is a or g or c or t
<220> FEATURE:
<221> NAME/KEY: misc_feature
<222> LOCATION: 162
<223> OTHER INFORMATION: n is a or g or c or t
<220> FEATURE:
<221> NAME/KEY: misc_feature
<222> LOCATION: 171
<223> OTHER INFORMATION: n is a or g or c or t
<220> FEATURE:
<221> NAME/KEY: misc_feature
<222> LOCATION: 180
<223> OTHER INFORMATION: n is a or g or c or t
<220> FEATURE:
<221> NAME/KEY: misc_feature
<222> LOCATION: 216
<223> OTHER INFORMATION: n is a or g or c or t
<220> FEATURE:
<221> NAME/KEY: misc_feature
<222> LOCATION: 231
<223> OTHER INFORMATION: n is a or g or c or t
<220> FEATURE:
<221> NAME/KEY: misc_feature
<222> LOCATION: 234
<223> OTHER INFORMATION: n is a or g or c or t
<220> FEATURE:
<221> NAME/KEY: misc_feature
<222> LOCATION: 237
<223> OTHER INFORMATION: n is a or g or c or t
<220> FEATURE:
<221> NAME/KEY: misc_feature
<222> LOCATION: 240
<223> OTHER INFORMATION: n is a or g or c or t
<220> FEATURE:
<221> NAME/KEY: misc_feature
<222> LOCATION: 255
<223> OTHER INFORMATION: n is a or g or c or t

<400> SEQUENCE: 53
gayaayggng aygtntgyca rgaytgyath caratggtna cngayathca racngcngtn     60
mgnacnaayw snacnttygt ncargcnytn gtngarcayg tnaargarga rtgygaymgn    120
ytnggnccng gnatggcnga yathtgyaar aaytayathw sncartayws ngarathgcn    180
athcaratga tgatgcayat gcargaycar carccnaarg arathtgygc nytngtnggn    240
ttytgygayg argtn                                                    255

<210> SEQ ID NO 54
<211> LENGTH: 2724
<212> TYPE: DNA
<213> ORGANISM: Homo sapiens

<400> SEQUENCE: 54
cgcgctatgt acgccctctt cctcctggcc agcctcctgg gcgcggctct agccggcccg     60
gtccttggac tgaaagaatg caccaggggc tcggcagtgt ggtgccagaa tgtgaagacg    120
```

-continued

```
gcgtccgact gcggggcagt gaagcactgc ctgcagaccg tttggaacaa gccaacagtg      180
aaatcccttc cctgcgacat atgcaaagac gttgtcaccg cagctggtga tatgctgaag      240
gacaatgcca ctgaggagga gatccttgtt tacttggaga agacctgtga ctggcttccg      300
aaaccgaaca tgtctgcttc atgcaaggag atagtggact cctacctccc tgtcatcctg      360
gacatcatta aaggagaaat gagccgtcct ggggaggtgt gctctgctct caacctctgc      420
gagtctctcc agaagcacct agcagagctg aatcaccaga agcagctgga gtccaataag      480
atcccagagc tggacatgac tgaggtggtg gccccccttca tggccaacat ccctctcctc      540
ctctaccctc aggacggccc ccgcagcaag ccccagccaa aggataatgg ggacgtttgc      600
caggactgca ttcagatggt gactgacatc cagactgctg tacggaccaa ctccacccttt    660 gtccaggcct tggtggaaca tgtcaaggag gagtgtgacc gcctgggccc tggcatggcc      720
gacatatgca agaactatat cagccagtat tctgaaattg ctatccagat gatgatgcac      780
atgcaaccca aggagatctg tgcgctggtt gggttctgtg atgaggtgaa agagatgccc      840
atgcagactc tggtccccgc caaagtggcc tccaagaatg tcatccctgc cctggaactg      900
gtggagccca ttaagaagca cgaggtccca gcaaagtctg atgtttactg tgaggtgtgt      960
gaattcctgg tgaaggaggt gaccaagctg attgacaaca acaagactga aaagaaata     1020 ctcgacgctt ttgacaaaat gtgctcgaag ctgccgaagt ccctgtcgga agagtgccag     1080
gaggtggtgg acacgtacgg cagctccatc ctgtccatcc tgctggagga ggtcagccct     1140
gagctggtgt gcagcatgct gcacctctgc tctggcacgc ggctgcctgc actgaccgtt     1200
cacgtgactc agccaaagga cggtggcttc tgcgaagtgt gcaagaagct ggtgggttat     1260
ttggatcgca acctggagaa aaacagcacc aagcaggaga tcctggctgc tcttgagaaa     1320
ggctgcagct tcctgccaga cccttaccag aagcagtgtg atcagtttgt ggcagagtac     1380
gagcccgtgc tgatcgagat cctggtggag gtgatggatc cttccttcgt gtgcttgaaa     1440
attggagcct gccctcggc ccataagccc ttgttgggaa ctgagaagtg tatatggggc      1500
ccaagctact ggtgccagaa cacagagaca gcagcccagt gcaatgctgt cgagcattgc     1560
aaacgccatg tgtggaacta ggaggaggaa tattccatct tggcagaaac cacagcattg     1620 gttttttttct acttgtgtgt ctgggggaat gaacgcacag atctgtttga ctttgttata     1680 aaatagggc tcccccacct cccccatttc tgtgtccttt attgtagcat tgctgtctgc      1740
aagggagccc ctagccctg gcagacatag ctgcttcagt gcccctttc tctctgctag       1800 atggatgttg atgcactgga ggtcttttag cctgcccttg catggcgcct gctggaggag     1860
gagagagctc tgctggcatg agccacagtt tcttgactgg aggccatcaa ccctcttggt     1920
tgaggccttg ttctgagccc tgacatgtgc ttgggcactg gtgggcctgg gcttctgagg     1980
tggcctcctg ccctgatcag ggaccctccc cgctttcctg ggcctctcag ttgaaccaaa     2040
gcagcaaaac aaaggcagtt ttatatgaaa gattagaagc ctggaataat caggcttttt     2100
aaatgatgta attcccactg taatagcata gggattttgg aagcagctgc tggtggcttg     2160
ggacatcagt ggggccaagg gttctctgtc cctggttcaa ctgtgatttg gctttcccgt     2220
gtctttcctg gtgatgcctt gtttgggggtt ctgtgggttt gggtgggaag agggcccatc    2280
tgcctgaatg taacctgcta gctctccgaa gccctgcggg cctggcttgt gtgagcgtgt     2340
ggacagtggt ggccgcgctg tgcctgctcg tgttgcctac atgtccctgg ctgttgaggc     2400
gctgcttcag cctgcacccc tccctttgtc tcatagatgc tccttttgac cttttcaaat     2460
```

-continued

| | | |
|---|---|---|
| aaatatggat ggcaagctcc taggcctctg cttcctggta gagggcggca tgccgaaggg | 2520 |
| tctgctgggt gtggattgga tgctggggtg tggggggttgg aagctgtctg tggcccactt | 2580 |
| gggcacccac gcttctgtcc acttctggtt gccaggagac agcaagcaaa gccagcagga | 2640 |
| catgaagttg ctattaaatt gacttcgtga tttttgtttt gcactaaagt ttctgtgatt | 2700 |
| taacaataaa attctgttag ccag | 2724 |

<210> SEQ ID NO 55
<211> LENGTH: 2171
<212> TYPE: DNA
<213> ORGANISM: Homo sapiens

<400> SEQUENCE: 55

| | | |
|---|---|---|
| cgcgctatgt acgccctctt cctcctggcc agcctcctgg gcgcggctct agccggcccg | 60 |
| gtccttggac tgaaagaatg caccaggggc tcggcagtgt ggtgccagaa tgtgaagacg | 120 |
| gcgtccgact gcggggcagt gaagcactgc ctgcagaccg tttggaacaa gccaacagtg | 180 |
| aaatcccttc cctgcgacat atgcaaagac gttgtcaccg cagctggtga tatgctgaag | 240 |
| gacaatgcca ctgaggagga gatccttgtt tacttggaga agacctgtga ctggcttccg | 300 |
| aaaccgaaca tgtctgcttc atgcaaggag atagtggact cctacctccc tgtcatcctg | 360 |
| gacatcatta aggagaaat gagccgtcct ggggaggtgt gctctgctct caacctctgc | 420 |
| gagtctctcc agaagcacct agcagagctg aatcaccaga agcagctgga gtccaataag | 480 |
| atcccagagc tggacatgac tgaggtggtg gccccccttca tggccaacat ccctctcctc | 540 |
| ctctaccctc aggacggccc ccgcagcaag ccccagccaa aggataatgg ggacgtttgc | 600 |
| caggactgca ttcagatggt gactgacatc cagactgctg tacggaccaa ctccaccttt | 660 |
| gtccaggcct tggtggaaca tgtcaaggag gagtgtgacc gcctgggccc tggcatggcc | 720 |
| gacatatgca agaactatat cagccagtat tctgaaattg ctatccagat gatgatgcac | 780 |
| atgcaaccca aggagatctg tgcgctggtt gggttctgtg atgaggtgaa agagatgccc | 840 |
| atgcagactc tggtccccgc caaagtggcc tccaagaatg tcatccctgc cctggaactg | 900 |
| gtggagccca ttaagaagca cgaggtccca gcaaagtctg atgtttactg tgaggtgtgt | 960 |
| gaattcctgg tgaaggaggt gaccaagctg attgacaaca acaagactga aaagaaata | 1020 |
| ctcgacgctt ttgacaaaat gtgctcgaag ctgccgaagt ccctgtcgga agagtgccag | 1080 |
| gaggtggtgg acacgtacgg cagctccatc ctgtccatcc tgctggagga ggtcagccct | 1140 |
| gagctggtgt gcagcatgct gcacctctgc tctggcacgc ggctgcctgc actgaccgtt | 1200 |
| cacgtgactc agccaaagga cggtggcttc tgcgaagtgt gcaagaagct ggtgggttat | 1260 |
| ttggatcgca acctggagaa aaacagcacc aagcaggaga tcctggctgc tcttgagaaa | 1320 |
| ggctgcagct tcctgccaga cccttaccag aagcagtgtg atcagtttgt ggcagagtac | 1380 |
| gagcccgtgc tgatcgagat cctggtggag gtgatggatc cttccttcgt gtgcttgaaa | 1440 |
| attggagcct gccctcggc ccataagccc ttgttgggaa ctgagaagtg tatatggggc | 1500 |
| ccaagctact ggtgccagaa cacagagaca gcagcccagt gcaatgctgt cgagcattgc | 1560 |
| aaacgccatg tgtggaacta ggaggaggaa tattccatct tggcagaaac cacagcattg | 1620 |
| gttttttttct acttgtgtgt ctgggggaat gaacgcacag atctgtttga ctttgttata | 1680 |
| aaaatagggc tcccccacct ccccatttc tgtgtccttt attgtagcat tgctgtctgc | 1740 |
| aagggagccc ctagccctg gcagacatag ctgcttcagt gccccttttc tctctgctag | 1800 |
| atggatgttg atgcactgga ggtcttttag cctgcccttg catggcgcct gctggaggag | 1860 |

-continued

```
gagagagctc tgctggcatg agccacagtt tcttgactgg aggccatcaa ccctcttggt      1920
tgaggccttg ttctgagccc tgacatgtgc ttgggcactg gtgggcctgg gcttctgagg      1980
tggcctcctg ccctgatcag ggaccctccc cgctttcctg ggcctctcag ttgaaccaaa      2040
gcagcaaaac aaaggcagtt ttatatgaaa gattagaagc ctggaataat caggcttttt      2100
aaatgatgta attcccactg taatagcata gggattttgg aagcagctgc tggtggcttg      2160
ggacatcagt g                                                           2171
```

<210> SEQ ID NO 56
<211> LENGTH: 35465
<212> TYPE: DNA
<213> ORGANISM: Homo sapiens

<400> SEQUENCE: 56

```
gatcttggct cactgcaacc tccgcctcca aggttcaagc gatcctccca cctcagcctc        60
ccaagtagct gggattacaa gcgtgtgcta tcacacctgg ctaattttta tattttggt       120
agagatgggg tttcaccttg ttggttaggc tggtcttgaa ctcctgacct caggtgatct       180
gcctgcctca gcctcccaaa gtgctgggat tacaggtgtg agccaccgcg cccagcctga       240
ccctttcttt ctctactggc aaaactcctg ctccttttta aagccaagct catgtcacct       300
cctctgtgaa gtcctcgctg actccccaag cggtcagtgt ctctctcgta tgggctcccc       360
ggccccctgca ctgctctcca tcacaccctg accactctgg gcagtggccc cctccccac       420
ccactgacta tgggctcctt gaaggcaggg cctgggtctg ccccatctct gtgtcccag       480
caatgctggg catgagtcag cctcagaaga catctgctga atggctgcaa accagaggaa       540
atatctccag cctcaggctg ggaccctccc cctctctcct cccacctctg acttcatacc       600
actcaccctc cagagtcttc aatgcccact attacttcac acagttggcc tgtgacaggc       660
aatcaggtca tcgtccacgg ctaccaggtg tttcatgtct actgtgactt ccaggaccac       720
aagccctttt gcgcccacca tgtcttcacc taagagatct tcaaagccca gtatgtctct       780
ggcacccagt ggatcctcca tgcccactgc ggatcccaag cctcctgcct ccttgaagtc       840
caccaaatca gcaacaccca acagatcctt agtgcccacc aaaccagcga catcccgtaa       900
ctcagtcatg agcccaagca gttccaagtc caccaaatcg accagtacaa aaagagcccc       960
ttctaaccgg cccagcagca ggtcccgagt ccgcagcaaa gcaagaacac ccagcagggt      1020
gagcaccgac accaggacca gcaaagccag caaggccagc gacgtgagat gccaccagcg      1080
gaggggcaca cacagccggg gtaggacacc tggcagaagg ggaagccgca gctccaagag      1140
gtcacccagc agggccagca ctcctggcag gataagaact catggtgcca gaccaggcat      1200
ggccagcagg gtgagaactc ccacttcaca gcaaaaaggg agccgggaa agagttacgg       1260
ccggcctaga accagcaaca gggaaaggag tgacagccag cctagaaatc tgagcaagaa      1320
gagttaccgc ccaccaggag gctcaggtat agggaggagt tccgagctgg ctgtaactcc      1380
cagtacagcc aagtgtcaaa ccccgactgg aattccctcc aaggagaaga gtgacaaccc      1440
atctccatcc tcatcaagga aggtgaagag ctacggtcag atgatcatcc ccagtaggga      1500
aaagagttac agccccactg aaatgtccag cagggtcaag agttataacc aggccagcac      1560
ccgcagcagg ccgcaaagtc acagccaatc tagaagcccc agaaggtcaa gaagtggcag      1620
tcagaagagg acgcacagca gagtgagaag tcacagttgg aagagaaacc atagcagggc      1680
aagaagtcgc acccggaagg gaattctgag ccagatggga agacacagcc agtctagaag      1740
```

```
ccacagcaag gggaaaagtc aaaaccaatc tagaaccccc agaagaggaa gaagtcacaa      1800
ctggtctaga aaccccagca aggaaagaag tcatagccat tccagaagct ccagcaaaga      1860
gagagatcac aggggatcta gcagccccag gaaggagagt ggtcgcagtc aatcaggaag      1920
ccccaacaag cagagagatc acagccgatc tagaagtccc aacaaggcga gagatcgcag      1980
ccgatctaga agtccctaca aggcgagaga tcgcagccga tctagaagtc ccaacaaggc      2040
gagagattgc agccgatcta gaagtcccta caaggcgaga gatcgcagcc gatctagaag      2100
tcccaacaag gcaagagatc atagccgatc tagaagtccc aacaaggcga gagatcgcag      2160
ccgatctaga agccccagca aggaaagaga tcacagccaa cttggaagcc ccagcaaaga      2220
gagagatcac agacgatcta gaagcccag caaggagaga cagtgcagac aatctagaag       2280
ctccagcaaa gagagagatc acagacgatc tagaagcccc agcaaggaga cagcgcag       2340 acaatctaga agccccaaca aggagagaga tcgcagccaa tctagaagcc ccagcgagga      2400
gagagagcac agacaatcca gaagcccag caaagagaga gatcgcagac gatggagaag       2460
ccccagcaag gagagagagc gcagacaatc tagaagctcc agcgaggaga gagatcacag      2520
ccgatctaga agccccaata gcagagtgg ttacagtcga cctagagcct ccagcaagga       2580
gaaagctcat agccgatcta gaaccccag caaagaagga aatcatagcc aatctagaac       2640
ctctagcaag gagagcgacc ccagtcaatc tacagtcccc agaagtcccg actgaagag      2700 atcccctact aggacaagca gtctcagtca gaatagaacc cctagcaaga caagcagcca      2760
ctccccatca acatttccca gtggggcca aaccctaagc caggatgaca gtcaagccga       2820
cgccaccacc tctaaggcca ccttacctgg ggaaaggtct tcatcatctt cttccaagct      2880
ggcgtagccc ccagtctcag ctggctcacg ggtctctgtc atgaccgggg gaggggacag      2940
gagacaggag cagagcagca gctgagcagc gtccctcccc ggccagctct ccacagccac      3000
acctccggcc acaagttctc taatacagga tgttggcagg tagagaggga tgctggatag      3060
ggggaaagga aagacctgtg atgattcaat aaattttac atagcaccca tccccaccaa       3120
gcccaactgt gtgctcactg ctggcatggg gcacagagga ccccagctct gtccctgact      3180
gtctacaggg tcttgactgc aagccctgcc cctctctagg tcttttttt ttttgagaca      3240 gagtctctct ctgttgccca ggctggagtg cagtggtgtg atctcagctc actgcaacct      3300
ccacctccca ggctcaagca attctcctac ctcagcttcc cgagtagctg gaactacaag      3360
tgtgcgtcct cacgcccggc taattttgta tttttagtag agatggggct tcaccatgtt      3420
ggccaggctg gctcgaact cctgacctca ggtgatccac atgcctcaac ctcgcaaagt       3480
gctgggatta taggcatgag ccaccgcacc cgtccccctc tctaggtctt aatttccgca      3540
tgtgggcaac aaggctgcct tctggttctt attcagtggg gtaggagag gtgacactcc       3600 aaatattcaa cagtggggac tggtgtgggc accaatcaga actgagagtg gagcgggacg      3660
gataccaggc cttaaccctt tagttgctgg accatgggga ggtctgggggt tggggaagtg      3720 ttatggggaa aaaaacccct caaactgtgt ttttcctcta ctctcacact atcacaacaa      3780
tcatcaacac agaattctgt gaccaaatgt gtgggctttt tccccacac actacacagc      3840 agacaacagc taggtgtccc ctccgattcc attccaacgc tgtccccaca cccagctaat      3900
ttttgtattt ttggaagaga cagggtttca ccatgttgcc cagagctcaa gcaatctgcc      3960
cacttcagcc ctccaaagtg ctgggattac aggcgtgagc caccacaccc gactttttta      4020
aaaaaataaa aataaggccg ggcgcagtga cccatgcctg taatcccagc actttgggag      4080
gccgaggtgg gcagatcacc tgagctcagg agtttgacac cagcctaggc aacatggcaa      4140
```

```
acttgtctct aaaaaaaaaa aaaaaattac aaaagttagc cggtgtggtg gcatgtgctt    4200
atagtcccag ctacctgaga ggctgaggca ggaggataaa ttgagcctgg aaggtcaagg    4260
ctgcagtgag ccgtgacctt gccactgcac tcaagcctgg atgacccatc ttacaaaaaa    4320 aaaattttg ctggagctgc tcacagaact caaggaaatg cttacttaga tttactggtt    4380
tattatagaa gatattgcaa agaacaaaga tgaagagatg tgtagggcaa ggtataaggg    4440
aaggggcagg gagcttcacg ccctccctgg ggtgctaccc tacaggaacc ctcaggtggt    4500
tagctatgcg gaagctctcc aaacccagtc ctcttgggtt tttacggagg ctttaagaca    4560
gcagcattgg gcatggactt ctctgaaaag tgtcttaaga ccaacaatca agaaggtggg    4620
gaagattaga gtcttgccct gggggcaggaa atggagggca ggaggaggtc agagagattc    4680
tgtttcttca gacctgcccc aggcctaagg tacacaacat tataacaaga gactgtaaca    4740
aaggctgtag gagttaccag ccaggaactg tggatgaaaa ccaatatatt tatatatata    4800
ataccacaag gggggtccaa agtggcagtt agggacaggg agtacttgtg tagcagtgac    4860
acaccaaccc atctggaagt attttaatat ttaaacaatt ggtatggcta tactagtttg    4920
tgattatcag ccttagttct gtatcaattg gcaagatagt gtctaggttt gccacactct    4980
agctgtgtag caccaagcaa agaacttaac ttctctagcc tgtttccttc tctggaagaa    5040 agggcttcc aggccttaac tcacgtactc cccataacta gactgggaat tatctccttt    5100
gtacagatga ggaaacagac acagaggtga taagtgagta gcccaaggtc accatctggt    5160
aagtggatga actaggattg gaagccagac ctttcataaa atgatttctc agctcaaaag    5220 gttttctga agattcagta ggctcactga tagaaattgc tggtgtgtgg ctggtattcc    5280
atcaagagtg gccattacta ctcccacccc tgccctcta taaactccag atgttccaga    5340
cctctcatct ctccctgtgc acacaaggcc ttttcacatc tgtgggtctt agtacaccca    5400
ctgttgctgt caagaatgtc ctcctcctcc tttttttttt tttttttgag atggagtctc    5460
actttgttgc ccaggctgga gtacagtagc gcgatctcag ctcactgcaa cctctaccct    5520
gcatcagcct cccagtagc tgggattaca ggcagccacc accaccatgc ccggctaatt    5580
ttttggtatt tttagtagag acagggtttc attatgtcag ccaggctggt ctcaaactcc    5640
tgacctcagg tgatccattt accttggcct cccagagtgc tgggattaca ggcaagagcc    5700
accacgccca gcctccttc ccctttttg gcctggagaa ctcctttcca cccttcaaag    5760
cccaccacaa acataagaac ctctatactt cttgcccgct gaaatactgc ctctgccagg    5820
aagccttctg tgacttctct ctctccctct tcaccaacgg accgccccg ccccccacca    5880 accccaccac acacacacac cactactgtc ttccactgta ctccctgaca gtagagaacc    5940
aagcagggcc agttgatgca gcctcagcta tatctcttac atgccaaggc ccatgcactg    6000
gggatacaat ggtggaaaat acatggtccc ttcaaagtct ggatgtcaag tttaatgctg    6060
gggactaaag agaaaagctt cagattgaaa cctggaggtg gctggggcaa aggaccattg    6120
gcatcattgg cagggcaact tcctaaagaa agcacctaaa tcttggcttt taaagacaga    6180
tttcataatt ggcagaggag aattctaatg atacccctat gcctacaggg ccccatctaa    6240
tttgggaatt ctactttata ccaagataag attgccagat ttagcaaata aaaacagaag    6300
acatccaatt aatttttttg tttgttttg ggttttttgtt gcggagatgg tgtctcacta    6360
tgttgcgaag gctgctgtca aattcctggc tcaaacaatc ctcctgcctt ggcctcccac    6420
ttcccaaagt gctgggatta caggcatgag ctaccacacc tggcccttat ttatttattt    6480
```

-continued

```
atttaattttt ctttttttggg acggagtgtc actctgtcgc ccaggttgga gcgcagtagc    6540
gcgatctcgg ctcactgcaa cctctgcctc ctgggttcaa gcgattatcc tgccccagcc    6600
tcccaagtag ctgggactac aggcgcgtgc caccatgccc ggctttttt ttttttttt      6660
ttttttttt gagacggagt cttgctctgt cgcccaggct ggagtgcagt ggcacgatct    6720
cggctcactg caagctccgc ctcctgggtt cacgccattc tcctgcctca gcttccgag    6780
tagctgggac tacaggcgcc tgccaccacg cccgactatt ttttgtattt ttagtagaga    6840
tggggtttca ccgtgttagc caggatgatc tcgatctcct gacctcgtga tccacccgcc    6900
tcggcctccc aaagtgctgg gattacaggc gtgagccacc gcgcccagcc tacttattta    6960
tattttttaa gagacagggt ctcgctcagt tgcccaggct ggagtgcagt agggtgatct    7020
gtaggaaagg ggcttccagg ccttaactca tgtactcccc cataaccagg ttgggaggtt    7080
agctcactgt aacctcaaac tcctgtgctc aaggtaccct actagcccct aggagagcag    7140
ctgggactac aggtatgcgc caccatgcca ggcttaattt ttactttttt ttttttttt    7200
tttttttgta gagacggggg tctcactata ttgcccaggc tggtcttgaa ctcctggtct    7260
caagcgatcc tcctgcctta gcctcccaaa gtattggtat cactgcaact agcccaaaga    7320
attaatatag ctatgttcca tgtgatattt gggacatact tttctaaaag gttgtatctt    7380
ttggatataa ttgtttatct gaaattcaaa tttaactaga cattgtatat tttatacggc    7440
aaccacacac ctgggacaat caagacattc cctgaagtta ccaggagaca atgcccatca    7500
gcctacactt ttccaagccc acgtcacaca aggcccttc cagagtattc cagacgtcag    7560
gtagggccat cccttggttc acaagtccca ctcctaccac gcctatggca gccaaactga    7620
aaggcaaaca cagtgctgga gaccccacaa tgccctgggc ctatagcagt caattcccaa    7680
gatgccccgc gtgaacacaa taggcacccg ttccaatgct cgagcaaaga gaccagggca    7740
aaaccttcca ctacgggaca ataacggcca gttcccacaa ttcgttgtgg cagttcttcc    7800
caggatgcct taggcctata gcgaccacct tcccagactc cccgtgtgga agcgctccaa    7860
gcctccagga cggtcagcgg caggtgtggg ataaaaggaa ccggtctcga caaggatctg    7920
ggacactctt tcccaggatg caccaggcct acgactagcg gaccgactcc cacagcgctt    7980
caaggcggag cgctcggttc tcccaggatg ccccagggcg gcacaaacgc gtaggggag    8040
aaaagaagc cctcgggtca ccacggcccc agaccgccgg ctccccggtg acgggagtcg    8100
tcgctcccat catgcagcgg ggccgtagcg cccgcttccc ggcatgcctc gcgcacccct    8160
gcccgggaca ctcaccggcg ccggcggccc ccgctccggc tctgcggcgg cggctgcacg    8220
cccagcctct gcgcctgcgt cgcaagtagg gtaggacagc gcgcagggg cgtgaagagc    8280
ctagggcgct tgcgcggcga gacggactag tcctgtagcg ctgtgggaag aggggctatg    8340
cgcgtcgggc cgtcgacgag acccgcgcgg ggggcgccgt gctttgcccc tcgctgcctg    8400
ggtttacttg gtacagcccg cggcccaaag gaacaagaag ctgaagggtt cgcgcgtgcg    8460
tgtgcggggc aggaacgcgc cttacaaaac tgggatgcgc tgggggtgga gggcgctagt    8520
tcggactgga tcctgggccc gaggcctgct tatttgcata tcctagcgc gggacaatga    8580
aaggcctccc gcactggaag gagtgatttg catattcccc ggagggcct tactccagag    8640
cgcagtgatt agcatatggc gggggcaacc tgagcaaagc gcatgcgcgc agggactgca    8700
gactgacgcg aagtgggtag ccttgtcttc gtagggatc agtttgcatc ctgagagagg    8760
gcacgagggc caggaccct cccaaccagg ataaaggttt attgatctcc taggtgtcag    8820
gccccatgct ggcggattct gtggtttctg cagtgaacca tactcctgta ctcacggcac    8880
```

```
cccagtcgaa ggagatacgc acctaattag acaactacta cccagaaggt cagacctgga   8940
gtgaggaaca caggggactg tgggagccta agaggcgctt gccccggcct ctggttctag   9000
aaagacttcc aggaggtggt gatccttaag ccaagtacga ataggagcca actagaatgg   9060
gaatgggtct ggcagaatga actgcaagcg ccaaggccca gaggccaaaa aaaaaaaaa   9120
aaaaatagaa gcgcatgttt tgattgagga agcaagagca gcttagtatg cctagaacct   9180
aactggagac gggaaatggt tctatagacg atgttagagt tcaactatgg ctacattcca   9240
gtcttcctgt aagtgacttt gtcacattct ggcttaaaac tcccccaaag ggatcccatt   9300
aggaaaaaaa aaaaatccaa aaatctttat catggcctca gggctataca cctggtctgg   9360
ccgtgcttat ctttctgacc ccacctactt cctcctccct ccatttctgt ccagctccac   9420
cttaccccaa actctttacc agctcgggcc tctgctcttg ccgttccctc cgcctgaaaa   9480
tgcttttccc tctgaccttt gaataccctac tcttgtgctc accattcata tcttggtaca   9540
gatgtcaatc tgagaggctt ttcctgatct ctccataata gcacttacac atttgactgg   9600
agttatggat aaatcgggat tggccatgag ttggtggtgg ttgtaactgg catgaagagt   9660
acatggggct gggcgcggtg gctcacgccc gtaatcccag cactttggga ggccgaggct   9720
ggtgtatcac ctgaggtcag gagcttgaga ccagcctggg caacatggtg aaaccctgcc   9780
tctattaaaa ctacaaaaat tagccagggg ttatgggggg tgcctgtaat ccttgctact   9840
tgggaggctg aggcacgaag atcacttgaa ccctggaggc agaggttgca ttgagtcgag   9900
attgagccac tgcactccag cctgggccac ccagcgagac tctgggtctc gcctgtaatc   9960
ccagcacttt gggaggccga ggcgggcgga tcacgtcaga agatcgagac catcctggcc  10020
atcctagacc atttctacta aaatacaaa aaaaaaaaa aaaaaattag ccgggcgtgg   10080
tggcaggcgc ctgtagtccc agctactcgg gaggctgagg caggagaatg gcgtgaacac  10140
gggaggcgga gcttgcagtg atccgagatg gcgctactgc actccagcct gggcgacaga  10200
gcgagacttg gtctcaaaaa aaagagtaca tgggacgtta ttgtcctgtc tactcctgtg  10260
ggtttgaagt tttccataat gacaatggca taccacatca ccatactctg catttatatt  10320
aatagttctt atcacaatct gaactttctt tgcttccttg ttttgagtgt tttcctcatg  10380
aaagcttcat gagggtaaga atggagtcgc ccttttttcac tttgggttct caatgcttag  10440
agcaggatca gatttcagat tagtgtagcg ctgtctttaa cacttaacat ttgcctgttt  10500
tattcaccat ggactctaga actttgagca gcacctggca catcgtaaga ggttattttt  10560
taaagttaga ataatacatc taaaatgtac atgaatgaat gagaggcctg ggatgccaga  10620
ctaaagagct ttgacttggt ctaaaggtga tggggagcta ggcaaaggtt ttgagagttt  10680
aactttaatt caaagttccc ttggagacta atgtctgggg taggggaag ccagggtaag  10740
ggtccgggcc atgaatggg gtagctcagt cgctatcaaa aagacaagac tgtgactatt  10800
tggctgaaga aatggccaaa cccaggtttc tggggaggtc gaggtaccct cagtgaggtc  10860
aggaccttct cctggcctat actgtccacc agcaaccatc acactcctcc ctcccctctc  10920
ccttagttcc cctcccaatg gtacagccct tgacagcagg acagacacac agccacccca  10980
aacacttgtt ctctcctcag tttaatggtg gttagtgaga ttgccaaaac cctctcccat  11040
tcccctcccc accccgtaca aaatgtgtgt gtggtttttt gttttttgtt ttttgttttt  11100
taacaagaaa aaggggcaa aagccaggaa tggggagagg ggggtgcaat ctgatatttt  11160
catacagact tttgattttt taatatatta tatataaaac catgaagacc acgaatcctc  11220
```

```
cccaaactcc tttccccctc cccgggggc  ctggaggaga gatggggaag gccccccag    11280 gagtgggtgg acagagagac aaatatggat gggacagacg ttgggggaga aggtagagag    11340 aagggagcc  caggaacctg gggaaggggg attggagaaa agggttgggg ctgtctccct    11400
cactgccccc atcaaagtta tgacacaaag acacagaatc cctatttcca cgccctcccc    11460
ccacccatcc ccccaccgtg caaacatggc tttgcaaaga agtgcccaga gctctgtgga    11520
actcttacaa tggctggcat ggggtctagg accccaaag  aaatctgtgt tcccctt ccc    11580 tgcccccccc acccttccca gaaactgacc ccctccccac aagacctggt tttgtagcct    11640
aggggccctg gccttccccc agttatcttc cccaacccaa atccctactg ccctcactgg    11700
acttgggggg tctggaccct tggcccctgc cccctggggg acccagacct ctgggccctc    11760
acttctggcc cttacagaga tccaggcatc caacaccccc atccctgccc aagcgtctga    11820
ggtgttagtg gtgggggag  aagcccacca tcccagactc tggtaaatgt ctttgctggt    11880
tccttgcagc tggcagtggg ggggacccca gcccaggccc aggcctaggc ctggggtggg    11940
gatagggtca gatgaagaat tcctctttcc tcttgtgtcc gtcgctgcca ttgaggaagg    12000
cttctcttgc ttctccctgt tcatccaagc cactggcttc gtgggtcaga taggaacctg    12060 aggggggtgac agaccccgg  ggcaggggg  acatatttgt ggatccagga gttggacaga    12120
agtataaggg aagagggaga cagacaagac acatgccagg cgaaggaaga gggagaaacg    12180
gaacacacag ggagaggcag agaaagaggt aaacagtggc agagaaagag gtaaaagcag    12240
aattaggaag actccaaaag ctcaccgaaa gtgccaccct tatcctttct cttggaggta    12300
tttccttgcc ctgctcccag cgaattcagc aattaggaaa ataaattgtt ttattcaaat    12360
ccatgctctt tttttcccct aattttttgt atttttagta gaaaaggggc tgcgccatgg    12420
tgcccaggct ggtctcgacc tcctagcttc tcaagtgctt tatccgcctt ggcctcccaa    12480
cgtgctggga ttacaggcgt gagccaccgc gcccaaccgc aaatctatgc ttttaattca    12540
gcttctaaat tctacccctt ttcgagtatt gtgccgaaag ccccgccccc tttgtcatct    12600
ccgcccccgg tgcggcggga tttggaatcc agagcctagg ctccgccctc tcgttaccct    12660
ggctctaggc cccgcctctt tccgagccct acaaccaacc aaccgtagag tccaggcccc    12720
gtcccactca cccttctgcc gtaccgagca ccagaccatg cccactagca cacatatgat    12780
cagaaacacc agcagcgcca ggatgccgcc cacaatggca tagggaaccg acgtctgagc    12840
ctctaccacc gcaccaggggt ctgccagagg gacacggcac aggaccaggt catcagagga    12900
cgatcccagt ctggccccat cgctgccaag cttttaagcc attctgcaca cgtctaaccg    12960 tgcccttta  tgtgccacac ccctcaaaaa ttactgccac cttgtagtct cttctctttc    13020
cagatgcttg ttggtttgta cactgcccga ccctcccct  gagtcatgtt acatttttcct   13080 tttcttttc  ttgttttctt ttgcagagac ggggtgtctca ctatgtggcc caggctgatc    13140
ttaaactcct gggctcaagc gatcctccgg cctaggcctc ccaaagtact gggattagag    13200
gcgtgagcga ccgcacccag ccatcccttt tcttttgact caagtttctt cctccactaa    13260
gaaacagagt ccaagaaaca ggtccaagtc ccttcccacc ttgtctaaaa cgctccaagt    13320
atttaaagtg ctgggcccaa ctaccaaaat ttctgcccca ccgtcataga gctaaacaca    13380
gaacagctgt gtgctagagc ccattccaac caccttacat atttagttca cataatcttc    13440
acaacagcct tgtttatatag gtgctattgt ttatttccac tttactgatg gtaaactga    13500 ggcgcagaca ggttcggtta cctgcaatag aatgcagcca acccgaattt gagcccccgcg   13560 ggccagtctg gtcccaaaac aaaaagaact ctgttggctg ccgaacccct gagttatgtg    13620
```

```
gcctctttgc tcaagccccg ccccgccac ctggcgcccc gccccgccc tcagtcggcc    13680 gcagcctgct ctcaccgtag accacaagta cgtagagcgc cctcgcatgg ccgtgcttat    13740
tggacgcctc gcaagtgtag gtgccgttat ccgcggatac cagacccggc agcgtgagcg    13800
tctctcccac ggcctccgcc ctctccggca aagactcatt cccgcggttc cagcggatct    13860
ggtttggcct gggtggggat aaagtatagt gagagttagg aaccgaggtg ccagcaccca    13920
attctgactt gtcaagaatc tagacatgca actctcatcc cgcagggacc tccaaataag    13980
aggcttcctg ctatctcttt cctttctgga aaaccaacag tcctgggcct acttccaccc    14040
atcaccaagg tctcaggaat tctagcccag gctgaacatg gtggcttatg cctgcaatcc    14100
cagcacttta ggaggctgag acgggaggac tgcttaaggc cagcagttcc agaccagcct    14160
gggcaacaca gggagacccc gtcactacaa ttaaaaaata ataataataa taataataat    14220
tctagccctc ccacgccatt ccatcctcag caaccaggag tctgaggctg cacagcttca    14280
gtattgggga gtctgagcct ccagattcct cctccctcag gatccaggag tccaggtccc    14340
agatccctat tcgtccaggt ccccagctct ctcctcctca ggacccagga atccaggtcc    14400
tagctccctg tttgtccagg tcctcagctc tctcctcctt aggacccagg agtccaagtc    14460
cctggtccct gttcttccag gtccccagct ttctcctcct gaggacgcag gaggccccca    14520
gagctcacct ggggttcccc gtgacagcac acgtcaacac cagcgtgtct ccctccctca    14580
ccacagcttg ggaggcatga atccggggccg tgggggagtc tgttaggcaa agtaagagg    14640 agagagtagt ttccaagcca tcgcagga caaggggac cctcgcgggt gcgggtggct    14700
ggcgttggga tcccttgggt cctggcccgc cggtcactta cactgcacat ccagcacgta    14760
ctgcgtctgc ttgctgtgtc cggagggcag cgcctggttc tgcgcctcac agatgatgat    14820
accaccgtcg tccttacggt ccacacgaaa ccgtactgtg cttgccacgc tccagaccctt    14880 gccatttttcc tggctgctgc tcactcctgc cacaccccgg tcagacactg tcaggccaca    14940
attccggctc catccaccca cccacccgag ccaacgccaa agcaggctat ttgccaagct    15000
ccacccctta cccacaggcc ccgcctcttg tcctccaagc tacgcccctc ccctaaccaa    15060
gcccacgtgc ctcctcccaa agctcttccc tcttcacgc tcatgctttc tcgtctatca    15120 atccattaa ttgctatata tataaaaaca taaatttata tatatactta gagacagggt    15180
ctcacaatgt tgggcaggtt gaactcctga cctcaagcaa tcctcccatc tcagcctccc    15240
aaagtgctag gactacaggc gtgagccacc gcgctcgaca tcaaccacta catattgaat    15300
gtccagtgtc tgtgaaaacc tgtggctcct ctccacatat aaacaacctc tcctaagtcc    15360
cacctcctcc ccatccttg tcagcactcg gcccagggta cctttcagct ccttgcggtc    15420
ccggtaccag cgcagggtgg cagccggacg ggaccgcgga acgaggcagc tgagctccac    15480
ctcgccgccc tctaccgcct gctcccggac ctccaccaca ggattctctg gggccactgc    15540
cgcagggaga agggaagtaa ggggttaaag aaggcacgaa cgtgggctca aagcgatcga    15600
gctgcctgtt cccagcgacc atagggaacc agggtcccag gtggcagggg tcaaagggga    15660
gaggtcagga gccagatgcc catccaggat gttaaaaata gccatggtct gaaagtctca    15720
ggagaagaga gaagcagaga agaaaggagg agaggatgcg tctgacaagg gggagggcgt    15780
tacctagtac cgtgagcgtg gcaatctggt ggtgggtgtc ttctgtgtag agctggcaga    15840
aatagccccc ctcgtcctcc aggcgggcat ctgagagccg gatccgcacc cggcgtgggg    15900
agaactcctc aagctggaaa cgctcatcct tcaaggctag agagagtgag ggggaaggtg    15960
```

-continued

```
tgaatttcgg gagtcctggc ctcacaagtc ccacccttcc gacaggagct tagagtccag    16020
ccctctgcct cttttctcca gccatatcta tgagtctgag gtgtccaact atttactccc    16080
ttgaggaccc agcattattc aagtcctcct gcctgcagga ccagcagtcc gggaccccag    16140 cccttcttc tccgagaccc aggagaccaa actctcaggt gtgtcctctt tcaggacatg    16200
ggagcctggg ccccagccct ctcttccttt aagactcctg agtctggtcc ccagcactca    16260
ccacgggtgc cattgaagaa gagggtctgc cgggctgggt tctggatgac aactatggac    16320
ccatcatact ggtgcagacg gcaggtgatc tcagccaccc caccctcagc cactgtcacg    16380
ttctctgtct gtacttcctg tcctgccct ggacgattag acaaagagac aggatagaag    16440
acttactgag agctgcaatt caatttttc tttctccctc ttccccatcc aaacctccaa    16500
tccctctctt tccctcatt cattccattg cactgaacat ttcctgcagg ctagagtcca    16560
ggacagggag gaaatctgct ccctactcta aagagctgc agtcaagatt tagtagaata    16620
tgctctaatg agggcagcac agggcacact aggagcccag agcaagggag gactattata    16680
gaattgccta gagagatggg tagccagaga gggctctgca agaaagctcc attggatctg    16740
gatcttaaag agtaagcagg aggctgagcg cggtggctca tgcctgtaat cccagcactt    16800
tgagaggccg aggtgggcgg atcgcaaggt caagagatag agaccatcct ggccaacatg    16860
gtgaaaccct gtcactacta aaatacaaa aaaaaaaaa aaattagctg ggtgtggtgg    16920
tgcgcacctg tagtcccagc tactcgggag gctgaggcag gggaatcgct tgaacccggg    16980
agttggaagt tgcagtgagc cgagatggag ccactgcact ccaggctggg cgacagagcg    17040
agactctgtc tcaaaaaaaa aagaaagaa aaaaagagt aagcaggagt tcacaaggtg    17100
tgggagactg ctgtgtgttc accaagcctc atctttcaca cctgggcaca tgttgtagcc    17160
cgtttgcaaa gatagccgta atattctcct gtccctggac atgccctttg caagttgatt    17220
ttgccattcc tcccattgag aaggcacttt gtccccctact agtctgggta agccttgaga    17280
gttgctttga ccaatagaat tgctagaaag tgatattgag cctaggcctg aagaggcctt    17340
gtagcttcca ctcctgccct aagactgttg catgaagata cccagactag tgtcttttgca    17400 gatgaacaat catggtgaaa gagaagccca gccggcagcc agcaccaatc gccagctgtg    17460
tgagtgtggc catcctggat catccagccc cagctgcccc accagctgac agcagccaca    17520
caagtgaccc cagttgagac caataaaaga tctgcccatc tgatacagcc caaactgctg    17580
aaccccagaa tcatgaacaa ataaggtggt ggttgttta agctcctaag ttgtgggtga    17640
tctgttctac tgctaaagtt aactgataca atacataatt aggctatact tcccagcatc    17700
ctttatagtt aggtggggcc atgtgaccaa ttctggccaa tgggatgtag gtggaagaga    17760
aacacctctt gcagcctgac ccatctccct cataatcctt cacactggct gaacagagag    17820
gactccaagg agcctagagg agggcagaat cacaagccag aaggaacctg ggtctctaac    17880
tgactgtccc ccatgacccg cctgtatagg actgtgtatat gagcaagaaa ataccttttt    17940
tgttaagcca ttgagattc aggggtgtct gttacagcct ttaacctacc ctgattaatc    18000
catcagaaaa acaaggtggg gaatctgaaa ccatcagaga aaagcattta ggaaagctga    18060
aagccaagac taatcatcag cattaatatc atcatctgtt gtcttcaaaa taacaataac    18120
ccccatagct accaattatt aggtacttgc agtgttagtc cctgtgctaa gggcattacc    18180
catataactt accttttaatc ctcacaatcc ctgtgtaagg tagacatgat tattatcatt    18240
attattatta ttttgggaca gagtattgct ctgttgccca ggctggagtg cagtggtgtg    18300
atctcagctc attgaaacct ccacctccca agttcaagcg attcttcagc ctcagcctcc    18360
```

```
caagtagctg gaattacagg catgcaccac catgccgggc taattttttat ttttagtaga    18420
gacagagttt agccatattg gcctggctgg tctcgaactc ctggcctcaa gtgatccgcc    18480
tgcctcagcc tcccaaagtc cagggattac aggtgcgacc caccgcgcct ggccaattat    18540
tattattatt tttaatttga dacaaggtca ggctggagtg cagtggcacg atctcagctc    18600
actgcaatgt ctgcctccca ggctcgagtg atcccacctc agcctcccca gtagctggaa    18660
ctacaggtgc acaacatcac acctggctaa cttttgtatt tttttagaga cggagtttca    18720
ccgtgttgcc caggctggtc ttgaacttgc gagctcaagt gaactgcctg cttcggcctc    18780
ccaaagtgct gggattacag gcatgagcca ctgtgcccgg cctgcgctat tattatcccc    18840
attttgcccg gcctgcgcta ctattatccc cattttcccc catttccatt tttcttttct    18900
tttttttttt tttttttttt tgagacattg tcttgctctg tcgcccaggc tagagtgcag    18960
tggtacgatc tcggctcact gcaacctcca cttcccgggt tcaagcaatt ctcctgcctc    19020
agcctcccaa gtagctggga ttataggcac ctgccactgc acttggctaa tctttgtgtt    19080
tttagtaaag acgggtctc accatcttgg ccaggctggt ctggaactcc tgacctcgtg    19140
atccacccgc ctcggcctcc caaagtgctg ggattacagg cttgagctat cgtgtcctgc    19200
tcccattccc attttatagg tgagaaaatt ggcccacaga gatgaaatga cttgcccaag    19260
ttcacagcca agagtggcag tgccaaaatc ttcgtccaaa tctctgattc tgtatcctga    19320
atctgtatat ccactcctgg ctgtctggat taagtgtcca tcattggcag ggggttgtga    19380
gagccgcttg tgatgggcct cgaatgccaa cctaggagat ttgctttcat cctaagggcc    19440
agtgaaggtt ttgaagcagg aatatgccat gattagatct ggctatttgt ctttaagtgc    19500
tggataacta tccatgtctt ttacattcag gtgctgggtt gcattcattc aggagtattt    19560
cctgagcatc acgtaggttt tcaggggctg agtagtcaga gatgagttag atgaggtccc    19620
tgccctttaa gatttatggg aagtaggaa ccaatcacgg taatcaaaag tgttatgtgg    19680
ctgggcacgg tggctcacac ctgtaatccc agcactttgg gaggccgagg tgggcggatc    19740
acaaggtcag gagttcgaga ccagcctgac caacatggtg aaaccccgtc tgtactaaaa    19800
atacaaaaat tagccaggtg tggtggtggg tgcttgtaat tccagctact caggaggctg    19860
aggcataaga atcgcttgaa cctgggaggc agaggttgca gtgagccaag atcgcgccac    19920
tgcagtccag cctgggtgac agagcaagac tccgtttcaa aaagaaaaa aaaaaagaa    19980
ataaataaaa gaaagtgtta tgttttctgt aagagggtag gtaacctaat ttggaagtta    20040
aggggtagaa aagattattt ctgggggatg gagacagaga cttctggctt cctattctga    20100
catccatttt tccctttctc ctcagtaaaa gaaaagaaca ctggttgtat tttatggttg    20160
cactatgtcc agcagaaaaa ggcattcctc agtctccttg cagcaaggta aagccatctg    20220
ataaaatttt gtccagttgg atataagcca aaatgttgcg tgacaatttt gggaggactt    20280
cctgaaacag gtggacaaac ccttttttcta ctgagtcacc tttgtgccac ctggaactaa    20340
cagtgtgacg cgtggaattt aggcagccat attgaaccat gaggacaaga gcagtgggga    20400
tggcggaacc aagagctgga aggtgcctga gtctctggtg aagatgtgga gctgctgtaa    20460
cagccctcaa ctcctagttc tggacttctt ttatgtttta gtgtaacgct ttgggtattt    20520
ttatttttttt aatttatttt agagatgagg tctcactatg ttgcctaggc tggactcaaa    20580
ctcttatgct caagcagtcc tcctgcctca gcttcatgag tagctgaaac tatagcactt    20640
tgggtatttc agccactgtt tgaggttttt ctagcacctc ctggaatatc aagcttaaca    20700
```

```
tgtccaatcc ttgccccaga tattttcctc cccaaatttt ctcaatctca ataaatgtca    20760
ccaccatcca cctggttgct caggtcaaaa acctagaaat cattcaagtt ctctcccttt    20820
ccctcatccc caatatccat tccatcagca acatctgtcc attctacctc caagacatat    20880
cccagatctc atcacctttg tctgcctctc ctaccctcac tctcatccag catcatccct    20940
cacctggact ctgcaaaagc ctactcgtgg gtctgtctgc atccctgtct gcctcctcca    21000
gggccattct ccacccagtg gccggatcga ttttcaaag aggtaaatca gatcaattca     21060
cctttctgct taaaaccctc cgagggctgc ccgtaacatg tagaataaaa tagaaccccc    21120
ttcccgggga cttcaaggtg ctatatggcc tggcccttg ctgaccttac ttcactctgg     21180
gctcgctagc cttgctgtcc ctcaaacatg ctgagctcgc tcccaccaca gggccttttc    21240
ccttttcttc cttctgcctg gaatgttctt ctccccacct cccaagcccc atcttcccag    21300
ggctgactcc tgttcccatt tgggtctcaa atcatatcag taccttctca gagaggcctt    21360
ccctcactgc tcatcccttc acctttagaa cactttcttt tcttttaaga acaaagtca    21420 gcccagtgcg gtggctcacg cctgtaatac cagcactttt gagaggccaa ggcgggcaga    21480
tcacctcagg tcaggagttc aagaccagcc tggccaacgt ggcgaaaccc cgtctctact    21540 aaaaaatac aaaaattagc taggcagtgg tagcccgggc tactcaggag gctgaggcag     21600
aattgcttga acccaggagg cagaggttgc agtgagccga gattgagcca ctgcacccca    21660
acctgggtga cagagagaga ctctgtctca aaaaaaaaa aaaaaaaag agacagggta      21720 ttgctctgtc acccaggctg gagtgcagtg gtgcaatcat ggctcactgc agcctcgaac    21780
tcctgggctc aagccatcct cccacctcag cctcctaagt agctgagatt ataggctcct    21840
cccaccacac ctggctaatt tttgtgcttt ttgtggagac acagattctc catgttgccc    21900
aggctggtct ccaactcctg ggtcaaagg atcctcctgc ctcggcttcc caaagtgctg     21960
ggattacagg cgtgagccac tgcgcctggc ccagaacact tgctatttcc tcaccattgc    22020
tttatttctt ctatgaagat ttcactggaa ttatcagatt aatttgctta tttgtttact    22080
gtctgtttgt cacccatgac tggaatgtat actctaggaa ggcagggata taatccaatg    22140
ggtttactgc tgcaccccta gtacccagaa gagtgcttgg cacctgataa gtgtctgggg    22200
aacttgctac atgaattaca tgtgtcagat gggatatctg ttcgtctttc ttctctcttt    22260 tttcttctc tctttctctc tctctttctt tctctttctt tcttttttct ttttttgaga    22320
taaggtctcg ctctgtcacc caggctagag tgcagtggtg caatcatggc tcactgcaac    22380
cttgaacatg tgggctcaag cgatcctccc acctcaggct accaaatagc taagactaca    22440
gaggtgcgta gctatgccca gctaattaaa aaaaaaaaa tttttttttt ttttagaga     22500 tgggggtctc aatatcttgc ccaggttggt cttgaactcc taggctcaag caatccccct    22560
gccttggcct cccaaagtgc tgggattata ggcatgagcc attgcagctg gcccagacag    22620
aatctcattt cagcccgaca actttgtgac atcattattt tcatcttaaa cacctaggtt    22680
gatcccagct caaccacttg ccatctgtgt gacctgtggg caagtgacct tacctttcgg    22740
agcctcagtt gccccatcta taaaatggga atgatgccag tgcctgcctc ataaggatga    22800
gccccgctcc tgaagctcag ggagccctct ctgcaaggct gttttagtgc aacctccgga    22860
aacatgccca tgcatgtgaa aactggcatg cacattctgg tgcttttaaa acatctcga    22920 agcctatcca cagatcctgg acctcaagac tggttcagtg ctagcccccc attttacaga    22980
tgtggagaat gaggcttagc gggtcccagg caagtcagtg gcaaaactca ccatctcctg    23040
ggagccatca ggttcctctg gatctgcccc caccaaattt atccctgct ctctgcttga     23100
```

```
gggtgcacat gggtgaggg tgggggtctt ttgttttact ccctccccct cctgaggagt   23160
cagtaaccaa cagtgtctgt gcctggaata ttaatgtctc agcagctttt gtttgggggg   23220
ttgggggtgg tggggcggg actttctggt cagagagggg ctgagctttg gggactgagg   23280
cactggccct ttaaactgtg ttgacagcca ggagtcgtca tggggatggt gcttggaaaa   23340
ggggacaggg agggtttggg aaagagtggc ggagcaggta atgcgtaaga cccaggaatc   23400
cagcccccaa ctacctcctc tcccaggacc caggagtcta ggctcccagc ccctcctcca   23460
tcaggttcca ggagtctgga accccggctt ctttccgcct tagacccagg aattcagccc   23520
ccaaccacct cctctctcag gttcccgaaa tccagacccc tagccccctt ctcgatcagg   23580
acccaggagt ctgggctgtc agcagcccct ccttcaaac ctaggagtca gagcccccag   23640
ccctctccta gcttagacac aggagtctgg gcctccagcc cctcctcct tcaggaccca   23700
ggagccaggg gtccagagta cacagctggt ggatgtttcc acggagacta agcagggtgg   23760
ggggagcgct tcctgggtcc tgagtcagcg aatacccaag ggagtctcaa ggtcatagtt   23820
ccgggaaggt caccaccacc ccctctgtat ccgctcccca gggggctcct ggcatcctgc   23880
ctccttcccc cttcctccct tagggaggtg gtacatccct gcgtcctgac tgaaccccc   23940
tcagccccc atcaatggcg gagtccgaac atcctcgcac aaagcgtcaa ttcttcccca   24000
gctcagcctt gtgaaggcgc ctgtattcgc aggacctagg cgtcagggtc tcagccctc   24060
ctccctcaga aacctgcagt ggaatccccc gcctccagcc ccttcctccc tcaggaccca   24120
ggagtctgta tcctcatccc ttcctccctc aagacctagg agtgtggact cccagccccc   24180
ttttccttcc ggacacagga gttccagccc tcggccctct cctctcttaa acccaggggt   24240
ctaagacccc agcctcctcc tccctcaaac tcaggagtct aagatcccag gcccctcctc   24300
cctcagactc aggagtctaa gatcccaggc ccctcctccc tcagactcag gagtctaaga   24360
ccccaggccc ctcctccctc agactcagga gtctaagatc ccaggcccct cctccctcag   24420
acccaggagt ctaagacccc agccctcct ccctcagact caggagtcta gacccagc    24480
ccctcctccc tcagactcag gagtctaaga ccccagccc ctcctccctg acccaggag   24540
cctaagacct cagcccctc ctccttgaga cccaggagtc taagaccta gctccctcct   24600
cctttagacc cattagtcca ggcccccaga ccctcctcca tcagacccag gagtccaggc   24660
ccccagcccc tcctccatca gatccagccc ctcctctcct gaaaacttt gactctaact   24720
ccccagtcct caaccctag aagcacagtc ctgcctttcc tcaatcctct gtcccctccc   24780
atctggggac ctaggcatca ggtgggggcg taggggtgag tcagcaacct cacacacaaa   24840
gtccccgctg tgccccac attcctggga tattcgggac tccctggatt ccaggcctca   24900
ggcccagcca gggagtgggg agtcccccag aggtcctccc tgggtgtggg gtacgagagg   24960
aattcctgct ccgggaaggg tgcaggcctg cactgagctc cctctgtccg aacctccacg   25020
cccagtgccc tctattcacc ccctcttccc agaagagccc aggctcagca cctgcccctt   25080
gccccactgg gtgcccacgg aggagcctgc gtgcctgctc cctatgggcc tggggtctgc   25140
acaggcggaa atcagtgggt gcttccgttc tgatgccaca ggccattgga tgctggcggg   25200
tctgactgtc tccaggccac cccccacccc tcccagagag agaaagctgc ctttgtgttc   25260
tccaagatgg ggacaggcca ggctcgcacg acattaaccc agcctaggc cccagccctg    25320
ctgtgtctaa ggtcttggaa tccactgcag aacctgaccc ccaccccag gctctgggga   25380
cacaggcgcc tggctcatgg gtgggtgggt ggggggtca gtgatagaaa cctccaaaac   25440
```

```
ctgttccttg gggtgactca caatggaggg agggtccccc tattctcaag agtggctggt   25500
cagaatttta gcaggaaaaa gtgagtcacc ctgggaagga acattatttt agggaccaac   25560
aactgccccc tccacaagac ccctcaactc ctaatagcct ctctattctt tctttgtatt   25620
ggatatctgt ttcctctcct cctttctgtt ctacccagtt tctggctgcg ggtcccattt   25680
ctgcctgggt gcatccctgg gcaggcaacc catccctccc tcttgctttc tctcctctgc   25740
ccaccctgga tccttctttg ggcataaatc tcatcttctt ctgctatgct cagaagatga   25800
atgaaccagg agagagagaa catgttttta aaatggcgca aatgcacccc atctcccccg   25860
attcctgctg gctgggcaag gtgagagagg aagaagtgac taagagagaa atgtgggaac   25920
aacagatacc ccctaaaatg tggtagccaa ggccactgag aaatatccaa tggaaaggag   25980
agcaggaagg gccctccaag accacatgct acagcctcct accccatgct ttacagaacg   26040
ggaaagtaag gcccagagag ggacaaggac tgatgcaaaa ttatactaaa gggtcctggg   26100
taaggcttgg acccaagttc cttagctccc agctgagagc tcttcccatg acaccaagct   26160
cagtttctac tggtaaaagc cacatactat ttactttaga gaaagtttac agagagggtt   26220
agggtgccag gaagcagtga cttggaaatc aaacgaggga cagggctgta gacctaactc   26280
ccagaagcac cagagaaagg cttttgcacg gggcgggtgg tcaccttaag ctatattctg   26340
atcctgagaa ttcaaagtct gatgattcta agctgtcagg attctaaatg tcatagatgt   26400
caagatccag gaactccaag acatcaagat ttcacgattt ttaagacgtc aagatgctag   26460
catgctaaca ccatcacggt tctagaactt taaaggtgtc aagattctaa agccttctgg   26520
attctagaat cctgtagatg tcagcattct aaagtaccat caggttcttt atttactgga   26580
ttcattagtt ccaggattct atgagcctgg tgtttagcct aaaaaataaa gataaattaa   26640
aattgatgga aatgtcactg aggtaccaaa gttctcatct gggaaattgt ggcatgtctg   26700
ttgtaaagaa aggaggtaat gatgcaagtt ctaaagcagt cacagaagac tagagaagaa   26760
agaaagacag tgagaggaca gctttgcccc tcatcctggc cgaggtgagg atggctctgc   26820
ctcaaaccct ggagtgggga acatgtaacc gcactcaact tgccagaaac cccttcacgg   26880
tctgagctgg cgttcccttt catgtcactg agttcaacat cctcacttta cagaaagaga   26940
aacagaagcc tggagagagg aaggtgttta ccattggctg cgatggcaaa tgcaagagc   27000
caagatttaa gcccaggccg ccagccccat gccacctggt tataactcct ctcaccaatc   27060
tctgccgaac acccagccct cctgcttctg cctagccacc ttccaatcct ctgttccttc   27120
caaaagtggc cttatccacc agggaggggt gacccgtggc aggttcaaga cttacacagt   27180
gtgagagtgt gtgtgggtga catttcctga ccttgtcccc attctcaggg tcacccaacc   27240
tcgggggtct ccagcttctc acagtgtgtg atgagggtat gtggatggct ccctggatgt   27300
cctggacagg ggcttctctg tgagtcaagc ctgggtgtgt gaatgggtga gcagggtttg   27360
gagaggcatt cgctgaatcc acgtgtgtgc ctacacgcca aggtccccca ttctcacttc   27420
cccacacaca tgcacacaga tgttcccctc cagggctctt tagaatgccc tgcctgactg   27480
aattcctctt caggggcaca gagggataga gagaggagg aagtaggat gggaatggga   27540
gatcccggga tggaggctgt aagcgtagag agaggaggca cagcagaaag acagggatgg   27600
agatagtggg acagaaagg gggaaagaga caggtgacag aaagggttag agaaacgagt   27660
gacagaaaga caggggacag agacaagggg atgggcaga tagggacag agaaaagggg   27720
acagaaaaac aagggtgaca gcgagacaga gacaggggcc aagaataggg gcagagaggg   27780
aggcagaaa tccgggggaa agagaataga caggatgatg gagggacag agtgacccag   27840
```

-continued

```
gaaaagggga cagagaccag gggacagagg taggggacaa agacagaata gatgaggaac     27900
accgaggcaa gaagagaggg agacagacag aaggagggac aggacttcga gactgaggga     27960
tagaggacaa gggtagggg acgaggagcc agacgggggg gttcagagac gggcggacag      28020
agggacgcag agactggaca gaaggacagc gggaccggcc tggggagggc ggacttgtgt     28080
gtgtaggggg gtctcgggcc ctttgtcccc gccgggatcc agcctgcgcg ggtgggggg     28140 ctgcggcacg gcggccgggc cccgcgcccc ctcccccgct cgtcgctccc ggctcccggc     28200
ccgcgctgcg ctttgtcccg gggagggggc ccggcccggc cccgcgcgca ttgttcggcc     28260
tctgcggccc cgaggctgcc gggctgtcac cacagcgcgc ccccgcccc agcccggccg      28320 gccgaccccg gccccgacc ctacctggcc ccgccgcggc cgcccacagc agcagcagcg      28380
gccactggaa gcgccgggcc cggcccatgg tgccgccgcc gccgccgccg ccgctcgctc     28440
ccggcccggc acctgcaccg cccgcgccgc ccgccccgcc ccccgcgccc cgccccctgc     28500
ccgcccgggg gcgggcgcc gaggccgggg cggggccggg gaggggaggg ggagacggag      28560
gagaggcccg gagacaatcg gggggacggc acggtgggg aacggtgcgg ggtgcgaaag      28620
ctggagagga gagggtgag gagggcggga aggggtgcgc gggagggcga cagcggcgtg      28680
ggagcaggtg ggggatctcg gtgagcgcgg gaaatggagg gtgttgggtg agggtgctgc     28740
gtgcgggccc aggtgctgcg cgcgagggtg cggagttgct ggcatgcagg gtgcttgcgc     28800
tgcgcggagg ggagggtggc agggtgttgc tggaggctgt gcgagggtgg gggcgcgggc     28860
gtcgtggggt gcggtgtgtg cgaagggaga gcgtggccag cgtgacgggg gagcgtaagg     28920
gagggagtgc gacgtgggaa aggtgagtgt gagaggcgtg ctgcgggcag gtgggtgtct     28980
ggagtctagc gagaggctgt gagctgagcc accgggacag gggaggctgc agctggaggt     29040
ccggagggtc cggaggtcga ggcaggtcaa ggatctccca gggcagggcg aggctggggc     29100
tcaggagtgg ggtggggtca gttccctccc tccctctctc ctgtcctgac ctgaaacccc     29160
cgtgtttccg cgtcattctc cgggagggg cccctgaaag tgaactaact ggaaggaagc      29220
ctgaatcctg ggtcccagga gggagaggct cctgtgaaca ccttccaagc cctggcgtcc     29280
cctctcctcc ctgctgtctc cctgccccag cctctctccc tctctctgca tgtatttgcc     29340
tctgcccttc ctctctcccc atctttgagg gtgactcacc cctccagact taggtccctt     29400
ctccctcctg ggagtgggtt tccctgagcc cacttctgtg acaccctgta gacctgatgc     29460
gggatcatta cctatgggac ccagaaagag tgagaaacca tggaaagaag gcctcgacct     29520
ctctcatgcc catttgtcag gcaaactgag gtccagaagt gccaattatg aacatctttc     29580
cttcccccct cccccctccc cgcccagacg gagtctcgct ctgttgccca ggctggagtg     29640
cagtggcacg atctcgactc actgcaacct ctgcctccca ggttccagtg attctcctgc     29700
ctcagcctcc cgagtagctg agattacagg cgcccgccac catgcctagc taatttttat     29760 attttagta gagacggagt tttgccatgc tggccaggct ggtcttgaac tccttacctc      29820
aggtgatcca tctgtctggc ctcccaaagt gctggattac aggcgtgagc caccatgcct     29880
ggctgaaaat ccttactttt tattccgact aaaaaatttt acatccagtc ccacaaggga     29940
cttcagcttc acacacccctt tctgtcctca gtacccagct cccagtatcc tttctgacct     30000
caaaaccata gctaccatca accettgtgt cccaggacca tggctcccag tgtcttctct     30060
gtcctcaggg tccaagctcc catcaactcc tgtgtcctca ggaccacggc tcccagcatc     30120
ctctctgtcc ttcaggtcca agctcccatc aaccctgtg aagcaggacc atggctccca     30180
```

```
gcatcctctc tgtcctcagg gtccaagctc ctatcaactc ctgtgtcccc aggacgatgg    30240
ctccagcaat cctctctgtc ctgagagccc aagcttctaa ctgcccctgt gtccccagat    30300
ccatagccct gagcaacttc cttctttttc agtcctcagc ttcccagctt ctgtagactt    30360
gggaagagat agtctctaat cctctttcca gggctcacat tctgtgactt ttgctagatg    30420
ggagaggaat gtttgatctg cctttggaat actggtccaa ggggtaacta gtagttgcct    30480
tttcccgcag gagccaatag gcccgctcac tctgtgctct gacagatgtc tcctgctcca    30540
gctgaagggg aaccttggga gatgttggtt tggttctcac ctgtcatcct taagtcccac    30600
cattccatgt gaagacatca caagagtagt ggtcctgacg ggcgcgttgg ctcacacctg    30660
taatcccagc actttgggag gccaaggtgg gccgatcact tgaggtcagg agtttgagac    30720
cagcctgacc aaccggccaa catggtgaaa caccatcttt accaaaaaaa aaaaaaaaa    30780 ttagcaaggc gtggtggcac gtgcctgtaa tcccagctgg tcggaaggct gaggcatgag    30840
aatcccctga acttgggagg cagaggttgc agtgagctaa gatcatgcca ctgcactcca    30900
gcctgggtga cagaatgaga ctcagtctaa ataataataa taataataat aataataata    30960
ataataataa taaatagaat agtggtcctg tccccatcct acttcagggt accctgtcca    31020 ttagggatttt agtgcaagtg acagcaagtg caacccaact ggtttgagag aaagagaact    31080
ggttcacaca taacaaaaag tccttctatg gctggctttg gcgaggtctg tcaatctctg    31140
tcctaaggat gcatggctcc cctcctgtag caagatggct ggcagatacc cctggggcca    31200
gattcatatt tggggtgatt aagattctgc aagagagaga caacctttat ttcacacagc    31260
ttttcaattg ttgcctgtcc ctggtgagac tcggagacct agctcttgcc tggtttctaa    31320
actttcaata acaccgtttt tgcttaagtc agcacaaaca gattttattt cttgcaagca    31380
aagattcctg aacaacaact tcagagccgt taacaatgag gtcctgatca caagctatgg    31440
tataggacgt gagaaatttg tccctagcct caatatctgc tggagggcat catggaataa    31500
gtatttctat cctctgatcc ccactgtagg gcatcatggg atatataatc ctaaccttca    31560
atctctgcca tagagtttca taggcaatgc agtcctagcc tcaatatgtt gtagggaatt    31620
atgggaaagg tgaaattatc ctcaattata atacagagca tctcagaaaa tgtcgtttta    31680
gcctcatctc tgctgtaggg catcatggga gatatacttc tggcccaatt tttgttgtaa    31740
gttgccatag aagatgcagt cttccttcc ttcccttttt tcttttcttt ctttctttct    31800 ttttttttt ttttattatg tagagacagg gtctctcgct atgttgccca ggctggtcct    31860
gaactcctgg gctcaagcag ttctcctgcc ttggcctccc aaagtgctgg gattacaggc    31920
aagagccatt gcacccagtc ccttctctcc tttctttctt catcacctgc catattccag    31980
gcactaggaa taaatcatca agtaaataaa cggccttacc ctccctggca attataatgg    32040
ggaaagttag ctaaaaacaa acaaaaatta ctgttccatt taaccatcgc tgaataacaa    32100 aatacccccag aacgtagtgg tgtgaaacaa caaccttta attttatgat tctgtgagtc    32160
aggaattgga gcaggattgg tgtgtatctg cttcatgatg aactggagcc aaaaatgaac    32220
tagctggaac agctggagat ggaggggagg ggcatcaagg gccatatatc taaggctggt    32280
ggttggtgtt gtgggttttg aatagtgtcc tccaagtaaa atatatgttg aagttctagc    32340
ccctggtatc tgtacatgtg accttatttg gaaataaaat ctttgcaaat gtaattcact    32400
tttttgtttg tttgtttgtt tgctcgagac tgagtctcgc tctgtcaccc aggctggagt    32460
gcagtggcat gatctcggct cactgtaacc ttcacctcct gggttcaagc gattctcctg    32520
cctcagcctc ccaagtagct gggattatag gcacgtgtca ccatgcccag ctaattttg    32580
```

```
tattttcagt agggacgggg tttcaccatg ttggccaggc tggtctcgaa ctcctgacct    32640
caaatgatct gccacctcag cctcccaaag tgctgggatt ataggcatgg ggcactgcat    32700
cctgcccaga tgtgattaac ttctaacccc tggtatcttt gcatgtgact ttatttggaa    32760
ataaggtggg ttttttttctt gttttttttt ttttttttga dacagtttca ctttgtcgct    32820
caggctggag ttcagttgca taatctcagc tcactgaaac ctctgcctcc gaggctcaag    32880
cgatcctccc gcctcagtct cccgagtcac tgggactacg gcaagcgcc accacacccg    32940 gctaattgtt gcagtttttg tagagatggg gttttgccat gttgcccagg cggtctccaa    33000
ttgccaccct caagcaattc atccgcctcg gcctcccaga gtgctggaat tataggtgtg    33060
agccatggcg cccggccaga aagtctttgc agatttagtt gaattaatga ctaaatgttt    33120
ccatgctgag ttagagtggg ctctaaatcc aatgattgat atgggggttat aaggagagat    33180 atttggagac atagccacag tcccagggaa ggtggacatt ggaagacaga ggtagggatt    33240
agagtgatgc agctacaagc caaggaatgg caaagattgc tggcagtccc tcagaagcaa    33300
aggagaggca aggaagggtt cttcccctga gactttttt ttttttttttg agacggagtc    33360 tcactgctgt cagcctcagc tggagtgcaa tggcgcgatc tcggctcact gcaacctctg    33420
cctcccaggt tccagcaatt ctcctgcctc agcctcccga gtaactgaga ttacaggcac    33480
ccgccaccat gcctggctag ttttttgcatt tttagtagag atgggatttc accctgttgg    33540
ccaggctggt ctcgaactcc tgacctcagg tgatccaccc gcctcggcct cccaaagtgc    33600
tgggattaca ggtgtcagcc ccggagactt taaaagcatg gctcttcccc tgacgcttta    33660
aaagcgtggc tcttcccgtg agacttcaac accttggttt tggacattta gcattcagaa    33720
ctgtgagaga acaagtttct agtgtgtgtg tgtgtgtgtg tgtgtgtgtg tgtgtgtgtg    33780
tgtgtgtgta tgtgttttag acagaggctc attctgttgc ccaggctgga gtgcagtggt    33840
tcaatctcgg ctcactgcaa actccgcttc tcagattcaa gtgattctta tgcctcagcc    33900
tcccaagtag ctggaattac agaggagcgc catcacagcc ggctattttt tttttttttt    33960
tttgtacttt tagtagagac agggtttcac tgtgttggcc aggctggtct caaattcctg    34020
gcctcaagtg atatgcctgc cttggcctcc caaagtgctg ggattacagg tgtaagccac    34080
cacacctggc ctaagtttct gtgtgtgtgt gtgtgtgttt tgttttgttt tttttttttt    34140
tttgagtgga gtctcgctct gttgcccagg ctggagtgca gtggcatgat ctcgactcac    34200
tgcaagctcc gcctcccggg ttcacgccat tctcctgcct cagcctcccg agtagctggg    34260
actacaggca cccaccacca cgcccagtta attttttgta ttttttaatag tgacagggtt    34320 tcatcatgtt agccaggatg gtctcgatct cctgacctcg tgatccgccc gcctcagcct    34380
cccgaattgc tgggattaca ggcatgagcc accaaacccg gccaagtttc tgtggtttta    34440
agccaccttg cttgtaagat ttgtgtgtgt gtgtttttaa tttttatttt ttaagtatta    34500
tgaatacata atagtggtgt atatttacag gacatatgta atatggtttt gggttttagt    34560
gttttttttt tggagacaga gtctggctct gttgcccagg ctggagtaca gtggtgggat    34620
catggctcac tgcagccttg acctcccggg ctcaagggat cctcctgcct cagcctccca    34680
tgtaactagg accacaggca tgccccacca catccagcca ttttttttt attttttagtg    34740 gagatgaggt ctcactgtgt tgcccaggct gatcttgaac tcctgagctc aagagatctt    34800
cctttctcac cctcccaaag tgctaggact acaggcatga gccactgtgc ctgtccttcc    34860
atgatgtttt gatataggca cacaatgtgt tagtttataa agtttgtaat aatttatcac    34920
```

| | |
|---|---:|
| aggcagccct aggaaactaa tatagccaag tttcctgttt cttctctata tcacatctgc | 34980 |
| tggggctaca tgtccaaggt ggcttcttca cccacttgtc tggtgcctgg gctgagatgg | 35040 |
| ctgaaacatc tggggctcta tctccacatg gcatttatac atgagtagct tgggcttcct | 35100 |
| cacagcatgg tggtctcagg gcagtagtac ttttacatgg caaccagctt ccccagagtg | 35160 |
| agcgttctaa gattcagaaa gtgaaaaatg aaagtttctt aaaacttggt tccagaacat | 35220 |
| agcacagcaa aacttccacc acattctact ggtcaaagca gtcacagagt cactcatatt | 35280 |
| caagaggcag aagtacagac ctcacttctt taagccacta cagtgacagg tggtgatatg | 35340 |
| tcattagaga aagccctaaa caagaacctt gtccctcacc tgcccccaaa taccatggaa | 35400 |
| gatgtctttt ttttttttt tttttttttg gggatagtct cactgtgtca tgcagtggtg | 35460 |
| tgatc | 35465 |

<210> SEQ ID NO 57
<211> LENGTH: 14327
<212> TYPE: DNA
<213> ORGANISM: Homo sapiens

<400> SEQUENCE: 57

| | |
|---|---:|
| ggccggcgag cgggcggctg cgggcggcgc ggagcgggcg gcgcggagcg agcgagcgag | 60 |
| agagcggcgc gggccgggcc atggggtggc gggcgccggg cgcgctgctg ctggcgctgc | 120 |
| tgctgcacgg gcggctgctg cggtgaccc atgggctgag ggcatacgat ggcttgtctc | 180 |
| tgcctgagga catagagacc gtcacagcaa gccaaatgcg ctggacacat tcgtaccttt | 240 |
| ctgatgatga gtacatgctg ctgacagca tctcaggaga cgacctgggc agtggggacc | 300 |
| tgggcagcgg ggacttccag atggtttatt tccgagccct ggtgaatttc actcgctcca | 360 |
| tcgagtacag ccctcagctg gaggatgcag gctccagaga gtttcgagag gtgtccgagg | 420 |
| ctgtggtaga cacgctggag tcggagtact tgaaaattcc cggagaccag gttgtcagtg | 480 |
| tggtgttcat caaggagctg gatggctggg tttttgtgga gctcgatgtg ggctcggaag | 540 |
| ggaatgcgga tggtgctcag attcaggaga tgctgctcag ggtcatctcc agcggctctg | 600 |
| tggcctccta cgtcacctct ccccagggat tccagttccg acgcctgggc acagtgcccc | 660 |
| agttcccaag agcctgcacg gaggccgagt ttgcctgcca cagctacaat gagtgtgtgg | 720 |
| ccctggagta tcgctgtgac cggcggcccg actgcaggga catgtctgat gagctcaatt | 780 |
| gtgaggagcc agtcctgggt atcagcccca cattctctct ccttgtggag acgacatctt | 840 |
| taccgccccg gccagagaca accatcatgc gacagccacc agtcacccac gctcctcagc | 900 |
| ccctgcttcc cggttccgtc aggccctgc cctgtgggcc ccaggaggcc gcatgccgca | 960 |
| atgggcactg catccccaga gactacctct gcgacgaca ggaggactgc gaggacggca | 1020 |
| gcgatgagct agactgtggc cccccgccac cctgtgagcc aacgagttc ccctgcggga | 1080 |
| atggacattg tgccctcaag ctgtggcgct gcgatggtga ctttgactgt gaggaccgaa | 1140 |
| ctgatgaagc caactgcccc accaagcgtc ctgaggaagt gtgcgggccc acacagttcc | 1200 |
| gatgcgtctc taccaacatg tgcatcccag ccagcttcca ctgtgacgag gagcgcgact | 1260 |
| gtcctgaccg gagcgacgag tttggctgca tgccccccca ggtggtgaca cctccccggg | 1320 |
| agtccatcca ggcttcccgg ggccagacag tgacctccac ctgcgtggcc attggcgtcc | 1380 |
| ccaccccat catcaattgg aggctcaact ggggccacat cccctctcat cccagggtga | 1440 |
| cagtgaccag cgagggtggc cgtggcacac tgatcatccg tgatgtgaag gagtcagacc | 1500 |
| agggtgccta cacctgtgag gccatgaacg cccgggggcat ggtgtttggc attcctgacg | 1560 |

-continued

```
gtgtccttga gctcgtccca caacgaggcc cctgccctga cggccacttc tacctggagc    1620
acagcgccgc ctgcctgccc tgcttctgct ttggcatcac cagcgtgtgc cagagcaccc    1680
gccgcttccg ggaccagatc aggctgcgct ttgaccaacc cgatgacttc aagggtgtga    1740
atgtgacaat gcctgcgcag cccggcacgc caccctctc ctccacgcag ctgcagatcg     1800
acccatccct gcacgagttc cagctagtag acctgtcccg ccgcttcctc gtccacgact    1860
ccttctgggc tctgcctgaa cagttcctgg gcaacaaggt ggactcctat ggcggctccc    1920
tgcgttacaa cgtgcgctac gagttggccc gtggcatgct ggagccagtg cagcggccgg    1980
acgtggtcct cgtgggtgcc gggtaccgcc tcctctcccg aggccacaca cccacccaac    2040
ctggtgctct gaaccagcgc caggtccagt tctctgagga gcactgggtc catgagtctg    2100
gccggccggt gcagcgcgcg gagctgctgc aggtgctgca gagcctggag gccgtgctca    2160
tccagaccgt gtacaacacc aagatggcta gcgtgggact tagcgacatc gccatggata    2220
ccaccgtcac ccatgccacc agccatggcc gtgcccacag tgtggaggag tgcagatgcc    2280
ccattggcta ttctggcttg tcctgcgaga gctgtgatgc ccacttcact cgggtgcctg    2340
gtgggcccta cctgggcacc tgctctggtt gcagttgcaa tggccatgcc agctcctgtg    2400
accctgtgta tggccactgc ctgaattgcc agcacaacac ggaggggcca cagtgcaaca    2460
agtgcaaggc tggcttcttt ggggacgcca tgaaggccac ggccacttcc tgccggccct    2520
gcccttgccc atacatcgat gcctcccgca gattctcaga cacttgcttc ctggacacgg    2580
atggccaagc cacatgtgac gcctgtgccc aggctacac tggccgccgc tgtgagagct     2640
gtgccccgg atacgagggc aaccccatcc agcccggcgg gaagtgcagg cccgtcaacc    2700
aggagattgt gcgctgtgac gagcgtggca gcatggggac ctccggggag gcctgccgct    2760
gtaagaacaa tgtggtgggg cgcttgtgca atgaatgtgc tgacggctct ttccacctga    2820
gtacccgaaa ccccgatggc tgcctcaagt gcttctgcat gggtgtcagt cgccactgca    2880
ccagctcttc atggagccgt gcccagttgc atggggcctc tgaggagcct ggtcacttca    2940
gcctgaccaa cgccgcaagc acccacacca ccaacgaggg catcttctcc cccacgcccg    3000
gggaactggg attctcctcc ttccacagac tcttatctgg accctacttc tggagcctcc    3060
cttcacgctt cctggggac aaggtgacct cctatggagg agagctgcgc ttcacagtga     3120
cccagaggtc ccagccgggc tccacacccc tgcacgggca gccgttggtg gtgctgcaag    3180
gtaacaacat catcctagag caccatgtgg cccaggagcc cagcccggc cagcccagca     3240
ccttcattgt gccttttccgg gagcaagcat ggcagcggcc cgatgggcag ccagccacac   3300
gggagcacct gctgatggca ctggcaggca tcgacaccct cctgatccga gcatcctacg    3360
cccagcagcc cgctgagagc agggtctctg gcatcagcat ggacgtggct gtgcccgagg    3420
aaaccggcca ggacccgcgc ctggaagtgg aacagtgctc ctgccacccc gggtaccgtg    3480
ggccgtcctg ccaggactgt gacacaggct acacgcac gcccagtggc ctctacctgg      3540
gtacctgtga acgctgcagc tgccatggcc actcagaggc ctgcgagcca gaaacaggtg    3600
cctgccaggg ctgccagcat cacacggagg gccctcggtg tgagcagtgc agccaggat     3660
actacgggga cgcccagcgg gggacaccac aggactgcca gctgtgcccc tgctacggag    3720
accctgctgc cggccaggct gcccacactt gttttctgga cacagacggc caccccacct    3780
gtgatcgtg ctcccaggc cacagtgggc gtcactgtga gaggtgcgcc cctggctact       3840
atggcaaccc cagccagggc cagccatgcc agagagacag ccaggtgcca gggcccatag    3900
```

-continued

```
gctgcaactg tgaccccaa ggcagcgtca gcagccagtg tgatgctgct ggtcagtgcc    3960
agtgcaaggc ccaggtagaa ggcctcactt gcagccactg ccggcccac cacttccacc    4020 tgagtgccag caacccagac ggctgcctgc cctgcttctg tatgggcatc acccagcagt    4080
gcgccagctc tgcctacaca cgccacctga tctccaccca ctttgcccct ggggacttcc    4140
aaggctttgc cctggtgaac ccacagcgaa acagccgcct gacaggagaa ttcactgtgg    4200
aacccgtgcc cgagggtgcc cagctctctt ttggcaactt gcccaactc ggccatgagt    4260 ccttctactg gcagctgccg gagacatacc agggagacaa ggtggcggcc tacggtggga    4320
agttgcgata caccctctcc tacacagcag gcccacaggg cagcccactc tcggaccccg    4380
atgtgcagat cacgggcaac aacatcatgc tagtggcctc ccagccagcg ctgcagggcc    4440
cagagaggag gagctacgag atcatgttcc gagaggaatt ctggcgccgg cccgatgggc    4500
agccggccac acgcgagcac ctcctgatgg cactggccga cctggatgag ctcctgatcc    4560
gggccacgtt ctcctccgtg ccgctggtgg ccagcatcag cgcagtcagc ctggaggtcg    4620
cccagccggg gccctcaaac agacccgcg ccctcgaggt ggaggagtgc cgctgcccgc    4680
caggctacat cggtctgtcc tgccaggact gtgcccccgg ctacacgcgc accgggagtg    4740
ggctctacct cggccactgc gagctatgtg aatgcaatgg ccactcagac ctgtgccacc    4800
cagagactgg ggcctgctcg caatgccagc acaacgccgc aggggagttc tgcgagcttt    4860
gtgcccctgg ctactacgga gatgccacag ccgggacgcc tgaggactgc cagccctgtg    4920
cctgcccact gaccaaccca gagaacatgt tttcccgcac ctgtgagagc ctgggagccg    4980
gcgggtaccg ctgcacggcc tgcgaacccg gctacactgg ccagtactgt gagcagtgtg    5040
gcccaggtta cgtgggtaac cccagtgtgc aaggggggcca gtgcctgcca gagacaaacc    5100
aagccccact ggtggtcgag gtccatcctg ctcgaagcat agtgccccaa ggtggctccc    5160
actccctgcg gtgtcaggtc agtgggagcc caccccacta cttctattgg tcccgtgagg    5220
atgggcggcc tgtgcccagc ggcacccagc agcgacatca aggctccgag ctccacttcc    5280
ccagcgtcca gccctcggat gctggggtct acatttgcac ctgccgtaat ctccaccaat    5340
ccaataccag ccgggcagag ctgctggtca ctgaggctcc aagcaagccc atcacagtga    5400
ctgtggagga gcagcggagc cagagcgtgc gccccggagc tgacgtcacc ttcatctgca    5460
cagccaaaag caagtcccca gcctataccc tggtgtggac ccgcctgcac aacgggaaac    5520
tgcccacccg agccatggat ttcaatggca tcctgaccat cgcaacgtc cagctgagtg    5580 atgcaggcac ctacgtgtgc accggctcca acatgtttgc catggaccag ggcacagcca    5640
ctctacatgt gcaggcctcg ggcaccttgt ccgcccccgt ggtctccatc catccgccac    5700
agctcacagt gcagcccggg caactggcgg agttccgctg cagcgccaca gggagcccca    5760 cgcccacccct cgagtggaca gggggccccg gcggccagct ccctgcgaag gcacaaatcc    5820
acggcggcat cctgcgcctg ccagctgtcg agccacgga tcaggcccag tacttgtgcc    5880
gagcccacag cagcgctggg cagcaggtgg ccagggctgt gctccacgtg catggggcg    5940 gtgggcccag agtccaagtg agcccagaga ggacccaggt ccacgcaggc cggaccgtca    6000
ggctgtactg cagggctgca ggcgtgccta cgccaccat cacctggagg aaggaagggg    6060
gcagcctccc accacaggcc cggtcagagc gcacagacat cgcgacactg ctcatcccag    6120
ccatcacgac tgctgacgcc ggcttctacc tctgcgtggc caccagccct gcaggcactg    6180
cccaggcccg gatgcaagtg gttgtccttt cagcctcaga tgccagccca ccgggggtca    6240
agattgagtc ctcatcgcct tctgtgacag aagggcaaac actcgacctc aactgtgtgg    6300
```

```
tggcagggtc agcccatgcc caggtcacct ggtacaggcg aggggggtagc ctgcctcccc   6360
acacccaggt gcacggctcc cgtctgcggc tcccccaggt ctcaccagct gattctggag   6420
aatatgtgtg ccgtgtggag aatggatcgg cccccaagga ggcctccatt actgtgtctg   6480
tgctccacgg cacccattct ggccccagct acaccccagt gcccggcagc acccggccca   6540
tccgcatcga gccctcctcc tcacacgtgg cggaagggca gaccctggat ctgaactgcg   6600
tggtgcccgg gcaggcccac gcccaggtca cgtggcacaa gcgtggggggc agcctccctg   6660
cccggcacca gacccacggc tcgctgctgc ggctgcacca ggtgacccccg ccgactcag   6720
gcgagtatgt gtgccatgtg gtgggcacct ccggccccct agaggcctca gtcctggtca   6780
ccatcgaagc ctctgtcatc cctggaccca tcccacctgt caggatcgag tcttcatcct   6840
ccacagtggc cgagggccag accctggatc tgagctgcgt ggtggcaggg caggcccacg   6900
cccaggtcac atggtacaag cgtgggggca gcctccctgc ccggcaccag gttcgtggct   6960
cccgcctgta catcttccag gcctcacctg ccgatgcggg acagtacgtc tgccgggcca   7020
gcaacggcat ggaggcctcc atcacggtca cagtaactgg gacccagggg gccaacttag   7080
cctaccctgc cggcagcacc cagcccatcc gcatcgagcc ctcctcctcg caagtggcgg   7140
aagggcagac cctggatctg aactgcgtgg tgcccgggca gtcccatgcc caggtcacgt   7200
ggcacaagcg tgggggcagc ctccctgtcc ggcaccagac ccacggctcc ctgctgagac   7260
tctaccaagc gtccccccgcc gactcgggcg agtacgtgtg ccgagtgttg ggcagctccg   7320
tgcctctaga ggcctctgtc ctggtcacca ttgagcctgc gggctcagtg cctgcacttg   7380
gggtcacccc cacggtccgg atcgagtcat cgtcttcgca agtggccgag gggcagaccc   7440
tggacctgaa ctgcctcgtt gctggtcagg cccatgccca ggtcacgtgg cacaagcgcg   7500
ggggcagcct cccggcccgg caccaggtgc atggctcgag gctacgcctg ctccaggtga   7560
cccccagctga ttcaggggag tacgtgtgcc gtgtggtcgg cagctcaggt acccaggaag   7620
cctcagtcct tgtcaccatc agcagcgcc ttagtggctc ccactcccag ggtgtggcgt   7680
accccgtccg catcgagtcc tcctcagcct ccctggccaa tggacacacc ctggacctca   7740
actgcctggt tgccagccag gctccccaca ccatcacctg gtataagcgt ggaggcagct   7800
acccagccg gcaccagatc gtgggctccc ggctgcggat ccctcaggtg actccggcag   7860
actcgggcga gtacgtgtgt cacgtcagta acggtgcagg ctcccgggag acctcgctca   7920
tcgtcaccat ccaggcagc ggttcctccc acgtgcccag cgtctcccca ccgatcagga   7980
tcgagtcgtc ttcccccacg gtggtggaag ggcagacctt ggatctgaac tgcgtggtcg   8040
ccaggcagcc ccaggctatc atcacatggt acaagcgtgg gggcagcctt ccctcccgac   8100
accagaccca tggctcccac ctgcggttgc accaaatgtc tgtggctgac tcgggcgagt   8160
atgtgtgccg ggccaacaac aacatcgatg ccctggaggc ctccatcgtc atctccgtct   8220
cccctagcgc cggcagcccc tccgcccctg gcagctccat gcccatcaga attgagtcat   8280
cctcctcaca cgtggccgaa gggagagaccc tggatctgaa ctgcgtggtc cccgggcagg   8340
cccatgccca ggtcacttgg cacaagcgtg ggggcagcct cccagtcac catcagaccc   8400
gcggctcacg gctgcggctg caccatgtgt ccccggccga ctcgggtgaa tacgtgtgcc   8460
gggtgatggg cagctctggc cccctggagg cctcagtcct ggtcaccatc gaagcctctg   8520
gctcaagtgc tgtccacgtc cccgcccag gtggagcccc accatccgc atcgagccct   8580
cctcctcccg agtggcagaa gggcagaccc tggatctgaa gtgcgtggtg cccgggcagg   8640
```

```
cccacgccca ggtcacatgg cacaagcgtg gaggaaacct ccctgcccgg caccaggtcc    8700
acggcccact gctgaggctg aaccaggtgt ccccggctga ctctggcgag tactcgtgcc    8760
aagtgaccgg aagctcaggc accctggagg catctgtcct ggtcacaatt gagccctcca    8820
gcccaggacc cattcctgct ccaggactgg gccagcccat ctacatcgag gcctcctctt    8880
cacacgtgac tgaagggcag actctggatc tgaactgtgt ggtgcccggg caggcccatg    8940
cccaggtcac gtggtacaag cgcgggggca gcctccccgc ccggcaccag acccatggct    9000
cccagctgcg gctccacctc gtctcccctg ccgactcagg cgagtatgtg tgtcgtgcag    9060
ccagcggccc aggccctgag caagaagcct ccttcacagt caccgtcccg cccagtgagg    9120
ggtcttccta ccgccttagg agcccggtca tctccatcga cccgcccagc agcaccgtgc    9180
agcagggcca ggatgccagc ttcaagtgcc tcatccatga cggggcagcc cccatcagcc    9240
tcgagtggaa gacccggaac caggagctgg aggacaacgt ccacatcagt cccaatggct    9300
ccatcatcac catcgtgggc acccggccca gcaaccacgg tacctaccgc tgcgtggcct    9360
ccaatgccta cggtgtggcc cagagtgtgg tgaacctcag tgtgcacggg cccctacag    9420 tgtccgtgct ccccgagggc cccgtgtggg tgaaagtggg aaaggctgtc accctggagt    9480
gtgtcagtgc cggggagccc cgctcctctg ctcgttggac ccggatcagc agcaccctg    9540 ccaagttgga gcagcggaca tatgggctca tggacagcca cgcggtgctg cagatttcat    9600
cagctaaacc atcagatgcg ggcacttatg tgtgccttgc tcagaatgca ctaggcacag    9660
cacagaagca ggtggaggtg atcgtggaca cgggcgccat ggccccaggg gcccctcagg    9720
tccaagctga agaagctgag ctgactgtgg aggctggaca cacggccacc ttgcgctgct    9780
cagccacagg cagccccgcg cccaccatcc actggtccaa gctgcgttcc ccactgccct    9840
ggcagcaccg gctggaaggt gacacactca tcatacccg ggtagcccag caggactcgg    9900
gccagtacat ctgcaatgcc actagccctg ctgggcacgc tgaggccacc atcatcctgc    9960
acgtggagag cccaccatat gccaccacgg tcccagagca cgcttcggtg caggcagggg   10020
agacggtgca gctccagtgc ctggctcacg ggacaccccc actcaccttc agtggagcc   10080 gcgtgggcag cagccttcct gggagggcga ccgccaggaa cgagctgctg cactttgagc   10140
gtgcagcccc tgaggactca ggccgctacc gctgccgggt caccaacaag gtgggctcag   10200
ccgaggcctt tgcccagctg ctcgtccaag gccctcccgg ctctctccct gccacctcca   10260
tcccagcagg gtccacgccc accgtgcagg tcacgcctca gctagagacc aagagcattg   10320
gggccagcgt tgagttccac tgtgctgtgc ccagcgacca gggtacccag ctccgttggt   10380
tcaaggaagg gggtcagctg cctccgggtc acagcgtgca ggatgggtg ctccgaatcc   10440 agaacttgga ccagagctgc caagggacgt atatatgcca ggcccatgga ccttggggga   10500
aggcccaggc cagtgcccag ctggttatcc aagccctgcc ctcggtgctc atcaacatcc   10560
ggacctctgt gcagaccgtg gtggttggcc acgccgtgga gttcgaatgc ctggcactgg   10620
gtgaccccaa gcctcaggtg acatggagca agttggagg gcacctgcgg ccaggcattg   10680
tgcagagcgg aggtgtcgtc aggatcgccc acgtagagct ggctgatgcg ggacagtatc   10740
gctgcactgc caccaacgca gctggcacca caatccca cgtcctgctg cttgtgcaag   10800
ccttgcccca gatctcaatg ccccaagaag tccgtgtgcc tgctggttct gcagctgtct   10860
tcccctgcat agcctcaggc tacccccactc ctgacatcag ctggagcaag ctggatggca   10920
gcctgccacc tgacagccgc ctggagaaca acatgctgat gctgccctca gtccgacccc   10980
aggacgcagg tacctacgtc tgcaccgcca ctaaccgcca gggcaaggtc aaagcctttg   11040
```

```
cccacctgca ggtgccagag cgggtggtgc cctacttcac gcagaccccc tactccttcc   11100
taccgctgcc caccatcaag gatgcctaca ggaagttcga gatcaagatc accttccggc   11160
ccgactcagc cgatgggatg ctgctgtaca atgggcagaa gcgagtccca gggagcccca   11220
ccaacctggc caaccggcag cccgacttca tctccttcgg cctcgtgggg ggaaggcccg   11280
agttccggtt cgatgcaggc tcaggcatgg ccaccatccg ccatcccaca ccactggccc   11340
tgggccattt ccacaccgtg accctgctgc gcagcctcac ccagggctcc ctgattgtgg   11400
gtgacctggc cccggtcaat gggacctccc agggcaagtt ccaggcctg gatctgaacg    11460 aggaactcta cctgggtggc tatcctgact atggtgccat ccccaaggcg gggctgagca   11520
gcggcttcat aggctgtgtc cgggagctgc gcatccaggg cgaggagatc gtcttccatg   11580
acctcaacct cacggcgcac ggcatctccc actgcccac ctgtcgggac cggccctgcc    11640
agaatggcgg tcagtgccat gactctgaga gcagcagcta cgtgtgcgtc tgcccagctg   11700
gcttcaccgg gagccgctgt gagcactcgc aggccctgca ctgccatcca gaggcctgtg   11760
ggcccgacgc cacctgtgtg aaccggcctg acggtcgagg ctacacctgc cgctgccacc   11820
tgggccgctc ggggttgcgg tgtgaggaag gtgtgacagt gaccacccc tcgctgtcgg    11880 gtgctggctc ctacctggca ctgcccgccc tcaccaacac acaccacgag ctacgcctgg   11940
acgtggagtt caagccactc gcccctgacg gggtcctgct gttcagcggg gggaagagcg   12000
ggcctgtgga ggacttcgtg tccctggcga tggtgggcgg ccacctggag ttccgctatg   12060
agttggggtc agggctggcc gttctgcgga gcgccgagcc gctggccctg ggccgctggc   12120
accgtgtgtc tgcagagcgt ctcaacaagg acggcagcct gcgggtgaat ggtggacgcc   12180
ctgtgctgcg ctcctcgccc ggcaagagcc agggcctcaa cctgcacacc ctgctctacc   12240 tgggggggtgt ggagccttcc gtgccactgt ccccggccac caacatgagc gctcacttcc  12300
gcggctgtgt gggcgaggtg tcagtgaatg caaacggct ggacctcacc tacagtttcc    12360
taggcagcca gggcatcggg caatgctatg atagctcccc atgtgagcgc cagccttgcc   12420
aacatggtgc cacgtgcatg cccgctggcg agtatgagtt ccagtgcctg tgtcgagatg   12480
gattcaaagg agacctgtgt gagcacgagg agaaccctg ccagctccgt gaaccctgtc    12540
tgcatggggg cacctgccag ggcacccgct gcctctgcct ccctggcttc tctgccccac   12600
gctgccaaca aggctctgga catggcatag cagagtccga ctggcatctt gaaggcagcg   12660
ggggcaatga tgcccctggg cagtacggag cctatttcca cgatgatggc ttcctcgcct   12720
tccctggcca tgtcttctcc aggagcctgc ccgaggtgcc cgagaccatc gagctggagg   12780
ttcggaccag cacagccagt ggcctcctgc tctggcaggg tgtggaggtg ggagaggccg   12840
gccaaggcaa ggacttcatc agcctcgggc ttcaagacgg gcaccttgtc ttcaggtacc   12900
agctgggtag tggggaggcc cgcctggtct ctgaggaccc catcaatgac ggcgagtggc   12960
accgggtgac agcactgcgg gagggccgca gaggttccat ccaagtcgac ggtgaggagc   13020
tggtcagcgg ccggtcccca ggtcccaacg tggcagtcaa cgccaagggc agcgtctaca   13080
tcggcggagc ccctgacgtg gccacgctga ccgggggcag attctcctcg ggcatcacag   13140
gctgtgtcaa gaacctggtg ctgcactcgg cccgacccgg cgcccgccc ccacagcccc    13200 tggacctgca gcaccgcgcc caggccgggg ccaacacacg cccctgcccc tcgtaggcac   13260
ctgcctgccc cacacggact cccggggcac gccccagccc gacaatgtcg agtatattat   13320
tattaatatt attatgaatt tttgtaagaa accgaggcga tgccacgctt tgctgctacc   13380
```

```
gccctgggct ggactggagg tgggcatgcc accctcacac acacagctgg gcaaagccac   13440
aaggctggcc agcaaggcag gttggatggg agtgggcacc tcagaaagtc accaggactt   13500
ggggtcagga acagtggctg ggtgggccca gaactgcccc cactgtcccc ctacccaccg   13560
atggagcccc cagatagagc tgggtggcct gtttctgcag cccttgggca gttctcactc   13620
ctaggagagc caacctcggc ttgtgggctg gtgccccaca gctacctgag acgggcatcg   13680
caggagtctc tgccacccac tcaggattgg gaattgtctt tagtgccggc tgtggagcaa   13740
aaggcagctc accctgggc aggcggtccc catccccacc agctcgtttt tcagcacccc    13800
cacccacctc cacccagccc ctggcacctc tctggcaga ctcccctcc taccacgtcc     13860 tcctggcctg cattcccacc ccctcctgcc agcacacagc ctgggtccc tccctcaggg    13920 gctgtaaggg aaggcccacc ccaactctta ccaggagctg ctacaggcag agcccagcac   13980
tgatagggcc ccgcccaccg ggccccgccc accccaggcc acatccccac ccatctggaa   14040
gtgaaggccc agggactcct ccaacagaca acggacggac ggatgccgct ggtgctcagg   14100
aagagctagt gccttaggtg ggggaaggca ggactcacga ctgagagaga gaggaggggg   14160
atatgaccac cctgccccat ctgcaggagc ctgaagatcc agctcaagtg ccatcctgcc   14220
agtggccccc agactgtggg gttgggacgc ctggcctctg tgtcctagaa gggacccctcc  14280 tgtggtcttt gtcttgattt ttcttaataa acggtgctat ccccgcc                14327
```

<210> SEQ ID NO 58
<211> LENGTH: 15
<212> TYPE: PRT
<213> ORGANISM: Homo sapiens

<400> SEQUENCE: 58

Ile Pro Thr Gly Glu Pro Cys Pro Glu Pro Leu Arg Thr Tyr Gly
1               5                   10                  15

<210> SEQ ID NO 59
<211> LENGTH: 13
<212> TYPE: PRT
<213> ORGANISM: Homo sapiens

<400> SEQUENCE: 59

Ile Glu Ser Val Leu Ser Ser Ser Gly Lys Arg Leu Gly
1               5                   10

<210> SEQ ID NO 60
<211> LENGTH: 18
<212> TYPE: PRT
<213> ORGANISM: Homo sapiens

<400> SEQUENCE: 60

Ala Thr Pro Ala Gln Ala His Leu Lys Lys Pro Ser Gln Leu Ser Ser
1               5                   10                  15

Phe Ser

<210> SEQ ID NO 61
<211> LENGTH: 15
<212> TYPE: PRT
<213> ORGANISM: Homo sapiens

<400> SEQUENCE: 61

Arg Ile Gln Ala Met Ile Pro Lys Gly Ala Leu Arg Val Ala Val
1               5                   10                  15

```
<210> SEQ ID NO 62
<211> LENGTH: 15
<212> TYPE: PRT
<213> ORGANISM: Homo sapiens

<400> SEQUENCE: 62

Gly Ile Cys Gln Cys Leu Ala Glu Arg Tyr Ser Val Ile Leu Leu
 1               5                  10                  15

<210> SEQ ID NO 63
<211> LENGTH: 17
<212> TYPE: PRT
<213> ORGANISM: Homo sapiens

<400> SEQUENCE: 63

Glu Lys Met His Glu Gly Asp Glu Gly Pro Gly His His His Lys Pro
 1               5                  10                  15

Gly

<210> SEQ ID NO 64
<211> LENGTH: 13
<212> TYPE: PRT
<213> ORGANISM: Homo sapiens

<400> SEQUENCE: 64

Asp Leu Gln Asn Phe Leu Lys Lys Glu Asn Lys Asn Glu
 1               5                  10

<210> SEQ ID NO 65
<211> LENGTH: 19
<212> TYPE: PRT
<213> ORGANISM: Homo sapiens

<400> SEQUENCE: 65

Val Lys Leu Gly His Pro Asp Thr Leu Asn Gln Gly Glu Phe Lys Glu
 1               5                  10                  15

Leu Val Arg

<210> SEQ ID NO 66
<211> LENGTH: 48
<212> TYPE: DNA
<213> ORGANISM: Homo sapiens
<220> FEATURE:
<221> NAME/KEY: misc_feature
<222> LOCATION: 6
<223> OTHER INFORMATION: n is a or g or c or t
<220> FEATURE:
<221> NAME/KEY: misc_feature
<222> LOCATION: 27
<223> OTHER INFORMATION: n is a or g or c or t
<220> FEATURE:
<221> NAME/KEY: misc_feature
<222> LOCATION: 36
<223> OTHER INFORMATION: n is a or g or c or t
<220> FEATURE:
<221> NAME/KEY: misc_feature
<222> LOCATION: 39
<223> OTHER INFORMATION: n is a or g or c or t
<220> FEATURE:
<221> NAME/KEY: misc_feature
<222> LOCATION: 42
<223> OTHER INFORMATION: n is a or g or c or t
<220> FEATURE:
<221> NAME/KEY: misc_feature
<222> LOCATION: 48
<223> OTHER INFORMATION: n is a or g or c or t

<400> SEQUENCE: 66
```
ttywsntggg ayaaytgytt ygarggnaar gayccngcng tnathmgn        48

<210> SEQ ID NO 67
<211> LENGTH: 48
<212> TYPE: DNA
<213> ORGANISM: Homo sapiens
<220> FEATURE:
<221> NAME/KEY: misc_feature
<222> LOCATION: 6
<223> OTHER INFORMATION: n is a or g or c or t
<220> FEATURE:
<221> NAME/KEY: misc_feature
<222> LOCATION: 9
<223> OTHER INFORMATION: n is a or g or c or t
<220> FEATURE:
<221> NAME/KEY: misc_feature
<222> LOCATION: 12
<223> OTHER INFORMATION: n is a or g or c or t
<220> FEATURE:
<221> NAME/KEY: misc_feature
<222> LOCATION: 18
<223> OTHER INFORMATION: n is a or g or c or t
<220> FEATURE:
<221> NAME/KEY: misc_feature
<222> LOCATION: 27
<223> OTHER INFORMATION: n is a or g or c or t
<220> FEATURE:
<221> NAME/KEY: misc_feature
<222> LOCATION: 30
<223> OTHER INFORMATION: n is a or g or c or t
<220> FEATURE:
<221> NAME/KEY: misc_feature
<222> LOCATION: 33
<223> OTHER INFORMATION: n is a or g or c or t
<220> FEATURE:
<221> NAME/KEY: misc_feature
<222> LOCATION: 39
<223> OTHER INFORMATION: n is a or g or c or t
<220> FEATURE:
<221> NAME/KEY: misc_feature
<222> LOCATION: 45
<223> OTHER INFORMATION: n is a or g or c or t
<220> FEATURE:
<221> NAME/KEY: misc_feature
<222> LOCATION: 48
<223> OTHER INFORMATION: n is a or g or c or t

<400> SEQUENCE: 67
taywsnytnc cnaarwsnga rttygcngtn ccngayytng arytnccn        48

<210> SEQ ID NO 68
<211> LENGTH: 16
<212> TYPE: PRT
<213> ORGANISM: Homo sapiens

<400> SEQUENCE: 68

Phe Ser Trp Asp Asn Cys Phe Glu Gly Lys Asp Pro Ala Val Ile Arg
 1               5                  10                  15

<210> SEQ ID NO 69
<211> LENGTH: 585
<212> TYPE: DNA
<213> ORGANISM: Homo sapiens
<220> FEATURE:
<221> NAME/KEY: misc_feature
<222> LOCATION: 6
<223> OTHER INFORMATION: n is a or g or c or t
<220> FEATURE:
<221> NAME/KEY: misc_feature
<222> LOCATION: 9
<223> OTHER INFORMATION: n is a or g or c or t
<220> FEATURE:
<221> NAME/KEY: misc_feature
<222> LOCATION: 12

-continued

```
<223> OTHER INFORMATION: n is a or g or c or t
<220> FEATURE:
<221> NAME/KEY: misc_feature
<222> LOCATION: 21
<223> OTHER INFORMATION: n is a or g or c or t
<220> FEATURE:
<221> NAME/KEY: misc_feature
<222> LOCATION: 24
<223> OTHER INFORMATION: n is a or g or c or t
<220> FEATURE:
<221> NAME/KEY: misc_feature
<222> LOCATION: 42
<223> OTHER INFORMATION: n is a or g or c or t
<220> FEATURE:
<221> NAME/KEY: misc_feature
<222> LOCATION: 48
<223> OTHER INFORMATION: n is a or g or c or t
<220> FEATURE:
<221> NAME/KEY: misc_feature
<222> LOCATION: 51
<223> OTHER INFORMATION: n is a or g or c or t
<220> FEATURE:
<221> NAME/KEY: misc_feature
<222> LOCATION: 57
<223> OTHER INFORMATION: n is a or g or c or t
<220> FEATURE:
<221> NAME/KEY: misc_feature
<222> LOCATION: 60
<223> OTHER INFORMATION: n is a or g or c or t
<220> FEATURE:
<221> NAME/KEY: misc_feature
<222> LOCATION: 66
<223> OTHER INFORMATION: n is a or g or c or t
<220> FEATURE:
<221> NAME/KEY: misc_feature
<222> LOCATION: 72
<223> OTHER INFORMATION: n is a or g or c or t
<220> FEATURE:
<221> NAME/KEY: misc_feature
<222> LOCATION: 75
<223> OTHER INFORMATION: n is a or g or c or t
<220> FEATURE:
<221> NAME/KEY: misc_feature
<222> LOCATION: 78
<223> OTHER INFORMATION: n is a or g or c or t
<220> FEATURE:
<221> NAME/KEY: misc_feature
<222> LOCATION: 81
<223> OTHER INFORMATION: n is a or g or c or t
<220> FEATURE:
<221> NAME/KEY: misc_feature
<222> LOCATION: 84
<223> OTHER INFORMATION: n is a or g or c or t
<220> FEATURE:
<221> NAME/KEY: misc_feature
<222> LOCATION: 90
<223> OTHER INFORMATION: n is a or g or c or t
<220> FEATURE:
<221> NAME/KEY: misc_feature
<222> LOCATION: 93
<223> OTHER INFORMATION: n is a or g or c or t
<220> FEATURE:
<221> NAME/KEY: misc_feature
<222> LOCATION: 99
<223> OTHER INFORMATION: n is a or g or c or t
<220> FEATURE:
<221> NAME/KEY: misc_feature
<222> LOCATION: 108
<223> OTHER INFORMATION: n is a or g or c or t
<220> FEATURE:
<221> NAME/KEY: misc_feature
<222> LOCATION: 114
<223> OTHER INFORMATION: n is a or g or c or t
<220> FEATURE:
<221> NAME/KEY: misc_feature
<222> LOCATION: 17
<223> OTHER INFORMATION: n is a or g or c or t
<220> FEATURE:
<221> NAME/KEY: misc_feature
```

-continued

```
<222> LOCATION: 120
<223> OTHER INFORMATION: n is a or g or c or t
<220> FEATURE:
<221> NAME/KEY: misc_feature
<222> LOCATION: 123
<223> OTHER INFORMATION: n is a or g or c or t
<220> FEATURE:
<221> NAME/KEY: misc_feature
<222> LOCATION: 126
<223> OTHER INFORMATION: n is a or g or c or t
<220> FEATURE:
<221> NAME/KEY: misc_feature
<222> LOCATION: 129
<223> OTHER INFORMATION: n is a or g or c or t
<220> FEATURE:
<221> NAME/KEY: misc_feature
<222> LOCATION: 132
<223> OTHER INFORMATION: n is a or g or c or t
<220> FEATURE:
<221> NAME/KEY: misc_feature
<222> LOCATION: 135
<223> OTHER INFORMATION: n is a or g or c or t
<220> FEATURE:
<221> NAME/KEY: misc_feature
<222> LOCATION: 138
<223> OTHER INFORMATION: n is a or g or c or t
<220> FEATURE:
<221> NAME/KEY: misc_feature
<222> LOCATION: 141
<223> OTHER INFORMATION: n is a or g or c or t
<220> FEATURE:
<221> NAME/KEY: misc_feature
<222> LOCATION: 144
<223> OTHER INFORMATION: n is a or g or c or t
<220> FEATURE:
<221> NAME/KEY: misc_feature
<222> LOCATION: 153
<223> OTHER INFORMATION: n is a or g or c or t
<220> FEATURE:
<221> NAME/KEY: misc_feature
<222> LOCATION: 156
<223> OTHER INFORMATION: n is a or g or c or t
<220> FEATURE:
<221> NAME/KEY: misc_feature
<222> LOCATION: 162
<223> OTHER INFORMATION: n is a or g or c or t
<220> FEATURE:
<221> NAME/KEY: misc_feature
<222> LOCATION: 165
<223> OTHER INFORMATION: n is a or g or c or t
<220> FEATURE:
<221> NAME/KEY: misc_feature
<222> LOCATION: 171
<223> OTHER INFORMATION: n is a or g or c or t
<220> FEATURE:
<221> NAME/KEY: misc_feature
<222> LOCATION: 174
<223> OTHER INFORMATION: n is a or g or c or t
<220> FEATURE:
<221> NAME/KEY: misc_feature
<222> LOCATION: 180
<223> OTHER INFORMATION: n is a or g or c or t
<220> FEATURE:
<221> NAME/KEY: misc_feature
<222> LOCATION: 195
<223> OTHER INFORMATION: n is a or g or c or t
<220> FEATURE:
<221> NAME/KEY: misc_feature
<222> LOCATION: 198
<223> OTHER INFORMATION: n is a or g or c or t
<220> FEATURE:
<221> NAME/KEY: misc_feature
<222> LOCATION: 201
<223> OTHER INFORMATION: n is a or g or c or t
<220> FEATURE:
<221> NAME/KEY: misc_feature
<222> LOCATION: 204
<223> OTHER INFORMATION: n is a or g or c or t
<220> FEATURE:
```

```
<221> NAME/KEY: misc_feature
<222> LOCATION: 213
<223> OTHER INFORMATION: n is a or g or c or t
<220> FEATURE:
<221> NAME/KEY: misc_feature
<222> LOCATION: 219
<223> OTHER INFORMATION: n is a or g or c or t
<220> FEATURE:
<221> NAME/KEY: misc_feature
<222> LOCATION: 222
<223> OTHER INFORMATION: n is a or g or c or t
<220> FEATURE:
<221> NAME/KEY: misc_feature
<222> LOCATION: 228
<223> OTHER INFORMATION: n is a or g or c or t
<220> FEATURE:
<221> NAME/KEY: misc_feature
<222> LOCATION: 237
<223> OTHER INFORMATION: n is a or g or c or t
<220> FEATURE:
<221> NAME/KEY: misc_feature
<222> LOCATION: 240
<223> OTHER INFORMATION: n is a or g or c or t
<220> FEATURE:
<221> NAME/KEY: misc_feature
<222> LOCATION: 243
<223> OTHER INFORMATION: n is a or g or c or t
<220> FEATURE:
<221> NAME/KEY: misc_feature
<222> LOCATION: 246
<223> OTHER INFORMATION: n is a or g or c or t
<220> FEATURE:
<221> NAME/KEY: misc_feature
<222> LOCATION: 252
<223> OTHER INFORMATION: n is a or g or c or t
<220> FEATURE:
<221> NAME/KEY: misc_feature
<222> LOCATION: 255
<223> OTHER INFORMATION: n is a or g or c or t
<220> FEATURE:
<221> NAME/KEY: misc_feature
<222> LOCATION: 258
<223> OTHER INFORMATION: n is a or g or c or t
<220> FEATURE:
<221> NAME/KEY: misc_feature
<222> LOCATION: 261
<223> OTHER INFORMATION: n is a or g or c or t
<220> FEATURE:
<221> NAME/KEY: misc_feature
<222> LOCATION: 264
<223> OTHER INFORMATION: n is a or g or c or t
<220> FEATURE:
<221> NAME/KEY: misc_feature
<222> LOCATION: 273
<223> OTHER INFORMATION: n is a or g or c or t
<220> FEATURE:
<221> NAME/KEY: misc_feature
<222> LOCATION: 285
<223> OTHER INFORMATION: n is a or g or c or t
<220> FEATURE:
<221> NAME/KEY: misc_feature
<222> LOCATION: 297
<223> OTHER INFORMATION: n is a or g or c or t
<220> FEATURE:
<221> NAME/KEY: misc_feature
<222> LOCATION: 300
<223> OTHER INFORMATION: n is a or g or c or t
<220> FEATURE:
<221> NAME/KEY: misc_feature
<222> LOCATION: 303
<223> OTHER INFORMATION: n is a or g or c or t
<220> FEATURE:
<221> NAME/KEY: misc_feature
<222> LOCATION: 306
<223> OTHER INFORMATION: n is a or g or c or t
<220> FEATURE:
<221> NAME/KEY: misc_feature
<222> LOCATION: 309
<223> OTHER INFORMATION: n is a or g or c or t
```

```
-continued

<220> FEATURE:
<221> NAME/KEY: misc_feature
<222> LOCATION: 312
<223> OTHER INFORMATION: n is a or g or c or t
<220> FEATURE:
<221> NAME/KEY: misc_feature
<222> LOCATION: 318
<223> OTHER INFORMATION: n is a or g or c or t
<220> FEATURE:
<221> NAME/KEY: misc_feature
<222> LOCATION: 321
<223> OTHER INFORMATION: n is a or g or c or t
<220> FEATURE:
<221> NAME/KEY: misc_feature
<222> LOCATION: 324
<223> OTHER INFORMATION: n is a or g or c or t
<220> FEATURE:
<221> NAME/KEY: misc_feature
<222> LOCATION: 327
<223> OTHER INFORMATION: n is a or g or c or t
<220> FEATURE:
<221> NAME/KEY: misc_feature
<222> LOCATION: 330
<223> OTHER INFORMATION: n is a or g or c or t
<220> FEATURE:
<221> NAME/KEY: misc_feature
<222> LOCATION: 333
<223> OTHER INFORMATION: n is a or g or c or t
<220> FEATURE:
<221> NAME/KEY: misc_feature
<222> LOCATION: 339
<223> OTHER INFORMATION: n is a or g or c or t
<220> FEATURE:
<221> NAME/KEY: misc_feature
<222> LOCATION: 345
<223> OTHER INFORMATION: n is a or g or c or t
<220> FEATURE:
<221> NAME/KEY: misc_feature
<222> LOCATION: 354
<223> OTHER INFORMATION: n is a or g or c or t
<220> FEATURE:
<221> NAME/KEY: misc_feature
<222> LOCATION: 357
<223> OTHER INFORMATION: n is a or g or c or t
<220> FEATURE:
<221> NAME/KEY: misc_feature
<222> LOCATION: 360
<223> OTHER INFORMATION: n is a or g or c or t
<220> FEATURE:
<221> NAME/KEY: misc_feature
<222> LOCATION: 363
<223> OTHER INFORMATION: n is a or g or c or t
<220> FEATURE:
<221> NAME/KEY: misc_feature
<222> LOCATION: 366
<223> OTHER INFORMATION: n is a or g or c or t
<220> FEATURE:
<221> NAME/KEY: misc_feature
<222> LOCATION: 369
<223> OTHER INFORMATION: n is a or g or c or t
<220> FEATURE:
<221> NAME/KEY: misc_feature
<222> LOCATION: 372
<223> OTHER INFORMATION: n is a or g or c or t
<220> FEATURE:
<221> NAME/KEY: misc_feature
<222> LOCATION: 375
<223> OTHER INFORMATION: n is a or g or c or t
<220> FEATURE:
<221> NAME/KEY: misc_feature
<222> LOCATION: 378
<223> OTHER INFORMATION: n is a or g or c or t
<220> FEATURE:
<221> NAME/KEY: misc_feature
<222> LOCATION: 384
<223> OTHER INFORMATION: n is a or g or c or t
<220> FEATURE:
<221> NAME/KEY: misc_feature
<222> LOCATION: 387
```

```
<223> OTHER INFORMATION: n is a or g or c or t
<220> FEATURE:
<221> NAME/KEY: misc_feature
<222> LOCATION: 390
<223> OTHER INFORMATION: n is a or g or c or t
<220> FEATURE:
<221> NAME/KEY: misc_feature
<222> LOCATION: 396
<223> OTHER INFORMATION: n is a or g or c or t
<220> FEATURE:
<221> NAME/KEY: misc_feature
<222> LOCATION: 402
<223> OTHER INFORMATION: n is a or g or c or t
<220> FEATURE:
<221> NAME/KEY: misc_feature
<222> LOCATION: 405
<223> OTHER INFORMATION: n is a or g or c or t
<220> FEATURE:
<221> NAME/KEY: misc_feature
<222> LOCATION: 408
<223> OTHER INFORMATION: n is a or g or c or t
<220> FEATURE:
<221> NAME/KEY: misc_feature
<222> LOCATION: 417
<223> OTHER INFORMATION: n is a or g or c or t
<220> FEATURE:
<221> NAME/KEY: misc_feature
<222> LOCATION: 420
<223> OTHER INFORMATION: n is a or g or c or t
<220> FEATURE:
<221> NAME/KEY: misc_feature
<222> LOCATION: 423
<223> OTHER INFORMATION: n is a or g or c or t
<220> FEATURE:
<221> NAME/KEY: misc_feature
<222> LOCATION: 426
<223> OTHER INFORMATION: n is a or g or c or t
<220> FEATURE:
<221> NAME/KEY: misc_feature
<222> LOCATION: 432
<223> OTHER INFORMATION: n is a or g or c or t
<220> FEATURE:
<221> NAME/KEY: misc_feature
<222> LOCATION: 435
<223> OTHER INFORMATION: n is a or g or c or t
<220> FEATURE:
<221> NAME/KEY: misc_feature
<222> LOCATION: 438
<223> OTHER INFORMATION: n is a or g or c or t
<220> FEATURE:
<221> NAME/KEY: misc_feature
<222> LOCATION: 441
<223> OTHER INFORMATION: n is a or g or c or t
<220> FEATURE:
<221> NAME/KEY: misc_feature
<222> LOCATION: 444
<223> OTHER INFORMATION: n is a or g or c or t
<220> FEATURE:
<221> NAME/KEY: misc_feature
<222> LOCATION: 447
<223> OTHER INFORMATION: n is a or g or c or t
<220> FEATURE:
<221> NAME/KEY: misc_feature
<222> LOCATION: 450
<223> OTHER INFORMATION: n is a or g or c or t
<220> FEATURE:
<221> NAME/KEY: misc_feature
<222> LOCATION: 453
<223> OTHER INFORMATION: n is a or g or c or t
<220> FEATURE:
<221> NAME/KEY: misc_feature
<222> LOCATION: 459
<223> OTHER INFORMATION: n is a or g or c or t
<220> FEATURE:
<221> NAME/KEY: misc_feature
<222> LOCATION: 462
<223> OTHER INFORMATION: n is a or g or c or t
<220> FEATURE:
<221> NAME/KEY: misc_feature
```

-continued

```
<222> LOCATION: 465
<223> OTHER INFORMATION: n is a or g or c or t
<220> FEATURE:
<221> NAME/KEY: misc_feature
<222> LOCATION: 471
<223> OTHER INFORMATION: n is a or g or c or t
<220> FEATURE:
<221> NAME/KEY: misc_feature
<222> LOCATION: 474
<223> OTHER INFORMATION: n is a or g or c or t
<220> FEATURE:
<221> NAME/KEY: misc_feature
<222> LOCATION: 480
<223> OTHER INFORMATION: n is a or g or c or t
<220> FEATURE:
<221> NAME/KEY: misc_feature
<222> LOCATION: 489
<223> OTHER INFORMATION: n is a or g or c or t
<220> FEATURE:
<221> NAME/KEY: misc_feature
<222> LOCATION: 492
<223> OTHER INFORMATION: n is a or g or c or t
<220> FEATURE:
<221> NAME/KEY: misc_feature
<222> LOCATION: 495
<223> OTHER INFORMATION: n is a or g or c or t
<220> FEATURE:
<221> NAME/KEY: misc_feature
<222> LOCATION: 501
<223> OTHER INFORMATION: n is a or g or c or t
<220> FEATURE:
<221> NAME/KEY: misc_feature
<222> LOCATION: 504
<223> OTHER INFORMATION: n is a or g or c or t
<220> FEATURE:
<221> NAME/KEY: misc_feature
<222> LOCATION: 507
<223> OTHER INFORMATION: n is a or g or c or t
<220> FEATURE:
<221> NAME/KEY: misc_feature
<222> LOCATION: 510
<223> OTHER INFORMATION: n is a or g or c or t
<220> FEATURE:
<221> NAME/KEY: misc_feature
<222> LOCATION: 513
<223> OTHER INFORMATION: n is a or g or c or t
<220> FEATURE:
<221> NAME/KEY: misc_feature
<222> LOCATION: 516
<223> OTHER INFORMATION: n is a or g or c or t
<220> FEATURE:
<221> NAME/KEY: misc_feature
<222> LOCATION: 519
<223> OTHER INFORMATION: n is a or g or c or t
<220> FEATURE:
<221> NAME/KEY: misc_feature
<222> LOCATION: 522
<223> OTHER INFORMATION: n is a or g or c or t
<220> FEATURE:
<221> NAME/KEY: misc_feature
<222> LOCATION: 525
<223> OTHER INFORMATION: n is a or g or c or t
<220> FEATURE:
<221> NAME/KEY: misc_feature
<222> LOCATION: 531
<223> OTHER INFORMATION: n is a or g or c or t
<220> FEATURE:
<221> NAME/KEY: misc_feature
<222> LOCATION: 534
<223> OTHER INFORMATION: n is a or g or c or t
<220> FEATURE:
<221> NAME/KEY: misc_feature
<222> LOCATION: 540
<223> OTHER INFORMATION: n is a or g or c or t
<220> FEATURE:
<221> NAME/KEY: misc_feature
<222> LOCATION: 549
<223> OTHER INFORMATION: n is a or g or c or t
<220> FEATURE:
```

-continued

```
<221> NAME/KEY: misc_feature
<222> LOCATION: 552
<223> OTHER INFORMATION: n is a or g or c or t
<220> FEATURE:
<221> NAME/KEY: misc_feature
<222> LOCATION: 558
<223> OTHER INFORMATION: n is a or g or c or t
<220> FEATURE:
<221> NAME/KEY: misc_feature
<222> LOCATION: 561
<223> OTHER INFORMATION: n is a or g or c or t
<220> FEATURE:
<221> NAME/KEY: misc_feature
<222> LOCATION: 564
<223> OTHER INFORMATION: n is a or g or c or t
<220> FEATURE:
<221> NAME/KEY: misc_feature
<222> LOCATION: 570
<223> OTHER INFORMATION: n is a or g or c or t
<220> FEATURE:
<221> NAME/KEY: misc_feature
<222> LOCATION: 573
<223> OTHER INFORMATION: n is a or g or c or t
<220> FEATURE:
<221> NAME/KEY: misc_feature
<222> LOCATION: 576
<223> OTHER INFORMATION: n is a or g or c or t
<220> FEATURE:
<221> NAME/KEY: misc_feature
<222> LOCATION: 582
<223> OTHER INFORMATION: n is a or g or c or t
<220> FEATURE:
<221> NAME/KEY: misc_feature
<222> LOCATION: 585
<223> OTHER INFORMATION: n is a or g or c or t

<400> SEQUENCE: 69
gaygcnccng gncartaygg ngcntaytty caygaygayg gnttyytngc nttyccnggn       60
caygtnttyw snmgnwsnyt nccngargtn ccngaracna thgarytnga rgtnmgnacn      120
wsnacngcnw snggnytnyt nytntggcar ggngtngarg tnggngargc nggncarggn      180
aargayttya thwsnytngg nytncargay ggncayytng tnttymgnta ycarytnggn      240
wsnggngarg cnmgnytngt nwsngargay ccnathaayg ayggngartg gcaymgngtn      300
acngcnytnm gngarggnmg nmgnggnwsn mgncargtng ayggngarga rytngtnwsn      360
ggnmgnwsnc cnggnccnaa ygtngcngtn aaygcnaarg gnwsngtnta yathggnggn      420
gcnccngayg tngcnacnyt nacnggnggn mgnttywsnw snggnathac nggntgygtn      480
aaraayytng tnytncayws ngcnmgncca ggngcnccnc cnccncarcc nyt

-continued

```
<220> FEATURE:
<221> NAME/KEY: misc_feature
<222> LOCATION: 27
<223> OTHER INFORMATION: n is a or g or c or t
<220> FEATURE:
<221> NAME/KEY: misc_feature
<222> LOCATION: 30
<223> OTHER INFORMATION: n is a or g or c or t
<220> FEATURE:
<221> NAME/KEY: misc_feature
<222> LOCATION: 33
<223> OTHER INFORMATION: n is a or g or c or t
<220> FEATURE:
<221> NAME/KEY: misc_feature
<222> LOCATION: 36
<223> OTHER INFORMATION: n is a or g or c or t
<220> FEATURE:
<221> NAME/KEY: misc_feature
<222> LOCATION: 42
<223> OTHER INFORMATION: n is a or g or c or t
<220> FEATURE:
<221> NAME/KEY: misc_feature
<222> LOCATION: 45
<223> OTHER INFORMATION: n is a or g or c or t
<220> FEATURE:
<221> NAME/KEY: misc_feature
<222> LOCATION: 48
<223> OTHER INFORMATION: n is a or g or c or t
<220> FEATURE:
<221> NAME/KEY: misc_feature
<222> LOCATION: 54
<223> OTHER INFORMATION: n is a or g or c or t
<220> FEATURE:
<221> NAME/KEY: misc_feature
<222> LOCATION: 63
<223> OTHER INFORMATION: n is a or g or c or t
<220> FEATURE:
<221> NAME/KEY: misc_feature
<222> LOCATION: 66
<223> OTHER INFORMATION: n is a or g or c or t
<220> FEATURE:
<221> NAME/KEY: misc_feature
<222> LOCATION: 69
<223> OTHER INFORMATION: n is a or g or c or t
<220> FEATURE:
<221> NAME/KEY: misc_feature
<222> LOCATION: 72
<223> OTHER INFORMATION: n is a or g or c or t
<220> FEATURE:
<221> NAME/KEY: misc_feature
<222> LOCATION: 78
<223> OTHER INFORMATION: n is a or g or c or t
<220> FEATURE:
<221> NAME/KEY: misc_feature
<222> LOCATION: 81
<223> OTHER INFORMATION: n is a or g or c or t
<220> FEATURE:
<221> NAME/KEY: misc_feature
<222> LOCATION: 12
<223> OTHER INFORMATION: n is a or g or c or t
<220> FEATURE:
<221> NAME/KEY: misc_feature
<222> LOCATION: 105
<223> OTHER INFORMATION: n is a or g or c or t
<220> FEATURE:
<221> NAME/KEY: misc_feature
<222> LOCATION: 111
<223> OTHER INFORMATION: n is a or g or c or t
<220> FEATURE:
<221> NAME/KEY: misc_feature
<222> LOCATION: 114
<223> OTHER INFORMATION: n is a or g or c or t
<220> FEATURE:
<221> NAME/KEY: misc_feature
<222> LOCATION: 117
<223> OTHER INFORMATION: n is a or g or c or t
<220> FEATURE:
<221> NAME/KEY: misc_feature
<222> LOCATION: 126
```

```
-continued

<223> OTHER INFORMATION: n is a or g or c or t
<220> FEATURE:
<221> NAME/KEY: misc_feature
<222> LOCATION: 132
<223> OTHER INFORMATION: n is a or g or c or t
<220> FEATURE:
<221> NAME/KEY: misc_feature
<222> LOCATION: 144
<223> OTHER INFORMATION: n is a or g or c or t
<220> FEATURE:
<221> NAME/KEY: misc_feature
<222> LOCATION: 150
<223> OTHER INFORMATION: n is a or g or c or t
<220> FEATURE:
<221> NAME/KEY: misc_feature
<222> LOCATION: 153
<223> OTHER INFORMATION: n is a or g or c or t
<220> FEATURE:
<221> NAME/KEY: misc_feature
<222> LOCATION: 159
<223> OTHER INFORMATION: n is a or g or c or t
<220> FEATURE:
<221> NAME/KEY: misc_feature
<222> LOCATION: 174
<223> OTHER INFORMATION: n is a or g or c or t
<220> FEATURE:
<221> NAME/KEY: misc_feature
<222> LOCATION: 177
<223> OTHER INFORMATION: n is a or g or c or t
<220> FEATURE:
<221> NAME/KEY: misc_feature
<222> LOCATION: 186
<223> OTHER INFORMATION: n is a or g or c or t
<220> FEATURE:
<221> NAME/KEY: misc_feature
<222> LOCATION: 198
<223> OTHER INFORMATION: n is a or g or c or t
<220> FEATURE:
<221> NAME/KEY: misc_feature
<222> LOCATION: 201
<223> OTHER INFORMATION: n is a or g or c or t
<220> FEATURE:
<221> NAME/KEY: misc_feature
<222> LOCATION: 213
<223> OTHER INFORMATION: n is a or g or c or t
<220> FEATURE:
<221> NAME/KEY: misc_feature
<222> LOCATION: 216
<223> OTHER INFORMATION: n is a or g or c or t
<220> FEATURE:
<221> NAME/KEY: misc_feature
<222> LOCATION: 219
<223> OTHER INFORMATION: n is a or g or c or t
<220> FEATURE:
<221> NAME/KEY: misc_feature
<222> LOCATION: 225
<223> OTHER INFORMATION: n is a or g or c or t
<220> FEATURE:
<221> NAME/KEY: misc_feature
<222> LOCATION: 228
<223> OTHER INFORMATION: n is a or g or c or t
<220> FEATURE:
<221> NAME/KEY: misc_feature
<222> LOCATION: 231
<223> OTHER INFORMATION: n is a or g or c or t
<220> FEATURE:
<221> NAME/KEY: misc_feature
<222> LOCATION: 234
<223> OTHER INFORMATION: n is a or g or c or t
<220> FEATURE:
<221> NAME/KEY: misc_feature
<222> LOCATION: 237
<223> OTHER INFORMATION: n is a or g or c or t
<220> FEATURE:
<221> NAME/KEY: misc_feature
<222> LOCATION: 240
<223> OTHER INFORMATION: n is a or g or c or t
<220> FEATURE:
<221> NAME/KEY: misc_feature
```

```
<222> LOCATION: 255
<223> OTHER INFORMATION: n is a or g or c or t
<220> FEATURE:
<221> NAME/KEY: misc_feature
<222> LOCATION: 261
<223> OTHER INFORMATION: n is a or g or c or t
<220> FEATURE:
<221> NAME/KEY: misc_feature
<222> LOCATION: 270
<223> OTHER INFORMATION: n is a or g or c or t
<220> FEATURE:
<221> NAME/KEY: misc_feature
<222> LOCATION: 273
<223> OTHER INFORMATION: n is a or g or c or t
<220> FEATURE:
<221> NAME/KEY: misc_feature
<222> LOCATION: 276
<223> OTHER INFORMATION: n is a or g or c or t
<220> FEATURE:
<221> NAME/KEY: misc_feature
<222> LOCATION: 282
<223> OTHER INFORMATION: n is a or g or c or t
<220> FEATURE:
<221> NAME/KEY: misc_feature
<222> LOCATION: 288
<223> OTHER INFORMATION: n is a or g or c or t
<220> FEATURE:
<221> NAME/KEY: misc_feature
<222> LOCATION: 297
<223> OTHER INFORMATION: n is a or g or c or t
<220> FEATURE:
<221> NAME/KEY: misc_feature
<222> LOCATION: 300
<223> OTHER INFORMATION: n is a or g or c or t
<220> FEATURE:
<221> NAME/KEY: misc_feature
<222> LOCATION: 324
<223> OTHER INFORMATION: n is a or g or c or t
<220> FEATURE:
<221> NAME/KEY: misc_feature
<222> LOCATION: 327
<223> OTHER INFORMATION: n is a or g or c or t
<220> FEATURE:
<221> NAME/KEY: misc_feature
<222> LOCATION: 330
<223> OTHER INFORMATION: n is a or g or c or t
<220> FEATURE:
<221> NAME/KEY: misc_feature
<222> LOCATION: 333
<223> OTHER INFORMATION: n is a or g or c or t
<220> FEATURE:
<221> NAME/KEY: misc_feature
<222> LOCATION: 339
<223> OTHER INFORMATION: n is a or g or c or t
<220> FEATURE:
<221> NAME/KEY: misc_feature
<222> LOCATION: 348
<223> OTHER INFORMATION: n is a or g or c or t
<220> FEATURE:
<221> NAME/KEY: misc_feature
<222> LOCATION: 369
<223> OTHER INFORMATION: n is a or g or c or t
<220> FEATURE:
<221> NAME/KEY: misc_feature
<222> LOCATION: 375
<223> OTHER INFORMATION: n is a or g or c or t
<220> FEATURE:
<221> NAME/KEY: misc_feature
<222> LOCATION: 387
<223> OTHER INFORMATION: n is a or g or c or t
<220> FEATURE:
<221> NAME/KEY: misc_feature
<222> LOCATION: 393
<223> OTHER INFORMATION: n is a or g or c or t
<220> FEATURE:
<221> NAME/KEY: misc_feature
<222> LOCATION: 396
<223> OTHER INFORMATION: n is a or g or c or t
<220> FEATURE:
```

-continued

```
<221> NAME/KEY: misc_feature
<222> LOCATION: 405
<223> OTHER INFORMATION: n is a or g or c or t
<220> FEATURE:
<221> NAME/KEY: misc_feature
<222> LOCATION: 411
<223> OTHER INFORMATION: n is a or g or c or t
<220> FEATURE:
<221> NAME/KEY: misc_feature
<222> LOCATION: 414
<223> OTHER INFORMATION: n is a or g or c or t
<220> FEATURE:
<221> NAME/KEY: misc_feature
<222> LOCATION: 417
<223> OTHER INFORMATION: n is a or g or c or t
<220> FEATURE:
<221> NAME/KEY: misc_feature
<222> LOCATION: 423
<223> OTHER INFORMATION: n is a or g or c or t
<220> FEATURE:
<221> NAME/KEY: misc_feature
<222> LOCATION: 429
<223> OTHER INFORMATION: n is a or g or c or t
<220> FEATURE:
<221> NAME/KEY: misc_feature
<222> LOCATION: 432
<223> OTHER INFORMATION: n is a or g or c or t
<220> FEATURE:
<221> NAME/KEY: misc_feature
<222> LOCATION: 438
<223> OTHER INFORMATION: n is a or g or c or t
<220> FEATURE:
<221> NAME/KEY: misc_feature
<222> LOCATION: 444
<223> OTHER INFORMATION: n is a or g or c or t
<220> FEATURE:
<221> NAME/KEY: misc_feature
<222> LOCATION: 450
<223> OTHER INFORMATION: n is a or g or c or t
<220> FEATURE:
<221> NAME/KEY: misc_feature
<222> LOCATION: 456
<223> OTHER INFORMATION: n is a or g or c or t
<220> FEATURE:
<221> NAME/KEY: misc_feature
<222> LOCATION: 462
<223> OTHER INFORMATION: n is a or g or c or t
<220> FEATURE:
<221> NAME/KEY: misc_feature
<222> LOCATION: 465
<223> OTHER INFORMATION: n is a or g or c or t
<220> FEATURE:
<221> NAME/KEY: misc_feature
<222> LOCATION: 471
<223> OTHER INFORMATION: n is a or g or c or t
<220> FEATURE:
<221> NAME/KEY: misc_feature
<222> LOCATION: 477
<223> OTHER INFORMATION: n is a or g or c or t
<220> FEATURE:
<221> NAME/KEY: misc_feature
<222> LOCATION: 480
<223> OTHER INFORMATION: n is a or g or c or t
<220> FEATURE:
<221> NAME/KEY: misc_feature
<222> LOCATION: 483
<223> OTHER INFORMATION: n is a or g or c or t
<220> FEATURE:
<221> NAME/KEY: misc_feature
<222> LOCATION: 486
<223> OTHER INFORMATION: n is a or g or c or t
<220> FEATURE:
<221> NAME/KEY: misc_feature
<222> LOCATION: 492
<223> OTHER INFORMATION: n is a or g or c or t
<220> FEATURE:
<221> NAME/KEY: misc_feature
<222> LOCATION: 504
<223> OTHER INFORMATION: n is a or g or c or t
```

-continued

<220> FEATURE:
<221> NAME/KEY: misc_feature
<222> LOCATION: 507
<223> OTHER INFORMATION: n is a or g or c or t
<220> FEATURE:
<221> NAME/KEY: misc_feature
<222> LOCATION: 513
<223> OTHER INFORMATION: n is a or g or c or t
<220> FEATURE:
<221> NAME/KEY: misc_feature
<222> LOCATION: 525
<223> OTHER INFORMATION: n is a or g or c or t
<220> FEATURE:
<221> NAME/KEY: misc_feature
<222> LOCATION: 531
<223> OTHER INFORMATION: n is a or g or c or t
<220> FEATURE:
<221> NAME/KEY: misc_feature
<222> LOCATION: 534
<223> OTHER INFORMATION: n is a or g or c or t
<220> FEATURE:
<221> NAME/KEY: misc_feature
<222> LOCATION: 537
<223> OTHER INFORMATION: n is a or g or c or t
<220> FEATURE:
<221> NAME/KEY: misc_feature
<222> LOCATION: 549
<223> OTHER INFORMATION: n is a or g or c or t
<220> FEATURE:
<221> NAME/KEY: misc_feature
<222> LOCATION: 555
<223> OTHER INFORMATION: n is a or g or c or t
<220> FEATURE:
<221> NAME/KEY: misc_feature
<222> LOCATION: 564
<223> OTHER INFORMATION: n is a or g or c or t
<220> FEATURE:
<221> NAME/KEY: misc_feature
<222> LOCATION: 576
<223> OTHER INFORMATION: n is a or g or c or t
<220> FEATURE:
<221> NAME/KEY: misc_feature
<222> LOCATION: 579
<223> OTHER INFORMATION: n is a or g or c or t
<220> FEATURE:
<221> NAME/KEY: misc_feature
<222> LOCATION: 582
<223> OTHER INFORMATION: n is a or g or c or t
<220> FEATURE:
<221> NAME/KEY: misc_feature
<222> LOCATION: 588
<223> OTHER INFORMATION: n is a or g or c or t
<220> FEATURE:
<221> NAME/KEY: misc_feature
<222> LOCATION: 594
<223> OTHER INFORMATION: n is a or g or c or t
<220> FEATURE:
<221> NAME/KEY: misc_feature
<222> LOCATION: 597
<223> OTHER INFORMATION: n is a or g or c or t

<400> SEQUENCE: 70
atgaartggg tntgggcnyt nytnytnytn gcngcntggg cngcngcnga rmgngaytgy 60
mgngtnwsnw snttymgngt naargaraay ttygayaarg cnmgnttyws nggnacntgg 120
taygcnatgg cnaaraarga yccngarggn ytnttyytnc argayaayat hgtngcngar 180
ttywsngtng aygaracngg ncaratgwsn gcnacngcna arggnmgngt nmgnytnytn 240
aayaaytggg aygtntgygc ngayatggtn ggnacnttya cngayacnga rgayccngcn 300
aarttyaara tgaartaytg gggngtngcn wsnttyytnc araarggnaa ygaygaycay 360
tggathgtng ayacngayta ygayacntay gcngtncart aywsntgymg nytnytnaay 420
ytngayggna cntgygcnga ywsntaywsn ttygtnttyw snmgngaycc naayggnytn 480

```
ccnccngarg cncaraaaat hgtnmgncar mgncargarg arytntgyyt ngcnmgncar    540
taymgnytna thgtncayaa yggntaytgy gayggnmgnw sngarmgnaa yytnytn       597
```

<210> SEQ ID NO 71
<211> LENGTH: 579
<212> TYPE: DNA
<213> ORGANISM: Homo sapiens
<220> FEATURE:
<221> NAME/KEY: misc_feature
<222> LOCATION: 9
<223> OTHER INFORMATION: n is a or g or c or t
<220> FEATURE:
<221> NAME/KEY: misc_feature
<222> LOCATION: 12
<223> OTHER INFORMATION: n is a or g or c or t
<220> FEATURE:
<221> NAME/KEY: misc_feature
<222> LOCATION: 21
<223> OTHER INFORMATION: n is a or g or c or t
<220> FEATURE:
<221> NAME/KEY: misc_feature
<222> LOCATION: 24
<223> OTHER INFORMATION: n is a or g or c or t
<220> FEATURE:
<221> NAME/KEY: misc_feature
<222> LOCATION: 27
<223> OTHER INFORMATION: n is a or g or c or t
<220> FEATURE:
<221> NAME/KEY: misc_feature
<222> LOCATION: 30
<223> OTHER INFORMATION: n is a or g or c or t
<220> FEATURE:
<221> NAME/KEY: misc_feature
<222> LOCATION: 36
<223> OTHER INFORMATION: n is a or g or c or t
<220> FEATURE:
<221> NAME/KEY: misc_feature
<222> LOCATION: 39
<223> OTHER INFORMATION: n is a or g or c or t
<220> FEATURE:
<221> NAME/KEY: misc_feature
<222> LOCATION: 42
<223> OTHER INFORMATION: n is a or g or c or t
<220> FEATURE:
<221> NAME/KEY: misc_feature
<222> LOCATION: 45
<223> OTHER INFORMATION: n is a or g or c or t
<220> FEATURE:
<221> NAME/KEY: misc_feature
<222> LOCATION: 48
<223> OTHER INFORMATION: n is a or g or c or t
<220> FEATURE:
<221> NAME/KEY: misc_feature
<222> LOCATION: 51
<223> OTHER INFORMATION: n is a or g or c or t
<220> FEATURE:
<221> NAME/KEY: misc_feature
<222> LOCATION: 54
<223> OTHER INFORMATION: n is a or g or c or t
<220> FEATURE:
<221> NAME/KEY: misc_feature
<222> LOCATION: 57
<223> OTHER INFORMATION: n is a or g or c or t
<220> FEATURE:
<221> NAME/KEY: misc_feature
<222> LOCATION: 60
<223> OTHER INFORMATION: n is a or g or c or t
<220> FEATURE:
<221> NAME/KEY: misc_feature
<222> LOCATION: 63
<223> OTHER INFORMATION: n is a or g or c or t
<220> FEATURE:
<221> NAME/KEY: misc_feature
<222> LOCATION: 69
<223> OTHER INFORMATION: n is a or g or c or t
<220> FEATURE:
<221> NAME/KEY: misc_feature

```
<222> LOCATION: 75
<223> OTHER INFORMATION: n is a or g or c or t
<220> FEATURE:
<221> NAME/KEY: misc_feature
<222> LOCATION: 84
<223> OTHER INFORMATION: n is a or g or c or t
<220> FEATURE:
<221> NAME/KEY: misc_feature
<222> LOCATION: 87
<223> OTHER INFORMATION: n is a or g or c or t
<220> FEATURE:
<221> NAME/KEY: misc_feature
<222> LOCATION: 93
<223> OTHER INFORMATION: n is a or g or c or t
<220> FEATURE:
<221> NAME/KEY: misc_feature
<222> LOCATION: 96
<223> OTHER INFORMATION: n is a or g or c or t
<220> FEATURE:
<221> NAME/KEY: misc_feature
<222> LOCATION: 99
<223> OTHER INFORMATION: n is a or g or c or t
<220> FEATURE:
<221> NAME/KEY: misc_feature
<222> LOCATION: 105
<223> OTHER INFORMATION: n is a or g or c or t
<220> FEATURE:
<221> NAME/KEY: misc_feature
<222> LOCATION: 126
<223> OTHER INFORMATION: n is a or g or c or t
<220> FEATURE:
<221> NAME/KEY: misc_feature
<222> LOCATION: 135
<223> OTHER INFORMATION: n is a or g or c or t
<220> FEATURE:
<221> NAME/KEY: misc_feature
<222> LOCATION: 138
<223> OTHER INFORMATION: n is a or g or c or t
<220> FEATURE:
<221> NAME/KEY: misc_feature
<222> LOCATION: 141
<223> OTHER INFORMATION: n is a or g or c or t
<220> FEATURE:
<221> NAME/KEY: misc_feature
<222> LOCATION: 147
<223> OTHER INFORMATION: n is a or g or c or t
<220> FEATURE:
<221> NAME/KEY: misc_feature
<222> LOCATION: 150
<223> OTHER INFORMATION: n is a or g or c or t
<220> FEATURE:
<221> NAME/KEY: misc_feature
<222> LOCATION: 153
<223> OTHER INFORMATION: n is a or g or c or t
<220> FEATURE:
<221> NAME/KEY: misc_feature
<222> LOCATION: 156
<223> OTHER INFORMATION: n is a or g or c or t
<220> FEATURE:
<221> NAME/KEY: misc_feature
<222> LOCATION: 159
<223> OTHER INFORMATION: n is a or g or c or t
<220> FEATURE:
<221> NAME/KEY: misc_feature
<222> LOCATION: 165
<223> OTHER INFORMATION: n is a or g or c or t
<220> FEATURE:
<221> NAME/KEY: misc_feature
<222> LOCATION: 171
<223> OTHER INFORMATION: n is a or g or c or t
<220> FEATURE:
<221> NAME/KEY: misc_feature
<222> LOCATION: 177
<223> OTHER INFORMATION: n is a or g or c or t
<220> FEATURE:
<221> NAME/KEY: misc_feature
<222> LOCATION: 180
<223> OTHER INFORMATION: n is a or g or c or t
<220> FEATURE:
```

-continued

```
<221> NAME/KEY: misc_feature
<222> LOCATION: 183
<223> OTHER INFORMATION: n is a or g or c or t
<220> FEATURE:
<221> NAME/KEY: misc_feature
<222> LOCATION: 186
<223> OTHER INFORMATION: n is a or g or c or t
<220> FEATURE:
<221> NAME/KEY: misc_feature
<222> LOCATION: 192
<223> OTHER INFORMATION: n is a or g or c or t
<220> FEATURE:
<221> NAME/KEY: misc_feature
<222> LOCATION: 195
<223> OTHER INFORMATION: n is a or g or c or t
<220> FEATURE:
<221> NAME/KEY: misc_feature
<222> LOCATION: 198
<223> OTHER INFORMATION: n is a or g or c or t
<220> FEATURE:
<221> NAME/KEY: misc_feature
<222> LOCATION: 201
<223> OTHER INFORMATION: n is a or g or c or t
<220> FEATURE:
<221> NAME/KEY: misc_feature
<222> LOCATION: 204
<223> OTHER INFORMATION: n is a or g or c or t
<220> FEATURE:
<221> NAME/KEY: misc_feature
<222> LOCATION: 207
<223> OTHER INFORMATION: n is a or g or c or t
<220> FEATURE:
<221> NAME/KEY: misc_feature
<222> LOCATION: 210
<223> OTHER INFORMATION: n is a or g or c or t
<220> FEATURE:
<221> NAME/KEY: misc_feature
<222> LOCATION: 213
<223> OTHER INFORMATION: n is a or g or c or t
<220> FEATURE:
<221> NAME/KEY: misc_feature
<222> LOCATION: 216
<223> OTHER INFORMATION: n is a or g or c or t
<220> FEATURE:
<221> NAME/KEY: misc_feature
<222> LOCATION: 219
<223> OTHER INFORMATION: n is a or g or c or t
<220> FEATURE:
<221> NAME/KEY: misc_feature
<222> LOCATION: 222
<223> OTHER INFORMATION: n is a or g or c or t
<220> FEATURE:
<221> NAME/KEY: misc_feature
<222> LOCATION: 225
<223> OTHER INFORMATION: n is a or g or c or t
<220> FEATURE:
<221> NAME/KEY: misc_feature
<222> LOCATION: 228
<223> OTHER INFORMATION: n is a or g or c or t
<220> FEATURE:
<221> NAME/KEY: misc_feature
<222> LOCATION: 231
<223> OTHER INFORMATION: n is a or g or c or t
<220> FEATURE:
<221> NAME/KEY: misc_feature
<222> LOCATION: 234
<223> OTHER INFORMATION: n is a or g or c or t
<220> FEATURE:
<221> NAME/KEY: misc_feature
<222> LOCATION: 237
<223> OTHER INFORMATION: n is a or g or c or t
<220> FEATURE:
<221> NAME/KEY: misc_feature
<222> LOCATION: 246
<223> OTHER INFORMATION: n is a or g or c or t
<220> FEATURE:
<221> NAME/KEY: misc_feature
<222> LOCATION: 252
<223> OTHER INFORMATION: n is a or g or c or t
```

-continued

```
<220> FEATURE:
<221> NAME/KEY: misc_feature
<222> LOCATION: 255
<223> OTHER INFORMATION: n is a or g or c or t
<220> FEATURE:
<221> NAME/KEY: misc_feature
<222> LOCATION: 258
<223> OTHER INFORMATION: n is a or g or c or t
<220> FEATURE:
<221> NAME/KEY: misc_feature
<222> LOCATION: 270
<223> OTHER INFORMATION: n is a or g or c or t
<220> FEATURE:
<221> NAME/KEY: misc_feature
<222> LOCATION: 273
<223> OTHER INFORMATION: n is a or g or c or t
<220> FEATURE:
<221> NAME/KEY: misc_feature
<222> LOCATION: 276
<223> OTHER INFORMATION: n is a or g or c or t
<220> FEATURE:
<221> NAME/KEY: misc_feature
<222> LOCATION: 279
<223> OTHER INFORMATION: n is a or g or c or t
<220> FEATURE:
<221> NAME/KEY: misc_feature
<222> LOCATION: 294
<223> OTHER INFORMATION: n is a or g or c or t
<220> FEATURE:
<221> NAME/KEY: misc_feature
<222> LOCATION: 300
<223> OTHER INFORMATION: n is a or g or c or t
<220> FEATURE:
<221> NAME/KEY: misc_feature
<222> LOCATION: 312
<223> OTHER INFORMATION: n is a or g or c or t
<220> FEATURE:
<221> NAME/KEY: misc_feature
<222> LOCATION: 315
<223> OTHER INFORMATION: n is a or g or c or t
<220> FEATURE:
<221> NAME/KEY: misc_feature
<222> LOCATION: 321
<223> OTHER INFORMATION: n is a or g or c or t
<220> FEATURE:
<221> NAME/KEY: misc_feature
<222> LOCATION: 342
<223> OTHER INFORMATION: n is a or g or c or t
<220> FEATURE:
<221> NAME/KEY: misc_feature
<222> LOCATION: 345
<223> OTHER INFORMATION: n is a or g or c or t
<220> FEATURE:
<221> NAME/KEY: misc_feature
<222> LOCATION: 354
<223> OTHER INFORMATION: n is a or g or c or t
<220> FEATURE:
<221> NAME/KEY: misc_feature
<222> LOCATION: 360
<223> OTHER INFORMATION: n is a or g or c or t
<220> FEATURE:
<221> NAME/KEY: misc_feature
<222> LOCATION: 363
<223> OTHER INFORMATION: n is a or g or c or t
<220> FEATURE:
<221> NAME/KEY: misc_feature
<222> LOCATION: 366
<223> OTHER INFORMATION: n is a or g or c or t
<220> FEATURE:
<221> NAME/KEY: misc_feature
<222> LOCATION: 372
<223> OTHER INFORMATION: n is a or g or c or t
<220> FEATURE:
<221> NAME/KEY: misc_feature
<222> LOCATION: 378
<223> OTHER INFORMATION: n is a or g or c or t
<220> FEATURE:
<221> NAME/KEY: misc_feature
<222> LOCATION: 384
```

-continued

```
<223> OTHER INFORMATION: n is a or g or c or t
<220> FEATURE:
<221> NAME/KEY: misc_feature
<222> LOCATION: 387
<223> OTHER INFORMATION: n is a or g or c or t
<220> FEATURE:
<221> NAME/KEY: misc_feature
<222> LOCATION: 390
<223> OTHER INFORMATION: n is a or g or c or t
<220> FEATURE:
<221> NAME/KEY: misc_feature
<222> LOCATION: 393
<223> OTHER INFORMATION: n is a or g or c or t
<220> FEATURE:
<221> NAME/KEY: misc_feature
<222> LOCATION: 399
<223> OTHER INFORMATION: n is a or g or c or t
<220> FEATURE:
<221> NAME/KEY: misc_feature
<222> LOCATION: 402
<223> OTHER INFORMATION: n is a or g or c or t
<220> FEATURE:
<221> NAME/KEY: misc_feature
<222> LOCATION: 405
<223> OTHER INFORMATION: n is a or g or c or t
<220> FEATURE:
<221> NAME/KEY: misc_feature
<222> LOCATION: 417
<223> OTHER INFORMATION: n is a or g or c or t
<220> FEATURE:
<221> NAME/KEY: misc_feature
<222> LOCATION: 429
<223> OTHER INFORMATION: n is a or g or c or t
<220> FEATURE:
<221> NAME/KEY: misc_feature
<222> LOCATION: 432
<223> OTHER INFORMATION: n is a or g or c or t
<220> FEATURE:
<221> NAME/KEY: misc_feature
<222> LOCATION: 438
<223> OTHER INFORMATION: n is a or g or c or t
<220> FEATURE:
<221> NAME/KEY: misc_feature
<222> LOCATION: 441
<223> OTHER INFORMATION: n is a or g or c or t
<220> FEATURE:
<221> NAME/KEY: misc_feature
<222> LOCATION: 444
<223> OTHER INFORMATION: n is a or g or c or t
<220> FEATURE:
<221> NAME/KEY: misc_feature
<222> LOCATION: 450
<223> OTHER INFORMATION: n is a or g or c or t
<220> FEATURE:
<221> NAME/KEY: misc_feature
<222> LOCATION: 459
<223> OTHER INFORMATION: n is a or g or c or t
<220> FEATURE:
<221> NAME/KEY: misc_feature
<222> LOCATION: 462
<223> OTHER INFORMATION: n is a or g or c or t
<220> FEATURE:
<221> NAME/KEY: misc_feature
<222> LOCATION: 465
<223> OTHER INFORMATION: n is a or g or c or t
<220> FEATURE:
<221> NAME/KEY: misc_feature
<222> LOCATION: 471
<223> OTHER INFORMATION: n is a or g or c or t
<220> FEATURE:
<221> NAME/KEY: misc_feature
<222> LOCATION: 477
<223> OTHER INFORMATION: n is a or g or c or t
<220> FEATURE:
<221> NAME/KEY: misc_feature
<222> LOCATION: 480
<223> OTHER INFORMATION: n is a or g or c or t
<220> FEATURE:
<221> NAME/KEY: misc_feature
```

-continued

```
<222> LOCATION: 483
<223> OTHER INFORMATION: n is a or g or c or t
<220> FEATURE:
<221> NAME/KEY: misc_feature
<222> LOCATION: 489
<223> OTHER INFORMATION: n is a or g or c or t
<220> FEATURE:
<221> NAME/KEY: misc_feature
<222> LOCATION: 492
<223> OTHER INFORMATION: n is a or g or c or t
<220> FEATURE:
<221> NAME/KEY: misc_feature
<222> LOCATION: 495
<223> OTHER INFORMATION: n is a or g or c or t
<220> FEATURE:
<221> NAME/KEY: misc_feature
<222> LOCATION: 498
<223> OTHER INFORMATION: n is a or g or c or t
<220> FEATURE:
<221> NAME/KEY: misc_feature
<222> LOCATION: 507
<223> OTHER INFORMATION: n is a or g or c or t
<220> FEATURE:
<221> NAME/KEY: misc_feature
<222> LOCATION: 516
<223> OTHER INFORMATION: n is a or g or c or t
<220> FEATURE:
<221> NAME/KEY: misc_feature
<222> LOCATION: 519
<223> OTHER INFORMATION: n is a or g or c or t
<220> FEATURE:
<221> NAME/KEY: misc_feature
<222> LOCATION: 522
<223> OTHER INFORMATION: n is a or g or c or t
<220> FEATURE:
<221> NAME/KEY: misc_feature
<222> LOCATION: 525
<223> OTHER INFORMATION: n is a or g or c or t
<220> FEATURE:
<221> NAME/KEY: misc_feature
<222> LOCATION: 528
<223> OTHER INFORMATION: n is a or g or c or t
<220> FEATURE:
<221> NAME/KEY: misc_feature
<222> LOCATION: 531
<223> OTHER INFORMATION: n is a or g or c or t
<220> FEATURE:
<221> NAME/KEY: misc_feature
<222> LOCATION: 534
<223> OTHER INFORMATION: n is a or g or c or t
<220> FEATURE:
<221> NAME/KEY: misc_feature
<222> LOCATION: 540
<223> OTHER INFORMATION: n is a or g or c or t
<220> FEATURE:
<221> NAME/KEY: misc_feature
<222> LOCATION: 543
<223> OTHER INFORMATION: n is a or g or c or t
<220> FEATURE:
<221> NAME/KEY: misc_feature
<222> LOCATION: 546
<223> OTHER INFORMATION: n is a or g or c or t
<220> FEATURE:
<221> NAME/KEY: misc_feature
<222> LOCATION: 561
<223> OTHER INFORMATION: n is a or g or c or t
<220> FEATURE:
<221> NAME/KEY: misc_feature
<222> LOCATION: 564
<223> OTHER INFORMATION: n is a or g or c or t
<220> FEATURE:
<221> NAME/KEY: misc_feature
<222> LOCATION: 567
<223> OTHER INFORMATION: n is a or g or c or t
<220> FEATURE:
<221> NAME/KEY: misc_feature
<222> LOCATION: 570
<223> OTHER INFORMATION: n is a or g or c or t
<220> FEATURE:
```

-continued

<221> NAME/KEY: misc_feature
<222> LOCATION: 576
<223> OTHER INFORMATION: n is a or g or c or t

<400> SEQUENCE: 71

```
atgcarwsny tnatgcargc nccnytnytn athgcnytng gnytnytnyt ngcnacnccn     60
gcncargcnc ayytnaaraa rccnwsncar ytnwsnwsnt tywsntggga yaaytgytty    120
garggnaarg ayccngcngt nathmgnwsn ytnacnytng arccngaycc nathgtngtn    180
ccnggnaayg tnacnytnws ngtngtnggn wsnacnwsng tnccnytnws nwsnccnytn    240
aargtngayy tngtnytnga raargargtn gcnggnytnt ggathaarat hccntgyacn    300
gaytayathg gnwsntgyac nttygarcay ttytgygayg tnytngayat gytnathccn    360
acnggngarc cntgyccnga rccnytnmgn acntayggny tnccntgyca ytgyccntty    420
aargarggna cntaywsnyt nccnaarwsn garttygcng tnccngayyt ngarytnccn    480
wsntggytna cnacnggnaa ytaymgnath garwsngtny tnwsnwsnws nggnaarmgn    540
ytnggntgya thaarathgc ngcnwsnytn aarggnath                           579
```

<210> SEQ ID NO 72
<211> LENGTH: 16
<212> TYPE: PRT
<213> ORGANISM: Homo sapiens

<400> SEQUENCE: 72

```
Tyr Ser Leu Pro Lys Ser Glu Phe Ala Val Pro Asp Leu Glu Leu Pro
  1               5                  10                  15
```

<210> SEQ ID NO 73
<211> LENGTH: 193
<212> TYPE: PRT
<213> ORGANISM: Homo sapiens

<400> SEQUENCE: 73

```
Met Gln Ser Leu Met Gln Ala Pro Leu Leu Ile Ala Leu Gly Leu Leu
  1               5                  10                  15

Leu Ala Thr Pro Ala Gln Ala His Leu Lys Lys Pro Ser Gln Leu Ser
             20                  25                  30

Ser Phe Ser Trp Asp Asn Cys Asp Glu Gly Lys Asp Pro Ala Val Ile
         35                  40                  45

Arg Ser Leu Thr Leu Glu Pro Asp Pro Ile Val Val Pro Gly Asn Val
     50                  55                  60

Thr Leu Ser Val Val Gly Ser Thr Ser Val Pro Leu Ser Ser Pro Leu
 65                  70                  75                  80

Lys Val Asp Leu Val Leu Glu Lys Glu Val Ala Gly Leu Trp Ile Lys
                 85                  90                  95

Ile Pro Cys Thr Asp Tyr Ile Gly Ser Cys Thr Phe Glu His Phe Cys
            100                 105                 110

Asp Val Leu Asp Met Leu Ile Pro Thr Gly Glu Pro Cys Pro Glu Pro
        115                 120                 125

Leu Arg Thr Tyr Gly Leu Pro Cys His Cys Pro Phe Lys Glu Gly Thr
    130                 135                 140

Tyr Ser Leu Pro Lys Ser Glu Phe Val Val Pro Asp Leu Glu Leu Pro
145                 150                 155                 160

Ser Trp Leu Thr Thr Gly Asn Tyr Arg Ile Glu Ser Val Leu Ser Ser
                165                 170                 175
```

-continued

```
Ser Gly Lys Arg Leu Gly Cys Ile Lys Ile Ala Ala Ser Leu Lys Gly
            180                 185                 190

Ile

<210> SEQ ID NO 74
<211> LENGTH: 83
<212> TYPE: PRT
<213> ORGANISM: Homo sapiens

<400> SEQUENCE: 74

Gly Asp Val Cys Gln Asp Cys Ile Gln Met Val Thr Asp Ile Gln Thr
 1               5                  10                  15

Ala Val Arg Thr Asn Ser Thr Phe Val Gln Ala Leu Val Glu His Val
            20                  25                  30

Lys Glu Glu Cys Asp Arg Leu Gly Pro Gly Met Ala Asp Ile Cys Lys
        35                  40                  45

Asn Tyr Ile Ser Gln Tyr Ser Glu Ile Ala Ile Gln Met Met Met His
    50                  55                  60

Met Gln Asp Gln Gln Pro Lys Glu Ile Cys Ala Leu Val Gly Phe Cys
65                  70                  75                  80

Asp Glu Val

<210> SEQ ID NO 75
<211> LENGTH: 115
<212> TYPE: PRT
<213> ORGANISM: Homo sapiens

<400> SEQUENCE: 75

Met Thr Cys Lys Met Ser Gln Leu Glu Arg Asn Ile Glu Thr Ile Ile
 1               5                  10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Asp Leu Asp Thr Asn Ala Asp Lys Gln Leu Ser Phe Glu Glu Phe
65                  70                  75                  80

Ile Met Leu Met Ala Arg Leu Thr Trp Ala Ser His Glu Lys Met His
                85                  90                  95

Glu Gly Asp Glu Gly Pro Gly His His His Lys Pro Gly Leu Gly Glu
            100                 105                 110

Gly Thr Pro
        115
```

USE OF A POLYPEPTIDE FOR DETECTING, PREVENTING OR TREATING A PATHOLOGICAL CONDITION ASSOCIATED WITH A DEGENERATIVE, NEUROLOGICAL OR AUTOIMMUNE DISEASE

BACKGROUND

The present invention relates in particular to the use of at least one polypeptide to obtain a diagnostic, prognostic, prophylactic or therapeutic composition for for detecting, preventing or treating a pathological condition associated with a degenerative and/or autoimmune and/or neurological disease.

According to the invention, the expression degenerative disease is understood to mean a disease in which a process of cell death or of cell destruction is associated with physiological and/or clinical disorders. Alzheimer's disease, amyotrophic lateral sclerosis and Parkinson's disease are classified amongst neurogenerative diseases. The expression autoimmune disease is understood to mean a hyperactivity of the immune system toward one or more autoantigens. Multiple sclerosis (MS), rheumatoid arthritis (RA) and lupus erythematosus are classified among autoimmune diseases.

Multiple sclerosis is a chronic disease of the central nervous system in humans which progresses through a succession of phases of remission and of flare-up or in a regular progression and whose anatomicopathological characteristic consists in the formation of well delimited demyelination zones in the white substance of the brain and of the spinal cord.

At the histological level, these zones exhibit, at the early stage of the lesional process, a degradation of the periaxonal myelin associated with an impairment of the glial cells responsible for this demyelination.

Inflammatory macrophage activation causing the microglial cells (resident tissue macrophages of the central nervous system), as well as, probably, macrophages from infiltrated blood monocytes, is associated with this demyelination process and contributes to the destruction of the myelinated sheets. At the center of the demyelinated zone, there is a relative depletion of glial cells whereas a proliferation of astrocytes develops at the periphery and can invade the demyelinated plaque in order to generate a fibrous or gliotic plaque. These sclerotic structures are responsible for the name given to the disease.

Another characteristic of these plaques is their almost systematic association with a vascular element around which they develop.

At the histological level, a frequent alteration of the blood-brain barrier (BBB) consisting of capillary endothelium is observed. One of the key elements in maintaining the BBB consists of the underlying presence of cytoplasmic extensions of the astrocytes, called astrocytic feet. Possibly, the astrocytic feet induce the formation or allow the maintenance of tight joining structures which ensure the cohesion of the capillary endothelial barrier concretizing the BBB. However, various pathological models report the alteration of the BBB and a depletion of the astrocytic feet.

Moreover, in the lesional process in MS, the alteration of the BBB contributes toward amplifying the associated inflammatory response by the influx of lymphoid cells from the bloodstream. The contribution of the inflammation associated with the immune cells is important in MS and participates in the lesional process.

The etiology of MS is the source of a current debate because the disease could have various origins. Hypotheses have been emitted on a bacterial and/or viral origin. Moreover, as described in patent application WO 95/21859, H. Perron et al. have been led to investigate one or more effector agents for the pathogenic process resulting in the typical formation of demyelination plaques and in astrocytic gliosis. In the context of this study, they demonstrated the presence, in the cerebrospinal fluid (CSF) and the serum of MS patients, of at least one factor which exhibits a toxic activity toward human or animal astrocyte and oligodendrocyte cells. This toxic activity is characterized by a cytomorphological disorganization of the network of intermediate filaments and/or a degradation of the proteins of said filaments and/or a cell death by apoptosis of the glial cells. They established a significant correlation between the in vitro detection of this toxic activity in samples of CSF and of serum of MS patients and multiple sclerosis by a quantitative calorimetric assay with methyltetrazolium bromide (MTT) of the live cells, as described in patent application WO 95/21859. Moreover, C. Malcus-Vocanson et al. have shown that urine is a very favorable biological fluid for the detection of the activity of this toxic factor and developed a method using flow cytometry to detect and/or quantify the adherent glial cells which are dead through apoptosis. All the information relating to this method is described in patent application WO 98/11439, whose content is incorporated by way of reference.

Trials were carried out starting with a protein fraction of CSF and of urine from MS patients in order to try to identify this toxic factor. The protein content of each fraction was separated on a 12% SDS-PAGE gel and observed after silver staining of the gel. Among the proteins observed, a protein fraction centered over an apparent molecular weight of about 21 kD was found not predominantly associated with the toxic activity detected in vitro and a fraction centered over an apparent molecular weight of about 17 kD was found predominantly associated with the toxic activity.

Injection of the fraction from the SCF of MS patients into the brain of Lewis rats and postmortem histological observation of brain sections of the rats made it possible to observe, three months after the injection, an apoptosis of the astrocytic population and the formation of demyelination plaques. All the information is contained in patent application WO 97/33466, whose content is incorporated by way of reference. These observations are in accordance with those which have been made on the brain sections of patients suffering from MS, after biopsy (N. Benjelloun et al. Cell. Mol. Biol., 1998, 44(4), 579–583).

SUMMARY

The present inventors have now identified and analyzed the proteins associated with this toxic activity toward glial cells in biological samples from MS patients, in particular in urine, cerebrospinal fluid and serum.

After purification of the proteins and separation on SDS-TRICINE gel, the inventors have demonstrated the presence of four bands of interest having different apparent molecular weights, of 8, 14, 18 and 20 kD respectively, corresponding to at least five different protein families. The proteins of these families were then analyzed by mass spectrometry and/or sequencing and a search for homology in data banks (NCBI, Basic Blast Search, Protein Blastp, the protein sequences are entered in a FASTA format into the nr database, the algorithm used is Matrix BLOSUM62, the identity called "Identities" corresponds to the number of identical amino acids, given as a percentage, and the positivity "Positives" corresponds to the amino acids exhibiting biological equivalence according to the abovementioned parameters of the software, given as a percentage). These proteins belong to the protein families of Perlecan, of the precursor of the retinol-binding plasma protein, of the GM2 activator protein, of calgranulin and of saposin B. More precisely, the proteins are (i) for the 20 kD band, the C-terminal fragment of Perlecan which starts at amino acid 3464 and ends at amino acid 3707 (Murdoch A D et al. J Biol Chem, 1992, April 25; 267 (12):8544–47), and designated by a reference in the sequence identifier SEQ ID No. 2 (the full-length Perlecan protein being designated by a reference in SEQ ID No. 1), (ii) for the 20 kD band, the precursor of the retinol-binding plasma protein (Monaco H L et al., Science, 1995, 268 (5213):1039–1041) whose sequence is given in SEQ ID No. 4, (iii) for the 18 kD band, the GM2 activator protein (Furst W et al., Euro J Biochem, 1990, Sep. 24; 193(3):709–14) identified in SEQ ID No. 8, (iv) for the 14 kD band, calgranulin B (Lagasse. E et al., Mol Cell Biol, 1988, Jun.; 8(6):2402–10) identified in SEQ ID No. 17 and (v) for the 8 kD band, saposin B (Kleinschmidt T et al., Biol Chem Hoppe Seyler, 1988, December; 369(12):1361–5) represented in SEQ ID No. 24. They have also demonstrated the presence of variant sequences to said reference sequences, in particular for the 18 kD band a variant sequence of the GM2 activator protein designated by the reference SEQ ID No. 9. These variant protein sequences are the product of mutations at the level of the genes encoding said proteins or are the result of splicing phenomena. It should be noted, for example, that calprotectin is a variant of calgranulin B.

The C-terminal fragment of the Perlecan protein (SEQ ID No. 2) is encoded, for example, by the DNA nucleotide sequence SEQ ID No. 69, taking into account the genetic code. The precursor protein for the retinol-binding plasma protein (SEQ ID No. 4) is encoded, for example, by the DNA nucleotide sequence SEQ ID No. 70, taking into account the genetic code. The GM2 activator protein (SEQ ID No. 8) is encoded, for example, by the DNA nucleotide sequence SEQ ID No. 31, taking into account the genetic code. The peptides FSWDNCFEGK DPAVIR and YSLPKSEFAV PDLELP derived from the GM2 activator mutated polypeptide (SEQ ID No. 9) are encoded by the DNA nucleotide sequences SEQ ID No. 66 and SEQ ID No. 67, respectively, taking into account the genetic code. The calgranulin B protein (SEQ ID No. 17) is encoded, for example, by the DNA nucleotide sequence SEQ ID No. 42, taking into account the genetic code. The saposin B protein (SEQ ID No. 24) is encoded, for example, by the DNA nucleotide sequence SEQ ID No. 53, taking into account the genetic code.

The expression protein family is understood to mean all the proteins encoded from the same DNA gene and which result from a differential multiple splicing of the gene and/or of a different reading frame. The DNA gene is transcribed with alternative splicing phenomena, leading to the translation of different primary sequences of proteins. All these proteins belong to the same protein family. The term "protein family" also includes proteins which exhibit at least 70% identity, preferably at least 80% identity and advantageously at least 98% identity with a reference protein sequence of the family.

The expression multiple splicing is understood to mean a splicing occurring at least once in the nucleotide region of interest.

For example, the expression precursor protein family for the retinol-binding plasma protein designates the protein family comprising at least the proteins or fragments of proteins having the sequence SEQ ID No. 4, SEQ ID No. 5, SEQ ID No. 6, SEQ ID No. 7, and the proteins encoded by the corresponding gene according to different reading frames.

For example, the expression GM2 activator protein family designates the protein family comprising at least the proteins or fragments of proteins having the sequence SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, and the proteins encoded by the corresponding gene according to different reading frames, which result from a differential multiple splicing of the gene and/or of a different reading frame.

For example, the expression calgranulin B protein family designates the protein family comprising at least the proteins or fragments of proteins having the sequence SEQ ID No. 17, SEQ ID No. 18, SEQ ID No. 19, SEQ ID No. 20, SEQ ID No. 21, SEQ ID No. 22, SEQ ID No. 23, and the proteins encoded by the corresponding gene according to different reading frames, which result from a differential multiple splicing of the gene and/or of a different reading frame. The proteins MRP14 (SEQ ID No. 17) and MRP8 (SEQ ID No. 18) have a different protein sequence while being encoded by the same gene; they belong to the same protein family.

For example, the expression saposin B protein family designates the protein family comprising at least the proteins or fragments of proteins having the sequence SEQ ID No. 24, SEQ ID No. 25, SEQ ID No. 26, SEQ ID No. 27, SEQ ID No. 28, SEQ ID No. 29, and the proteins encoded by the corresponding gene according to different reading frames, which result from a differential multiple splicing of the gene and/or of a different reading frame.

The expression nucleic acid family encoding a protein is understood to mean all the cDNA and/or RNA nucleic sequences transcribed from the same DNA gene and which result from a differential multiple splicing. The DNA gene is transcribed with differential splicing phenomena and leads to the synthesis of different nucleic acids (cDNA, RNA) of different sequences. All these cDNA and mRNA sequences are considered to belong to the same nucleic acid family.

For example, the expression nucleic acid family encoding the precursor protein family for the retinol-binding plasma protein designates the nucleic acid family comprising at least the nucleic acids or fragments having the sequence SEQ ID No. 30.

For example, the expression nucleic acid family encoding the GM2 activator protein family designates the nucleic acid family comprising at least the nucleic acids or fragments having the sequences SEQ ID No. 31, SEQ ID No. 32, SEQ ID No. 33, SEQ ID No. 34, SEQ ID No. 35, SEQ ID No. 36, SEQ ID No. 37, SEQ ID No. 38, SEQ ID No. 39, SEQ ID No. 40, SEQ ID No. 41 which result from a differential multiple splicing of the gene and/or of a different reading frame.

For example, the expression nucleic acid family encoding the calgranulin B protein family designates the nucleic acid family comprising at least the nucleic acids or fragments having the sequences SEQ ID No. 42, SEQ ID No. 43, SEQ ID No. 44, SEQ ID No. 45, SEQ ID No. 46, SEQ ID No. 47, SEQ ID No. 48, SEQ ID No. 49, SEQ ID No. 50, SEQ ID No. 51, SEQ ID No. 52 which result from a differential multiple splicing of the gene and/or of a different reading frame.

For example, the expression nucleic acid family encoding the saposin B protein family designates the nucleic acid family comprising at least the nucleic acids or fragments having the sequences SEQ ID No. 53, SEQ ID No. 54, SEQ ID No. 55 which result from a differential multiple splicing of the gene and/or of a different reading frame.

The expression "splicing" is understood to mean a mechanism of excision of the introns and of joining of the exons during the maturation of the transcripts and the expression "differential splicing" is understood to mean the existence of several schemes for splicing of a primary transcript resulting in the formation of different messenger RNAs and capable of leading to the synthesis of several different proteins (Kaplan and Delpech, Biologie Moléculaire et Médecine, 1993, $2^{nd}$ edition, Médecine et Sciences, Flammarion, pages 73–77). This phenomenon is widely described in the scientific literature. By way of example, there may be mentioned the model of the genes which encode the heavy and light immunoglobulin chains, the model of the gene for dystrophin, the model of the gene for alpha-amylase, the gene for myelin, and the like.

It is known that the eukaryotic genes in particular comprise regions (exons) which encode fragments of the protein encoded by said gene and other regions (introns) which do not have a protein equivalent. This is due to the fact that the genes are first transcribed to a "primary" RNA which is then cut by splicing enzymes at the level of specific nucleotide sites (splicing sites). These enzymes then join the regions encoding the protein, thus reconstituting a "secondary" RNA from which the intron regions have been removed. Moreover, depending on the cellular phenotypes (and therefore the tissues or the differentiation), these enzymes are not all expressed, and thus the same RNA may be differently spliced in the cells of the same individual, thus generating proteins with differences in sequence. However, these phenomena may also be applied to nucleotide regions which are completely coding (exons), but which, according to different possible splicings, will generate several different proteins from the same nucleotide region by the phenomenon of differential splicing between the different protein products.

Furthermore, it is known that nucleotide regions may have several reading frames according to the three potential frames of the genetic code. Thus, the presence of several initiation codons for translation in several reading frames and/or a splicing of primary RNA joining nucleotide sequences present in different reading frames on the DNA, allows the same DNA region to generate protein products with no mutual relationship from the point of view of the peptide sequence.

Finally, the genetic polymorphism existing between individuals of the same species and/or individual mutations can create or eliminate splicing sites from a given DNA region, and thus modify the sequence and the structure of the protein product(s) normally produced by this region.

Thus, the combination of these different phenomena can allow the same nucleotide sequence corresponding to a DNA segment, identified as determining a genetic region of interest in a given study, to comprise the information which is necessary and sufficient to define a whole family of RNA spliced according to different and alternative schemes, in various reading frames and, thereby obviously, proteins and polypeptides having "mosaic" sequences according to one reading frame or even according to the three potential frames and mutations possibly linked to genetic polymorphism.

An example of this phenomenon may be represented by the nucleotide region of the HIV-1 retrovirus env gene. Indeed, several different proteins are encoded by segments of the same sequence: for example, the envelope glycoprotein, and the regulatory proteins TAT, REV, NEF, VIF.

It is also known that proteins may result from the assembly of identical subunits (homodimers, homomultimers) or different subunits (heterodimers, heteromultimers). Thus, the various protein products encoded by the same DNA region may also assemble with each other to constitute multimeric complex protein entities. This phenomenon is in addition to the preceding ones and, when a protein is identified by a peptide fragment, it is possible to logically identify all the other constituent elements of this complex protein and the spliced RNA and DNA segments encoding them, as well as all the members of the family of protein products and their assemblies. Another example is provided by the human DNA region encoding the family of MRP14, calgranulin B, MRP8, calprotectin and psoriasin proteins, and the like.

Accordingly, the subject of the present invention is the use of at least one polypeptide comprising at least one fragment of a protein to obtain a diagnostic, prognostic, prophylactic or therapeutic composition for detecting, prognosticating, preventing or treating a pathological condition associated with a degenerative and/or autoimmune disease, said protein being chosen from proteins whose peptide sequence in the native state corresponds to SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28 and SEQ ID No. 29 and the peptide sequences which exhibit at least 70% identity, preferably at least 80% identity and advantageously at least 98% identity with any of the abovementioned peptide sequences, and the peptide sequences or the fragments of said sequences belonging to the same family of proteins chosen from Perlecan, the precursor of the retinol-binding plasma protein, GM2 activator protein, calgranulin B and saposin B. In specific embodiments, at least two abovementioned polypeptides are used in combination in order to obtain a diagnostic, prognostic, prophylactic or therapeutic composition for detecting, prognosticating, preventing or treating a pathological condition associated with a degenerative and/or autoimmune disease.

The invention also relates to the use of at least one polypeptide comprising at least one fragment of a protein to obtain a diagnostic, prognostic, prophylactic or therapeutic composition for detecting, prognosticating, preventing or treating a pathological condition associated with a degenerative and/or autoimmune disease, said protein being chosen from the proteins whose peptide sequence in the native state corresponds to SEQ ID No. 2, SEQ ID No. 4, SEQ ID No. 8, SEQ ID No. 17 and SEQ ID No. 24 and the peptide sequences which exhibit at least 70% identity, preferably at least 80% identity and advantageously at least 98% identity with any one of the abovementioned peptide sequences. Advantageously, the five polypeptides which correspond to the above definition are used in combination.

Preferably, the peptide sequence of said polypeptide comprises, or consists of, a sequence chosen from any one of SEQ ID No. 2, SEQ ID No. 4, SEQ ID No. 8, SEQ ID No. 17 and SEQ ID No. 24.

The invention also relates to the use of at least one fragment of one of the abovementioned polypeptides for the preparation of an immunogenic peptide, said peptide comprising all or part of at least one of the sequences designated by the references SEQ ID Nos. 58 to 65 and being used for the production of monoclonal antibodies.

The subject of the invention is also the use of at least one nucleotide fragment to obtain a diagnostic, prognostic, prophylactic or therapeutic composition for detecting, prognosticating, preventing or treating a pathological condition associated with a degenerative and/or autoimmune disease, according to which said nucleotide fragment is chosen from fragments which encode at least one fragment of a protein, said protein being chosen from proteins whose peptide sequence in the native state corresponds to SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28 and SEQ ID No. 29 and the peptide sequences which exhibit at least 70% identity, preferably at least 80% and advantageously at least 98% identity with any one of the above peptide sequences, and the fragments complementary to said fragments, and the peptide sequences or the fragments of said sequences belonging to the same family of proteins chosen from Perlecan, the precursor of the retinol-binding plasma protein, GM2 activator protein, calgranulin B and saposin B. It is within the capability of persons skilled in the art to determine the nucleic sequences of the nucleotide fragments from the peptide sequences and the genetic code, this forming part of their general knowledge.

Preferably, said nucleotide fragment encodes a protein which, in the native state, consists of a sequence chosen from any one of the sequences SEQ ID Nos. 1 to 8 and SEQ ID Nos. 10 to 29 cited above, and among the peptide sequences or the fragments of said sequences belonging to the same family of proteins chosen from Perlecan, the precursor of the retinol-binding plasma protein, GM2 activator protein, calgranulin B and saposin B.

Another subject of the invention is the use of at least one nucleotide fragment to obtain a diagnostic, prognostic, prophylactic or therapeutic composition for detecting, prognosticating, preventing or treating a pathological condition associated with a degenerative and/or neurological and/or autoimmune disease according to which said fragment is a fragment of a nucleic sequence chosen from any one of SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, SEQ ID No. 39, SEQ ID No. 40, SEQ ID No. 41, SEQ ID No. 42, SEQ ID No. 43, SEQ ID No. 44, SEQ ID No. 45, SEQ ID No. 46 and SEQ ID No. 47, SEQ ID No. 48, SEQ ID No. 49 and SEQ ID No. 50, SEQ ID No. 51, SEQ ID No. 52, SEQ ID No. 53, SEQ ID No. 54, SEQ ID No. 55, SEQ ID No. 56, SEQ ID No. 57, SEQ ID No. 67, SEQ ID No. 66, SEQ ID No. 69, SEQ ID No. 70 and SEQ ID No. 71, and their complementary sequences.

The invention also relates to the use of a ligand specific for a polypeptide or for a nucleotide fragment as defined above to obtain a diagnostic, prognostic, prophylactic or therapeutic composition for detecting, prognosticating, preventing or treating a pathological condition associated with a degenerative and/or autoimmune disease.

The expression ligand is understood to mean any molecule capable of combining with a polypeptide, such as a monoclonal antibody, a polyclonal antibody, a receptor, a substrate with enzymatic activity, or an enzyme for which said polypeptide is a cofactor. The production of polyclonal or monoclonal antibodies forms part of the general knowledge of persons skilled in the art. There may be mentioned, by way of reference, Köhler G. and Milstein C. (1975): Continuous culture of fused cells secreting antibody of predefined specificity, Nature 256:495–497 and Galfre G. et al. (1977) Nature, 266:522–550 for the production of monoclonal antibodies and Roda A., Bolelli G. F.: Production of high-titer antibody to bile acids, Journal of Steroid Biochemistry, Vol. 13, pp. 449–454 (1980) for the production of polyclonal antibodies.

The expression ligand is also understood to mean any molecule capable of combining with a nucleotide fragment, such as a partially or completely complementary nucleotide fragment, a complementary polynucleotide, or an anti-nucleic acid antibody. The production of nucleotide fragments or of polynucleotides forms part of the general knowledge of persons skilled in the art. There may be mentioned in particular the use of restriction enzymes, and chemical synthesis on an automated synthesizer, for example on synthesizers marketed by the company Applied Biosystem. Moreover, techniques for the production of anti-nucleic acid antibodies are known. There may be mentioned, by way of examples, Philippe Cros et al., Nucleic Acides Researc, 1994, Vol. 22, No. 15, 2951–2957; Anderson, W. F. et al. (1988) Bioessays, 8(2), 69–74; Lee, J. S. et al. (1984) FEBS Lett., 168, 303–306; Malfoy, B. et al. (1982) Biochemistry, 21(22), 5463–5467; Stollar, B. D. et al., J. J. (eds) Methods in Enzymology, Academic Press, pp. 70–85; Traincard, F. et al. (1989) J. Immunol. Meth., 123, 83–91 and Traincard, F. et al. (1989) Mol. Cell. Probes, 3, 27–38).

The subject of the invention is also a method for detecting at least one protein associated with a degenerative and/or autoimmune disease in a biological sample in which the biological sample is brought into contact with at least one ligand specific for at least one polypeptide, said polypeptide comprising at least one fragment of a protein and said protein being chosen from the proteins whose peptide sequence in the native state corresponds to SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28 and SEQ ID No. 29 and the peptide sequences which exhibit at least 70% identity, preferably at least 80% identity and advantageously at least 98% identity with any one of the peptide sequences SEQ ID No. 1 to SEQ ID No. 8 and SEQ ID No. 10 to 29, and the peptide sequences or fragments of said sequences belonging to the same family of proteins chosen from Perlecan, the precursor of the retinol-binding plasma protein, GM2 activator protein, calgranulin B and saposin B, and then the formation of a complex between said polypeptide and said ligand is detected. Said ligand is advantageously a monoclonal antibody, a polyclonal antibody, a receptor, a substrate with enzymatic activity or an enzyme for which said polypeptide is a cofactor.

Likewise, the invention relates to a method for detecting at least one ligand associated with a degenerative and/or autoimmune disease, in a biological sample, characterized in that the biological sample is brought into contact with at least one polypeptide comprising at least one fragment of a protein, said protein being chosen from the proteins whose peptide sequence in the native state corresponds to SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28 and SEQ ID No. 29 and the peptide sequences which exhibit at least 70% identity, preferably at least 80% identity and advantageously at least 98% identity with any one of the peptide sequences SEQ ID No. 1 to SEQ ID No. 8 and SEQ ID Nos. 10 to SEQ ID No. 29, and the peptide sequences or the fragments of said sequences belonging to the same family of proteins chosen from Perlecan, the precursor of the retinol-binding plasma protein, GM2 activator protein, calgranulin B and saposin B, and then the formation of a complex between said polypeptide and said ligand is detected. The ligand is any molecule which satisfies the conditions previously described.

Preferably, in the methods described above, the sequence of the polypeptide comprises or consists of a peptide sequence chosen from any one of SEQ ID No. 1 to 8 and SEQ ID No. 10 to 29 above and the peptide sequences or the fragments of said sequences belonging to the same family of proteins chosen from Perlecan, the precursor of the retinol-binding plasma protein, GM2 activator protein, calgranulin B and saposin B.

The invention also relates to a novel polypeptide which comprises at least one fragment of a protein whose peptide sequence corresponds to SEQ ID No. 9, said fragment exhibiting at least one mutation, in particular at least two mutations, in relation to the reference sequence SEQ ID No. 8. The polypeptide is advantageously chosen from the polypeptides which comprise the amino acid sequence FSWDNCFEGKDPAVIR, designated by the reference SEQ ID No. 68, and the amino acid sequence YSLPKSEFAVP-DLELP, designated by the reference SEQ ID No. 72.

In particular, said polypeptide comprises or consists of SEQ ID No. 9. This polypeptide is used to obtain a diagnostic, prognostic, prophylactic or therapeutic composition for detecting, prognosticating, preventing or treating a pathological condition associated with a degenerative and/or autoimmune disease, alone or as a mixture with at least one polypeptide as defined above.

One of the subjects of the invention is also a nucleotide fragment which encodes the fragment of the protein whose peptide sequence corresponds to SEQ ID No. 9, said fragment of said protein exhibiting at least one mutation, in particular two mutations relative to the reference sequence SEQ ID No. 8. Said nucleotide fragment in particular comprises or consists of a fragment which encodes SEQ ID No. 9. This fragment is used to obtain a diagnostic, prognostic, prophylactic or therapeutic composition for detecting, preventing or treating a pathological condition associated with a degenerative and/or autoimmune disease, alone or as a mixture with at least one nucleotide fragment as defined above.

The subject of the invention is also a method for detecting at least one ligand associated with a degenerative and/or autoimmune disease, in a biological sample, according to which the biological sample is brought into contact with at least the polypeptide which comprises or consists of SEQ ID No. 9 or a mixture of polypeptides comprising this polypeptide and at least one polypeptide as described above, and then the formation of a complex or of complexes between the polypeptide(s) and the corresponding ligand(s) is detected; it is to be understood that the expression ligand is understood to mean a molecule which satisfies the above-mentioned conditions.

The invention also relates to a method for detecting at least the reference polypeptide SEQ ID No. 9 or a fragment of said polypeptide, this fragment comprising at least one and preferably two mutations in relation to the reference sequence SEQ ID No. 8, in a biological sample according to which the biological sample is brought into contact with at least one ligand specific for said polypeptide, and then the formation of a complex between said polypeptide and said ligand is detected. The definition of ligand corresponds to that defined above. It may be, inter alia, a monolonal antibody, a polyclonal antibody, a substrate with enzymatic activity or an enzyme for which said polypeptide is a cofactor, or a receptor.

It is also possible to bring the biological sample into contact with a ligand specific for the reference polypeptide SEQ ID No. 9 and at least one ligand specific for at least one other polypeptide as defined above, and then the formation of complexes between said polypeptides and said ligands specific for said polypeptides is detected; it being understood that the expression ligand is understood to mean a molecule which satisfies the conditions described above.

Another subject of the invention is a nucleotide fragment encoding all or part of the polypeptide SEQ ID No. 9, and its use to obtain a diagnostic, prognostic, prophylactic or therapeutic composition for detecting, prognosticating, preventing or treating a pathological condition associated with a degenerative and/or autoimmune disease, optionally in combination with at least one nucleotide fragment as defined above, and the fragments complementary to said fragments.

The expression polypeptide fragment is understood to mean at least all or part of the peptide sequence of a protein, in particular a polypeptide fragment which comprises between about 5 and 15 amino acids and more precisely between about 5 and 10 amino acids and 6 and 15 amino acids. The expression nucleotide fragment is understood to mean at least all or part of a nucleotide sequence, it being understood that the expression nucleotide sequence covers DNA and RNA sequences.

In particular, the expression polypeptide or nucleotide fragment is understood to mean either fragments associated with the same molecular unit, or fragments in a molecular complex comprising several homologous or heterologous subunits obtained naturally or artificially, in particular by differential multiple splicing or by selective synthesis.

The invention also relates to a method for detecting at least one polypeptide as defined above, according to which a sample of a biological fluid is collected from a patient having a pathological condition associated with a degenerative and/or neurological and/or autoimmune disease and, optionally after purification of said sample of biological fluid, the mass profile obtained from the biological fluid is analyzed by mass spectrometry and compared with a reference mass profile.

The present invention also relates to the use of at least one polypeptide of the invention to define therapeutically effective agents, and the use of these agents to prevent and/or treat an autoimmune and/or neurological and/or degenerative disease, and in particular multiple sclerosis.

Thus, other subjects of the invention are the following:

Use of at least one polypeptide comprising at least one fragment of a protein to test the efficacy of a therapeutic agent, said protein being chosen from the proteins whose peptide sequence in the native state corresponds to SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28 and SEQ ID No. 29, the peptide sequences which exhibit at least 70% identity, preferably at least 80% identity and advantageously at least 98 identity with any one of the peptide sequences SEQ ID No. 1 to 29, and the peptide sequences or the fragments of said sequences belonging to the same family of proteins chosen from Perlecan, the precursor of the retinol-binding plasma protein, GM2 activator protein, calgranulin B and saposin B;

Use of at least one polypeptide comprising at least one fragment of a protein to define a biological material for the preparation of a pharmaceutical composition for treating a degenerative and/or neurological and/or autoimmune disease, such as multiple sclerosis, said protein being chosen from the proteins whose peptide sequence in the native state corresponds to SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28 and SEQ ID No. 29, the peptide sequences which exhibit at least 70% identity, preferably at least 80% identity and advantageously at least 98 identity with any one of the peptide sequences SEQ ID No. 1 to 29, and the peptide sequences or the fragments of said sequences belonging to the same family of proteins chosen from Perlecan, the precursor of the retinol-binding plasma protein, GM2 activator protein, calgranulin and saposin;

According to an advantageous variant of one of the preceding uses, the polypeptide is chosen from SEQ ID No. 2, 4, 8, 9, 17, 24;

Use of at least one nucleotide fragment to test the efficacy of a therapeutic agent for a pathological condition associated with a degenerative and/or neurological and/or autoimmune disease, according to which said nucleotide fragment is chosen from the fragments which encode at least one fragment of a protein, said protein being chosen from the proteins whose peptide sequence in the native state corresponds to SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28 and SEQ ID No. 29, the peptide sequences which exhibit at least 70% identity, preferably at least 80% and advantageously at least 98% identity with any one of the peptide sequences SEQ ID No. 1 to 29, and the fragments complementary to said fragments and the fragments which encode the peptide sequences or the fragments of said sequences belonging to the same family of proteins chosen from Perlecan, the precursor of the retinol-binding plasma protein, GM2 activator protein, calgranulin B and saposin B.

Use, to test the efficacy of a therapeutic agent for a pathological condition associated with a degenerative and/or neurological and/or autoimmune disease, of recombinant proteins and/or proteins encoded by all or part of the nucleotide fragments defined in the above paragraph;

Use of at least one nucleotide fragment for the preparation of a pharmaceutical composition for treating a degenerative and/or neurological and/or autoimmune disease, such as multiple sclerosis, according to which said nucleotide fragment is chosen from fragments which encode at least one fragment of a protein, said protein being chosen from the proteins whose peptide sequence in the native state corresponds to SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28 and SEQ ID No. 29, the peptide sequences which exhibit at least 70% identity, preferably at least 80% and advantageously at least 98% identity with any one of the peptide sequences SEQ ID No. 1 to 29, and the fragments complementary to said fragments and the fragments which encode the peptide sequences or the fragments of said sequences belonging to the same family of proteins chosen from Perlecan, the precursor of the retinol-binding plasma protein, GM2 activator protein, calgranulin B and saposin B;

Use, for the preparation of a pharmaceutical composition for treating a degenerative and/or neurological and/or autoimmune disease, such as multiple sclerosis, of recombinant proteins and/or proteins encoded by all or part of the nucleotide fragments defined in the preceding paragraph.

Advantageously, said nucleotide fragment used encodes said protein.

Preferably, the peptide sequence of said protein in the native state consists of a sequence chosen from any one of SEQ ID No. 1 to 29, the peptide sequences which exhibit at least 70% identity, preferably at least 80% identity and advantageously at least 98 identity with any one of the peptide sequences SEQ ID No. 1 to 29, and the peptide sequences or the fragments of said sequences belonging to the same family of proteins chosen from Perlecan, the precursor of the retinol-binding plasma protein, GM2 activator protein, calgranulin B and saposin B. The polypeptides are preferably chosen from SEQ ID No. 2, 4, 8, 9, 17, 24.

Use of at least one nucleotide fragment to test the efficacy of a therapeutic agent for a pathological condition associated with a degenerative and/or neurological and/or autoimmune disease, according to which said fragment is a fragment of a nucleic sequence chosen from any one of SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, SEQ ID No. 39, SEQ ID No. 40, SEQ ID No. 41, SEQ ID No. 42, SEQ ID No. 43, SEQ ID No. 44, SEQ ID No. 45, SEQ ID No. 46 and SEQ ID No. 47, SEQ ID No. 48, SEQ ID No. 49 and SEQ ID No. 50, SEQ ID No. 51, SEQ ID No. 52, SEQ ID No. 53, SEQ ID No. 54, SEQ ID No. 55, SEQ ID No. 56, SEQ ID No. 57, SEQ ID No. 66, SEQ ID No. 67, SEQ ID No. 69, SEQ ID No. 70, SEQ ID No. 71, and their complementary sequences.

Use of at least one nucleotide fragment for the preparation of a pharmaceutical composition for treating a degenerative and/or neurological and/or autoimmune disease, such as multiple sclerosis, according to which said fragment is a fragment of a nucleic sequence chosen from any one of SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, SEQ ID No. 39, SEQ ID No. 40, SEQ ID No. 41, SEQ ID No. 42, SEQ ID No. 43, SEQ ID No. 44, SEQ ID No. 45, SEQ ID No. 46 and SEQ ID No. 47, SEQ ID No. 48, SEQ ID No. 49 and SEQ ID No. 50, SEQ ID No. 51, SEQ ID No. 52, SEQ ID No. 53, SEQ ID No. 54, SEQ ID No. 55, SEQ ID No. 56, SEQ ID No. 57, SEQ ID No. 66, SEQ ID No. 67, SEQ ID No 68, SEQ ID No. 69, SEQ ID No. 70, SEQ ID No. 71, and their complementary sequences.

The nucleic sequence is preferably chosen from SEQ ID No. 30, 31, 42, 53.

Use of lycorine for the preparation of a composition for preventing and/or treating a degenerative and/or neurological and/or autoimmune disease.

The expression therapeutic efficacy is understood to mean the clinical and biological benefit acquired after administration of a therapeutic agent for the purpose of improving or even curing the disease. This benefit is manifested, inter alia, by a reduction in the clinical and biological signs, and in the pathological effects of the disease after clinical analysis by the doctor and/or biological analyses, such as magnetic resonance imaging, analysis of the oligoclonal bands in the cerebrospinal fluid, analysis of evoked potentials and the test for detection of gliotoxicity called bioassay, whose principle is described in patent application WO 98/11439 cited above. This reduction in the clinical signs and pathological effects should result in a benefit for the patient (Schwartz and Lazar, 1995, Elements de statistique médicale et biologique, eds Flammarion; Lazar and Schwartz, 1995, Eléments de statistique médicale et biologique, eds Flammarion). The disease studied is preferably multiple sclerosis.

The expression composition for prophylactic and/or therapeutic use is understood to mean any composition which comprises an effective therapeutic agent. These therapeutic agents are capable (i) of qualitatively and/or quantitatively influencing the biological activity and/or the function of the proteins of interest identified in the present invention, preferably the gliotoxic activity and/or (ii) modulating and/or inhibiting the expression of these proteins and/or (iii) reducing the concentration of these proteins in an extracellular and/or intracellular compartment, and/or substituting a nonpathogenic form for a pathogenic, for example mutated, form of one of these proteins and/or modulating their attachment to at least one of their ligands; said ligand being a molecule which satisfies the criteria described above. Various therapeutic agents are produced based on the conventional approaches widely described in the literature. The various groups of therapeutic agents defined from the proteins of interest identified in this present invention are described below. Their prophylactic and/or therapeutic efficacy or activity is evaluated in vitro and/or in vivo.

Evaluation of the efficacy of a therapeutic agent in vitro: urine samples from healthy individuals and from patients suffering from multiple sclerosis, preferably in the active phase, are tested for their gliotoxic activity in vitro based on the bioassay protocol described in patent application WO 98/11439, cited above. The experiment is carried out in parallel by adding or otherwise, to the urine samples tested, the therapeutic agent whose efficacy is to be tested. Assays are carried out at various concentrations of this agent, and after various incubation times with the sample, at a temperature of about 37° C. or at room temperature, for each concentration of agent tested, before carrying out the bioassay test. The gliotoxic activity is determined for each crude or purified sample of control and patient's urine in the presence or in the absence of tested therapeutic agent. A prophylactic and/or therapeutic agent for multiple sclerosis is an agent which allows a reduction or an inhibition of the gliotoxic activity in a biological fluid from the patients, in particular in the urine. This reduction or inhibition is evaluated relative to the gliotoxic activity detected in the biological fluid of MS patients in the absence of the test agent which defines the upper limit and relative to the gliotoxic activity detected in the urine of a healthy individual which determines the lower limit (Schwartz and Lazar, 1995, Elements de statistique médicale et biologique, eds Flammarion; Lazar and Schwartz, 1995, Elements de statistique médicale et biologique, eds Flammarion). The therapeutic efficacy of several agents may be evaluated in combination in the same assay.

Evaluation of the efficacy of a therapeutic agent using an animal model: there are injected into an animal fractions of purified urine and/or at least one polypeptide of the invention and/or at least one protein obtained by genetic recombination which corresponds to at least one polypeptide of the invention and/or at least one synthetic polypeptide whose amino acid sequence corresponds to the sequence of at least one polypeptide of the invention. The injections are carried out, at various established concentrations, into mammalian animals such as mice or rats, preferably a Lewis rat according to the protocol described in patent application WO97/33466 cited above. Various concentrations of a fraction of crude or purified urine or of at least one polypeptide and/or one protein, as defined above, are injected into a series of animals by the intradermal, intravenous, intrathecal, intracerebral or intramuscular route, and the like. A negative control is carried out in parallel. The prophylactic and/or therapeutic agent to be evaluated and then injected at various concentrations and by various routes of administration to a mammalian animal, preferably to a mouse or to a rat. The injections are carried out as a single dose or as repeated doses, with various time intervals between each administration. A few hours to a few weeks after the administration, biological samples, preferably of blood, serum, cerebrospinal fluid, or urine, are collected. These samples are subjected to:

(i) a measurement of the gliotoxic activity by the bioassay, and/or (ii) a measurement of activity of the polypeptides and/or proteins of interest of the invention, alone or in combination, as described at least in: Li et al., 1983, Am J Hum Genet 35:629–634; Li et al., 1988 J Biol Chem 263:6588–6591; Li et al., 1981 J Biol Chem 256: 6234–6240; Li et al., 1976 J Biol Chem 251:1159; Kase et al., 1996, FebsLetters 393: 74–76; Kishimoto et al., 1992, J Lipid Res 33: 1255–1267; O'Brien et al., 1991 Faseb J 5: 301–308; Murthy et al., 1993 J Immunol 151: 6291–6301; Murao et al., 1990 Cell growth Differ 1: 447–454, and/or (iii) an assay of the polypeptides and/or proteins of interest, alone or in combination, by ELISA (Enzyme Linked-Immunosorbant Assay) and/or Western blotting, using antibodies or antibody fragments capable of binding to at least one of the polypeptides and/or proteins of the invention, or their fragment, and/or (iv) an assay of antibodies specific for the polypeptides and/or proteins of interest or their fragments, alone or in combination or the assay of at least one ligand capable of binding to the polypeptides and/or proteins of interest or their fragments, and/or (v) an assay of the "helper" and/or cytotoxic cellular immune response induced against the polypeptides and proteins of interest or their fragments and any immunogenic peptide derived from these polypeptides, proteins and fragments, by carrying out, for example, a test of activation in vitro of "helper" T lymphocyte cells specific for the antigen administered; by quantifying the cytotoxic T lymphocytes according to the so-called ELISPOT technique described by Scheibenbogen et al., 1997 Clinical Cancer Research 3: 221–226. Such a determination is particularly advantageous when it is desired to evaluate the efficacy of a vaccine approach for use in a given patient or for diagnosing and/or prognosticating a potential pathological condition by seeking to demonstrate an immune response naturally developed by the patient against the antigen, the polypeptides, the proteins of interest or the immunogenic fragments derived from these proteins.

The expression "ligand capable of binding to a protein" is understood to mean any molecule capable of recognizing the protein or a portion of the protein. This may be verified for example in vitro by Elisa and/or Western blot tests.

The expression "polypeptides and/or proteins of interest of the invention" designates the C-terminal fragment of Perlecan (SEQ ID No. 2), the precursor of the retinol-binding plasma protein (SEQ ID No. 4), the GM2 activator protein (SEQ ID No. 8), the mutated protein of the GM2 activator (SEQ ID No. 9), calgranulin B (SEQ ID No. 17), saposin B (SEQ ID No. 24), the proteins or fragments belonging to the family of the precursor of the retinol-binding plasma protein (for example SEQ ID No. 5 to 7), the proteins or fragments belonging to the family of the GM2 activator protein (for example SEQ ID No. 10 to 16), the proteins or fragments belonging to the family of calgranulin B protein (for example SEQ ID No. 18 to 23), the proteins or fragments belonging to the family of the saposin B protein (for example SEQ ID No. 25 to 29) and the peptide sequences which exhibit at least 70% identity, preferably at least 80% identity and advantageously at least 98% identity with any one of the peptide sequences SEQ ID No. 1 to 29.

The animal is then sacrificed and histological sections of various tissues are prepared, preferably brain sections. Various studies and observations are carried out in order to detect and/or quantify the characteristic effects of the polypeptides and/or active proteins associated with the gliotoxic fraction, that is to say an apoptosis of the glial cells, and/or the opening of the blood-brain barrier and/or a demyelination. The presence or the expression of the polypeptides and/or proteins of interest identified is also observed and/or quantified in these tissues:

(i) by conventional immunohistological analyses using ligands for the polypeptides and/or proteins of interest and/or their fragments and/or monoclonal or polyclonal antibodies or fragments of said which bind to the polypeptides and/or proteins of interest, or to their fragments, and/or (ii) by conventional in situ hybridization techniques using nucleic acid fragments or oligonucleotides defined from polypeptide and/or protein sequences of interest; and/or (iii) by PCR and/or RT-PCR amplification techniques in situ using nucleic acid fragments or primers defined from polypeptide and/or protein sequences of interest.

The expression antibodies capable of binding to a polypeptide, to a protein or to their fragments is understood to mean any monoclonal or polyclonal antibody and any fragment of said antibodies capable of recognizing the polypeptide, the protein or their fragments. The capacity of the antibodies to recognize said polypeptides, proteins or their fragments is verified in vitro, for example by ELISA and/or Western blotting. An antibody capable of binding to the saposin B protein (SEQ ID No. 24) or to any fragment of this protein is described by Misasi et al. 1998, J. Neuro-Chem. 71:2313 and Klein et al. 1994, BBRC 200: 1440–1448 or may be produced using conventional methods, for example those designated by references above for the production of monoclonal and polyclonal antibodies, by immunization starting with a natural protein, a recombinant protein, a synthetic polypeptide or their fragments. The immunogenic peptides for the production of anti-saposin B monoclonal antibodies are the peptides corresponding to the sequences SEQ ID No. 61 and SEQ ID No. 62.

For example, an antibody capable of binding to the GM2 activator protein (SEQ ID No. 8) or to any fragment of this protein is illustrated by Yuziuk et al., 1998 J Biol Chem 273: 66–72 or may be produced using conventional methods known to persons skilled in the art. This antibody may for example be produced after injecting into mice or rabbits the natural protein or any fragment, and/or the recombinant protein or any fragment, and/or peptides defined and synthesized from the protein sequence of the protein. The immunogenic peptides used for the production of anti-GM2 monoclonal antibodies are the reference peptides SEQ ID No. 58, SEQ ID No. 59 and SEQ ID No. 60. An antibody capable of binding to the galgranulin B protein (SEQ ID No. 17) or to any fragment of this protein is described by Saintigny et al., 1992 J Invest Dermatol 99: 639–644 and Goebeler et al. 1994 J Leukoc Biol 55: 259–261, or may be produced using conventional methods. The immunogenic peptides for the production of anti-calgranulin B monoclonal antibodies are the peptides corresponding to the sequences SEQ ID No. 63, SEQ ID No. 64 and SEQ ID No. 65. An antibody capable of binding to the mutated GM2 activator protein (SEQ ID No. 9) or to any fragment of this protein may be produced using the conventional methods defined above.

The expression natural protein and fragment is understood to mean any isolated, completely or partially purified protein obtained from a human or animal sample and any fragment obtained from this protein. For example, the natural protein corresponding to saposin B (SEQ ID No. 24) is obtained according to the technique described by Waring et al. 1998 Mol Genet Metab 63: 14–25; the natural protein corresponding to the GM2 activator protein (SEQ ID No. 8) according to the technique described by DeGasperi et al., 1989 Biochem J 260: 777–783, Vogel et al., 1987 Arch Biochem Biophys 259: 627–638, Mitsuyama, 1983 Hokkaido Igaku Zasshi 58: 502–512; Hirabayashi et al 1983 J Neurochem 40: 168–175, Conzelmann et al., 1979 Hoppe Seylers Z Physiol Chem 360: 1837–1849, Li et al., 1976 J Biol Chem 251: 1159–1163. The natural protein corresponding to calgranulin B (SEQ ID No. 17) is obtained according to the technique described by Hitomi et al., 1996 J Cell Sci 109: 805–815, Van den Bos et al. 1998 Protein Expr Purif 13: 313–318 and Raftery et al. 1996 Biochem J 316: 285–293.

The expression recombinant protein or fragment of a recombinant protein refers to any protein or protein fragment produced in a prokaryotic or eukaryotic cell from a nucleotide sequence encoding the protein or its fragment and transfected into the cell, this protein or its fragment then being purified. In general, any cell derived from a prokaryotic or eukaryotic organism may be used in the context of the present invention, but the cells derived from eukaryotic organisms are preferred. There may be mentioned, by way of example, CHO cells, COS cells, and Semliki cells. For the purposes of the present invention, said cell may be wild type or mutant. For example, the recombinant protein corresponding to saposin B (SEQ ID No. 24) may be obtained according to the techniques described by Zaltash et al. 1998 Bebbs letter 423: 1–4 and Qi et al. 1994 J Biol Chem 269: 16746–16753. Such a recombinant protein is at least available from Kase et al. 1996 Febs Lett 393: 74–76. The recombinant protein corresponding to the GM2 activator protein (SEQ ID No. 8) may be produced by the techniques described by Yuziuk et al. 1998 J Biol Chem 273: 66–72 and Bierfreund et al., 1999 Neurochem Res 24: 295–300. The recombinant protein corresponding to calgranulin B (SEQ ID No. 17) may be obtained according to the protocol by Longbottom et al. 1992 Biochim Biophys Acta 1120:215–222, Raftery et al. 1999 Protein Expr Purif 15:228–235. Such a recombinant protein is available at least from Klempt et al. 1997 Febs Letter 408:81–84.

The expression DNA nucleotide sequence or DNA nucleotide fragment encoding all or part of the saposin B protein (SEQ ID No. 24) is understood to mean the nucleic acid sequence SEQ ID No. 53 or a fragment of this sequence. The expression RNA nucleotide sequence or fragment encoding all or part of the saposin B protein (SEQ ID No. 24) is understood to mean any sequence deduced from the DNA sequence SEQ ID No. 53, taking into account the genetic code and the splicing phenomena.

The expression DNA nucleotide sequence or DNA nucleotide fragment encoding all or part of the GM2 activator protein (SEQ ID No. 8) is understood to mean the nucleic acid sequence SEQ ID No. 31 or a fragment of this sequence. The expression RNA nucleotide sequence or fragment encoding all or part of the GM2 activator protein (SEQ ID No. 8) is understood to mean any sequence deduced from the DNA sequence SEQ ID No. 31, taking into account the genetic code and the splicing phenomena.

The expression DNA nucleotide sequence or DNA nucleotide fragment encoding all or part of the calgranulin B protein (SEQ ID No. 17) is understood to mean the nucleic acid sequence SEQ ID No. 42 or a fragment of this sequence. The expression RNA nucleotide sequence or fragment encoding all or part of the calgranulin B protein (SEQ ID No. 17) is understood to mean any sequence deduced from the DNA sequence SEQ ID No. 42, taking into account the genetic code and the splicing phenomena.

The expression nucleotide sequence or fragment encoding all or part of the mutated protein (SEQ ID No. 9) is understood to mean the nucleic acid sequence deduced from the sequence SEQ ID No. 9, taking into account the genetic code. The expression RNA nucleotide sequence or fragment encoding all or part of this mutated B protein (SEQ ID No. 9) is understood to mean any sequence deduced from the DNA sequence, taking into account the genetic code and the splicing phenomena.

The expression protein activity is understood to mean a characteristic biological function of the protein. The protein activity may be demonstrated by techniques known to persons skilled in the art. For example, the activity of saposin B (SEQ ID No. 24) and of the proteins of the saposin B family (for example SEQ ID No. 25 to 29) may be detected using the protocols described by Li et al., 1983, Am J Hum Genet 35:629–634; Li et al., 1988 J Biol Chem 263: 6588–6591, Li et al., 1981 J Biol Chem 256: 6234–6240 and Li et al., 1976 J Biol Chem 251:1159. The expression activity of the GM2 activator protein (SEQ ID No. 8) and of the proteins of the same family (for example SEQ ID No. 10 to 16) is understood to mean at least the activity detected using the protocols described, for example, by Kase et al., 1996, Febs Letters 393: 74–76, Kishimoto et al., 1992, J Lipid Res 33:1255–1267 and O'Brien et al., 1991 Faseb J 5: 301–308. The expression activity of calgranulin B (SEQ ID No. 17) and the proteins of the same calgranulin B family (for example SEQ ID No. 18 to 23) and any is understood to mean at least the activity detected using the protocols described for example by Murthy et al., 1993 J Immunol 151: 6291–6301 and Murao et al., 1990 Cell growth Differ 1: 447–454.

Production of a transgenic animal, preferably murine, model for a human pathology can be technically achieved. Briefly, the transgenic animal is produced using the conventional techniques described and possesses, integrated into the genome, the nucleic acids encoding the proteins or their fragments.

Evaluation of the efficacy of a therapeutic agent and therapeutic monitoring ex vivo, in humans:

the therapeutic agents to be tested for a therapeutic activity and/or for therapeutic monitoring are administered by various routes to humans, such as the intradermal, intravenous, intramuscular, intracerebral or oral routes, and the like. Various doses are administered to human beings. The patient's clinical file at the time of the first administration is perfectly known. One or more administrations may be carried out with various time intervals between each administration which may range from a few days to a few years. Biological samples are collected at defined time intervals after administration of the therapeutic agent, preferably blood, serum, cerebrospinal fluid and urine. Various analyses are carried out using these samples. Immediately before the first administration of the therapeutic agent, these sample collections and these same analyses are again performed. A conventional clinical and biological examination (MRI, oligoclonal bands in cerebrospinal fluid, evoked potentials) is also carried out in parallel with the additional analyses which are described below, at various analytical times. The analyses carried out are:

(i) a measurement of the gliotoxic activity by bioassay starting with samples of serum, CSF and urine, and/or (ii) a measurement of the activity of proteins of interest identified in the present invention alone or in combination, as described for example by: Li et al., 1983, Am J Hum Genet 35:629–634; Li et al., 1988 J Biol Chem 263: 6588–6591; Li et al., 1981 J Biol Chem 256: 6234–6240; Li et al., 1976 J Biol Chem 251:1159; Kase et al., 1996, FebsLetters 393:74–76; Kishimoto et al., 1992, J Lipid Res 33: 1255–1267; O'Brien et al., 1991 Faseb J 5: 301–308; Murthy et al., 1993 J Immunol 151: 6291–6301; Murao et al., 1990 Cell growth Differ 1: 447–454; and/or (iii) an assay of the proteins of interest or of their fragments, alone or in combination, in the blood/serum, CSF or urine samples by ELISA and/or Western blotting, using antibodies or antibody fragments capable of binding to at least one of the proteins or to one of their fragments, and/or (iv) an assay of antibodies specific for the proteins of interest or of their fragments in blood/serum, CSF or urine samples, by ELISA and/or Western blotting using a natural protein or a fragment of the natural protein and/or a recombinant protein or a fragment of this recombinant protein, alone or in combination. Likewise, an assay of ligands capable of binding to the proteins of interest identified, alone or in combination, may be carried out, and/or (v) an assay of "helper" and/or cytotoxic cellular immune response induced against the proteins of interest and any immunogenic peptide derived from these proteins, for example by carrying out a test of activation in vitro of T lymphocyte cells specific for the antigen administered (example). For example, using a test of activation in vitro of helper T lymphocyte cells specific for the antigen administered (example); For example by quantifying the cytotoxic T lymphocytes according to the so-called ELISPOT technique described by Scheibenbogen et al., 1997 Clinical Cancer Research 3: 221–226. Such a determination is particularly advantageous when it is desired to evaluate the efficacy of a vaccine approach used in a given patient or to diagnose a potential pathological condition in a patient, seeking to demonstrate an immune response naturally developed by said patient against the antigen, the proteins of interest or any immunogenic fragment derived from these proteins, alone or in combination, and/or (vi) a detection of DNA and/or RNA fragments encoding the proteins or a fragment of proteins of interest by nucleotide hybridization according to techniques well known to persons skilled in the art (Southern blotting, Northern blotting, ELOSA "Enzyme-linked Oligosorbent Assay" (Katz J B et al., Am. J. Vet. Res., 1993 December; 54 (12):2021–6 and Francois Mallet et al., Journal of Clinical Microbiology, June 1993, p 1444–1449)) and/or by the DNA and/or RNA amplification method, for example by PCR, RT-PCR, using nucleic acid fragments encoding the sequence of the proteins of interest, and/or (vii) by tissue, preferably brain, biopsy and observation of the characteristic effects of the active proteins associated with the gliotoxic fraction, that is to say an apoptosis of the glial cells and/or the opening of the blood-brain barrier and/or the observation of demyelination phenomena, and/or (viii) by tissue biopsy or on circulating cells (blood, CSF), observation of the presence of proteins of interest and estimation of their expression by immunohistological observation on histological sections prepared from tissues, using ligands and/or antibodies or their fragments capable of binding to the proteins of interest, and/or (ix) by tissue biopsy or on circulating cells (blood, CSF), observation of the expression of the proteins of interest by in situ hybridization of the RNA molecules encoding the proteins of interest using nucleic acids defined using the sequences of the proteins of interest, and/or (x) by tissue biopsy or on circulating cells (blood, CSF), determination of the expression of the proteins of interest by amplification of these RNAs by conventional techniques such as, for example, RT-PCR, using nucleic acids defined using the sequences of the proteins of interest.

The expression "polypeptides and/or proteins of interest of the invention" designates the C-terminal fragment of Perlecan (SEQ ID No. 2), the precursor of the retinol-binding plasma protein (SEQ ID No. 4), the GM2 activator protein (SEQ ID No. 8), the mutated GM2 activator protein (SEQ ID No. 9), calgranulin B (SEQ ID No. 17), saposin B (SEQ ID No. 24), the proteins or fragments belonging to the family of the precursor of the retinol-binding plasma protein (for example SEQ ID No. 5 to 7), the proteins or fragments belonging to the family of the GM2 activator protein (for example SEQ ID No. 10 to 16), the proteins or fragments belonging to the calgranulin B protein family (for example SEQ ID No. 18 to 23), the proteins or fragments belonging to the saposin B protein family (for example SEQ ID No. 25 to 29), and the peptide sequences which exhibit at least 70% identity, preferably at least 80% identity and advantageously at least 98 identity with any one of the peptide sequences SEQ ID No. 1 to 29.

The expression DNA nucleic acid sequence or fragments encoding the "polypeptides and/or proteins of interest of the invention" designates the nucleic acid sequence encoding the C-terminal fragment of Perlecan (SEQ ID No. 2), the nucleic acid sequence encoding the precursor of the retinol-binding plasma protein (SEQ ID No. 4), the nucleic acid sequence (SEQ ID No. 31) encoding the GM2 activator protein (SEQ ID No. 8), the nucleic acid sequence encoding the mutated GM2 activator protein (SEQ ID No. 9), the nucleic acid sequence (SEQ ID No. 42) encoding calgranulin B (SEQ ID No. 17), the nucleic acid sequence (SEQ ID No. 53) encoding saposin B (SEQ ID No. 24), the DNA and RNA nucleic acid sequences (SEQ ID No. 30 to 57) encoding the proteins or fragments belonging to the family of the precursor of the retinol-binding plasma protein (for example SEQ ID No. 5 to 7), the proteins or fragments belonging to the family of the GM2 activator protein (for example SEQ ID No. 10 to 16), the proteins or fragments belonging to the calgranulin B protein family (for example SEQ ID No. 18 to 23), the proteins or fragments belonging to the saposin B protein family (for example SEQ ID No. 25 to 29).

A protein or a variant of a protein chosen more particularly from the sequences defined in the identifiers SEQ ID Nos. 2, 4, 8, 9, 17 and 24 or their fragments, or from the sequences corresponding to the proteins of the families of said sequences (SEQ ID No. 1, SEQ ID No. 3, SEQ ID No. 5 to 7, SEQ ID No. 10 to 16, SEQ ID No. 18 to 24, SEQ ID No. 25 to 29), and the peptide sequences which exhibit at least 70% identity, preferably at least 80% identity and advantageously at least 98 identity with any one of the peptide sequences SEQ ID No. 1 to 29, independently or in combination, exhibits a toxic effect directly or indirectly on cells, in particular on glial cells, which is demonstrated by the abovementioned bioassay. The autoantibodies produced in response to the presence of this protein or of these proteins are associated with the autoimmune process. Thus, the target of the therapeutic agent(s) is for example (i) the natural protein or the natural proteins or their variants with the aim of regulating their expression and/or their intracellular concentration and/or their concentration in the bloodstream, (ii) an antibody specific for at least such a protein. The therapeutic agent or the therapeutic agents defined eliminate the target directly, by inducing a specific immune response, and/or neutralize it.

The present invention therefore relates to a biological material for the preparation of a pharmaceutical composition for treating mammals suffering from degenerative and/or autoimmune and/or neurological pathological conditions, preferably multiple sclerosis, said composition comprising:

(i) either at least one natural protein and/or one recombinant protein or their fragments whose sequence corresponds to all or part of the sequences designated by the references SEQ ID No. 2, 4, 8, 9, 17 and 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29), and the peptide sequences which exhibit at least 70% identity, preferably at least 80% identity and advantageously at least 98 identity with any one of the peptide sequences SEQ ID No. 1 to 29, independently or in combination, (ii) or at least one ligand specific for at least one of said proteins or their fragments whose sequence corresponds to all or part of the sequences designated by the references SEQ ID No. 2, 4, 8, 9, 17 and 24, and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29), and the peptide sequences which exhibit at least 70% identity, preferably at least 80% identity and advantageously at least 98 identity with any one of the peptide sequences SEQ ID No. 1 to 29, independently or in combination, (iii) or at least one polyclonal or monoclonal antibody specific for at least one of said proteins or their fragments whose sequence corresponds to all or part of the sequences designated by the references SEQ ID No. 2, 4, 8, 9, 17 and 24, and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29), and the peptide sequences which exhibit at least 70% identity, preferably at least 80% identity and advantageously at least 98 identity with any one of the peptide sequences SEQ ID No. 1 to 29, independently or in combination, (iv) or at least one nucleic acid sequence comprising at least one gene of therapeutic interest whose nucleic sequence is deduced from the DNA and RNA sequences encoding all or part of the proteins whose sequences are designated by the references SEQ ID No. 2, 4, 8, 9, 17 and 24, and the DNA and/or RNA sequences (for example SEQ ID No. 30 to 57) encoding all or part of the proteins belonging to the same family of proteins chosen from Perlecan, the precursor of the retinol-binding plasma protein, GM2 activator protein, calgranulin B and saposin B, in association with elements ensuring the expression of said gene of therapeutic interest in vivo in target cells intended to be genetically modified by the nucleic sequence of the gene of therapeutic interest, (v) or at least one mammalian cell not naturally producing the protein of interest or the proteins of interest or any fragment of this or these protein(s) or of the antibodies specific for at least one of said proteins or of its fragments, said mammalian cell being genetically modified in vitro by at least one nucleic acid sequence or a fragment of a nucleic acid sequence or a combination of nucleic acid sequences corresponding to nucleic acid fragments derived from the same gene or from different genes, said nucleic sequence(s) being deduced from the DNA and RNA sequences encoding the proteins designated by the references SEQ ID No. 2, 4, 8, 9, 17 and 24, and the DNA and/or RNA sequences (for example SEQ ID No. 30 to 57) encoding all or part of the proteins belonging to the same family of proteins chosen from Perlecan, the precursor of the retinol-binding plasma protein, GM2 activator protein, calgranulin B and saposin B, said gene of therapeutic interest encoding all or part of the protein of interest, of a fragment of the protein of interest or of an antibody specific for the protein of interest which will be expressed at the surface of said mammalian cell (Toes et al., 1997, PNAS 94: 14660–14665). The pharmaceutical composition may contain a therapeutic agent alone directed against a target alone or agents taken in combination directed against several targets.

The expression "polypeptides and/or proteins of interest of the invention" designates the C-terminal fragment of Perlecan (SEQ ID No. 2), the precursor of the retinol-binding plasma protein (SEQ ID No. 4), the GM2 activator protein (SEQ ID No. 8), the mutated GM2 activator protein (SEQ ID No. 9), calgranulin B (SEQ ID No. 17), saposin B (SEQ ID No. 24), the proteins or fragments belonging to the family of the precursor of the retinol-binding plasma protein (for example SEQ ID No. 5 to 7), the proteins or fragments belonging to the family of the GM2 activator protein (for example SEQ ID No. 10 to 16), the proteins or fragments belonging to the calgranulin B protein family (for example SEQ ID No. 18 to 23), the proteins or fragments belonging to the saposin B protein family (for example SEQ ID No. 25 to 29 and the peptide sequences which exhibit at least 70% identity, preferably at least 80% identity and advantageously at least 98% identity with any one of the peptide sequences SEQ ID No. 1 to 29.

From the knowledge of the amino acid sequences of the proteins of interest identified in the present invention, it is within the capability of persons skilled in the art to define and use the molecules described above and/or any molecule capable of binding to said molecules, and/or any molecule capable of inhibiting said molecules. Thus, the present invention relates to the use of natural and/or recombinant proteins and/or of synthetic polypeptides and their fragments, of ligands capable of binding to said proteins or to their fragment(s), for example antibodies; proteins inhibiting the function and/or expression and/or binding of said proteins.

Use of natural protein(s) and/or peptide(s) and/or recombinant protein(s) and/or synthetic polypeptide(s) corresponding to the proteins of interest identified in the present invention.

The present invention relates to a biological material for the preparation of pharmaceutical compositions for treating mammals suffering from an autoimmune disease, preferably multiple sclerosis, comprising:

(i) either at least one natural protein and/or one recombinant protein and/or one synthetic polypeptide chosen from the proteins whose amino acid sequences are designated by the references SEQ ID No. 2, 4, 8, 9, 17 and 24, and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29), and the peptide sequences which exhibit at least 70% identity, preferably at least 80% identity and advantageously at least 98 identity with any one of the peptide sequences SEQ ID No. 1 to 29, alone or in combination, (ii) or at least one natural and/or synthetic fragment of these proteins of interest, for example an immunogenic fragment capable of inducing an immune response against a target polypeptide, (iii) or at least one mimotope peptide defined from the reference sequences SEQ ID No. 2, 4, 8, 9, 17 and 24, and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29), and the peptide sequences which exhibit at least 70% identity, preferably at least 80% identity and advantageously at least 98 identity with any one of the peptide sequences SEQ ID No. 1 to 29, or a combination of mimotopes, capable of inducing an immune response against the target polypeptide, (iv) or at least any protein or peptide capable of regulating in vivo the transcription and/or the translation of the proteins of interest (SEQ ID No. 2, 4, 8, 9, 17 and 24) and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98 identity with any one of the peptide sequences SEQ ID No. 1 to 29. The administration of these proteins and/or peptides alone or in combination can reestablish the concentration of a protein of interest in the body.

The immune response directed against a specific antigen may be divided into two distinct categories, one involving the antibodies (humoral type immune response), the other the cytotoxic effector cells such as for example the macrophages, the cytotoxic lymphocytes (CTL) or the killer (NK) cells as well as the "helper" T lymphocytes, in particular the CD4+ T lymphocytes (cellular type immune response). More particularly, the two types of response are distinguishable in that the antibodies recognize the antigens under their three-dimensional form whereas the T lymphocytes, for example, recognize peptide portions of said antigens, associated with glycoproteins encoded by the genes of the major histocompatibility complex (MHC), in particular the genes of the type I major histocompatibility complex which are ubiquitously expressed at the surface of the cells or the genes of the type II major histocompatibility complex which are specifically expressed at the surface of the cells involved in the presentation of antigens (APC). 1) According to a first aspect, the cellular type immune response is characterized in that the CD4+ type T cells (helper T cells), following a well-known activation phenomenon (for a review see Alberolalia 1997, Annu Rev Immunol 15, 125–154), produce cytokines which in turn induce the proliferation of APC cells capable of producing said cytokines, the cellular differentiation of the B lymphocytes capable of producing antibodies specific for the antigen, and the stimulation of the cytotoxic T lymphocytes (CTL). 2) According to a second aspect of the cellular immune response, the cytotoxic effector cells such as for example the CD8+ type lymphocytes (CTL) are activated a) after interaction with antigenic peptides bound to and presented by the glycoproteins carried by the ubiquitous cells and encoded by the genes belonging to the MHCI system, and b) optionally by the cytokines produced by the CD4+ cells.

The present invention relates to the administration of a protein or of a peptide derived from the proteins of interest (SEQ ID No. 2, 4, 8, 9, 17 and 24) or of their fragment(s), and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29), and the peptide sequences which exhibit at least 70% identity, preferably at least 80% identity and advantageously at least 98% identity with any one of the peptide sequences SEQ ID No. 1 to 29, alone or in combination, for the prophylaxy and/or the therapy of an autoimmune disease, such as multiple sclerosis. These administered proteins and peptides are characterized in that they must have lost their toxic activity, for example their gliotoxic activity, or must have lost their capacity to bind to a ligand, and may significantly induce an immune response mediated by the T lymphocytes and/or the antibodies directed against this protein are used. Such proteins are said to be "modified"; nevertheless, their immunogenicity is preserved. Such modified immunogenic molecules are obtained by a number of conventional treatments, for example chemical or heat denaturation, truncation or mutation with deletion, insertion or location of amino acids. An example of truncation consists in the truncation of amino acids at the carboxy-terminal end which may be up to 5–30 amino acids. The modified molecules may be obtained by synthetic and/or recombinant techniques or by chemical or physical treatments of the natural molecules.

The natural and/or recombinant proteins of interest identified in the present invention (SEQ ID No. 2, 4, 8, 9, 17 and 25), and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29), and the peptide sequences which exhibit at least 70% identity, preferably at least 80% identity and advantageously at least 98 identity with any one of the peptide sequences SEQ ID No. 1 to 29, or their fragment(s), are used in prophylactic and therapeutic vaccination against autoimmune diseases, preferably MS. A vaccine comprises an immunogenically effective quantity of the immunogenic protein in association with a pharmaceutically acceptable vehicle and optionally an adjuvant and/or a diluent. The pharmaceutically acceptable vehicles, adjuvants and diluents are well known to persons skilled in the art. There may be mentioned, by way of references, Remington's Pharmaceutical Sciences. The use of vaccine compositions is particularly advantageous in association with an early diagnosis of the disease. The immunogenic protein is used in the preparation of a medicament for prophylactic or therapeutic vaccination. The proteins of interest may be eliminated from the body without inducing undesirable side effects. The identification of such vaccine proteins or peptides is carried out as follows: the candidate molecules modified as described above (proteins which are natural or recombinant, peptides) are analyzed in a functional test to verify that they have lost their toxicity, for example their gliotoxic activity, using the test known as bioassay, and to verify their immunogenicity (i) by carrying out an in vitro test of proliferation of CD4+ T lymphocytes specific for the antigen administered (T cell assay) or an in vitro test of cytotoxicity of the CD8+ lymphocytes specific for the antigen administered and (ii) by measuring, inter alia, the amount of circulating antibodies directed against the natural protein. These modified forms are used to immunize humans by standard procedures with appropriate adjuvants.

The prepared vaccines are injectable, that is to say in liquid solution or in suspension. Optionally, the preparation may also be emulsified. The antigenic molecule may be mixed with excipients which are pharmaceutically acceptable and compatible with the active ingredient. Examples of favorable excipients are water, saline solution, dextrose, glycerol, ethanol or equivalents and their combinations. If desired, the vaccine may contain minor quantities of auxiliary substances such as "wetting" or emulsifying agents, pH buffering agents or adjuvants such as aluminum hydroxide, muramyl dipeptide or variations thereof. In the case of peptides, their coupling to a larger molecule (KLH, tetanus toxin) sometimes increases the immunogenicity. The vaccines are conventionally administered by injection, for example by subcutaneous or intramuscular injection. Additional formulations favorable with other modes of administration include suppositories and sometimes oral formulations.

In general, the concentration of the polynucleotide in the composition used for administration in vivo is from 0.1 µg/ml up to 20 mg/ml. The polynucleotide may be homologous or heterologous for the target cell into which it will be introduced.

The present invention also relates to the use of vaccines including molecules of nucleic acids which encode the proteins of interest or immunogenic peptides or their fragment(s), which are non-active, corresponding to the proteins of interest (SEQ ID No. 2, 4, 8, 9, 17 and 24) and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29. The nucleic acid vaccines, in particular the DNA vaccines, are generally administered in association with a pharmaceutically acceptable vehicle by intramuscular injection.

From the amino acid sequence of the proteins of interest described (SEQ ID No. 2, 4, 8, 9, 17 and 24) and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, peptides or fragments corresponding to all or part of the primary sequence of these proteins may be synthesized by conventional methods of peptide synthesis or obtained by genetic recombination.

Recombinant proteins corresponding to the proteins of interest, produced in a prokaryotic or eukaryotic cellular system, are available from various teams and are described in the literature. They may also be produced by persons skilled in the art from the knowledge of the sequences of the corresponding genes described in the literature and taking into account the degeneracy of the genetic code. All the protein sequences identified in the present invention are thus capable of being obtained by genetic recombination. The genes are cloned into suitable vectors. Different vectors are used to transform prokaryotic cells (for example E. coli) and eukaryotic cells (for example COS cells, CHO cells and Simliki cells). The recombinant proteins corresponding to the proteins of interest or to fragments of the proteins of interest may thus be produced in prokaryotic and/or eukaryotic cellular systems. In E. Coli cells, the recombinant proteins are produced with a polyhistidine tail. The insoluble protein fraction is solubilized in 8M urea. Enrichment of the product was carried out on nickel-chelated resin (Qiagen). The column was washed with decreasing concentrations of urea. The elution was carried out with imidazole in the absence of urea. The complete sequence of the proteins of interest may also be cloned into a suitable plasmid and then transferred into the vaccinia virus in order to obtain a recombinant virus.

Use of ligands capable of binding to the proteins of interest identified in the present invention.

The present invention relates to a biological material for the preparation of pharmaceutical compositions for treating mammals suffering from an autoimmune disease, preferably multiple sclerosis, comprising:

(i) either at least one ligand capable of binding to the proteins and/or fragments of the proteins chosen from the target proteins SEQ ID No. 2, 4, 8, 9, 14 and 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, the ligand being capable or not of inhibiting the protein activity, (ii) or at least one polyclonal or monoclonal antibody capable of binding to at least one protein or one of its fragments chosen from the target proteins SEQ ID No. 2, 4, 8, 9, 14 and 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29. This antibody may be neutralizing or not, that is to say capable or not of inhibiting the activity of the protein of interest. The ligand may be chosen from any molecule or molecule fragment capable of binding to the target proteins, for example the receptor for this proteins, the cofactors for these proteins, the polyclonal or monoclonal antibodies capable of binding to the proteins or any fragment of these proteins.

These antibodies are very useful in particular for allowing the use of therapeutic compositions because they lead, for example, to immune reactions directed specifically against immunodominant epitopes or against antigens exhibiting high variability. There are administered to the patient either neutralizing soluble antibodies in order to inhibit their function, or specific soluble antibodies in order to eliminate the peptide by formation of immune complexes. The invention describes the use of antibodies capable of specifically recognizing at least one protein described in the present invention for the treatment and/or for the therapeutic monitoring of a degenerative and/or neurological and/or autoimmune disease, preferably multiple sclerosis. These antibodies are polyclonal and preferably monoclonal. Preferably, these antibodies recognize the active site of the protein and, upon binding, inhibits the function of the protein. The capacity of the antibody to specifically bind to the protein is analyzed by conventional techniques which have been described, such as for example by ELISA or Western blot tests using the natural or synthetic immunogenic peptide or protein. The antibody titer is determined. The capacity of the antibody to neutralize the function of the protein may be analyzed by various means, for example by determining the reduction in the activity of the immunogenic peptide or protein in the presence of antibodies, preferably by determining the reduction in the gliotoxic activity using the bioassay test in vitro.

For example, the monoclonal antibodies directed against the target protein or a portion of this protein are produced by conventional techniques used to produce antibodies against surface antigens. Mice or rabbits are immunized (i) either with the natural or recombinant protein of interest, (ii) or with any immunogenic peptide of this protein of interest, (iii) or with murine cells which express the protein or the peptide of interest and the MHCII molecules.

The Balb/c murine line is the most frequently used. The immunogen is also a peptide chosen from the peptides defined from the primary sequences of the proteins of interest. For example, the following immunogen was prepared: the peptides SEQ ID Nos. 58, 59, 60 derived from the sequence of the GM2 activator protein, the peptides SEQ ID Nos. 61, 62 derived from the sequence of saposin B and the peptides SEQ ID Nos. 63, 64, 65 derived from calgranulin B were coupled to Keyhole Lymphet hemocyanin, abbreviated peptide-KLH, as support for its use in immunization, or coupled to human serum albumin, abbreviated peptide-HSA. The animals were subjected to an injection of peptide-KLH or of peptide-HSA using complete Freund's adjuvant (CFA). The sera and the hybridoma culture supernatants derived from animals immunized with each peptide were analyzed for the presence of anti-protein antibodies by an ELISA test using the initial proteins. The spleen cells of these mice were consequently recovered and fused with myeloma cells. Polyethylene glycol (PEG) is the fusion agent most frequently used. The hybridomas producing the most specific and the most sensitive antibodies are selected. The monoclonal antibodies may be produced in vitro by cell culture of the hybridomas produced or by recovering murine ascitic fluid after intraperitoneal injection of the hybridomas in mice. Whatever the mode of production, in supernatant or in ascites, it is then important to purify the monoclonal antibody. The methods of purification used are essentially ion-exchange gel filtration or exclusion chromatography, or even immunoprecipitation. For each antibody, the method which will make it possible to obtain the best yield should be chosen. A satisfactory number of anti-protein antibodies are targeted in functional tests in order to identify the most efficient antibodies for binding the protein of interest and/or for blocking the activity of the protein of interest. The monoclonal antibodies selected are humanized by standard "CDR grafting" methods (protocol performed by many companies, as a service). These humanized antibodies may be clinically tested in the patient. The efficiency of these antibodies may be monitored by clinical parameters.

The in vitro production of antibodies, of antibody fragments or of antibody derivatives, such as chimeric antibodies, produced by genetic engineering, in eukaryotic cells has been described (EP 120 694 or EP 125 023) and is also applicable to the present invention.

Use of molecules inhibiting the proteins of interest identified in the present invention.

The present invention relates to a biological material for the preparation of pharmaceutical compositions for treating mammals suffering from a degenerative and/or neurological and/or autoimmune disease, preferably multiple sclerosis, said composition comprising (i) either at least one molecule inhibiting the function of at least one protein chosen from the proteins identified in the present invention (SEQ ID No. 2, 4, 8, 9, 17, 24) and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, for example inhibiting the gliotoxic activity, (ii) or at least one molecule regulating the expression of at least one protein chosen from the proteins SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, for example to block transcription or translation, (iii) or at least one molecule regulating the metabolism of at least one protein chosen from the proteins SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, (iv) or at least one molecule regulating the expression and/or the metabolism of a ligand for at least one protein chosen from the proteins SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to SEQ ID No. 8 and SEQ ID No. 10 to 29 and the peptide sequences which exhibit at least 70% identity, preferably at least 80% identity and advantageously at least 98% identity with any one of the peptide sequences SEQ ID No. 1 to 29, for example a receptor or a cofactor. It is also possible to think that these proteins of the human body can be inhibited with no side effect.

Another important aspect of the invention relates to the identification and the evaluation of the therapeutic efficacy of natural and/or synthetic substances (i) capable of blocking and/or inhibiting the activity of the proteins of interest of the invention and/or of their fragment: SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29 and/or (ii) capable of inhibiting their metabolism such as the inhibitors of the corresponding metabolism, the inhibitors of enzymes activated by the coenzymes, (iii) capable of regulating the expression of the proteins of interest (SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, (iv) capable of inhibiting the function and/or the expression of the ligands for the proteins of interest SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, such as for example receptors. These substances may be used in prophylactic or therapeutic treatments of the disease. The invention also relates to methods for treating and preventing an autoimmune disease, for example MS, by administering effective quantities of these substances. The substances may be proteins, antibodies, small synthetic or natural molecules, derivatives of the proteins identified in this invention, lipids, glycolipids and the like. The small molecules may be screened and identified in a large quantity using chemical combinatory libraries. The invention also relates to pharmaceutical compositions comprising these substances in association with acceptable physiological carriers, and methods for the preparation of medicaments to be used in the therapy or in the prevention of autoimmune diseases including MS using these substances.

To identify inhibitory molecules of low molecular weight such as candidate drugs for degenerative and/or neurological and/or autoimmune diseases, such as multiple sclerosis, there are used the tests and protocols described in above and in the patent applications incorporated by way of reference, using samples collected from untreated or treated patients, untreated or treated animal models, or tissues of untreated or treated animal models. This aspect of the invention also includes a method for identifying substances capable of blocking or inhibiting the activity of the proteins of interest, comprising the introduction of these substances into a test in vitro or into an animal model in vivo. The molecules selected are tested at different concentrations. These inhibitors are also tested in toxicity and pharmaco-kinetic assays to know if they can represent valid candidate drugs. The substances tested for the inhibition or the blocking of the protein activities or for the expression of the proteins, in these screening procedures, may be proteins, antibodies, antibody fragments, small synthetic or natural molecules, derivatives of the proteins of interest and the like. The small molecules may be screened and identified in a large quantity using chemical combinatory libraries.

By way of example, there may be mentioned as inhibitory substances:

The inhibitors of the proteins identified in the present invention (SEQ ID No. 2, 4, 8, 9, 17, 24), the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, and the inhibitors of the fragments of said proteins. These inhibitors may be included in a prophylactic and therapeutic composition, in particular for the treatment of multiple sclerosis. For example, lycorine, an alkaloid extracted from Amaryllidaceae (e.g.: *Crinum asiaticum*) is used in vitro at a concentration of between 0.1 and 0.5 µg/ml and in vivo at a concentration of between 0.1 and 1 mg/kg/day. For example, Rolipram (trade name) and Ibudilast (trade name), which are two molecules of the same family of inhibitors of 4 (PDE4) phosphodiesterases, are used in vitro at concentrations of between 1 and 10 µM/l and in vivo at concentrations of between 10 mg/kg/day.

From the amino acid sequences of the proteins SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29), it is evident that it is possible to deduce the DNA and RNA nucleotide sequences (SEQ ID No. 30, 31, 42, 53) corresponding to the proteins of interest and the sequences encoding the proteins of the family of these proteins of interest (for example SEQ ID No. 32 to 41, SEQ ID No. 43 to 52, SEQ ID No. 54 to 57, SEQ ID No. 66 to 67), taking into account the genetic code and its degeneracy. Thus, the present invention relates to the use of these nucleotide sequences in the form:

of antisense sequences, of sequences encoding a therapeutic gene, of sequences which may be contained in a vector for carrying out cell transformation ex vitro and/or in vivo (gene therapy).

Use of nucleic acids deduced from the amino acid sequences of the proteins of interest identified in the present invention; antisense nucleic acids and/or nucleic acids encoding a therapeutic gene.

The present invention relates to a biological material for the preparation of pharmaceutical compositions for treating mammals suffering from a degenerative and/or neurological and/or autoimmune disease, in particular multiple sclerosis, the composition comprising (i) either at least one nucleic acid sequence capable of hybridizing with a nucleic acid sequence encoding the proteins of interest (SEQ ID No. 2, 4, 8, 9, 17, 24) and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, or their fragment(s), (ii) or at least one nucleic acid sequence comprising at least one gene of therapeutic interest encoding the proteins or a fragment of proteins (SEQ ID No. 2, 4, 8, 9, 17, 24), the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, and elements ensuring the expression of said gene in vivo in target cells intended to be genetically modified by said nucleic sequence.

The expression nucleic acid sequence is understood to mean a DNA and/or RNA fragment which is double-stranded or single-stranded, linear or circular, natural and isolated or synthetic, designating a precise succession of nucleotides, modified or otherwise, which makes it possible to define a fragment or a region of a nucleic acid chosen from the group consisting of a cDNA; a genomic DNA; a plasmid DNA; a messenger RNA. These nucleic acid sequences are deduced from the amino acid sequence of the proteins SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, using the genetic code. Because of the degeneracy of the genetic code, the invention also encompasses equivalent or homologous sequences. These defined sequences allow persons skilled in the art themselves to define the appropriate nucleic acids.

Accordingly, the present invention relates to a biological material for the preparation of pharmaceutical compositions comprising at least one nucleic acid sequence capable of hybridizing with a nucleic acid sequence encoding the proteins of interest or their fragment(s) (SEQ ID No. 2, 4, 8, 9, 17, 24) and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29.

The invention consists in defining and using nucleic acid molecules complementary to the DNA and/or RNA sequences encoding the proteins of interest or their fragment(s). These fragments correspond to ribozyme or antisense molecules and may be synthesized using automated synthesizers, such as those marketed by the company Applied Biosystem. The invention describes the use of these nucleic acids capable of hybridizing under stringent conditions with the DNA and/or RNA encoding the proteins of the invention or their fragment(s). Characteristic stringency conditions are those which correspond to a combination of the temperature and of the saline concentration chosen approximately between 12 and 20° C. under the Tm ("melting temperature") of the hybrid under study. Such molecules are synthesized and may be labeled using conventional labeling methods used for molecular probes, or may be used as primers in amplification reactions. The sequences which exhibit at least 90% homology relative to a reference sequence also form part of the invention, as well as the fragments of these sequences which have at least 20 nucleotides and preferably 30 contiguous nucleotides that are homologous with respect to a reference sequence. To reduce the proportion of natural or variant peptides, it is possible to envisage an antisense and/or ribozyme approach. Such an approach is widely described in the literature. Of course, such antisense molecules may constitute, as such, vectors. It is also possible to use vectors which comprise a nucleic acid sequence which encodes an antisense.

The present invention relates to a biological material for the preparation of pharmaceutical compositions for treating mammals suffering from a degenerative and/or neurological and/or autoimmune disease, such as multiple sclerosis, said composition comprising at least one nucleic acid sequence containing at least one gene of therapeutic interest and elements ensuring the expression of said gene in vivo in target cells intended to be genetically modified by said nucleic sequence.

These nucleic acid sequences and/or vectors (antisense or encoding a protein or a fragment of a protein) make it possible to target the cells in which the peptide is expressed, such as macrophage cells: (i) either by the use of a targeting molecule introduced on the vector, (ii) or by the use of a particular property of these cells.

Use of vectors comprising a gene of therapeutic interest corresponding to the genes for the proteins of interest identified in the present invention.

The present invention relates to a biological material for the preparation of pharmaceutical compositions for preventing and treating degenerative and/or neurological and/or autoimmune diseases, such as multiple sclerosis, the composition comprising a nucleic acid sequence comprising a gene of therapeutic interest and elements for expressing said gene of interest. The genes may be nonmutated or mutated. They may also consist of nucleic acids modified such that it is not possible for them to integrate into the genome of the target cell, or of nucleic acids stabilized with the aid of agents, such as spermine.

Such a gene of therapeutic interest encodes in particular:

(i) either at least one protein chosen from the proteins identified in the present invention (SEQ ID No. 2, 4, 8, 9, 17, 24) and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, or their fragment(s), (ii) or at least all or part of a polyclonal or mono-clonal antibody capable of binding to at least one protein or a protein fragment chosen from the proteins identified in the present invention (SEQ ID No. 2, 4, 8, 9, 17, 24) and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29. This may include in particular a native transmembrane antibody, or a fragment or derivative of such an antibody, as long as said antibody, antibody fragment or derivative is expressed at the surface of the genetically modified target cell of the mammal and is capable of binding to a polypeptide present at the surface of a cytotoxic effector cell or of a helper T lymphocyte involved in the process for activating such a cell, (iii) or at least one molecule inhibiting at least one protein or its fragments, said protein being chosen from the proteins identified (SEQ ID No. 2, 4, 8, 9, 17, 24) and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29; the proteins inhibiting the function and/or the metabolism and/or the binding of the proteins SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, (iv) or at least one ligand or any portion of a ligand capable of binding to at least one protein or one protein fragment chosen from the proteins identified (SEQ ID No. 2, 4, 8, 9, 17, 24) and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, and/or of inhibiting its function.

More particularly, the expression antibody fragment is understood to mean the F(ab)2, Fab', Fab, sFv fragments (Blazar et al., 1997, Journal of Immunology 159: 5821–5833; Bird et al., 1988 Science 242: 423–426) of a native antibody and the expression derivative is understood to mean, for example, a chimeric derivative of such an antibody (see for example the chimeras of the Mouse/Human anti-CD3 antibodies in Arakawa et al., 1996 J Biochem 120: 657–662 or the immunotoxins such as sFv-toxin by Chaudary et al 1989, Nature 339: 394–397). The expression transmembrane antibody is understood to mean an antibody in which at least the functional region capable of recognizing and binding to its specific antigen is expressed at the surface of the target cells in order to allow said recognition and binding. More particularly, the antibodies according to the present invention consist of fusion polypeptides comprising the amino acids defining said functional region and an amino acid sequence (transmembrane polypeptide) allowing anchoring within the membrane lipid double layer of the target cell or at the outer surface of this bilayer. The nucleic sequences encoding numerous transmembrane polypeptides are described in the literature. According to a most advantageous case, the nucleic acid sequence encoding the antibody heavy chain is fused with the nucleic acid sequence encoding the said transmembrane polypeptide.

The expression elements ensuring the expression of said gene in vivo refers in particular to the elements necessary to ensure the expression of said gene after its transfer into a target cell. This includes in particular promoter sequences and/or regulatory sequences which are efficient in said cell, and optionally the sequences required to allow expression at the surface of the target cells of said polypeptide. The promoter used may be a viral, ubiquitous or tissue-specific promoter or a synthetic promoter. By way of example, there may be mentioned promoters such as the promoters of the viruses RSV (Rous Sarcoma Virus), MPSV, SV40 (Simian Virus), CMV (Cytomegalovirus) or of the vaccinia virus, the promoters of the gene encoding muscle creatine kinase, actin. It is, in addition, possible to choose a promoter sequence specific for a given cell type, or activable under defined conditions. The literature provides a large amount of information relating to such promoter sequences.

Moreover, said nucleic acid may comprise at least two sequences, which are identical or different, exhibiting a transcriptional promoter activity and/or at least two genes, which are identical or different, situated relative to each other contiguously, apart, in the same direction or in the opposite direction, provided that the transcriptional promoter function or the transcription of said genes is not affected.

Likewise, in this type of nucleic acid construct, it is possible to introduce "neutral" nucleic sequences or introns which do not adversely affect the transcription and are spliced before the translational step. Such sequences and their uses are described in the literature (reference: PCT patent application WO 94/29471).

Said nucleic acid may also comprise sequences required for intracellular transport, for replication and/or for integration, for transcription and/or translation. Such sequences are well known to persons skilled in the art.

Moreover, the nucleic acids which can be used according to the present invention may also be nucleic acids modified such that it is not possible for them to integrate into the genome of the target cell or nucleic acids stabilized with the aid of agents, such as, for example, spermine, which, as such, have no effect on the efficiency of the transfection.

According to one embodiment of the invention, the nucleic acid sequence is a naked RNA or DNA sequence, that is to say which is free of any compound facilitating its introduction into cells (transfer of nucleic acid sequence). However, according to a second embodiment of the invention, to promote its introduction into the target cells and to obtain the genetically modified cells of the invention, this nucleic acid sequence may be in the form of a "vector" and more particularly in the form of a viral vector, such as, for example, an adenoviral vector, a retroviral vector, a vector derived from a poxvirus, in particular derived from the vaccinia virus or from the Modified Virus Ankara (MVA) or from a nonviral vector such as, for example, a vector consisting of at least one said nucleic acid sequence complexed or conjugated with at least one carrier molecular substance selected from the group consisting of a cationic amphiphile, in particular a cationic lipid, a cationic or neutral polymer, a practical polar compound chosen in particular from propylene glycol, polyethylene glycol, glycerol, ethanol, 1-methyl-L-2-pyrrolidone or their derivatives, and an aprotic polar compound chosen in particular from dimethyl sulfoxide (DMSO), diethyl sulfoxide, di-n-propyl sulfoxide, dimethyl sulfone, sulfolane, dimethylformamide, dimethylacetamide, tetramethylurea, acetonitrile or their derivatives. The literature provides a large number of examples of such viral and nonviral vectors.

Such vectors may in addition and preferably comprise targeting elements which can make it possible to direct the transfer of a nucleic acid sequence toward certain cell types or certain particular tissues such as cyto-toxic cells and antigen-presenting cells). They can also make it possible to direct the transfer of an active substance toward certain preferred intracellular compartments such as the nucleus, the mitochondria or the peroxisomes, for example. This may also include elements facilitating penetration into the cell or the lysis of intracellular compartments. Such targeting elements are widely described in the literature. This may include, for example, all or part of lectins, peptides, in particular the peptide JTS-1 (see PCT patent application WO 94/40958), oligonucleotides, lipids, hormones, vitamins, antigens, antibodies, ligands specific to membrane receptors, ligands capable of acting with an antiligand, fusogenic peptides, nuclear localization peptides or a composition of such compounds.

Use of cells transformed in vivo after injection of vectors containing at least one gene of therapeutic interest defined from the proteins of interest identified in the present invention (SEQ ID No. 2, 4, 8, 9, 17, 24) and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29.

The present invention relates to a biological material for the preparation of pharmaceutical compositions for preventing and treating mammals suffering from degenerative and/or neurological and/or autoimmune diseases, preferably multiple sclerosis, the composition comprising at least one vector containing a therapeutic gene as described below, capable of being introduced into a target cell in vivo and of expressing the gene of therapeutic interest in vivo. The advantage of this invention consists in the possibility of maintaining long term a basal level of molecules expressed in the patient treated. Vectors or nucleic acids encoding genes of therapeutic interest are injected. These vectors and nucleic acids should be transported up to the target cells and transfect these cells in which they have to be expressed in vivo.

The invention relates to the expression in vivo of nucleotide sequences and/or vectors as designated in the preceding paragraph, that is to say sequences corresponding to genes of therapeutic interest encoding in particular:

(i) either at least one protein chosen from the proteins identified in the present invention (SEQ ID No. 2, 4, 8, 9, 17, 24) and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, or their fragment(s), (i) or at least all or part of a polyclonal or mono-clonal antibody capable of binding to at least one protein chosen from the proteins identified in the present invention (SEQ ID No. 2, 4, 8, 9, 17, 24) and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29. This may include a native transmembrane antibody, or a fragment or derivative of such an antibody, as long as said antibody or antibody fragment or derivative is expressed at the surface of the genetically modified target mammalian cell and in that said antibody is capable of binding to a polypeptide present at the surface of a cytotoxic effector cell or of a helper T lymphocyte and involved in the process of activating such a cell. This may include antibody fragments expressed by cells capable of secreting said antibodies in the bloodstream of a mammal or patient carrying the cells genetically modified by the gene encoding the antibody, (ii) or at least one molecule inhibiting at least one protein chosen from the proteins identified (SEQ ID No. 2, 4, 8, 9, 17, 24) and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29; protein inhibiting the function and/or metabolism and/or binding of the proteins SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, (iii) or at least one ligand or any portion of the ligand capable of binding to at least one protein chosen from the proteins identified (SEQ ID No. 2, 4, 8, 9, 17, 24) and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, and/or of inhibiting its function.

According to a particular embodiment, this includes using gene therapy so as to direct the immune response against the target protein, peptide or molecule of interest, that is to say against any protein chosen from the proteins SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, their fragment(s) and/or against any molecule inhibiting the function and/or expression and/or metabolism of said proteins of interest, and/or ligands of said proteins such as, for example, the receptors. For that, it is evident that the cells to be targeted for the transformation with a vector are cells belonging to the immune system, either lymphocyte-type cells (CD4/CD8), or antigen-presenting cells (dendritic cells, macrophages and the like).

According to a particular embodiment, the antigen-presenting cells (APC) are genetically modified, in particular in vivo. APCs such as macrophages, dendritic cells, microgliocytes and astrocytes play a role in initiating the immune response. They are the first cellular components which capture the antigen, prepare it in the cell and express the transmembrane MHCI and MHCII molecules involved in presenting the immunogen to the CD4+ and CD8+ T cells, they produce specific secondary proteins which participate in activating the T cells (Debrick et al., 1991, J. Immunol 147: 2846; Reis et al., 1993, J Ep Med 178: 509; Kovacsovics-bankowski et al., 1993, PNAS 90: 4942; Kovacsovics-bankowski et al., 1995 Science 267: 243; Svensson et al., 1997, J Immunol 158: 4229; Norbury et al., 1997, Eur J Immunol 27: 280). For a vaccination, it may be advantageous to have a gene therapy system which can target the gene transfer into such APC cells, that is to say a gene which encodes a polypeptide which can, after its intracellular production and its "processing", be presented to the CD8+ and/or CD4+ cells by the molecules of the MHCI and MHCII complexes, respectively, at the surface of these cells.

It is chosen to express at the surface of the APC cells in vivo all or part of an antibody and/or of a ligand such as, for example, a receptor, capable of reacting with the target protein or peptide chosen from the proteins SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29. Such cells will then specifically phagocytose said protein or said peptide, the "processer" so that fragments of this peptide are present at the surface of the antigen-presenting cells.

The literature provides a large number of examples of genes encoding antibodies capable of reacting with polypeptides or receptors. It is within the capability of persons skilled in the art to obtain the nucleic acid sequences encoding such antibodies. There may be mentioned, for example, the genes encoding the light and heavy chains of the antibody YTH 12.5 (anti-CD3) (Routledge et al. 1991, Eur J Immunol 21: 2717–2725), of the anti-CD3 according to Arakawa et al; 1996, J. Biochem. 120: 657–662. The nucleic acid sequences of such antibodies are easily identifiable from the databases commonly used by persons skilled in the art. It is also possible, starting with hybridomas available from ATCC, to clone the nucleic acid sequences encoding the heavy and/or light chains of these various antibodies by amplification methods such as RT-PCR with the aid of specific oligonucleotides or techniques using cDNA libraries (Maniatis et al., 1982, Molecular cloning. A laboratory manual CSH Laboratory, Cold Spring Harbor, N.Y.). The sequences thus cloned are then available for their cloning into vectors. According to a preferred case of the invention, the nucleic acid sequence encoding the heavy chain of the antibody is fused by homologous recombination with the nucleic acid sequence encoding a transmembrane polypeptide such as the rabies glycoprotein or gp160 (Polydefkis et al., 1990, J Exp Med 171: 875–887). These molecular biology techniques have been fully described.

It is chosen to express at the surface of the APC cells in vivo immunogenic fragments corresponding to at least one proteins chosen from the proteins SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29. For that, it is possible to choose to cause the vector to express either the full-length polypeptide or, preferably, polypeptides selected to react with specific ligands and/or receptors. The immunogenic peptide encoded by the polynucleotide introduced into the cell of the vertebrate in vivo may be produced and/or secreted, made ready and then presented to an antigen-presenting cell (APC) in the context of the molecules of the MHC.

The APCs thus transferred in vivo induce an immune response directed against the immunogen expressed in vivo. The APCs possess different mechanisms for capturing the antigens: (a) capture of the antigens by membrane receptors such as the receptors for immuno-globulins (Fc) or for the complement which are available at the surface of the granulocytes, monocytes or macrophages allowing efficient delivery of the antigen into the intracellular compartments after phagocytosis mediated by the receptors. (b) entry into the APCs by pinocytosis in fluid phase, involving various mechanisms: micropinocytosis, that is to say the capture of small vesicles (0.1 μm) by the clathrin-coated pits, and macropinocytosis, that is to say the capture of larger vesicles (with a size varying graft 0.5 μm and about 6 μm) (Sallusto et al. 1995, J Exp Med 182: 389–400). While micropinocytosis constitutively exists in all cells, macropinocytosis is limited to cellular types such as, for example, the macrophages, dendritic cells, astrocytes, epithelial cells stimulated by growth factors (Racoosin et al., J Cell Sci 1992, 102: 867–880). In this invention, the expression cells capable of macropinocytosis is understood to mean the cells which can carry out the events described above and the cells which can capture macromolecules preferably between 0.5 μm and about 6 μm in the cytoplasm.

According to a particular embodiment, the cytotoxic effector cells or the helper T lymphocytes are genetically modified in particular in vivo so that they express at their surface a polypeptide corresponding to the proteins SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, ligands for said proteins, which are naturally not expressed by these cells and which are capable of inducing the process of activation of such cells, by introducing into these cells nucleic acid sequences containing the gene encoding such a polypeptide. In accordance with the present invention, it is also possible to select a nucleic acid sequence containing a gene of therapeutic interest encoding all or part of an antibody directed against a protein chosen from the proteins SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, capable of being expressed at the surface of the target cells of the patient to be treated, said antibody being capable of binding to a polypeptide which is naturally not expressed by these cytotoxic effector cells or helper T lymphocytes.

The expression cytotoxic effector cells is understood to designate the macrophages, astrocytes, cytotoxic T lymphocytes (CTL) and killer (NK) cells as well as their derivatives such as, for example, LAKs (Versteeg 1992 Immunology today 13: 244–247; Brittende et al 1996, Cancer 77: 1226–1243). The expression "helper T lymphocytes" is understood to designate in particular the CD4 cells which allow, after activation, the secretion of factors for activating the effector cells of the immune response. The polypeptides, and in particular the receptors expressed at the surface of these cells and which are involved in the activation of such cells, constitute in particular all or part of the TCR complex or CD3, all or part of the CD8, CD4, CD28, LFA-1, 4-1BB (Melero et al., 1998, Eur J Immunol 28: 1116–1121), CD47, CD2, CD1, CD9, CD45, CD30 and CD40 complexes, all or part of the cytokine receptors (Finke at al., 1998, Gene therapy 5: 31–39), such as IL-7, IL-4, IL-2, IL-15 or GM-CSF, all or part of the receptor complex for the NK cells such as for example NKAR, Nkp46, and the like; (Kawano et al., 1998 Immunology 95: 5690–5693; Pessino et al., 1998 J Exp Med 188: 953–960), Nkp44, all or part of the macrophage receptors such as for example the Fc receptor (Deo et al., 1997, Immunology Today 18: 127–135).

Numerous tools have been developed for introducing various heterologous genes and/or vectors into cells, in particular mammalian cells. These techniques may be divided into two categories: the first category involves physical techniques such as microinjection, electroporation or particle bombardment. The second category is based on the use of molecular and cell biology techniques with which the gene is transferred with a biological or synthetic vector which facilitates the introduction of the material into the cell in vivo. Nowadays, the most efficient vectors are the viral, in particular adenoviral and retroviral, vectors. These viruses possess natural properties for crossing the plasma membranes, avoiding degradation of their genetic material and introducing their genome into the nucleus of the cell. These viruses have been widely studied and some are already experimentally used in human applications in vaccination, immunotherapy, or to compensate for genetic deficiencies. However, this viral approach has limitations, in particular due to the restricted cloning capacity in these viral genomes, the risk of disseminating the viral particles produced in the body and the environment, the risk of artefactual mutagenesis by insertion into the host cell in the case of retroviruses, and the possibility of inducing a high inflammatory immune response in vivo during the treatment, which limits the number of injections possible (McCoy et al. 11995, Human Gene Therapy 6: 1553–1560; Yang et al., 1996 Immunity 1: 433–422). Other alternative systems to these viral vectors exist. The use of nonviral methods such as, for example, coprecipitation with calcium phosphate, the use of receptors which mimic the viral systems (for a summary see Cotten and Wagner 1993, Current Opinion in Biotechnology, 4: 705–710), or the use of polymers such as polyamidoamines (Haensler and Szoka 1993, Bioconjugate Chem 4: 372–379). Other nonviral techniques are based on the use of liposomes whose efficiency for the introduction of biological macromolecules such as DNA, RNA, proteins or active pharmaceutical substances has been widely described in the scientific literature. In this domain, teams have proposed the use of cationic lipids having a high affinity for the cell membranes and/or nucleic acids. Indeed, it has been shown that a nucleic acid molecule itself could cross the plasma membrane of some cells in vivo (WO 90/11092), the efficiency depending in particular on the polyanionic nature of the nucleic acid. Since 1989 (Felgner et al., Nature 337: 387–388), cationic lipids have been proposed to facilitate the introduction of large anionic molecules, which neutralizes the negative charges on these molecules and promotes their introduction into the cells. Various teams have developed such cationic lipids: DOTMA (Felgner et al., 1987, PNAS 84: 7413–7417), DOGS or Transfectam™ (Behr et al., 1989, PNAS 86: 6982–6986), DMRIE and DORIE (Felgner et al., 1993 methods 5: 67–75), DC-CHOL (Gao and Huang 1991, BBRC 179: 280–285), DOTAP™ (McLachlan et al., 1995, Gene therapy 2: 674–622) or Lipofectamine™, and the other molecules described in patents WO9116024, WO9514651, WO9405624. Other groups have developed cationic polymers which facilitate the transfer of macromolecules, in particular anionic macromolecules, into cells. Patent WO95/24221 describes the use of dendritic polymers, the document WO96/02655 describes the use of polyethyleneimine or polypropyleneimine and the documents U.S. Pat. No. 5,595,897 and FR 2719316, the use of polylysine conjugates.

Given that it is desired to obtain in vivo a transformation targeted toward a given cell type, it is evident that the vector used should be able to be "targeted" itself, as described above.

Use of cells transformed in vitro or ex vivo with vectors containing a gene of therapeutic interest defined in relation to the proteins of interest identified in the present invention (SEQ ID No. 2, 4, 8, 9, 17, 24) and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29.

The present invention relates to a biological material for the preparation of pharmaceutical compositions for preventing and treating degenerative and/or neurological and/or autoimmune diseases, preferably multiple sclerosis, the composition comprising at least one cell, in particular a cell not naturally producing antibodies, in a form allowing their administration into the body of a mammal, human or animal, as well as optionally their prior culture, said cell being genetically modified in vitro by at least one nucleic acid sequence containing at least one gene encoding in vivo:

(i) at least one protein chosen from the proteins SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29 and the peptide sequences which exhibit at least 70% identity, preferably at least 80% identity and advantageously at least 98% identity with any one of the peptide sequences SEQ ID No. 1 to 29, and any fragment, (ii) at least one peptide defined from the primary sequence of at least one protein chosen from the proteins SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, (iii) at least any molecule inhibiting the function and/or binding and/or expression of these proteins, (iv) at least one peptide derived from the primary sequence of a protein chosen from the proteins SEQ ID No. 2, 4, 8, 9, 17, 24 and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29, and capable of binding to at least one glycoprotein of the MHCI, (v) at least any antibody and any portion of antibody which are capable of binding to at least one protein chosen from the proteins SEQ ID No. 2, 4, 8, 9, 17, 24, and the peptide sequences or the fragments of said sequences belonging to the same family of proteins chosen from Perlecan, the precursor of the retinol-binding plasma protein, GM2 activator protein, calgranulin B and saposin B (for example SEQ ID No. 1, SEQ ID No. 3, SEQ ID No. 5 to 7, SEQ ID No. 10 to 16, SEQ ID No. 18 to 23, SEQ ID No. 25 to 29) and the peptide sequences which exhibit at least 70% identity, preferably at least 80% identity and advantageously at least 98% identity with any one of the peptide sequences SEQ ID No. 1 to 29.

More particularly, said target cell is obtained either from the mammal to be treated, or from a mammal other than that to be treated. In the latter case, it should be noted that said target cell will have undergone a treatment making it compatible with the mammal to be treated. The expression "mammal" is preferably understood to mean a human mammal. These cells are established as cell lines and are preferably MHCII+ or MHCII+-inducible such as the lymphocytes, monocytes, astrocytes and oligodendrocytes.

The invention also relates to the modified cells and to a method for preparing a cell as described above, characterized in that there is introduced into a mammalian cell not naturally producing antibodies, by any appropriate means, at least one nucleic acid sequence containing at least one gene of therapeutic interest and elements ensuring the expression of said gene in said cell, said gene of therapeutic interest containing a nucleic acid sequence encoding a molecule or a molecule fragment in vivo, as described immediately above. More particularly, it relates to prokaryotic cells, yeast cells and animal cells, in particular mammalian cells transformed with at least one nucleotide sequence and/or one vector as described above.

According to a particular embodiment, the cells (dendritic cells, macrophages, astrocytes, CD4+ T lymphocytes, CD8+ T lymphocytes, and the like) of the patient or allogenic cells are placed in contact with a purified preparation of the target polypeptide, the latter being internalized, made ready and presented at the cell surface associated with the MHCI and/or MHCII molecules and thus to induce a specific immune response against the peptide. The "activated" cells are then administered to the patient in whom they will induce an immune response specific for the antigens (a natural route is used for the immune response, but what the antigen-presenting cell is going to present is checked).

According to a particular embodiment, the antigen-presenting cells (dendritic cell, macrophage, astrocytes, and the like) are modified in vitro in order to express the antigens in the transformed cell which will associate with the MHCI and/or MHCII molecules and be presented at the surface of the cells to induce a perfectly targeted immune reaction in the patient in whom the modified cell is administered.

All the vaccine approaches are not always satisfactory and lead, for example, to limited immune reactions directed solely against immunodominant epitopes or against antigens exhibiting great variability. Likewise, the incorrect presentation of the antigens by the glycoproteins of the MHC system at the surface of the cells does not make it possible to develop in the treated patient a suitable anti-protein of interest immunity. To overcome these problems, some authors have proposed, in the context of such vaccine methods, to select the antigenic minimal fragments corresponding to the peptide portions capable of being specifically recognized by the cytotoxic T lymphocytes, expressing them in the cells so that they associate with the molecules of the MHCI and are presented at the surface of the cells in order to induce a perfectly targeted immune reaction in the treated patient (Toes et al. 1997, PNAS 94: 14660–14665). More particularly, it has been shown that epitopes of very small sizes (varying from 7 to about 13 amino acids), which are expressed from minigenes introduced into a vaccinia virus, could induce a cellular type immunization. It has moreover been shown that several minigenes could be conjointly expressed starting with the same vector (this particular construct is called "string of beads"). Such a construct has the advantage of inducing a synergistic CTL-type immune reaction (Whitton et al., 1993 J. of Virology 67: 348–352).

Protocol for bringing the cells and the antigenic fragment into contact:

The presentation of the antigenic fragments by the MHCI molecules depends on an identified intracellular method (see Groettrup et al., 1996 Immunology Today 17: 429–435 for a review) in which very short antigenic peptides (about 7–13 amino acids) are produced by degradation of a more complex polypeptide against which the final immune reaction will be directed. These short peptides are then combined with the MHCI or MHCII molecules to form a protein complex which is transported to the cell surface in order to present said peptides to the circulating cytotoxic T lymphocytes or to the circulating helper T lymphocytes, respectively. It should be noted, in addition, that the specificity of the MHCI or MHCII molecules toward the antigenic peptides varies as a function of the MHCI or MHCII molecules (example for MHCI: HLA-A, HLA-B, and the like) and the allele (example for MHCI: HLA-A2, HLA-A3, HLA-A11) which are considered. Within the same animal species, from one individual to another, there is great variability of the genes encoding the molecules of the MHC system (on this subject, see in particular George et al., 1995, Immunology Today 16: 209–212).

According to a particular embodiment, the cells, such as dendritic cells, macrophages, astrocytes, CD4+ T lymphocytes, CD8+ T lymphocytes, are modified so as to express at their surface antibodies specific for the targeted peptide. The peptide is neutralized with the antibodies expressed at the surface of the cells. These cells are preferably immune cells, preferably from the patient, are preferably cytotoxic and modified to express all or part of an antibody specific for the target polypeptide.

Isolation of mononucleated cells from peripheral blood:

In 1968, Boyum described a rapid technique which makes it possible, by centrifugation of blood on a density gradient, to separate the mononucleated cells (lymphocytes and monocytes) with a good yield (theoretical yield 50%, that is to say $10^6$ cells/ml of blood). 50 ml of peripheral blood sterilely collected in heparinized tubes are centrifuged for 20 minutes at 150 g at 20° C. The cells recovered are diluted in two volumes of initial peripheral blood of sterile PBS. 10 ml of this suspension are deposited on 3 ml of a Ficoll-Hypaque solution (medium for separation of the lymphocytes, Flow). After centrifuging for 20 minutes at 400 g and 20° C. without decelerating braking, the mononucleated cells sediment at the PBS-Ficoll interface, as an opalescent dense layer, whereas practically all the red blood cells and the polynuclear cells sediment at the bottom of the tube. The mono-nucleated cells are recovered and washed with sterile PBS.

Internalization of the antigens by the antigen-presenting cells:

Prior treatment of the antigen-presenting cells: the antigen-presenting cells are washed beforehand with PBS buffer containing 0.5% (w/v) BSA, then counted and they are then preincubated in the presence of various reduction inhibitors three times in PBS-0.5% BSA containing 10 µM to 10 mM final of DTNB (5,5'-dithio-bis-2-nitrobenzoic acid) or NEM (N-ethylmaleimide). The subsequent stages of binding of antigens to the cell surface or of internalization of antigens are also carried out in the presence of various concentrations of inhibitors.

Protocol for internalization of the antigens by the antigen-presenting cells:

$8 \times 10^6$ cells are internalized in the presence of saturating quantity of proteins radiolabeled with iodine 125 (1 µg) in microwells in 70 µl. After incubating for one hour at 4° C., with stirring, the antigens are bound to the surface of the cells. The cell suspension is washed twice in PBS-BSA and the cellular pellets are taken up in 70 µl of buffer and incubated at 37° C. for various periods ranging up to 2 hours. Cells and supernatants are separated by centrifugation at 800 g for 5 minutes 4° C. For longer incubation periods, the preliminary stage of prebinding of the antigens to the surface of the cells is eliminated. The cells are diluted in RPMI-10% FCS medium in the presence of 20 mM Hepes, at $10^6$ cells/ml. The cells are incubated in the presence of an excess of antigen for various periods at 37° C. (1 µg of molecules/ $5 \times 10^7$ monocyte/macrophage cells or $10^8$ B-EBV cells).

All the therapeutic agents defined in the context of the present invention are used for preventing and/or treating a degenerative and/or neurological and/or autoimmune disease, such as multiple sclerosis, alone or in combination. They may also be used to evaluate their efficacy in vitro or in vivo.

Administration of therapeutic agents in humans:

The biological material according to the invention may be administered in vivo in particular in injectable form. It is also possible to envisage injection by the epidermal, intravenous, intraarterial, intramuscular or intracerebral route with a syringe or any other equivalent means. According to another embodiment, by oral administration or any other means perfectly known to a person skilled in the art and applicable to the present invention. The administration may take place as a single dose or as a dose repeated once or several times after a certain time interval. The most appropriate route of administration and dosage vary as a function of various parameters such as, for example, the individual or the disease to be treated, the stage and/or the progression of the disease, or alternatively the nucleic acid and/or protein and/or peptide and/or molecule and/or cell to be transferred or the target organ/tissue.

To carry out the treatment of the mammal mentioned in the present invention, it is possible to have pharmaceutical compositions comprising a biological material as described above, advantageously combined with a pharmaceutically acceptable vehicle for administration to humans or to animals. The use of such carriers is described in the literature (see, for example, Remington's Pharmaceutical Sciences 16th ed. 1980, Mack Publishing Co). This pharmaceutically acceptable vehicle is preferably isotonic, hypotonic or exhibits low hypertonicity and has a relatively low ionic strength, such as for example a sucrose solution. Moreover, said composition may contain solvents, aqueous or partially aqueous vehicles such as sterile water, free of pyrogenic agents and dispersion media for example. The pH of these pharmaceutical compositions is suitably adjusted and buffered according to conventional techniques.

BRIEF DESCRIPTION OF THE DRAWINGS

FIG. 1 represents the amino acid sequence of the GM2AP protein (SEQ ID NO: 73), and the localization of the peptides, which is underlined, and which are used for the production of anti-GM2AP peptides antibodies.

FIG. 2 represents the amino acid sequence of the MRP14 protein (SEQ ID NO: 75), and the localization of the peptides, which is underlined, and which are used for the production of anti-MRP14 peptides antibodies.

FIG. 3 represents the amino acid sequence of the Saposin B protein (SEQ ID NO: 74), and the localization of the peptides, which is underlined, and which are used for the production of anti-Saposin B peptides antibodies.

FIG. 11A, the assay of the GM2AP protein in ng/ml in the urine of an MS patient in progressive remittent form (light-colored curve) and the gliotoxicity as a percentage of dead cells estimated by the MTT test (dark-colored curve); FIG. 11B, the assay of the Saposin B protein in µg/ml in the urine of an MS patient in progressive remittent form (light-colored curve) and the gliotoxicity as a percentage of dead cells estimated by the MTT test (dark-colored curve).

FIG. 13A, the assay of the GM2AP protein in ng/ml in the urine of an MS patient in progressive remittent form (light-colored curve) and the gliotoxicity as a percentage of dead cells estimated by the MTT test (dark-colored curve); FIG. 13B, the assay of the Saposin B protein in µg/ml in the urine of an MS patient in progressive form (light-colored curve) and the gliotoxicity as a percentage of dead cells estimated by the MTT test (dark-colored curve).

DETAILED DESCRIPTION OF EMBODIMENTS

EXAMPLES

Example 1

Collecting and Pooling of Urines

Figure 4:
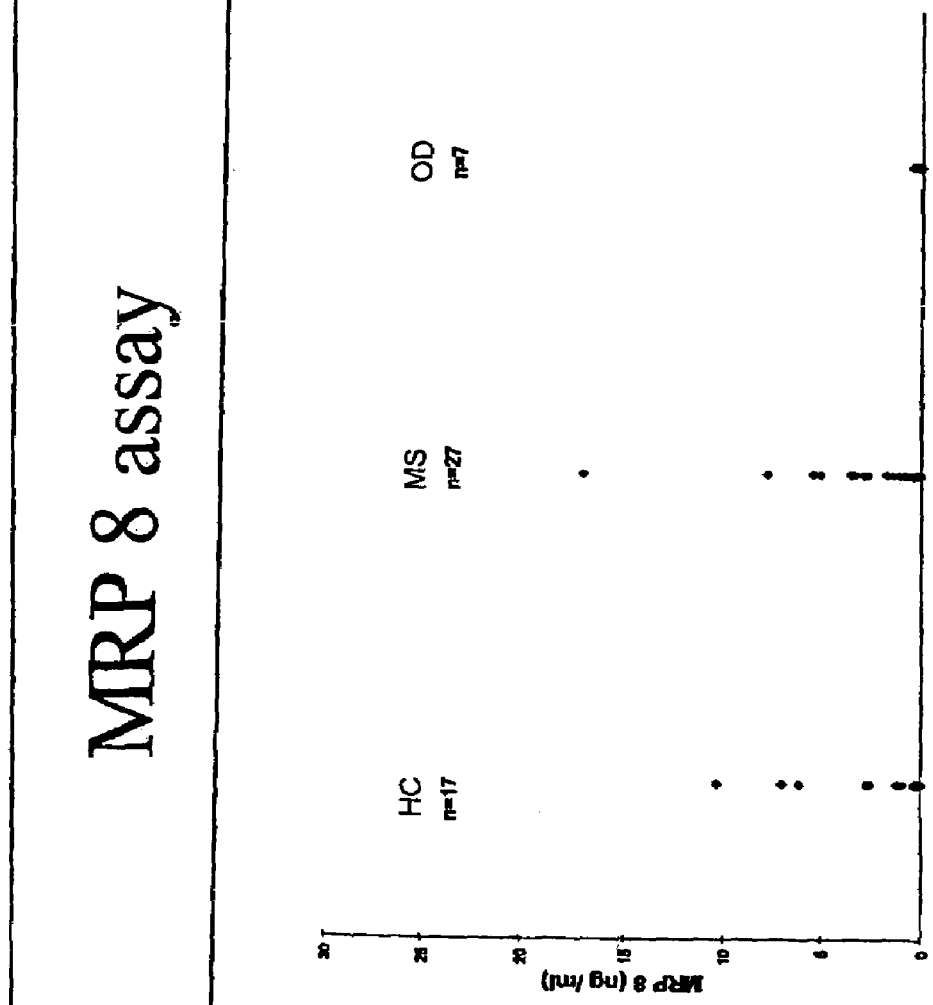
FIG. 4 represents the assay of the MRP8 protein (ng/ml—on the y-axis) in the urine of patients suffering from multiple sclerosis (MS), in the urine of patients suffering from other neurological diseases (OND) and in the urine of controls considered healthy (HC). n means the number of urine samples tested per category.

Urine samples of different volumes were collected from healthy individuals (MS-negative) having a priori no neurological or autoimmune disease. The toxic activity of each sample toward murine astrocyte cells was tested in vitro using the MTT test. In total, a pool of 20 liters of urine was formed (MS-negative pool). In parallel, urine samples of different volumes were collected from individuals suffering from multiple sclerosis (MS-positive) at various stages of the disease. The toxic activity of each sample toward murine astrocyte cells was tested in vitro using the MTT test. In total, a pool of 80 liters of urine was formed (MS-positive pool).

Example 2

Purification of the Urinary Proteins

The pools of MS-positive and MS-negative urine, collected and tested according to example 1, were purified in order to obtain a high protein concentration and to remove the high molecular weight proteins as far as possible.

Precipitation: precipitations with ammonium sulfate (Prolabo—ref. 21 333 365) were carried out on the pools of MS-positive and MS-negative urine. The percentage of 60% saturated ammonium sulfate per 40% of urine, that is 390 grams of ammonium sulfate per liter of urine, was used. Each pool was distributed into fractions of 1.8 liters in 2-liter bottles in order to improve the precipitation. The precipitation was carried out for 2×8 hours, at room temperature, with gentle stirring. After centrifugation of the pools of urine at 3 000 rpm for 10 min, at a temperature of 10° C., the pellet obtained is taken up in 20 mM Tris buffer containing 1 mM $CaCl_2$ and 0.25 M urea. The mixture was then centrifuged at 3 000 rpm for 10 min. The supernatant contains the concentrated proteins. It is either used immediately for the next stage, or frozen if the next stage cannot be performed continuously.

Ion-exchange chromatography: the solution containing the proteins was then passed over a DEAE fast Flow gel (marketed by PHARMACIA). This stage is carried out at low pressure on a PHARMACIA column filled with gel. The buffers are brought to the column by a peristaltic pump which allows a uniform flow rate. The buffer for equilibrating the column is 20 mM Tris buffer, pH 7. The fraction corresponding to the precipitation supernatant and containing an excessively high quantity of salts is dialyzed against this buffer before depositing on the column. Elution with a salt gradient makes it possible to recover the proteins. The elution gradient is performed in steps of 100, 200, 300, 500 mM NaCl in the buffer for equilibrating the column. The elution fractions are tested by the MTT test and only the positive fractions, that is the fraction eluted at 200 Mm NaCl, will be preserved. These fractions may be immediately treated or stored in the freeze-dried state.

Purification: steric exclusion chromatography based on the difference in size and shape of the proteins to be eluted was used. The fraction corresponding to the 200 mM NaCl elution is deposited on the column. During the elution, the proteins of low molecular mass are retained and therefore eluted later than the large molecules. The purifications were carried out on HPLC with a TosoHaas TSK Prep G 3000 SW column having a diameter of 21.5 mm and a length of 300 mm, the molecular mass exclusion limit is 500 000 daltons. The elution buffer used contains 100 mM phosphate, 100 mM sodium sulfate, at pH 6.8. The separation of the protein mixture was carried out in 60 min. Only the fraction corresponding to a mass of 15–20 000 daltons was preserved. This fraction is dialyzed in 20 mM Tris buffer containing 0.2 mM $CaCl_2$, pH 7.2, and then freeze-dried.

At each stage, only the fractions having a significant toxic activity were retained for the next stage. The toxic activity of the proteins was checked at each stage using the MTT test. Only the fractions having a significant toxic activity were retained for the additional purification stage described in example 3.

Example 3

Additional Purification of the Urinary Proteins by Reverse Phase Chromatography

Pools of urine from MS patients (MS-positive pool) and from non-MS patients (MS-negative pool), obtained after purification according to example 2, were taken up in distilled water and then diluted with a 0.2% TFA/10% acetonitrile solution in order to obtain a final concentration of about 130 to 140 µg/ml.

The separation by C8 reverse phase HPLC was carried out on a Brownlee Aquapore column (trade name) marketed by the company Perkin Elmer (column characteristics: 300 angstroms/7 µm/(100×4.6) mm). Two separate columns were used for the positive and negative pools respectively.

The injections were carried out by multiple injections of 250 µl. The proteins were eluted with a linear gradient from 5% to 15% of buffer B over 5 min, and then from 15% to 100% of buffer B over 95 min, at a flow rate of 0.5 ml/min. The separation buffers A and B used are the buffer 0.1% TFA (Pierce No. 28904)/MilliQ water and the buffer 0.09% TFA/80% acetonitrile (Baker) respectively. The detection was carried out by measuring the UV absorbence at 205 and 280 nm. Fractions were collected in 1.5 ml and 0.5–1 ml fractions in the zone of interest. The fractions were frozen after collection in dry ice.

The fractions collected were then dried in a speed vac and taken up in 100 µl of 0.1% TFA/30% acetonitrile, 20 µl of the fractions were transferred into 500 µl eppendorfs, dried and washed twice with 100 µl of MilliQ water and then dried again.

The toxic activity of the proteins contained in each fraction collected after elution was determined with the aid of the MTT test. Only fraction 21 exhibiting a significant toxic activity was retained. The number for this fraction corresponds to the order of elution as a function of the elution conditions stated in this example.

Example 4

Analysis of the Proteins Obtained by HPLC Separation on SDS-TRICINE Gel

The collection pool for fraction 21 obtained by HPLC, as described in example 3, and resulting from 20 injections of the MS-positive pool, was deposited on a precast 16% SDS-TRICINE gel of 10 wells and 1 mm thick (marketed by the company Novex). The conditions for using the gel correspond to those recommended by the supplier. The sample is taken up in 75 µl of 1 times concentrated sample buffer (SDS-TRICINE No. LC 1676, 1 ml two times concentrated+50 µl of β-mercapto-ethanol (Pierce) diluted ½ in water) and 25 µl of the sample are deposited on the gel in three portions. The collection pool for fraction 21 obtained from 6 injections of the MS-negative pool was deposited on the gel under the same conditions as described for the MS-positive pool. The migration on the two gels was carried out in parallel in the same migration tank (XCELL II NOVEX (trade name)) at a constant voltage of 125 mV for 2 hours. The tank is placed in a container containing ice. The gels were stained directly after migration by zinc/imidazole staining (staining kit 161-0440 marketed by the company BIORAD) so as to obtain a reversible negative staining. The protein bands are translucent on an opaque base.

Example 5

Digestion of the Gel Bands with Trypsin

All the protein bands visualized in the deposits of fraction 21 were cut out and subjected to proteolysis with trypsin.

The gel bands are cut out with a scalpel into slices of 1 mm and transferred into eppendorf tubes. The eppendorfs are subjected to a centrifugation peak so as to cause the gel pieces to fall and, after centrifugation, 100 µl of washing buffer (100 Mm $NH_4CO_3$/50% $CH_3CN$) are added to the gel pieces. After stirring for 30 min at room temperature, the supernatant is removed in fractions of 20 µl and the washing step is repeated twice. The eppendorfs are dried for 5 min in speed vac. 20 µg of trypsin (modified sequenal grade PROMEGA V5111) are taken up in 200 µl of digestion buffer (5 mM TRIS, pH 8) and are dissolved for 30 min at room temperature, with intermittent stirring, and 20 to 30 μl of resuspended trypsin are added to the gel pieces. The eppendorfs are centrifuged and stored in a hot room at 28° C. overnight. After digestion, the gel bands may be used immediately for the measurements of mass or frozen for subsequent use.

Example 6

Chemical Digestion of the Gel Bands with CNBR

In the event of a protein being resistant to enzymatic cleavages, in particular to the action of trypsin as described in example 5, the bands between 16 kD and 20 kD were treated with CNBR. The gel bands, already used for the digestions with trypsin, are dried for 5 to 10 min in speed vac.

A solution of CNBR (FLUKA) at 200 mg/ml was prepared in 70% formic acid (BAKER). 20 μl of this solution were used to rehydrate the gel pieces. The reaction was carried out for 20 h at room temperature and in the dark. The peptides are extracted for 3 times 30 min with 100 μl of 0.1% TFA/60% acetonitrile. The extraction solutions are combined and concentrated to 20 μl. These samples are diluted 5-fold in 0.1% TFA/water. The separation conditions are those described for the peptides from the digestion with trypsin.

Example 7

Analysis by MALDI-TOF Spectrometry

30 μl of extraction buffer (2% TFA/50% acetonitrile) are added to the samples. The eppendorfs to be analyzed are subjected to a centrifugation of 5 min, and then to a sonication of 5 min, and finally to a centrifugation of 1 min. On a stainless steel disk, 14 deposits of 0.5 μl of matrix (α-cyano-4-hydroxytranscinnamic acid at saturation in acetone) are carried out. A fine uniform microcrystalline layer is obtained. 0.5 μl of a solution of 2% TFA/water are deposited on this sublayer on the 14 deposits, and then 0.5 μl of sample to be analyzed are added. 0.5 μl of a solution at saturation with α-cyano-4-hydroxytranscinnamic acid acid in 50% acetonitrile/water is added to this drop thus formed. After drying at room temperature for 30 min, the crystalline deposits are washed with 2 μl of water which are immediately evacuated by a puff of air. All the spectra are obtained on a BRUKER BIFLEX (trade mark) mass spectrometer equipped with a reflectron. The measurements (90 to 120 laser shots on the entire deposit) are accumulated in order to obtain a mass spectrum which is most representative of all the peptides present in the matrix-sample sandwich. For each deposit, a calibration with the peptides from the autolysis of trypsin was made in order to be able to use a measurement accuracy of less than 100 ppm.

Searches in databanks were carried out in MS-FIT PROTEINPROSPECTOR (http://prospector.ucsf.edu). The common parameters used in these searches are (1) database: NCBInr, (2) a tolerance of 100–50 ppm, (3) the cysteins are not modified, (4) the methionines may be oxidized, (5) molecular weight range: 1 000–100 000 Da, (6) up to 3 cleavage sites may be ignored.

Example 8

N-Terminal Sequencing of the Digestion Peptides (i) Extraction and Separation by HPLC of the Digestion Peptides.

After the measurements of mass on the entire digestion, the rest of the peptides are extracted 3 times 30 min in a sonication bath with 0.1% TFA/60% acetonitrile. The extraction solutions are combined and dried up to 20 μl in speed vac. After dilution in 80 μl of buffer A (0.1% TFA/water), the extractions of the gel bands, digested with trypsin, are injected onto a C18/MZ-Vydac/(125×1.6) mm/5 μm column. The elution of the peptides is carried out at a flow rate of 150 μl/min, in a gradient ranging from 5% of buffer B (0.09% TFA/80% acetonitrile) to 40% of buffer B over 40 min, and then from 40% of buffer B to 100% of buffer B over 10 min. The detection is made by measuring the UV absorbence at 205 nm. The collection of the peaks is carried out in 500 μl eppendorf tubes. The fractions are stored on ice and, for the band of 18–20 kD of the MS-positive pool 21, analyzed by MALDI-TOF mass spectrometry.

(ii) N-Terminal Sequencing

The fractions corresponding only to a single mass peak were analyzed by Edman degradation on a sequencer (model 477A PERKIN ELMER/Applied Biosystems). The sequencing conditions are those described by the manufacturer. A microcartridge was used for depositing the samples and the PTH-amino acids are identified with an online HPLC system (model 120A PERKIN ELMER/Applied Biosystems).

The deposition of the fraction to be sequenced is made in several depositions of 15 μl with intermediate dryings. The tube which contained the peptide is washed with 15 μl of 85% formic acid (BAKER). The amino acid sequences still correspond to the masses measured. The peptides, whose masses do not correspond to the principal protein identified, were sequenced as a priority. In this manner, it was possible to identify up to three proteins in a gel band.

Example 9

Results and Discussion

After reversed HPLC of the MS-negative control pool and of the MS-positive pool, the toxic activity of each elution fraction was determined using the MTT test. Only fraction 21 of the MS-positive pool exhibits a toxic activity in vitro. Fraction 21 of the MS-negative control pool exhibits no toxic activity. The toxic activity of fraction 21 of the MS-positive pool was confirmed in vitro by FACS, as described in patent application WO 98/11439 on murine astrocyte cells.

The protein content of fraction 21 of the MS-negative control pool and of the MS-positive pool was observed after separation on 16% SDS-TRICINE gel and staining of the gel with zinc/imidazole. Proteins of high apparent molecular weights were found in the two fractions. On the other hand, five different bands of low apparent molecular weights are only visible in fraction 21 of the MS-positive pool (bands 8, 14, 18 and 20 kD). To each band there corresponds at least one protein and variants of said proteins which have an apparent molecular weight close to that of the native protein. These variant sequences exhibit a percentage homology or identity with the native sequences of at least 70%, preferably of at least 80% and advantageously of at least 98%.

The proteins of interest of fraction 21 of the MS-positive pool were then analyzed by mass spectrometry and/or sequencing and searching for homology in the databanks. The results show the presence of five protein bands migrating between 22 and 5 kD in fraction 21 of the MS-positive pool and variants of said proteins.

These proteins are the C-terminal fragment of Perlecan, which starts at amino acid 3464 and ends at amino acid 3707 of the complete protein sequence, identified in the sequence identifier SEQ ID No. 2, the precursor of the retinol-binding plasma protein whose sequence is given in SEQ ID No. 4, the GM2 activator protein identified in SEQ ID No. 8, calgranulin B identified in SEQ ID No. 17 and saposin B represented in SEQ ID No. 24. As described above, homologs or variants of said proteins were also identified by sequencing. These homologous or variant protein sequences are the product of mutations in the genes encoding said proteins. By way of example, SEQ ID No. 9 exhibits 99% homology or identity with SEQ ID No. 8 of the GM2 activator protein and the fragment of SEQ ID No. 9 which starts at amino acid 34 and ends at amino acid 202 exhibits 98.88% homology or identity with the fragment corresponding to the native protein identified in SEQ ID No. 8.

Example 10

Identification of the Proteins in a Urine Sample

Urine samples from an MS-negative individual and from an MS-positive patient were collected. These urine samples were purified according to the protocol described above. The final elution fractions 21 were analyzed separately by mass spectrometry. The mass profile of each fraction corresponding to each urine sample was compared with the mass profile obtained for the proteins identified in the preceding examples. The results show that for the urine sample from the MS-positive patient, the masses correspond to the molecules (i) C-terminal fragment of Perlecan, (ii) GM2 activator protein, (iii) calgranulin B and (iv) saposin B identified above. On the other hand, none of these masses was identified in the mass profile obtained after analysis of the urine sample obtained from the MS-negative individual. The method described can be used as a diagnostic assay.

Example 11

Western Blot Assay

Western blottings were carried out on different fractions of crude or purified urine as described in example 2. Urine samples from healthy individuals and from patients suffering from multiple sclerosis are tested in parallel. The samples are deposited on an electrophoresis gel which makes it possible to separate the various proteins according to their molecular mass under the action of an electric field. The Western blottings are carried out after transferring the proteins from the gel onto a membrane. To visualize the transferred proteins, the membrane is saturated with saturation buffer and then incubated with an antibody directly labeled with alkaline phosphatase. The antibody used is an anticalgranulin antibody (mouse monoclonal antibody, clone CF 145 subtype IgG 2b marketed by the company Valbiotech: reference MAS 696p batch PC96G696). The substrate for the enzyme is 3,3'-(1,1'-biphenyl)-4,4'-diazonium dichloride and sodium 2-naphthalenylphosphate (marketed under the name β Naphthyl acid phosphate Sigma ref. N7375 and Tetrazotized ô-dianisine D3502) is added for revealing the bands and visualizing the proteins linked to the antibody. A molecule with an apparent molecular mass of about 14 000 is revealed in the purified urines from patients suffering from MS, with a relatively intense signal. This protein corresponds to calgranulin B (apparent molecular mass: 14 kD). By contrast, no signal is observed from urine from healthy individuals. This observation confirms the presence of this protein specifically in the urines from patients suffering from MS and the use of a method of detection using an antibody recognizing the protein.

Example 12

Production of Monoclonal Antibodies

The production of monoclonal antibodies using ascites requires compatibility of the H-2 system between the hybridoma and the producing mouse. Twenty 6-week-old female Balb/c mice receive an injection of 0.5 ml of Pristane (2,6,10,14-tetramethylpentadecane acid) in their peritoneal cavity, for the production of ascites (Porter et al., 1972). One week to 10 days later, $5 \times 10^6$ to $10 \times 10^6$ hybridomas, diluted in 0.5 ml of sterile buffer containing 0.145 M NaCl, 10 mM $Na_2HPO_4$, 2.7 mM KCl and 1.5 mM $KH_2PO_4$ at pH 7.4, are injected by the intraperitoneal route. The ascites appear one to two weeks later. The ascitic fluids present in the peritoneal cavity are then collected with a syringe after incision of the peritoneum. The fluid collected is centrifuged at 3 000 g for 15 minutes at room temperature, filtered on gauze in order to remove the fat, and then buffered by adding ½₀th of its volume of 1M Tris-HCl at pH 8.0. This method makes it possible to obtain quantities of antibody 10 times higher than those obtained by hybridoma culture.

The immunoglobulins present in the ascitic fluid are released by the salts (ammonium sulfate or sodium sulfate). The ascitic fluid is precipitated with 40% ammonium sulfate. After 20 minutes in the cold, the solution is centrifuged for 15 minutes at 8 000 g at 4° C. The precipitate is washed and resuspended in the cold in a 40% ammonium sulfate solution and then centrifuged again. The new precipitate enriched with IgG is redissolved in PBS buffer and dialyzed overnight against the 25 mM Tris-HCl buffer containing 150 mM NaCl, pH 7.4. In parallel, an agarose-Protein A (or protein G) column (marketed in the freeze-dried form, Pierce) is extensively washed with the 25 mM Tris-HCl buffer containing 150 mM NaCl, pH 7.4. The solution enriched with IgG is deposited on the column and then the column is washed. The IgGs retained by the column are eluted at acidic pH (200 mM glycine, pH 2.8). The eluted fractions are neutralized with one volume of 1M Tris-Base, pH 10.5. The immunoglobulin content of each fraction collected is quantified by reading the absorbance at 280 nm (e 1%, 1 cm=14.0, Prahl and Porter 1968). The rich fractions are pooled. The degree of purification of the pooled IgGs is analyzed by acrylamide gel electrophoresis in the presence of SDS. The purified IgGs are dialyzed overnight against the 25 mM Tris-HCl buffer containing 150 mM NaCl, pH 7.4, sterilely filtered, aliquoted and stored at −20° C. Their final concentration is determined by reading the absorbance at 280 nm or by micro-BCA assay. The immunogenic peptides designated by the references SEQ ID No. 58, SEQ ID No. 54, SEQ ID No. 55, SEQ ID No. 56, SEQ ID No. 57, SEQ ID No. 58, SEQ ID No. 59, and SEQ ID No. 65 were used for the production of monoclonal antibodies, according to the protocol described above. However, it is in the capability of persons skilled in the art to define other protocols for the production of monoclonal antibodies, for example using the techniques described by Köhler and Milstein and by Galfre G. et al. previously cited or techniques derived therefrom.

Production of recombinant proteins and of polyclonal and monoclonal antibodies

Recombinant proteins:

The recombinant proteins GM2AP (SEQ ID NO. 73) and Saposin B (SEQ ID NO. 74) used to produce the calibration series for this study were produced in a prokaryotic system and purified from the clones of these two proteins obtained in our laboratory using the methods and protocols well known to persons skilled in the art.

Anti-GM2AP or Anti-Saposin B Antibodies:

The anti-GM2AP or anti-Saposin B antibodies used to carry out the study were produced in our laboratory or generously given.

Anti-Saposin B and anti-GM2AP polyclonal antibodies (Li et al., Glycoconjugate, 1984) were used for the study (cf the examples below): they are called SAP84 and GM2AP84.

Anti-GM2AP or anti-Saposin B polyclonal antibodies were produced and purified in the laboratory using the protocols and methods well known to persons skilled in the art: 50 µg of prokaryotic GM2AP or Saposin B protein purchased were injected into rabbits on days D0, D28 and D56; two booster injections were carried out once per month for two consecutive months. The two anti-GM2AP polyclonal antibodies and two anti-Saposin B polyclonal antibodies were thus obtained and their specificity toward the recombinant protein was verified by Western blotting and Elisa.

Anti-GM2AP or Saposin B peptides polyclonal antibodies were produced and purified in the laboratory using the protocols and methods well known to persons skilled in the art: 75 µg of GM2AP or Saposin B peptides defined, produced and coupled to KLH in our laboratory were injected on days D0, D28 and D56; several boosts were thus carried out once per month for 5 consecutive months with injection of 75 µg each time. Four anti-GM2AP peptides polyclonal antibodies, four anti-Saposin B peptides polyclonal antibodies and four anti-MRP14 peptides rabbit polyclonal antibodies were obtained and their specificity toward the recombinant protein was verified by Western blotting and by Elisa. The sequence of the GM2AP, Saposin B and MRP14 peptides chosen are described in FIGS. 1 to 3.

The following were obtained:

an antibody anti-mixture of two peptides of 13 and 15 amino acids of GM2AP: 189–190; an antibody anti-peptide of 18 amino acids of GM2AP: 191–192 (cf. FIG. 1), an antibody anti-mixture of two peptides of 13 and 19 amino acids of MRP14: 193; an antibody anti-peptide of 17 amino acids of MRP14: 195–196 (cf. FIG. 2), an antibody anti-mixture of three peptides of 12, 15 and 15 amino acids of Saposin B: 74–75; another antibody anti-mixture of 3 peptides of 12, 15 and 15 amino acids of Saposin B: 72–73 (cf. FIG. 3).

Anti-native fraction monoclonal antibodies were produced and purified in the laboratory using the protocols and methods well known to persons skilled in the art. The "native fraction" corresponds to the cytotoxic elution fraction obtained from the pool of 80 liters of urine from MS patients and after purification. It is the last elution fraction which contains the three proteins GM2AP, Saposin B, MRP14. 30 µg of this purification fraction were injected into three mice on days D0, D14, D28 and the sample collection was carried out on D38. After "screening" and cell fusion, protocols known to persons skilled in the art for establishing hybridomas and monoclonal antibodies, the hybridomas were reinjected into the mice and the ascitic fluid was recovered 10 days later. The antibodies were purified on sepharose-Protein A column and the specificity toward the fraction used for the immunization was verified by Western blotting and by Elisa. Thus, four monoclonal antibodies were obtained: 191C1A7, 3D3F9, 18C8C5 and 7D12A8.

Example 13

Assay of the MRP14 Proteins in the Urines by the ELISA Technique

The MRP14, MRP8 proteins and the MRP8/14 heterocomplex were assayed in human urines using (i) either an Elisa assay technique according to the method known to persons skilled in the art and using the anti-MRP antibodies described in the preceding examples; (ii) or the "MRP Enzyme Immunoassay" kit marketed by BMA Biomedicals AG, Augst, Switzerland, using the antibodies of the kit, the protocol being carried out according to the leaflet in the kit.

Detection of MRP14 and MRP8/14 in Urines

The assay was carried out using 17 urines of individuals from the active population (HC), 27 urines of patients suffering from multiple sclerosis (MS) and 7 urines of patients suffering from other neurological diseases (OND).

FIG. 4 illustrates the levels of MRP8 assayed in these urines: while the MRP8 concentration is practically zero in the OND urines, there is no real difference in distribution between the HC and MS urines. It should be noted, however, that the differences observed are practically negligible because the concentrations assayed are extremely low.

Figure 5:
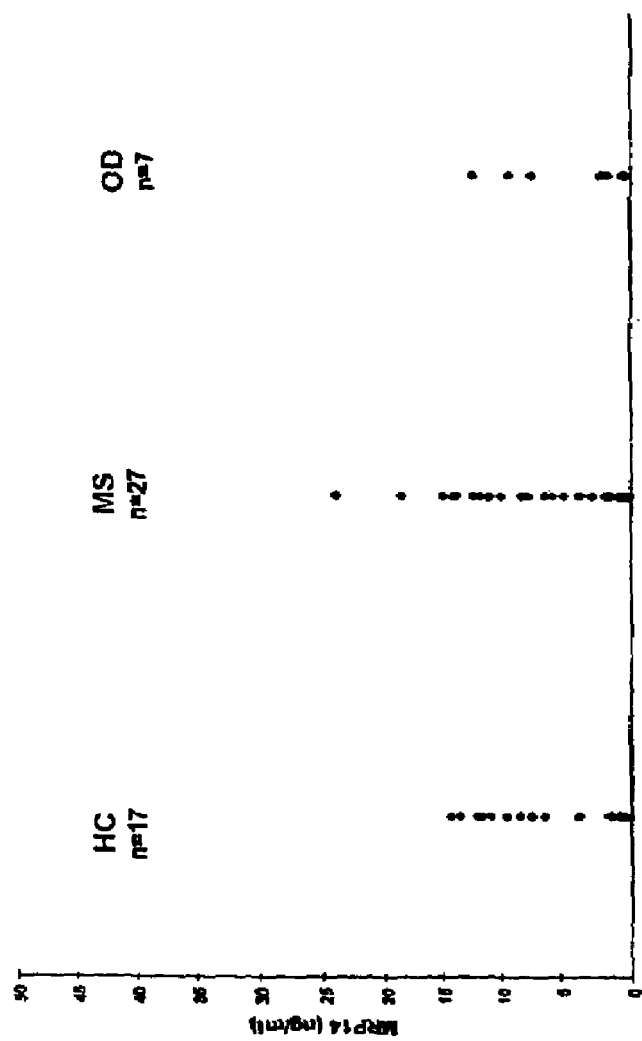
FIG. 5 represents the assay of the MRP14 protein (ng/ml—on the y-axis) in the urine of patients suffering from multiple sclerosis (MS), in the urine of patients suffering from other neurological diseases (OND) and in the urine of controls considered healthy (HC). n means the number of urine samples tested per category.

FIG. 5 illustrates the levels of MRP14 assayed in the same urines: while there are no real differences in the distribution of the concentrations between the HC and OND urines, the concentrations are higher in certain MS urines.

Figure 6:
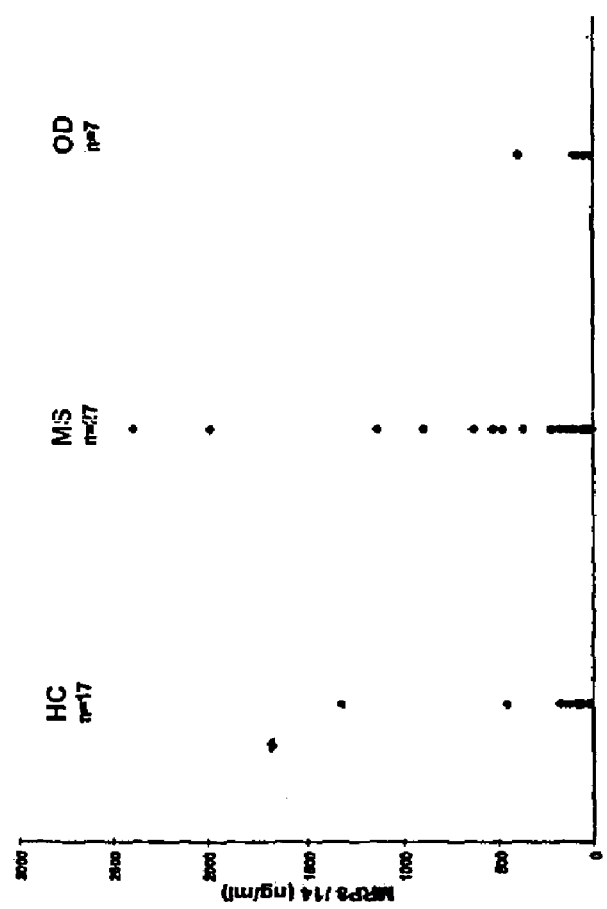
FIG. 6 represents the assay of the MRP8/14 protein (ng/ml—on the y-axis) in the urine of patients suffering from multiple sclerosis (MS), in the urine of patients suffering from other neurological diseases (OND) and in the urine of controls considered healthy (HC). n means the number of urine samples tested per category.

FIG. 6 illustrates the levels of MRP8/14 hetero-dimer assayed in the same urines: while there is no real difference between the concentrations of the HC and OND urines, higher concentrations are observed in certain MS urines, perhaps corresponding to a subpopulation of MS patients characterized by an activity of the disease. MRRP8/14 assayed in the urines is a marker for the activity of the MS disease characterized by an inflammation peak).

Figure 7:
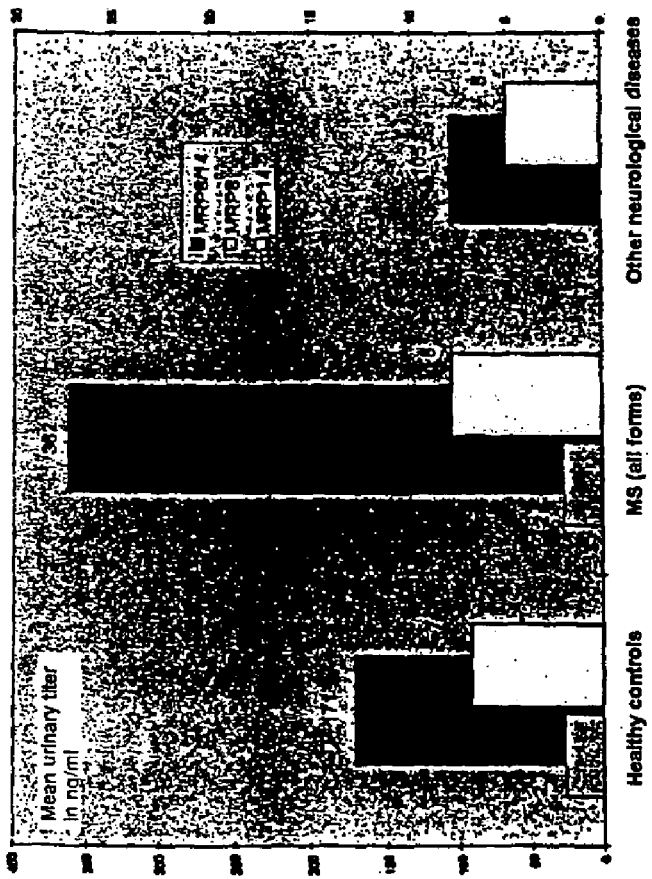
FIG. 7 represents the mean concentrations of the MRP8, MRP14 and MRP8/14 proteins (ng/ml—on the y-axis) in the urine of patients suffering from multiple sclerosis (MS), in the urine of patients suffering from other neurological diseases (OND) and in the urine of controls considered healthy (HC). n means the number of urine samples tested per category.

The recapitulative FIG. 7 confirms that there is no significant difference in MRP8 and MRP14 concentration between the HC, OND and MS urines, while a small difference in MRP8/14 concentration is observed between these urines, this concentration being higher on average in the MS urines and being a marker for the activity of the disease (inflammation peak).

Example 14

ELISA Protocols Used for the Assay of the GM2AP and Saposin B Proteins

The GM2AP or Saposin B proteins were assayed in human urines using anti-GM2AP or anti-Saposin B? polyclonal antibodies according to the Elisa protocol described by Gardas et al. (Glycoconjugate Journal 1, 37–42, 1984). The principal stages are briefly described below:

At each stage, the wells of a 96-well microplate are filled with 200 µl of the designated solution. The wells are first "coated" with a solution of GM2AP (prokaryotic recombinant protein) diluted to 50 ng/ml in a carbonate-bicarbonate buffer, pH 9.6. After incubating overnight at 4° C., the solution is removed and the wells are washed four times with PBS buffer pH 7.4 containing 0.05% Tween-20 (PBS-Tween). The microplates thus coated are stored at 4° C. for about 2 weeks.

The urine samples at three different dilutions (20×, 40× and 80× or other appropriate dilutions) are incubated with an appropriate dilution of the anti-GM2AP or anti-Saposin B rabbit polyclonal antibody overnight at 4° C. A standard series of dilutions of a recombinant protein ranging from 2.0 to 62.5 ng/ml is used to prepare the calibration series and are treated in the same manner. All the dilutions are made in PBS-Tween buffer containing 1 mg/ml of ovalbumin. Thus, 0.2 ml of each incubated solution is added to "coated" wells in duplicate and the plates are left for 2 hours at room temperature. The wells are then washed four times in PBS-Tween and again filled with a solution of anti-rabbit IgG goat antibodies coupled to peroxidase and diluted about 1 200-fold. After incubating for 2 hours at room temperature, the wells are washed four times in PBS-Tween and again filled with the staining reagent. The staining reagent consists of 100 mg of 2,2'-azino-di-(3-ethylbenzothiazoline) sulfonic acid and 10 µl of 30% hydrogen peroxide for one hour at room temperature and the degree of staining of each microwell is estimated by reading the absorbance at 405 nm.

A standard curve is constructed by placing on the x-axis the concentration of GM2AP in the calibration series or of Saposin B with a logarithmic scale and on the y-axis the percentage absorbance with a linear scale. The percentage absorbance of the sample is the absorbance ratio between the urine sample and the control which contains only the antiserum, without the soluble antigen.

A solution of recombinant protein GM2AP produced in a prokaryotic system, and having a concentration of 3 mg/ml, is diluted in 50 mM carbonate buffer, pH 9.6, and 50 µl are added to each well of a 96-well microplate, that is 50 µl per well of a solution at 0.5 µg/ml. The plates thus prepared are incubated overnight at room temperature. The anti-GM2AP polyclonal antibody produced in the laboratory (rabbit 79) was purified and diluted in PBS-0.05% Tween buffer in the presence of 10% horse serum. This solution is diluted 1/8 000. The solution is used to produce a calibration series with 8 series points covering concentrations from 0 to 500 ng/ml. A preincubation is carried out overnight at room temperature between 100 µl of antibody and 100 µl of urine sample to be assayed or of recombinant GM2AP or Saposin B protein solution serving for the calibration series. After washing the microplate in PBS-Tween, 50 µl of the incubation mixture are added per well, and then incubated for two hours at room temperature. The microplate is again washed in PBS-Tween, and then 50 µl of anti-rabbit IgG antibody coupled to peroxidase and diluted 1/5 000 are added to each microwell of the plate and incubated for two hours at room temperature. After further washings of the microplate, 100 µl of OPD are added to each well and incubated for 20 minutes at room temperature. The staining of each well, proportional to the concentration of GM2AP or of Saposin B recognized by the specific antibody used, is estimated by reading the absorbance.

A solution of recombinant protein GM2AP or Saposin B produced in a prokaryotic system, with a concentration of 3 mg/ml, is diluted in 50 mM carbonate buffer, pH 9.6, and 50 µl are added to each well of a 96-well microplate, that is 50 µl per well of a solution at 1.5 µg/ml. The plates thus prepared are incubated overnight at room temperature. The purified anti-GM2AP peptides polyclonal antibodies produced in the laboratory (rabbit 190 and rabbit 191) are used alone or as a mixture, diluted 1/1 000 for each, in PBS-0.05% Tween buffer in the presence of 10% horse serum. The calibration series is produced using the prokaryotic recombinant protein GM2AP or Saposin B diluted so as to cover the concentration range 0 to 1 500 ng/ml with 8 points. 100 µl of antibody (one antibody or the two together) are preincubated in the presence of 100 µl of urine sample to be tested or of recombinant GM2AP or Saposin B solution, overnight at room temperature. After washing the microplate in PBS-Tween, 50 µl of the incubation mixture are added per well and then incubated for two hours at room temperature. The microplate is again washed in PBS-Tween, and then 50 µl of anti-rabbit IgG antibody coupled to peroxidase, diluted 1/5 000, are added to each microwell of the plate and incubated for two hours at room temperature. After washing the microplate, 100 µl of OPD are added to each well and incubated for 20 minutes at room temperature. The staining of each well, proportional to the concentration of GM2AP or Saposin B recognized by the specific antibody used, is estimated by reading the absorbance.

Example 15

Assay of the GM2AP Proteins in the Urines

The GM2AP protein was assayed in the urines of 22 patients suffering from multiple sclerosis (MS), 5 patients suffering from other neurological diseases (OND) and 9 individuals chosen from the active population and taken during a medical visit (healthy), according to the Elisa protocol described below, using anti-GM2AP polyclonal antibodies. The MS patients selected for this study are confirmed patients, that is to say with various stages and profiles of the disease, and different treatments, and the like.

Figure 8:
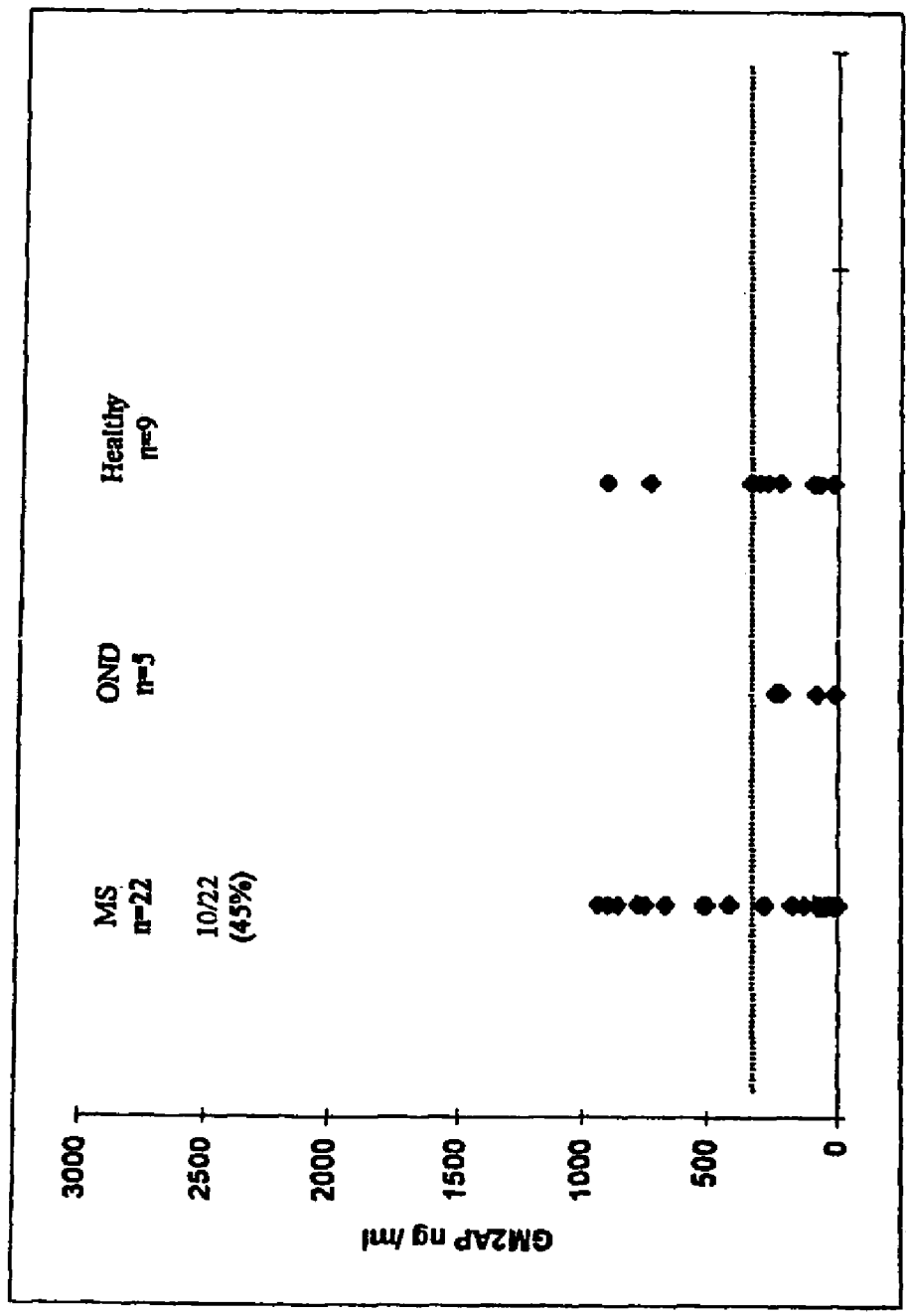
FIG. 8 represents the assay of the GM2AP protein (ng/ml—on the y-axis) in the urine of patients suffering from multiple sclerosis (MS), in the urine of patients suffering from other neurological diseases (OND) and in the urine of controls considered healthy (HC). n means the number of urine samples tested per category. MS means multiple sclerosis, OND means other neurological diseases and Healthy means samples from controls supposed healthy (HC).

The results of the assay are presented in FIG. 8. Whereas only 0/5 OND urines and 2/9 so-called "Healthy" urines have a GM2AP concentration greater than 200 ng/ml, 10/22 (that is 45%) have a concentration greater than 200 ng/ml.

These results indicate that while the GM2AP protein is present in a very low concentration (<400 ng/ml) in the urines of individuals from the active population, it is present in higher concentration in the urines of MS patients. However, 12 MS urines also exhibit low levels of GM2AP. Among these 12 patients, 10 are under treatment. The high urinary concentrations of GM2AP appear to be a marker for the MS pathology, and more precisely a marker for one stage or one form of the disease, for the activity of the disease, and is certainly influenced by any ongoing treatment. It should be noted that two individuals in the active population have high GM2AP concentrations (these two cases were voluntarily included in the study, because they both exhibited a gliotoxic activity in their urines unlike the other individuals of this same category). It is impossible to know if they are healthy individuals, or individuals suffering from a pathological condition, or individuals suffering from multiple sclerosis because the samples from the so-called "Healthy" individuals were collected anonymously, with no knowledge of their clinical file.

Higher urinary concentrations of GM2AP are detected in the urines of MS patients; a high concentration of GM2AP can then be a marker for the MS pathology, and more precisely for one form of the disease, for one stage of the disease, or for a period of activity, and may be influenced by any ongoing treatment. These high urinary concentrations of GM2AP may also have a predictive value for the onset of a worsening of the disease, or for a benign MS at the onset of a progression, and the like.

The absolute values of the GM2AP concentrations detected in the urines are dependent on the affinity and the specificity of the antibody used, but in general, the tendency between the three groups of individuals is preserved regardless of the antibody used.

Example 16

Assay of the Saposin B Proteins in the Urines

The Saposin B protein was detected in the same urine samples as those used to study the detection of GM2AP. The assays were carried out in parallel with those of GM2AP, in the same study, according to the Elisa protocol described below, using anti-Saposin B polyclonal antibodies.

Figure 9:
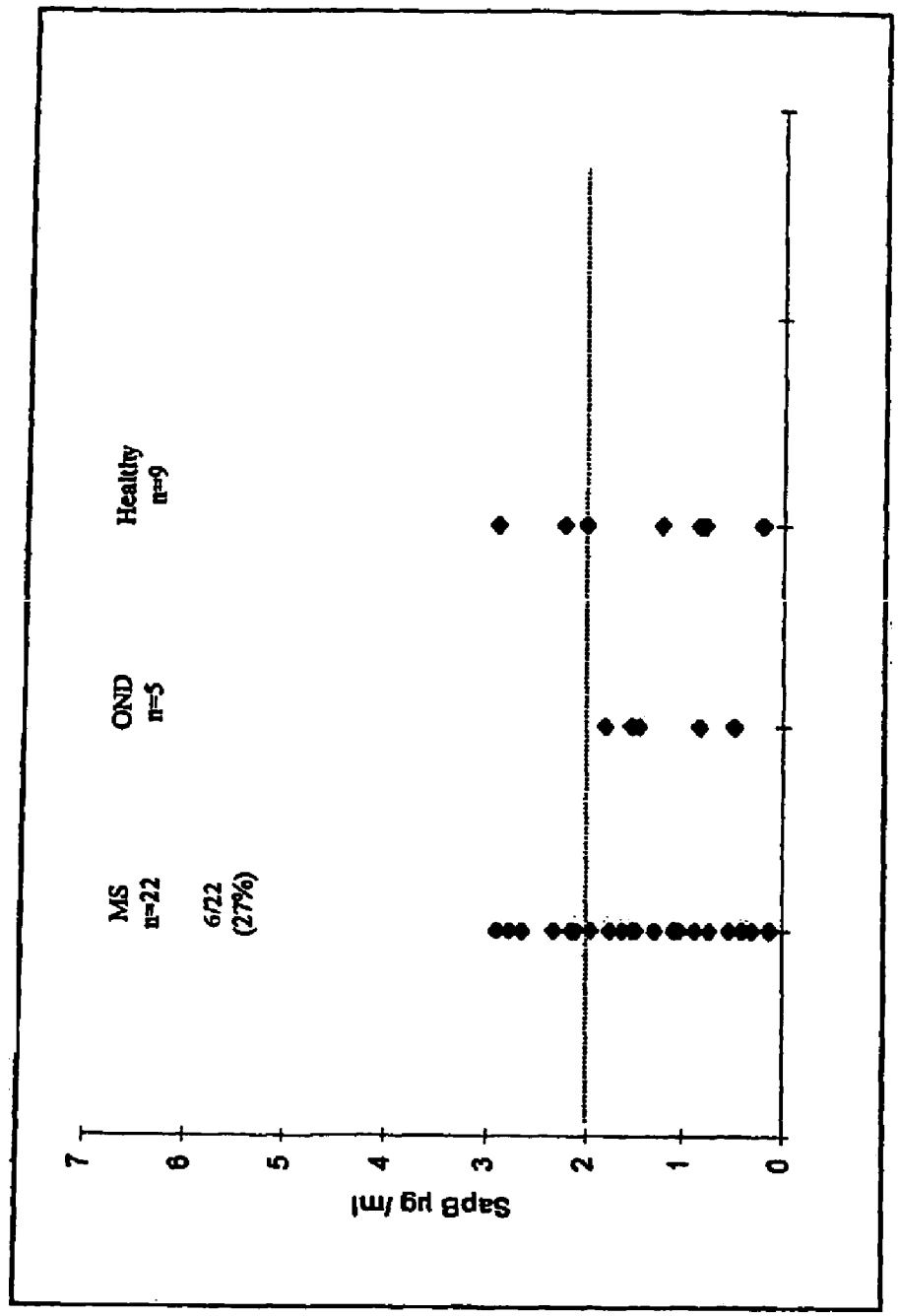
FIG. 9 represents the assay of the Saposin B protein (µg/ml—on the y-axis) in the urine of patients suffering from multiple sclerosis (MS), in the urine of patients suffering from other neurological diseases (OND) and in the urine of controls considered healthy (HC). n means the number of urine samples tested per category. MS means multiple sclerosis, OND means other neurological diseases and Healthy means samples from controls supposed healthy (HC).

The results of the Saposin B assay are presented in FIG. 9. 0/5 OND urines and 2/9 Healthy urines have a Saposin B concentration greater than 2 µg/ml, while 6/22 (that is 27%) exhibit a concentration greater than 2 µg/ml.

These results indicate that the Saposin B protein is present in each urine (so-called healthy population or so-called sick population) at significant concentrations, that is to say <2 µg/ml. These assay results are compatible with those described in the literature. However, even if Saposin B is present in each urine, it appears to be present in a higher concentration in certain MS urines. This increase in Saposin B concentration in the MS urines is perhaps masked by the basal concentration of this protein in the ordinary state. Thus, the high urinary concentrations of Saposin B appear to be a marker for the MS pathology, and more precisely a marker for one stage or one form of the disease, or for the activity of the disease, and is certainly influenced by any ongoing treatment. The Saposin B assayed alone appears, however, to be a marker which discriminates for one form or for one activity of the disease slightly less than GM2AP. It should again be noted that two individuals from the active population have high Saposin B concentrations and they are the same individuals who also had a high GM2AP concentration in their urine.

In conclusion, higher urinary concentrations of Saposin B are detected in the urines of MS patients; a high Saposin B concentration can therefore be a marker for the MS pathology, and more precisely for one form of the disease, for one stage of the disease, or for a period of activity, and may be influenced by any ongoing treatment. These high urinary GM2AP concentrations may also have a predictive value for an onset of a worsening of the disease, or for a benign MS at the beginning of a progression, and the like. However, in general, the high Saposin B concentrations alone appear to be markers which are less discriminatory than high GM2AP concentrations alone.

The absolute values of the Saposin B concentrations detected in the urines are dependent on the affinity and specificity of the antibody used, but in general, the tendency between the three groups of individuals is preserved regardless of the antibody used.

Example 17

Coassay of the GM2AP and Saposin B Proteins in the Urines

Figure 10:
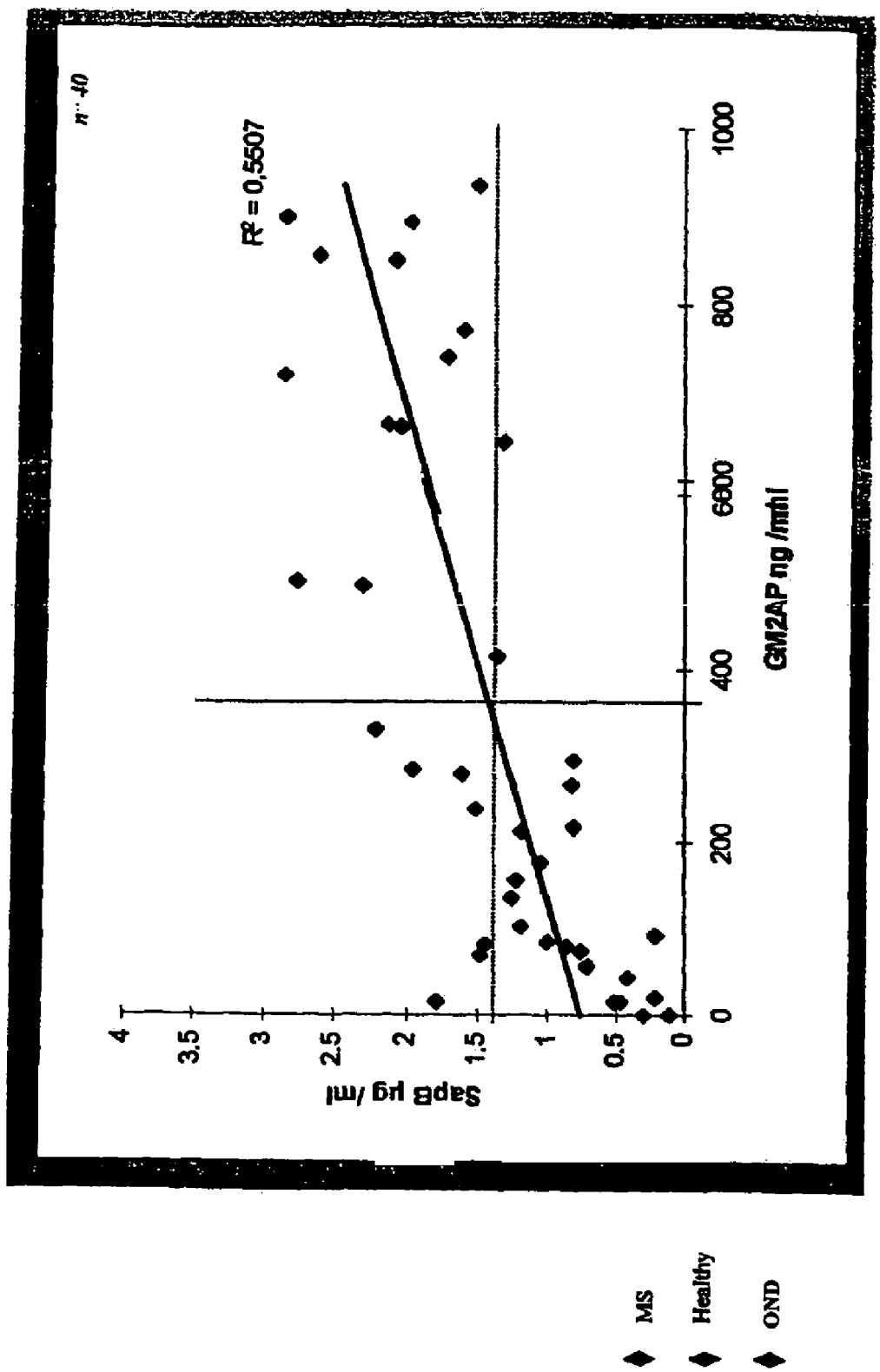
FIG. 10 represents the codetection of the Saposin B (µg/ml—on the y-axis) and GM2AP (ng/ml—on the x-axis) proteins in urine samples from MS patients, controls supposed healthy and patients suffering from other neurological diseases and the correlation observed between the levels of the two proteins.

FIG. 10 presents the GM2AP concentrations assayed in the urine samples described in FIG. 5 relative to the Saposin B concentration assayed in these same samples and described in FIG. 6. The MS samples (dark diamonds) and the OND and "Healthy" samples (white diamonds) are presented on this graph.

On this graph, it appears clearly that:

the higher the GM2AP concentration in the urines, the higher the Saposin B concentration. (We have shown that it is not a general case with other proteins and that it does not indicate a renal disturbance, with the assay of creatinine in parallel for each of the samples tested);

the high GM2AP and Saposin B concentrations are characteristic of the MS samples (with the exception of two urines from the active population, mentioned above). These joint high GM2AP and Saposin B concentrations are markers for the MS pathology, more precisely for a window of the disease (quadran on the right and at the top of the graph).

In conclusion, this analysis confirms that high urinary concentrations of GM2AP (>400 ng/ml) and of Saposin B (>2 µg/ml) are codetected in the urines of MS patients and may represent markers for the MS pathology, more precisely for one form of the disease, for one stage of the disease, or for a period of activity, and may be influenced by any ongoing treatment. It is advantageous to assay the two proteins in parallel in each sample, and to consider the two concentrations.

Figure 11:
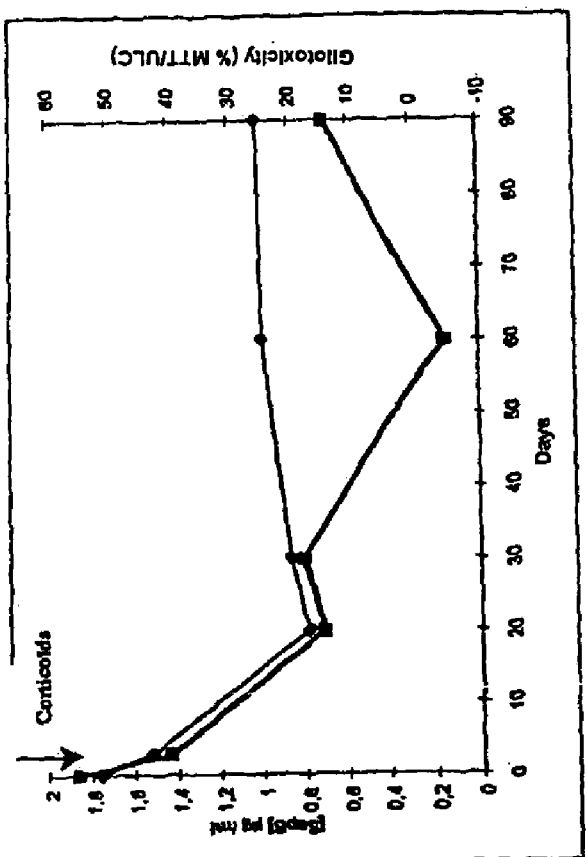
FIG. 11 represents.
Figure 11:
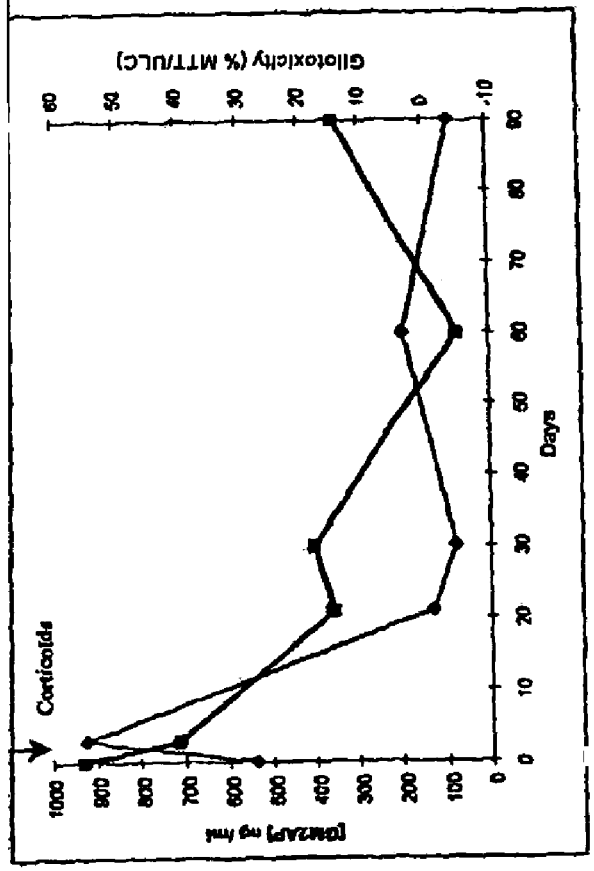
Figure 12:
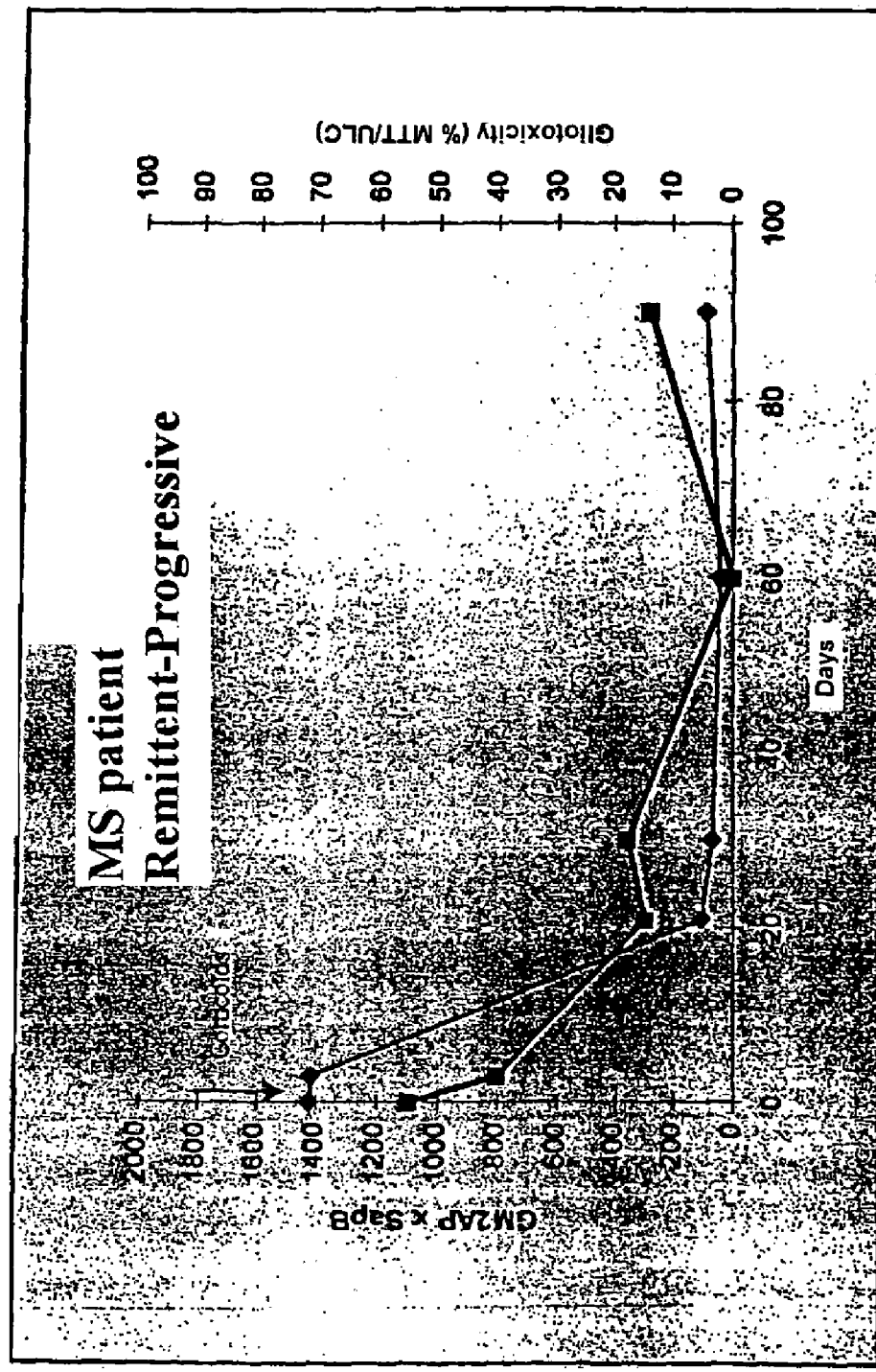
FIG. 12 represents the product of the concentrations of the GM2AP and saposin B proteins in ng×µg/ml² in the urine of an MS patient in progressive remittent form (light-colored curve) and the gliotoxicity as a percentage of dead cells estimated by the MTT test (dark-colored curve).

Assay of GM2AP and Saposin B in the Urine of Two Patients in the Form of Kinetics MS Patient No. 1—Progressive Remittent Form Urines of this patient were collected during the progression of his disease. The patient was hospitalized on D0 for an attack. He was subjected on D1 to a flash of corticoids and was then monitored over time from a clinical point of view (the flash provided clinical improvement). FIG. 11 shows the profile for the assay of GM2AP and of Saposin B in these urines during the progression, and FIG. 12 shows the profile of the product of the two GM2AP and Saposin B concentrations, indicating a codetection of high concentrations. The high GM2AP and Saposin B concentrations at the time of the attack and hospitalization decrease gradually over time after the flash of corticoids up to 90 days.

MS Patient No. 2—Progressive Form

Figure 13:
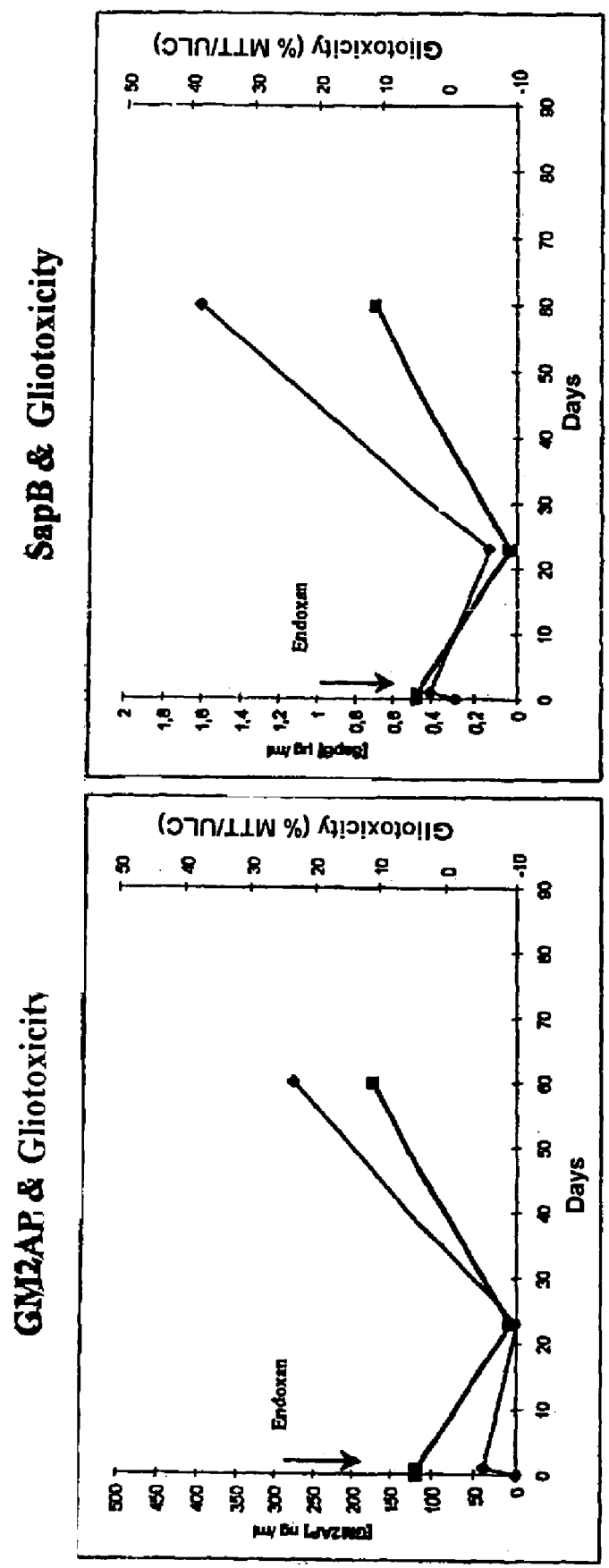
FIG. 13 represents.
Figure 14:
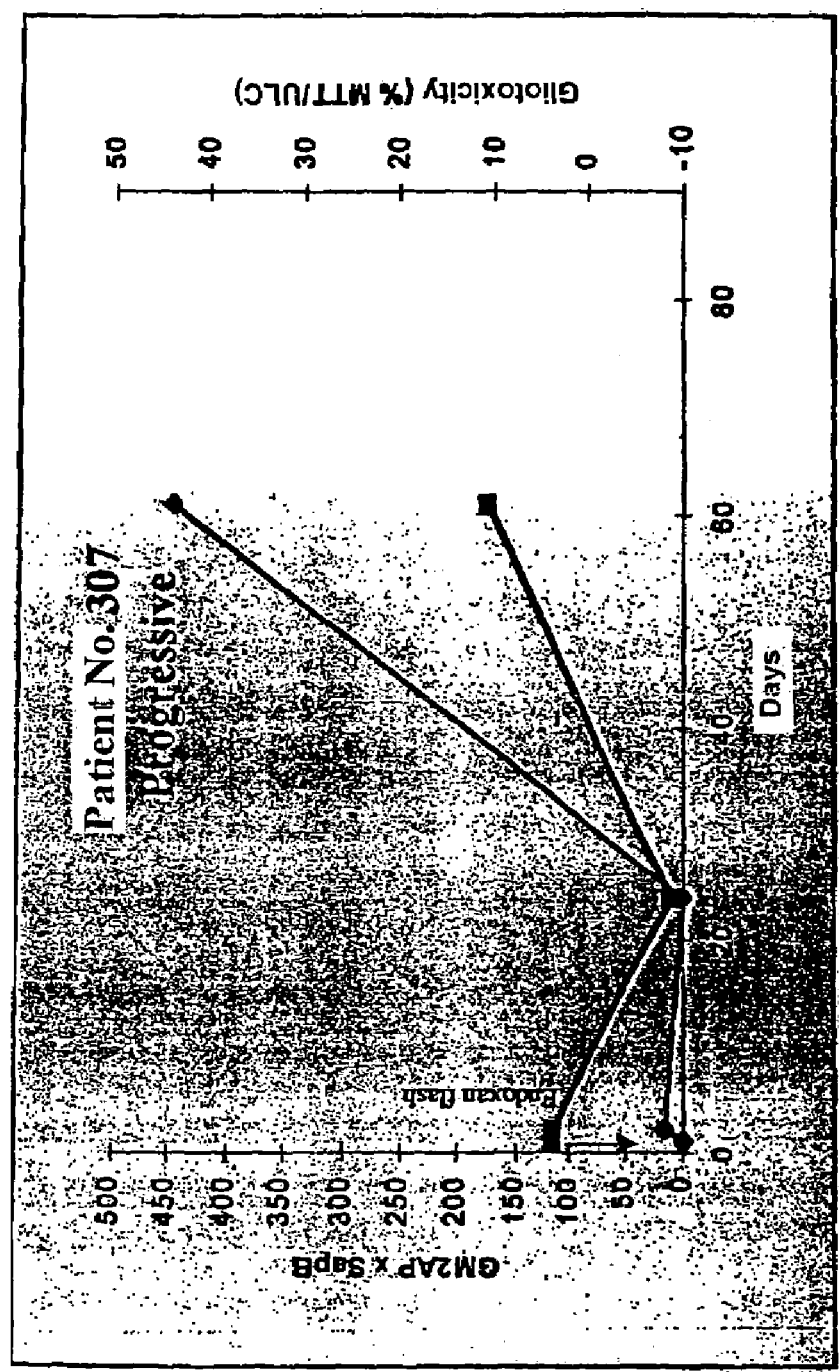
FIG. 14 represents the product of the concentrations of the GM2AP and saposin B proteins in ng×µg/ml² in the urine of an MS patient in progressive form (light-colored curve) and the gliotoxicity as a percentage of dead cells estimated by the MTT test (dark-colored curve).

Urines of this patient were collected during the progression of his disease. The patient was hospitalized on D0 for an attack. He was subjected on D1 to a flash of Endoxan and was then monitored over time from a clinical point of view (the flash provided clinical improvement and at D60, signs of a worsening of the disease were observed). FIG. 13 shows the profile for the assay of GM2AP and of Saposin B in these urines during the progression, and FIG. 14 shows the profile of the product of the two GM2AP and Saposin B concentrations, indicating a codetection of high concentrations. The high GM2AP and Saposin B concentrations at the time of the attack and hospitalization decrease gradually over time after the flash of Endoxan (also called cyclophosphamide) up to 23 days and appear to increase, becoming high at D60, thus showing a perfect correlation with the progression of the clinical signs.

These results confirm that:

high concentrations of GM2AP and Saposin B in the urines are markers for the MS pathology, and in particular the codetection of high concentrations of the two proteins together (indicated by the product of the two concentrations);

the high concentrations of GM2AP and Saposin B in the urines are markers for the activity of the disease (here during the attack) or are markers influenced by the immunosuppressive treatments such as corticoids and Endoxan which lower the concentrations.

This example illustrates the fact that these markers can be used, inter alia:

to carry out a therapeutic monitoring of a patient and evaluate the therapeutic benefits of a treatment for a given patient; or to predict a worsening of the disease, predict an activity peak, and the like to decide on an anticipated therapeutic resumption based on the clinical signs Example 18

Correlation Between the Detection of the MRP14, GM2AP and Saposin B Proteins in the Urines and the Gliotoxicity Measured in these Urines To verify a correlation between the presence of these proteins alone or in combination in the urines and the gliotoxicity of the urines, the concentrations of a protein of interest and the gliotoxicity of a sample of urines from patients suffering from multiple sclerosis (MS), from patients suffering from other neurological diseases (OND) and from individuals taken from the active population termed "Healthy" were assayed in parallel. Among the MS patients, patients are noted with various forms and stages of the disease, under treatment or otherwise, at various activities of the disease.

The MRP, GM2AP and Saposin B proteins were assayed in human urines according to the Elisa protocols described above. The assays analyzed in this example are those described in the preceding examples. Each urine sample analyzed in Elisa was analyzed by the MTT test to measure the gliotoxicity of each sample. The gliotoxicity is expressed as a percentage of dead cells (estimated by colorimetry using tetrazolium salts) of a murine astrocyte cell line (CLTT1.1) after 48 hours of incubation in the presence of centrifuged urine.

Figure 15:
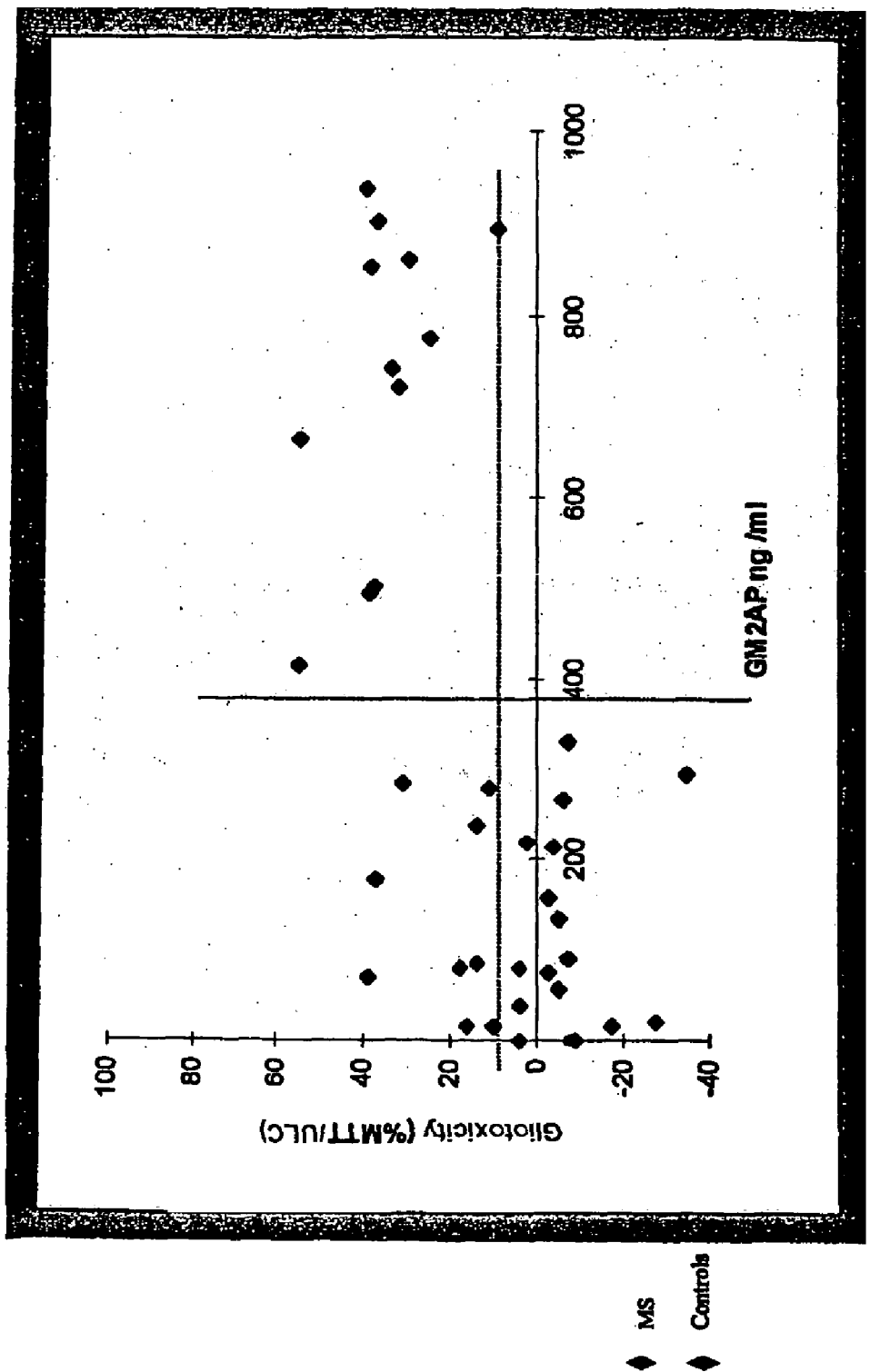
FIG. 15 represents the correlation between the concentrations of GM2AP in ng/ml α-axis) and gliotoxicity as a percentage of dead cells estimated by the MTT test (y-axis) determined in the urine of MS patients and of controls.

FIG. 15 represents the GM2AP concentration as a function of the gliotoxicity of the urines determined by the MTT test.

22 MS urines (gray diamonds), 5 OND urines (black diamonds) and 9 so-called "Healthy" urines (black diamonds) were presented on the graph. They are the same urines which were studied in examples 15 and 16. It is observed that all the control urines (OND and Healthy) have low levels of GM2AP (<400 ng/ml) and a low gliotoxicity (<15%), with the exception of a Healthy control urine (already commented upon in example 15) for which a high GM2AP concentration and gliotoxicity are observed.

The MS urines are divided into three subpopulations:

urines with low GM2AP concentration (<400 ng/ml) and low gliotoxicity (<15%), urines with low GM2AP concentration (<400 ng/ml) and gliotoxicity (>15%), that is essentially 3 urines, urines at high GM2AP concentration (>400 ng/ml) and high gliotoxicity (>15%).

These three subpopulations perhaps indicate MS subpopulations, that is to say different forms or stages of the disease, different activities of the disease, different therapeutic benefits, and the like.

However, it can be noted that all the urines having a high GM2AP concentration also have a high gliotoxicity.

In conclusion, a correlation is observed between high urinary GM2AP concentration and gliotoxicity (all the urines with a high GM2AP concentration are gliotoxic (10/10), and all the urines with a low GM2AP concentration are not gliotoxic (<15%), with the exception of 3 urines/12 MS). This indicates the involvement of the GM2AP protein in the mechanism of gliotoxicity, alone or in combination, in its natural or modified form, but which is recognizable by an anti-GM2AP antibody. Furthermore, the codetection of a high GM2AP concentration in the urines and of a high gliotoxicity correlates with one subpopulation of patients suffering from MS.

Figure 16:
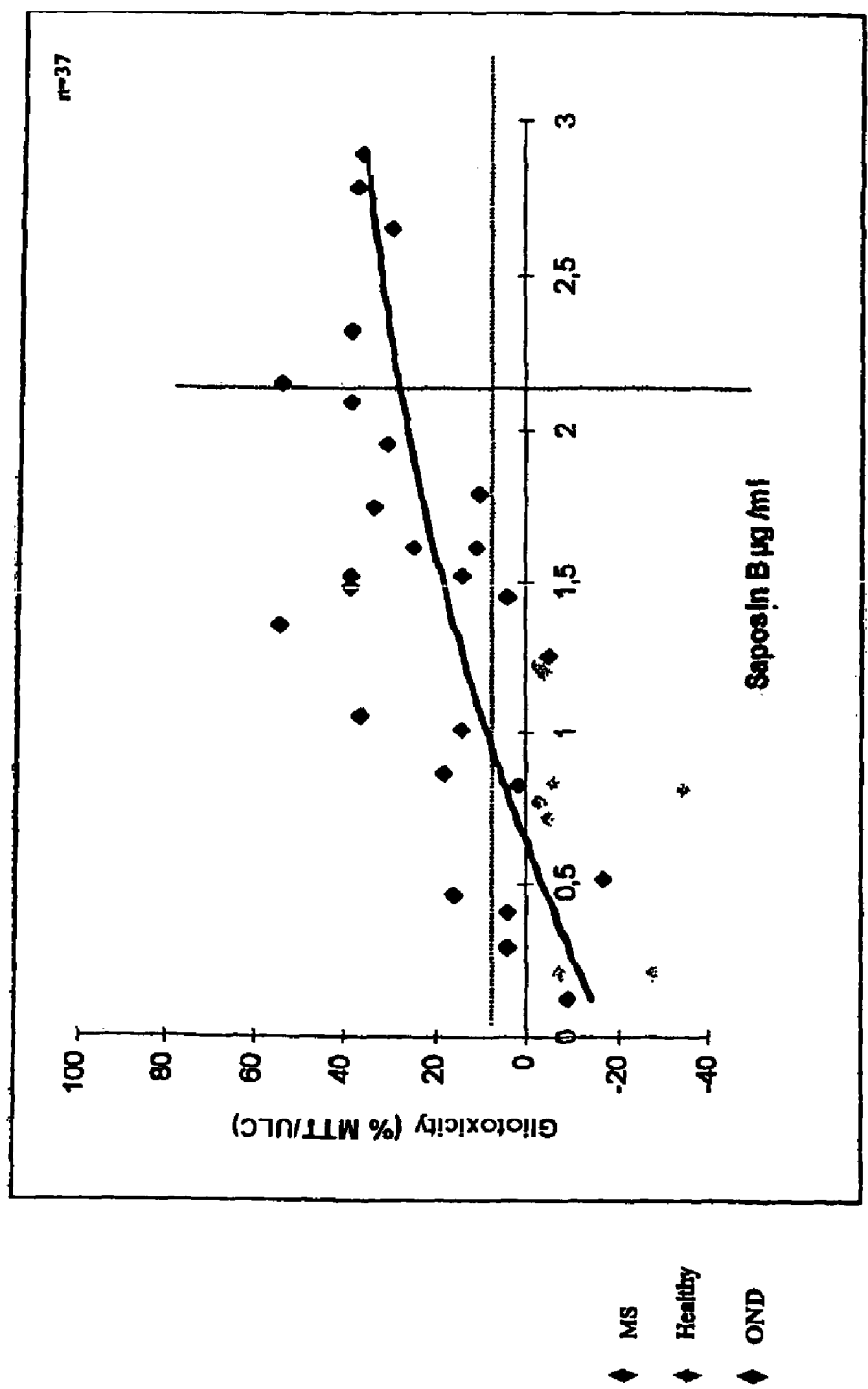
FIG. 16 represents the correlation between the concentrations of Saposin B in µg/ml (x-axis) and gliotoxicity as a percentage of dead cells estimated by the MTT test (y-axis) determined in the urine of MS patients and of controls.

FIG. 16 represents the Saposin B concentration as a function of the gliotoxicity of the urines determined by the MTT test.

22 MS urines (gray diamonds), 5 OND urines (black diamonds) and 9 so-called "Healthy" urines (light gray diamonds) were presented on the graph. They are the same urines which were studied in examples 15 and 16. It is observed that the richer the urines are in Saposin B, the more gliotoxic they are. There is a fairly clear correlation between the Saposin B concentration and the gliotoxicity of the urines.

In conclusion: a correlation is observed between high urinary Saposin B concentration and gliotoxicity. This indicates involvement of the Saposin B protein in the mechanism of gliotoxicity, alone or in combination, in its natural or modified form, but which is recognizable by the anti-Saposin B antibody used for the assay.

Figure 17:
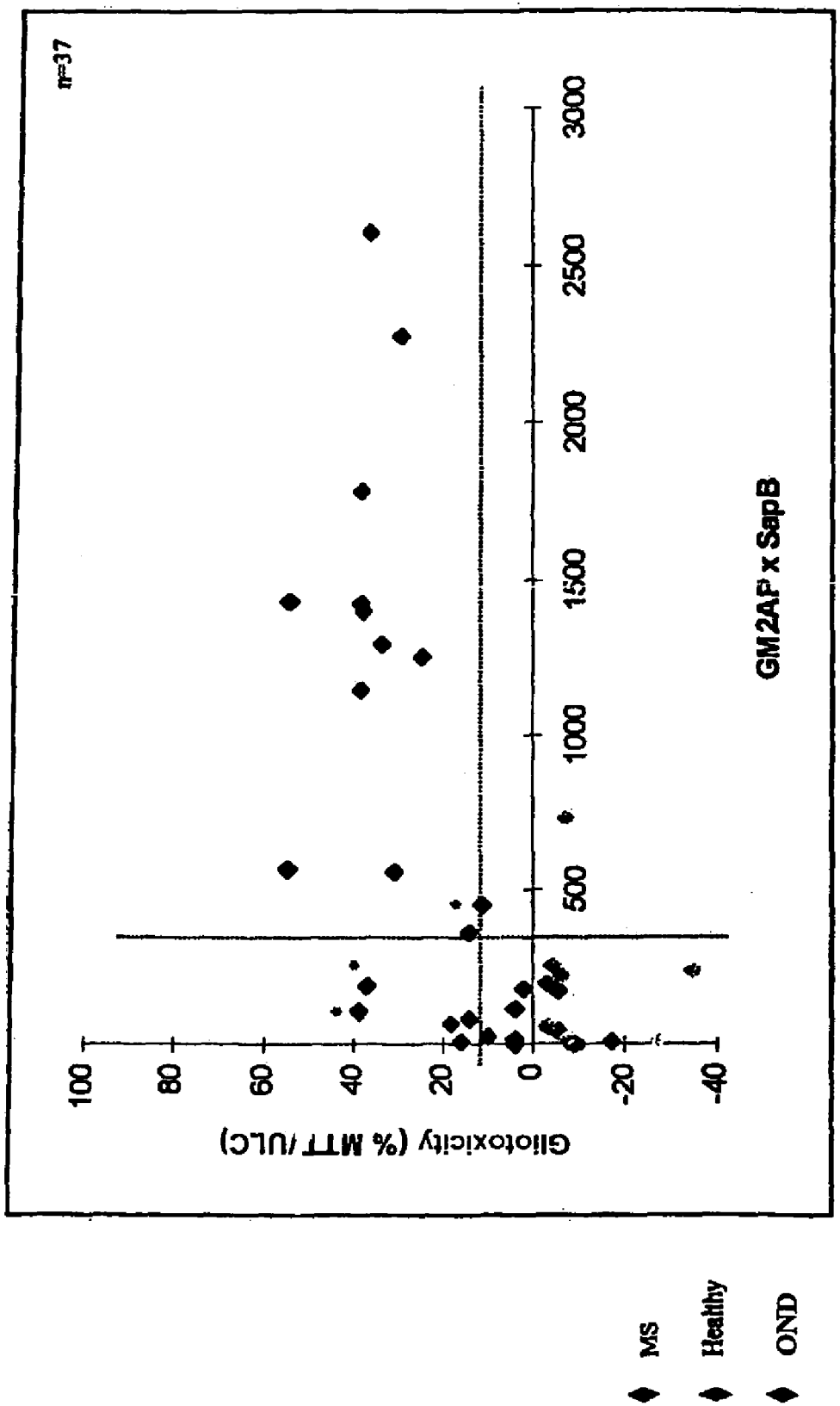
FIG. 17 represents the correlation between the product of the concentrations of GM2AP and Saposin B in ng×µg/ml² (x-axis) and gliotoxicity as a percentage of dead cells estimated by the MTT test (y-axis) determined in the urine of MS patients and of controls.

FIG. 17 represents the product of the GM2AP and Saposin B concentrations as a function of the gliotoxicity of the urines determined by the MTT test.

The 22 MS urines (gray diamonds), 5 OND urines (black diamonds) and 9 so-called "Healthy" urines (light gray diamonds) of examples 15 and 16 were presented in FIG. 17. The gliotoxicity of these urines is analyzed according to the product of the GM2AP and Saposin B concentrations, that is to say according to the codetection of the two proteins in the urines. A correlation is very clearly observed between the product of the two GM2AP and Saposin B concentrations and the gliotoxicity which is much higher than on considering only one protein. It is observed that 5/5 of the OND urines have a low product of GM2AP and Saposin B concentration and a low gliotoxicity; 8/9 "Healthy" urines have a low product of GM2AP and Saposin B concentration and/or a low gliotoxicity. On the other hand, essentially three subpopulations of MS urines are distinguished:

urines at low GM2AP.Saposin B concentration and low gliotoxicity (<15%), urines at high GM2AP.Saposin B concentration and high gliotoxicity (>15%).

Figure 18:
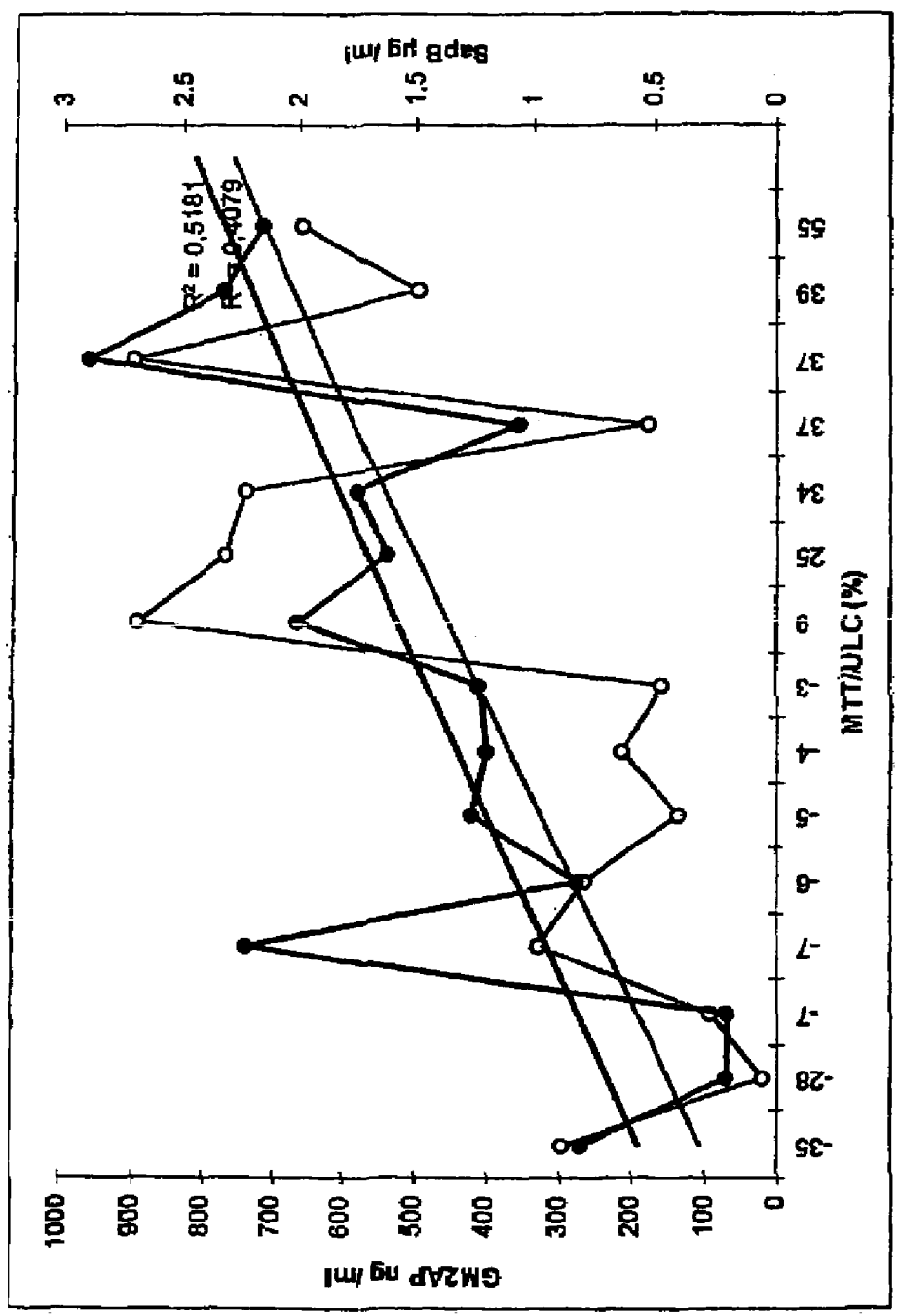
FIG. 18 represents the correlation between the concentrations of GM2AP (ng/ml—on the left-hand y-axis), the concentrations of Saposin B (µg/ml—right-hand y-axis) and the gliotoxicity as a percentage of dead cells estimated by the MTT test (x-axis). Two estimated correlation straight lines are represented on the graph. The lines in bold relate to the concentrations of saposin B; the lines in light black relate to the concentrations of GM2AP.

These two subpopulations perhaps indicate MS subpopulations, that is to say different forms or stages of the disease, different activities of the disease, different therapeutic benefits and the like. However, it is very important to note that all the urines having a high GM2AP and Saposin B concentration, that is to say having simultaneously a high GM2AP and Saposin B concentration, also have a high gliotoxicity. The two subpopulations of MS patients are all the more marked and clear when the three markers are considered together: gliotoxicity, high GM2AP concentration and high Saposin B concentration. This is confirmed in FIG. 18.

In conclusion: a correlation is observed between high urinary GM2AP and Saposin B concentration and gliotoxicity. All the urines with a high GM2AP and Saposin B concentration are gliotoxic, and all the urines with a low GM2AP and Saposin B concentration are not gliotoxic (<15%), with the exception of 2 urines/22 MS. This indicates the involvement of the two proteins GM2AP and Saposin together or in combination in the mechanism of gliotoxicity, in their natural or modified form, but which is recognizable by the anti-GM2AP and anti-Saposin B antibodies used for the assay. Furthermore, the codetection of a high urinary GM2AP and Saposin B concentration and of a high gliotoxicity correlates with a subpopulation of patients suffering from MS (stage, form, activity, treatment of the disease?), compared with another subpopulation. These three markers considered together make it possible to discriminate between two subpopulations of MS patients.

Variation of the gliotoxicity and of the GM2AP and Saposin B concentrations as a function of the progression of the disease in two patients after and during treatment The correlation between gliotoxicity, high GM2AP and Saposin concentration in the urines and MS pathology was also confirmed by measuring these three parameters in the urine of two patients during the progression of their disease.

Patient No. 1: MS remittent-progressive form, hospitalized on D0 for an attack and who had received a flash of corticoid on D1. After the flash, he showed a clinical improvement up to D90—(cf. FIGS. 11, 12), Patient No. 2: MS progressive form, hospitalized on D0 for an attack and having received a flash of Endoxan (also called cyclophosphamide) on D1. On D60, he shows new clinical signs of a worsening of his disease—(cf. FIGS. 13, 14).

The following were shown for the two patients:

a correlation between the urinary gliotoxicity and the clinical progression of the disease (when the clinical signs are severe, the gliotoxicity is high; when the clinical signs decrease following the treatment, the gliotoxicity decreases and becomes stationary; when the signs of a worsening appear after the treatment, the gliotoxicity appears to increase again), a correlation between the gliotoxicity level in the urines of patients and the GM2AP and Saposin B concentrations, and a correlation between the high GM2AP and Saposin B concentrations and the clinical progression of the disease.

In conclusion: the assay of the GM2AP and Saposin B proteins in the urines is a good discriminatory marker for a subpopulation of MS (stage, form, activity, treatment of the disease). The GM2AP and/or Saposin B proteins are involved in the mechanism of gliotoxicity, alone or in combination, in their natural form or in a form which is recognizable by the polyclonal antibodies used for their assay. As the GM2AP and Saposin B proteins are codetected in high concentration in the gliotoxic urines, it is possible that these two proteins act in combination to induce the gliotoxicity.

Example 19

Immunohistochemical Analysis of the Expression of the GM2A, SAPB, MRP14 and MRP8 Proteins in a Culture System Producing Gliotoxin In Vitro (Monocyte Cultures), and in Normal and Pathological Cerebral Tissue for MS and for Controls Protocol: Cultures of monocytes from a patient suffering from MS and from a healthy control were carried out in parallel, according to the present protocol described briefly. Starting with peripheral blood from these two volunteers collected over ACD, the PBMC (Peripheral Blood Mononuclear Cells) are isolated on Ficoll using the technique known to persons skilled in the art. The cells recovered (at the level of the ring) are washed twice in RPMI medium. The cells are then counted on Kovas slide and are inoculated in a primary bottle of 25 cm$^2$ or on Labteck slide (8 wells) (in permanox) in RPMI medium supplemented with 15% human AB serum on D0. The cells are cultured on "Labtek" type chamber slides in order to obtain a direct support for the analysis of the monocytes which adhere to the support and subsequently differentiate into macrophages. For the slides, $2 \times 10^6$ cells are then inoculated in an amount of $0.25 \times 10^6$ cells/well. For the bottles, $4 \times 10^6$ cells are inoculated in an amount of $0.25 \times 10^6$ cells/well. On D1, the cells in suspension are recovered and the Labteck wells or the bottles are washed twice with RPMI (previously heated to 37° C.) before adding RPMI medium supplemented with 5% human AB serum. On D1, D3, D6, D9, D12 or 14, D15, the culture medium is changed; the supernatants are collected and the cells bound to the slides using the techniques known to persons skilled in the art. At each change of medium, at least two slides were fixed in paraformaldehyde and stored for the immunohistochemical analysis.

Composition of the medium: RPMI (500 ml) with 15 ml of 200 mM glutamate, 5 ml 100 µM sodium pyruvate, 5 ml of nonessential amino acids (100×), antibiotics penicillin and streptomycin 100 000 U/µl and anti-human interferon antibodies at 100 U/µl.

Results: Four cultures of monocytes in vitro were thus studied in the form of kinetics: two cultures of monocytes derived from blood from control individuals and two cultures of monocytes derived from MS patients. At various culture times (D0, D1, D3, D6, D9, D12, was), the corresponding supernatants were also recovered. Once the kinetics was completed, the slides corresponding to the different days of culture were incubated in the presence of anti-GM2A, SAP-B, MRP-8 and MRP14 polyclonal antibodies. The gliotoxicity of each supernatant thus recovered was estimated by the MTT test. The concentration of GM2AP, MRP14 and Saposin B protein was also determined in each supernatant by the Elisa protocol as described in examples 13 and 14.

The immunofluorescence results on fixed cells are summarized below; it is possible to note:

an absence of expression of MRP8 at all the stages of the 2 cultures a clear expression of MRP-14 in the period between D9 and D15, found in the two cultures, although higher in the MS culture. This expression appears to correlate with a macrophage differentiation stage.

a very low expression (low intensity and low number of cells) is observed at the beginning of the culture in the control culture and probably corresponds to the physiological presence of GM2A in the macrophage lysosomes.

In the MS culture, a much more marked expression of GM2A (greater intensity and larger number of cells) is observed, with a relatively homogeneous cytoplasmic labeling between D3 and D6, disappears on D9 and is again noted on D14–D15 with an intense labeling localized at the cytoplasmic periphery, defining the inner contour of the plasma membrane. These observations are not found in all the control slides.

Analysis with the anti-SAP-B antibody did not make it possible to obtain an interpretable immunohistochemical labeling.

In the MS monocyte cultures already carried out, 3/3 had a gliotoxicity peak at D9 and 2/3 a smaller peak at D6, no peak being detected in the cultures of monocytes of 2/2 non-MS controls analyzed in parallel. Likewise, the assay of the MRP14, GM2AP and Saposin B proteins in the supernatant of the cell cultures during the kinetics showed that the SapB and GM2AP proteins are detected by Elisa in the supernatants of the MS monocytes and not in those of the control monocytes, on days D6 and especially D9 of the culture; the proteins are not detected beyond this kinetic. It should be noted that the antibodies used for the assay can recognize the physiological forms of the proteins, but also the complexed and/or modified forms.

It is therefore observed that the period D6–D9 during which the highest gliotoxicity is observed in the supernatant is covered by the period D3–D15 during which a less differentiated production of the negative control for GM2A is observed in the cells with quantitative and qualitative fluctuations of its cellular expression (quantity of expression and cellular localization).

Example 20

Immunohistological Technique on Brain Sections in Paraffin

The histological sections prepared in paraffin are made paraffin free in xylene and alcohol before undergoing a pretreatment intended to unmask the antigens; this pretreatment may correspond to (i) twice 5 minutes under microwave (750W) in the presence of a sodium citrate, citric acid buffer, (ii) a treatment with acid by incubating for 15 minutes in a 1% periodic acid solution or by incubating for 5 minutes in a 99% formic acid solution. The endogenous peroxidases are then blocked by incubating the slides for 30 minutes in 1% hydrogen peroxide, followed by extensive washing in water for 15 minutes. The background noise is blocked by incubating the slides for 30 minutes in the presence of PBS-0.03% Triton, 10% Donkey serum (for the polyclonal antibodies) or 10% Goat serum (for the monoclonal antibodies). Labeling with the primary antibody is carried out by applying 100 to 200 µl of primary antibody solution per slide (0.5 to 5 µg/ml according to the titer) in PBS-0.03% Triton and then incubating for 2 hours at room temperature. The slides are then rinsed 3 times in PBS-Triton for 10 minutes. Secondary antibody labeling is carried out using biotinylated antibodies capable of binding specifically to the primary antibodies, for example anti-rabbit IgG or anti-mouse IgG antibodies diluted in PBS-0.03% Triton. The slides are washed and incubated in a solution for 2 hours (2 µl streptavidin-biotin-peroxide complex, 1 600 µl PBS-0.03% Triton). The slides are again washed before being revealed, protected from light, in buffer A and then rinsed with water before microscope observation. Buffer A for 5 slides: 25 ml 0.05M Tris, pH 7.6, 2.5 ml 1M Imidazole, 15 ml sterile water, 2 ml DAB 5 mg/ml, 5 ml 10% ammonium nickel, 30 µl 1% $H_2O_2$.

The same antibodies were used for an immunohistochemical study, according to the technique briefly described below, on paraffined slides obtained by microtome section of brain collected post mortem from MS and from controls who had died from non-neurological pathologies.

The results of the analysis are summarized below:

There is no labeling of the "non-MS" and MS brains in the "normal" (non-lesioned) white substance and gray substance with the different anti-MRP8, MRP14 and GM2A antibodies. A nonspecific reactivity did not make it possible to interpret the results with the anti-saposin B antibody in this immunohistochemical application.

On the other hand, the following are noted in the plaque zones of MS brains:

an anti-MRP14 reactivity in the macrophage and microglial cells, having a relatively homogeneous distribution over the entire stretch of the demyelination zones (plaques), a lower (less frequent) anti-MRP8 reactivity essentially linked to perivascular lymphoid infiltrates a clear anti-GM2A reactivity in the macrophages and microgliocytes of the plaque zones, with a particular density in the zones constituting the "glial wall" at the peripheral limit of a plaque. Labeling of a few astrocytes was also observed in the demyelination zones.

These different observations show that there is a particular hyperexpression of MRP-14 and GM2A proteins in the cultures of MS monocytes producing a gliotoxic activity in their supernatant, as well as in the zones defining demyelination plaques in the MS brains. They therefore reflect the reality of the coincidence between their abnormal coexpression, the production of gliotoxic activity and the demyelination lesions.

Furthermore, their abnormal production in the context of MS, in macrophage blood cells as well as in those of the brain, indicates that it is justified to carry out their assay in biological fluids to correlate their quantity with the lesional and inflammatory activity of MS.

Example 21

Measurement of the Activity of the T Cells by Proliferation of the T Cells (Sredni et al., 1981).

The T cells are washed twice in culture medium in order to remove any trace of IL2 present in the initial culture medium. B lymphocytes (EBV-LCL) or monocytes/macrophages taken as antigen-presenting cells are irradiated at 10 000 rads, and washed twice with culture medium (RPMI). $2 \times 10^4$ T cells ($2 \times 10^5$ cells/ml) and $2 \times 10^4$ irradiated autologous B cells ($2 \times 10^5$ cells/ml) are incubated together in the presence of an increasing antigen concentration range in a final volume of 200 µl in microwells. After 48 hours of culture at 37° C., 1 µCi of 3H-thymidine in 50 µl of RPMI medium is added to each well. The T cells, the only cells which divide, incorporate the tritiated thymidine into the DNA. After 18 hours of culture, the cells of each microwell are harvested on glass wool pastilles by aspiration. After osmotic lysis of the cells, the radioactivity incorporated into the DNA is absorbed onto the pastilles (cell Harvester 530, Inotech). Each dried pastille is placed in a plastic tube which contains 2 ml of scintillant; the radioactivity b adsorbed on each of the pastilles is quantified in a liquid scintillation beta counter (LKB Rackbeta 1217). The results are expressed as an arithmetic mean of cpm/culture ("counts per minute").

Example 22

Protocol for Detecting the Association Between the Peptides and the Histocompatibility Molecules (Approach APC Transformed with a Peptide Binding to MHC I).

1) Materials:

The sources of histocompatibility molecules are currently of two main types: mutant cells and purified histocompatibility molecules.

The mutant cell used is the human T2 cell which and a variant of the T1 line produced by fusion of the CEM T lymphoma and of the 721.174 B lymphoma (Salter and Cresswell Embo J 1986, 5: 943–949). This cell, which lacks peptide transporters, contains heavy chains of class I molecules free of peptides which will be able to accept exogenous peptides.

Class I histocompatibility molecules purified by affinity chromatography from human B cell lines transformed with EBV can also be used. In this case, the endogenous peptides should be removed by a treatment with 1.5 M urea and 12.5 mM sodium hydroxide (pH 11.7) for 1 hour at 4° C., followed by their removal by a desalting column (PDLO, Pharmacia). The histo-compatibility molecules are immediately placed in contact with the peptides to be tested in a PBS buffer with 0.05% Tween 20, 2 mM EDTA, 0.1% NP40 and 6 mM CHAPS, in the presence of 2 μg/ml B2m to facilitate reassociation (Gnjatic et al., Eur J Immunol 1995 25: 1638–1642).

The peptides tested have in general 8 to 10 residues, sometimes 11 or 12. They were synthesized by Néosystems (Strasbourg), or by Chiron mimotopes (Victoria, Australia). They are used at concentrations varying from 100 μM to 0.1 nM.

2) Protocol for assembly (Connan et al., Eur J Immunol 1994, 24: 777; Couillin et al. Eur J Immunol 1995, 25: 728–732).

Aliquots of 8.105 cells in a volume of 64 μl, distributed in Eppendorf microfuge tubes, are brought into contact with a lysis buffer containing 10 mM PBS, pH 7.5, 1% NP40, protease inhibitors (1 mM PMSF, 100 μM iodoacetamide, 2 μg/ml aprotinin, 10 μM leupeptin, 10 μM pepstatin and 10 μg/ml trypsin inhibitor). The lysis is performed in the presence of the peptides to be tested for 30 minutes or 1 hour at 37° C. After removing the nonsolubilized material by centrifugation at 15 000 revolutions/minute at 4° C., the supernatant and supplemented with 140 μl of PBS containing 0.05% Tween 20, 3 mM of sodium azide, 1 mM PMSF and 10 mg/ml of bovine albumin. Each sample is incubated for 20 hours at 4° C. in 2 wells of a microtiter plate of the Nunc type, Maxisorb, previously coated with a monoclonal antibody (10 μg/ml in PBS) which recognizes the histocompatibility molecules having conforming conformation(s) for the presentation of peptides and similar to that (those) present at the surface of the cells. The antibody-coated plate is saturated beforehand with bovine albumin at 10 mg/ml in PBS-Tween before placing the sample. The second antibody which allows the detection of the assembly of the histo-compatibility molecules is directed against B2m. It is coupled either to biotin (NHS-LC biotin, Pierce) or to alkaline phosphatase (P-552, Sigma) and is incubated at 2 μg/ml for one hour at 37° C. In the case of the use of biotin, an incubation of 45 minutes at 20–25° C. with streptavidin coupled to alkaline phosphatase (E-2636, Sigma) is carried out. The activity of alkaline phosphatase is measured using, as substrate, 4-methyl-umbelliferyl phosphate (M-8883, Sigma) at 100 μM in 50 mM diethanolamine, pH 9.5 with 1 mM MgCl$_2$. The reading is carried out at 340/460 nm with the aid of a cytofluorimeter.

3) Stability of the HLA/peptide complexes:

The stability of the abovementioned complexes was studied because it determines the good presentation of the antigen and the induction of the T response. To this effect, either purified HLA or the T2 cell lysate was used. With purified HLA, the endogenous peptides were removed (as described in 2)) and then it was brought into contact with the peptide to be tested in an Eppendorf tube at 37° C., for periods varying from a few minutes to several days. The following incubation phase on a 96-well plate (as described in 2) with the anti-HLA antibody is performed for one hour at 37° C. The revealing is carried out in a conventional manner. With the T2 cell lysate, all the incubations are also carried out at 37° C., after addition of all the protease inhibitors.

What is claimed is:

1. A polypeptide comprising at least one fragment of SEQ ID NO: 9, said fragment comprising at least one of SEQ ID NO: 68 or SEQ ID NO: 72.

2. The polypeptide as claimed in claim 1, characterized in that it comprises SEQ ID NO: 9.

3. The polypeptide as claimed in claim 1, characterized in that it consists of SEQ ID NO: 9.

4. A method for detecting at least one ligand associated with multiple sclerosis, in a biological sample, characterized in that the biological sample is brought into contact with at least one polypeptide as defined in claim 1, and then the formation of a complex between said polypeptide and the ligand is detected.

5. The method as claimed in claim 4, characterized in that the biological sample is in addition brought into contact with at least one polypeptide comprising at least one fragment of a protein chosen from proteins whose peptide sequence in the native state is selected from the group consisting of SEQ ID NO: 1 to SEQ ID NO: 8 and SEQ ID NO: 10 to SEQ ID NO: 29 and peptide sequences which exhibit at least 70% identity with any one of SEQ ID NO: 1 to SEQ ID NO: 8 and SEQ ID NO: 10 to SEQ ID NO: 29.

6. The method as claimed in claim 4, characterized in that said ligand is an antibody, a receptor, a substrate for enzymatic activity or an enzyme for which said polypeptide is a cofactor.

7. The method as claimed in claim 4, characterized in that the biological sample is urine, cerebrospinal fluid or serum.

8. A method for detecting at least one polypeptide as defined in claim 1, in a biological sample, characterized in that the biological sample is brought into contact with at least one ligand that specifically binds to said polypeptide, and then the formation of a complex between said polypeptide and said ligand is detected, wherein said ligand is selected from the group consisting of an antibody, a substrate with enzymatic activity, an enzyme for which said polypeptide is a cofactor and a receptor.

9. The method as claimed in claim 8, characterized in that the biological sample is urine, cerebrospinal fluid or serum.

10. A nucleotide fragment, characterized in that it encodes a polypeptide as defined in claim 1.

* * * * *